(12) United States Patent
Martin

(10) Patent No.: US 12,268,704 B2
(45) Date of Patent: Apr. 8, 2025

(54) HIPPO REGULATION OF CARDIAC VASCULARITY, FIBROSIS, AND INFLAMMATION

(71) Applicant: Baylor College of Medicine, Houston, TX (US)

(72) Inventor: James F. Martin, Houston, TX (US)

(73) Assignee: Baylor College of Medicine, Houston, TX (US)

(*) Notice: Subject to any disclaimer, the term of this patent is extended or adjusted under 35 U.S.C. 154(b) by 1022 days.

(21) Appl. No.: 17/049,891

(22) PCT Filed: Apr. 23, 2019

(86) PCT No.: PCT/US2019/028777
§ 371 (c)(1),
(2) Date: Oct. 22, 2020

(87) PCT Pub. No.: WO2019/209865
PCT Pub. Date: Oct. 31, 2019

(65) Prior Publication Data
US 2021/0322454 A1    Oct. 21, 2021

Related U.S. Application Data

(60) Provisional application No. 62/661,325, filed on Apr. 23, 2018.

(51) Int. Cl.
A61K 31/713    (2006.01)
A61P 9/10      (2006.01)
C12N 15/63     (2006.01)
C12N 15/86     (2006.01)
C12Q 1/68      (2018.01)

(52) U.S. Cl.
CPC .............. *A61K 31/713* (2013.01); *A61P 9/10* (2018.01); *C12N 15/63* (2013.01); *C12N 15/86* (2013.01)

(58) Field of Classification Search
None
See application file for complete search history.

(56) References Cited

U.S. PATENT DOCUMENTS

2016/0312219 A1    10/2016    Martin et al.

OTHER PUBLICATIONS

Liu et al. Int. J. Biol. Sci. vol. 19(11):3428-3440, 2023.*
Conrad et al. "Myocardial Fibrosis and Stiffness with Hypertrophy and Heart Failure in the Spontaneously Hypertensive Rat", Circulation< Jan. 1, 1995, vol. 91, No. 1; pp. 161-170.
Matsui et al. "Lats2 Is a Negative Regulator of Myocyte Size in the Heart", Circulation Research, Nov. 21, 2008, Epub Oct. 16, 2008, vol. 103, No. 11; pp. 1309-1318.

* cited by examiner

*Primary Examiner* — Sean McGarry
(74) *Attorney, Agent, or Firm* — Norton Rose Fulbright US LLP

(57) ABSTRACT

Embodiments of the disclosure encompass methods and compositions related to modulating the Hippo pathway to inhibit fibrosis and/or inflammation in a tissue and/or organ of an individual in need thereof. In specific embodiments, the disclosure concerns modulation of LATS1, LATS2, or both, such as providing to the individual an effective amount of one or more agents that increase the levels of LATS1, LATS2, or both in the individual. In specific cases, cardiac fibrosis is treated with effective levels of vector(s) comprising LATS1, LATS2, or both.

11 Claims, 164 Drawing Sheets
Specification includes a Sequence Listing.

Podoplanin p-Yap DAPI

Podoplanin a-actinin DAPI

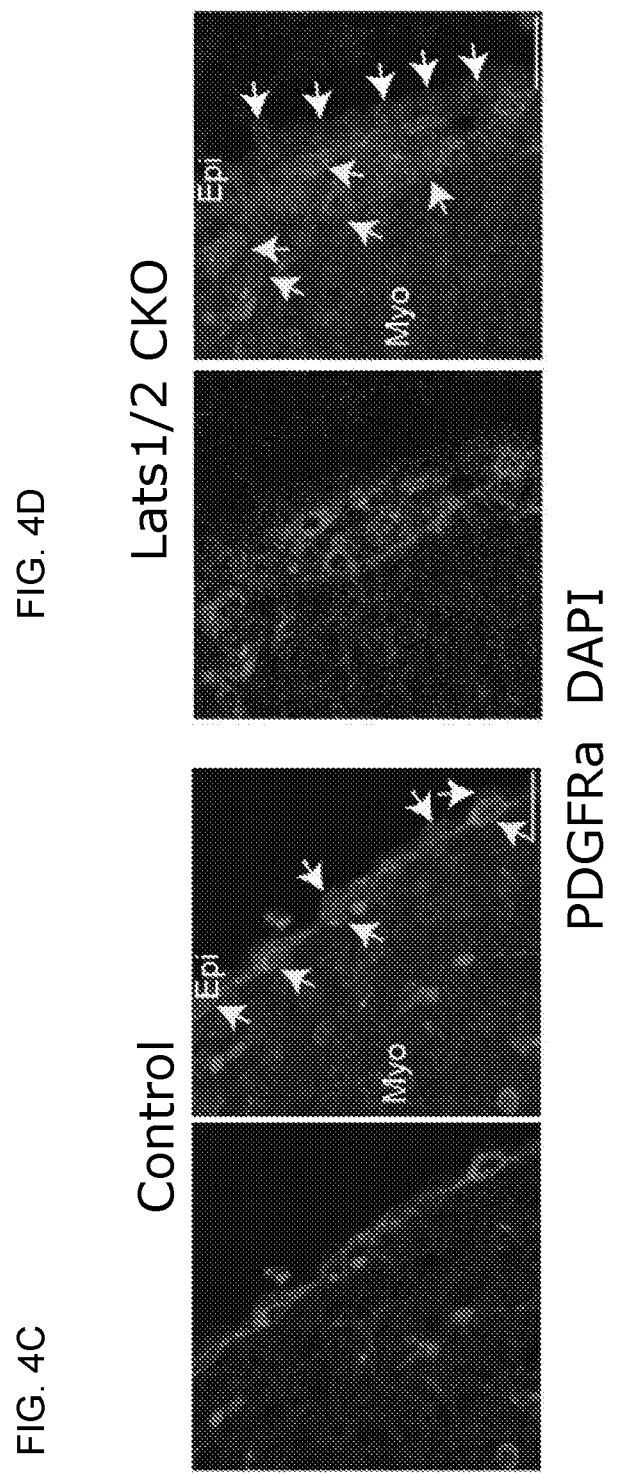

| E14.5 hearts | GFP+PDGFRa+ (cell events) | GFP+ (cell events) | % |
|---|---|---|---|
| Control (4 hearts) | 691 | 1564 | 44.2 |
| Lats1/2 CKO (4 hearts) | 547 | 1708 | 32* |

*p<0.0001

GFP Vimentin DAPI

FIG. 8A

| Injection/Harvest | Survival Rate of Lats1/2 CKO |
|---|---|
| E11.5/E14.5 | 11/11 |
| E11.5/E15.5 | 7/11 |
| E11.5/E16.5 | 1/10 * + |

*Snai2*

FIG. 9F

| E14.5 hearts from one litter of embryos | Epicardial cells (cell number) | pSmad2/3$^{high}$ (cell number) | % |
|---|---|---|---|
| Control | 45 | 22 | 48.31* |
| Lats1/2CKO | 49 | 37 | 75.89 |

*$p<0.05$ by Chi-square test pan-Keratin DAPI

GFP DAPI

Wt1 CTnt DAPI

Yap1 occupied anchors
H3K27Ac HiChIP

Control        *Lats1/2* CKO

Control

Lats1/2 CKO

Lyz GFP DAPI

Ligand-Receptor Pairs

Sorted GFP+ cells on low attachment culture for 24hr cTnT YaP DAPI

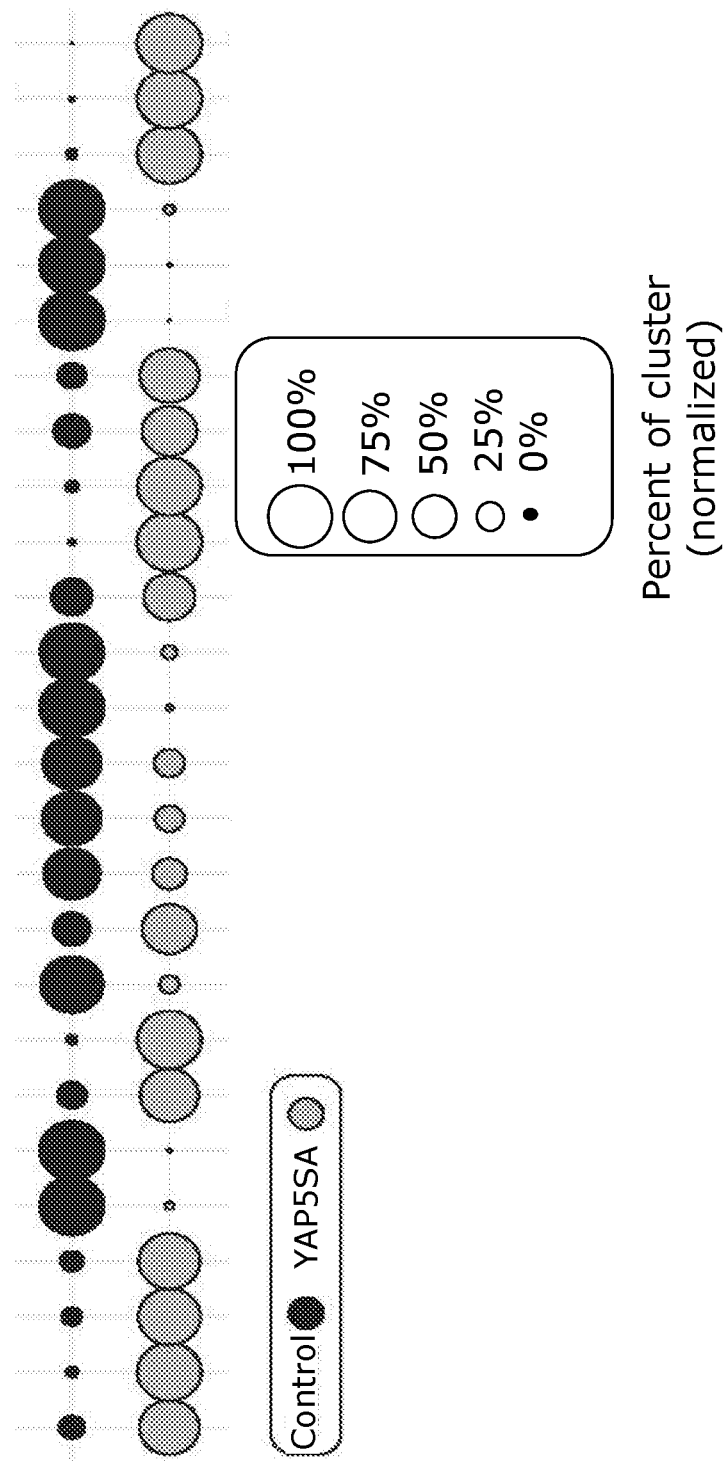

Lyz2

Ccr2

Il6

Serpina3n

Amotl2

Tgfb2

Acta2

Col 12a1

FIG. 26G

|          | Control      | Lats1/2 CKO  | P-value |
|----------|--------------|--------------|---------|
| G1       | 80.73±6.33%  | 63.9±7.94%   | 0.018*  |
| S        | 7.60±1.28%   | 20.4±2.86%   | 0.023*  |
| G2/M     | 8.91±2.11%   | 12.06±2.55%  | 0.106   |
| Super G2 | 1.17±1.02%   | 2.23±2.37%   | 0.106   |

Serpina3N GFP DAPI

Plac8 GFP DAPI

GFP Tunel DAPI

HIPPO REGULATION OF CARDIAC VASCULARITY, FIBROSIS, AND INFLAMMATION

CROSS-REFERENCE TO RELATED APPLICATIONS

This application is a national phase application under 35 U.S.C. § 371 that claims priority to International Application No. PCT/US2019/028777 filed Apr. 23, 2019, which claims priority to U.S. Provisional Patent Application 62/661,325, filed Apr. 23, 2018, both of which are incorporated by reference herein in their entirety.

STATEMENT REGARDING FEDERALLY SPONSORED RESEARCH OR DEVELOPMENT

This invention was made with government support under HL118761 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 22, 2020, is named Sequence_Listing.txt and is 37,774 bytes in size.

TECHNICAL FIELD

Embodiments of the disclosure include at least the fields of cell biology, molecular biology, cardiology, physiology, biochemistry, and medicine.

BACKGROUND

The epicardium, cells covering the outer layer of the heart, originates from the extra-cardiac proepicardium. The proepicardium is compartmentalized into populations that give rise to cardiac endothelium and mesenchymal cells: fibroblasts and smooth muscle (Katz et al., 2012; Acharya et al., 2012). At mouse embryonic day (E)9.5, proepicardial cells attach to myocardium, spread as a continuous epithelial sheet, and form a single cell layer covering the entire myocardium. The epicardium expresses a number of important genes including signaling molecules such as Retinaldehyde dehydrogenase 2 (Raldh2), and genes encoding transcription factors: Wilms tumor 1 (Wt1), transcription factor 21 (Tcf21), T-box18 (Tbx18), and multiple C/EBP transcription factor family members (Acharya et al., 2012; Cai et al., 2008; Guadix et al., 2011; Huang et al., 2012; Zhou et al., 2008).

A subset of epicardial cells delaminate, undergo EMT and generate epicardial-derived cells (EPDCs). In mammals, EPDCs emanating from Wt1-expressing lineage primarily give rise to vascular smooth muscle cells and fibroblasts, two supporting cell types that are important for coronary vascular and myocardial development. EPDCs first populate the subepicardial space between epicardium and myocardium, forming the subepicardial mesenchyme, and invade the myocardium where they differentiate into supporting cells of the heart (Wessels and Perez-Pomares, 2004).

Although adult epicardial cells are quiescent, they are activated upon injury and contribute to the repair process by expressing developmental programs in the injured adult heart (Zhou et al., 2011; Huang et al., 2012; Lepilina et al., 2006). Activated adult epicardium is a source of pro-inflammatory signals after myocardial infarction. In the adult heart C/EBP factors activate pro-inflammatory signals after injury whereas Yap and Taz, two Hippo-pathway effectors, may promote anti-inflammatory response to injury (Huang et al., 2012; Ramjee et al., 2017).

The Hippo signaling pathway, an organ size control pathway, inhibits cell proliferation and promotes apoptosis (Halder and Johnson, 2011). Hippo pathway components include ste-20 family kinases Mst1 and Mst2 (Mst1/2), which complex with scaffold adaptor protein Salvador (Sav) to phosphorylate the nuclear dbf2-related (NDR) family kinases Lats1 and Lats2 (Lats1/2). Yap and Taz, Hippo pathway effectors, are transcriptional co-factors that are substrates for Lats1/2 kinases. Upon phosphorylation by Lats1/2 kinases, Yap and Taz are excluded from the nucleus and transcriptional activity is inhibited. Removing Hippo pathway components in embryonic or adult myocardium releases the downstream effector Yap from Hippo-dependent suppression, promoting cardiomyocyte (CM) proliferation and tissue regeneration (Heallen et al., 2013; Heallen et al., 2011; Morikawa et al., 2015).

The present disclosure satisfies a long felt need in the art of treatment of fibrosis and inflammation, particularly aspects related to fibroblast development, including for cardiac fibrosis.

BRIEF SUMMARY

Embodiments of the disclosure include methods and compositions related to inhibiting fibrosis and/or inflammation. The fibrosis and inflammation may be in cardiac tissue and heart. In particular embodiments, members of the Hippo signaling pathway are modulated to impact cardiac fibroblast development and homeostasis such that fibrosis and inflammation are at least improved. In particular embodiments, the Hippo pathway kinases Lats1/2 (which refers to either or both of Lats1 and Lats2) are utilized to promote the transition from epicardial progenitors to fibroblasts, thereby improving or preventing fibrosis and inflammation. In adult resting cardiac fibroblasts, Lats1/2 inhibit transition from fibroblasts to inflammatory myofibroblasts thereby preventing fibrosis and inflammation.

In specific embodiments, one or more agents that increase Lats1/2 levels in cardiac cells of cardiac tissue or the heart in need thereof are delivered to the respective tissue or organ. The one or more agents may be of any kind. In specific embodiments, the agents are themselves Lats1/2 polynucleotides and/or polypeptides, and delivery of the agents to the tissue or organ results in improvement of the fibrosis and/or inflammation, including a reduction in the level of fibrosis and/or inflammation, a delay in onset or prevention of onset of further fibrosis and/or inflammation, and so forth. The Lats1/2 polynucleotides and/or polypeptides may be delivered by any suitable material, such as in, on, or with a vector, in some cases.

In particular embodiments, the fibrosis and/or inflammation is in the heart. As described herein, studies revealed the association of Lats1/2 with cardiac fibroblast development, homeostasis, and prevention of inflammation. Single cell transcriptomics were utilized to investigate Lats1/2 function in epicardial progenitor cell diversification and adult cardiac fibroblasts. A high-throughput single cell (sc) RNA-sequence (seq) platform, Drop-seq, was adopted to characterize E13.5 and E14.5 adult cardiac cellular composition and heterogeneity in Lats1/2 deficient and control hearts (Macosko et al., 2015). The data revealed that Lats1/2 activity is required for epicardial-derived cells (EPDC) progression from a transient subepicardial mesenchyme to fully differentiated cardiac fibroblasts and provides insight into mechanisms coordinating fibroblast development with coronary vascular remodeling in heart development. The data also showed that in the adult cardiac fibroblast Lats1/2 prevented fibrosis and inflammation in the adult heart.

In one embodiment, there is a method of inhibiting fibrosis and/or inflammation in a tissue or organ, comprising the step of contacting the tissue or organ with one or more agents that increase the level of Large tumor suppressor kinase 1 (LATS1), Large tumor suppressor kinase 2 (LATS2), or both in the tissue or organ. In specific cases, the fibrosis and/or inflammation is in the heart. The tissue or organ may be cardiac or heart. In some cases, the fibrosis in the heart is from a myocardial infarction. In some cases, the method is an in vitro method.

Agents of the disclosure may be a nucleic acid. In specific cases, the nucleic acid encodes LATS1 or a functional fragment or derivative thereof, LATS2 or a functional fragment or derivative thereof, or both. The nucleic acid may be a vector comprising an expression construct that encodes LATS1, an expression construct that encodes LATS2, or an expression construct the encodes LATS1 and LATS2 separated by a 2A or IRES element. LATS1 functional derivatives may be at least 75, 76, 77, 78, 79, 80, 81, 82, 83, 84, 85, 86, 87, 88, 89, 90, 91, 92, 93, 94, 95, 96, 97, 98, or 99% identical to SEQ ID NO:2. LATS2 functional derivatives may be at least 75, 76, 77, 78, 79, 80, 81, 82, 83, 84, 85, 86, 87, 88, 89, 90, 91, 92, 93, 94, 95, 96, 97, 98, or 99% identical to SEQ ID NO:4. In specific cases, the LATS1 nucleic acid comprises SEQ ID NO:1 or is at least 75, 76, 77, 78, 79, 80, 81, 82, 83, 84, 85, 86, 87, 88, 89, 90, 91, 92, 93, 94, 95, 96, 97, 98, or 99% identical to SEQ ID NO:1. The functional fragment of LATS1 may be at least 100, 200, 250, 300, 400, 500, 600, 700, 750, 800, 900, 950, 1000, 1050, or 1100 amino acids in length. In some cases, the LATS2 nucleic acid comprises SEQ ID NO:3 or is at least 75, 76, 77, 78, 79, 80, 81, 82, 83, 84, 85, 86, 87, 88, 89, 90, 91, 92, 93, 94, 95, 96, 97, 98, or 99% identical to SEQ ID NO:3. The functional fragment of LATS2 may be at least 100, 200, 250, 300, 400, 500, 600, 700, 750, 800, 900, 950, 1000, or 1050 amino acids in length. Any vectors include viral vectors (adenoviral vector, an adeno-associated viral vector, a lentiviral vector, or a retroviral vector, for example) or non-viral vectors (plasmid, retrotransposon, nanoparticle, liposome, or combination thereof).

In some cases, the agent is a polypeptide. The agent may be a LATS1 polypeptide, LATS2 polypeptide, or both. The LATS1 polypeptide may comprise or be SEQ ID NO:2 or is at least 75, 76, 77, 78, 79, 80, 81, 82, 83, 84, 85, 86, 87, 88, 89, 90, 91, 92, 93, 94, 95, 96, 97, 98, or 99% identical to SEQ ID NO:2. The LATS2 polypeptide may comprise or be SEQ ID NO:4 or is at least 75, 76, 77, 78, 79, 80, 81, 82, 83, 84, 85, 86, 87, 88, 89, 90, 91, 92, 93, 94, 95, 96, 97, 98, or 99% identical to SEQ ID NO:4.

Embodiments of the disclosure include compositions comprising one or more agents that increase the level of Large tumor suppressor kinase 1 (LATS1), Large tumor suppressor kinase 2 (LATS2), or both in the tissue or organ for use in inhibiting fibrosis and/or inflammation in a tissue or organ.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing, in which:

(FIG. 1A) E15.5 histology showed reduced compacted myocardium in Lats1/2 CKO. Panels on right are high magnification views of boxed area in panels on left. (FIG. 1B) Coronary vessels visualized by Pecam-1 at E14.5. Lats1/2 CKO had decreased vessel coverage (asterisks) and blood islands (arrows) on ventral and lateral heart. (FIG. 1C) Pecam-1 IF. (FIG. 1D) Quantitation of vasculature in FIG. 1C. (FIG. 1E) Podoplanin labels epicardium and Lats1/2 CKO hearts had increased nuclear Yap in epicardium (white arrowheads) and subepicardium (yellow arrowheads). (FIG. 1F) Quantification of Yap subcellular localization. (FIG. 1G) Lats1/2 CKO had decreased p-Yap in epicardium (white arrows) and subepicardium (yellow arrows). (FIG. 1H-FIG. 1I) Lats1/2 CKO hearts with reduced Yap/Taz were normal at E15.5. Scale bar: FIG. 1A left panels 400 µm; right panels 80 µm; FIG. 1B 500 µm; FIG. 1C upper panels 200 µm, bottom panels 100 µm, FIG. 1E 25 µm, FIG. 1G 50 µm, FIG. 1H 200 µm. Data: means±SD. *P<0.1: Mann-Whitney U test. LA: left atrium; RV: right ventricle; LV: left ventricle; IVS: interventricular septum. RV: right ventricle; LV: left ventricle; N: Nuclear Yap; N/C Nuclear/Cytoplasmic Yap; C: Cytoplasmic Yap; Epi: epicardium; Myo: myocardium.

(FIG. 2A) two-dimensional tSNE representation of 18,757 single-cell transcriptomes colored by experimental group. (FIG. 2B) tSNE visualization of graph-based clustering carried out on control and Lats1/2 CKO. (FIG. 2C) Classification and merging of clusters shown in FIG. 2B. Red blood cells and platelets, cluster 16, are removed. (FIG. 2D) Differentially expressed genes (rows) across final 18,166 cells (columns). (FIG. 2E) Sunburst plot of E13.5-E14.5 cardiac cell composition. Cell classes are colored according to FIG. 2C. (FIG. 2F) Lats1/2 CKO and control single-cell composition for individual clusters. Phylogenetic tree of each identified cell type based on 3,217 expressed genes with high dispersion (>2 standard deviations above average dispersion) (left). Dot plot showing relative proportion of cells belonging to each genotype at E13.5 and E14.5 time points colored according to FIG. 2A. Dot size represents percentage of cells within each identity class. Numbers on dots are cell numbers in corresponding cluster and numbers below each genotype are cell numbers analyzed in each group (middle, Chi-squared analysis, * p-value<0.0025). Violin plot of gene expression for representative markers of each categorical class colored according to FIG. 2C (right). Mφ Macrophages; Art. EC, arterial endothelial cells; VEC, vascular endothelial cells; EndoV EC, endocardial valve cells; Endo EC, endocardial cells; Pro. EC, proliferating endocardial cells; AVC CMs, atrioventricular canal CMs; Trab. CM, trabecular CMs; CMs, standard CMs; Pro. CM, proliferating CMs; EPI, epicardial cells; Valve Mes., valve Mesenchymal cells; AVCu, atrioventricular cushion mesenchymal cells; Pro. AVCu, proliferating atrioventricular cushion mesenchymal cells; SMC, smooth muscle cells; FB, fibroblasts; C20, cluster number 20.

(FIG. 3A) Subsetting and clustering of epicardial and epicardial-derived cells. (Right) View of experimental identity for each single-cell, colored as in FIG. 2A. (FIG. 3B) tSNE plot of Lats1/2 CKO enriched clusters. Epicardial cells (EPI), fibroblasts (FB), cluster number 20 (C20), vascular endothelial cells (VEC), and fibroblast cluster 2 (FB2) which resemble pericytes. (FIG. 3C) Heatmap of differentially expressed genes from FB, VEC, EPI, C20, and FB2 clusters. Rows are genes and columns represent single-cells. Red indicates high relative expression. (FIG. 3D) Gene expression projected across tSNE. Black indicates high gene expression and cluster identities and boundaries are set in background and colored according to FIG. 3B. (FIG. 3E) Pseudotime trajectory of epicardial cells, fibroblasts, and C20. Cells are colored by experimental groups across epicardial to fibroblast differentiation axis (top). Pseudotime score is assigned to individual cells. Cells with a dark color and bright color represent start and end of pseudotime respectively (bottom). (FIG. 3F) tSNE from FIG. 2B is colored by individual cells pseudotime placement and arrow represents epicardium to fibroblast developmental trajectory shown in FIG. 3E. (FIG. 3G) The Monocle2 minimum spanning tree is the underlying black line, and critical node is denoted as 'X' with dashed arrows representing the bifurcation of Branch A (fibroblast) and Branch B (C20) (top panel). Hierarchical clustering of genes with branch-specific trends in gene expression across pseudotime. (top three: gene expression pattern enriched in Branch A; bottom three: gene expression pattern enriched in Branch B) (bottom panel). (FIG. 3H) GO analysis of genes identified from branch B, C20-specific, in FIG. 3G. Color represents each GO term. (FIG. 3I) Motif enrichment of Branch B, C20, specific genes. Expression of each transcription factor is in percent of cells above threshold in C20. Red indicates high expression. (FIG. 3J) Expression and cell density plots of key transcriptional regulators across pseudotime. Points are each colored by cluster identity from FIG. 3B, and FIG. 3G. (FIG. 3K) Tead1 target gene visualization and annotation. GO categories assigned and color coordinated based on FIG. 3H.

FIGS. 4A-4H. C20 is located in subepicardium and expands in Lats1/2 CKO hearts. See also FIG. 11. (FIG. 4A-FIG. 4B) Podoplanin labels epicardium (white arrows) and α-actinin labels myocardium. The intervening region is subepicardium and Lats1/2 CKO showed expanded subpicardium weakly stained by Podoplanin (yellow arrows). (FIG. 4C-FIG. 4D) PDGFR-α rarely labels epicardium (white arrows) and extensively labels subepicardium (yellow arrows). Lats1/2 CKO hearts had thickened PDGFR-α positive subepicardium. (FIG. 4E-FIG. 4G) Wt1, Dpp4, and Collagen I labels epicardium (white arrows) and subepicardium (yellow arrows) in Lats1/2 CKO hearts. Lats1/2 CKO hearts had expanded Wt1 positive subepicardium. Scale bar: FIG. 4A, FIG. 4C, FIG. 4E-FIG. 4G, 25 μm. In FIG. 4B and FIG. 4H, data are means±SD. *P<0.1 Mann-Whitney U test.

(FIG. 5A-FIG. 5B) A reduction of epicardial-derived fibroblasts was observed in Lats1/2 CKO hearts. Epicardial-derived fibroblasts are labelled (arrowheads) by GFP and PDGFR-α double positive staining. Other epicardial-derived lineages are indicated (arrows) by GFP single positive staining. Panels on left are a higher magnification view of boxed area in panels on right. (FIG. 5B-FIG. 5C) FACS analysis quantification of percentage of epicardial derived fibroblasts (*P<0.0001: Chi-square test). (FIG. 5D-FIG. 5E) Fibroblast marker Vimentin showed decreased epicardial derived fibroblasts in Lats1/2 CKO hearts. (epicardial derived fibroblasts: arrowheads, other epicardial derived lineages: arrows). Panels on left are higher magnification of boxed area in panels on right. Data are means±SD. *P<0.1, Mann-Whitney U test. Scale bar: 50 μm.

(FIG. 6A) Cardiac fibroblast labelled with PDGFR-α in control and Dhrs3$^{-/-}$ hearts at E14.5. Dhrs3$^{-/-}$ exhibited more fibroblasts in myocardium (arrows). Right two panels are high magnification of left two panels. (FIG. 6B) Quantification of FIG. 6A. (FIG. 6C) Vasculature of Sitagliptin treated E14.5 embryonic hearts were visualized by Pecam-1. Ventral side of Lats1/2 CKO hearts treated with Sitagliptin exhibited some blood islands (arrows), but dorsal side showed comparable vessel coverage. Vessel phenotype was partially suppressed compared with FIG. 1B. (FIG. 6D) Pecam-IF of Sitagliptin treated E14.5 heart. Vessel phenotype was partially suppressed compared with FIG. 1C. (FIG. 6E) Quantification of vessel pattern in FIG. 6D. Junction density was reduced in Lats1/2 CKO hearts treated with Sitagliptin, but vessel percentage and Mean E lacunarity have no difference between Lats1/2 CKO and controls. (FIG. 6F) Primary epicardial cells growing on 4 kPa and 20 kPa stiffness hydrogel showing cell shape and Yap localization. (FIG. 6G) PDGFR-α expression in primary epicardial cells on different stiffness. (FIG. 6H) Quantification of 6F, 6G. Scale bar: 6A, 50 μm, 6C, 400 μm, 6D, 200 μm, 6F-6G, 50 μm. In FIG. 6B, FIG. 6E and FIG. 6I, data are means±SD. Statistics: Mann-Whitney U test.

FIGS. 8A-8F. Knocking out Lats1/2 leads to embryonic lethality at E15.5. (FIG. 8A) Cre activity was induced at E11.5 by tamoxifen injection. Lats1/2 CKO survival rate was at different harvest time series. *P<0.001 between E16.5 and E14.5, Fisher's exact test. $^{+}$P<0.05 between E16.5 and E15.5, Fisher's exact test. (FIG. 8B-FIG. 8C) Gross heart morphology and H&E stained sections from at E14.5 and E15.5. (FIG. 8D-FIG. 8F) Non-cardiac defects in Lats1/2 CKO at E15.5, including hemorrhage (yellow arrowheads) and herniated liver (L) and intestine (I). Scale bar: FIG. 8B 400 µm; FIG. 8C left panel 500 µm; right panel 100 µm; FIG. 8D 2000 µm; FIG. 8E-FIG. 8F 1000 µm.

FIGS. 9A-9F. Control experiments to validate coronary vessel development defects in Lats1/2 CKO and EMT factors expression in epicardium and EPDC. (FIG. 9A) Wt1$^{CreERT2/+}$; Rosa26$^{mTmG}$ injected with Tamoxifen (TAM) exhibited well-formed coronary vasculature compared with Rosa26$^{mTmG}$ littermate at E14.5. (FIG. 9B) Wt1$^{CreERT2/+}$; Lats1/2$^{f/f}$ hearts exhibited organized coronary vessel injected with vehicle control peanut oil compared with Lats1/2$^{f/f}$ littermate at E15.0. (FIG. 9C-FIG. 9D) EMT factors Twist1 and Snai2 detected by in situ probe at E14.5. (FIG. 9E) pSmad2/3 activity in epicardium. White arrowheads point to pSmad2/3 high-expressing epicardial cells (pSmad2/3$^{high}$) and yellow arrowheads point to pSmad2/3 low-expressing epicardial cells. Lats1/2 CKO hearts exhibited more pSmad2/3$^{high}$ epicardial cells. (FIG. 9F) Quantification of pSmad2/3$^{high}$ epicardial cells. Scale bar: 9A-9B, 400 µm, 9C-9E, 25 µm.

(FIG. 10A) Quality control metrics for individual Drop-seq experiments. (Left) Violin plots displaying the number of genes and Unique Molecular Identifiers (UMI) per individual cell with total statistics listed at top (combined data set). (Right) Number of genes and UMI per cell plotted against each other. Plots and points all colored according to FIG. 2A. (FIG. 10B) Heatmap of top differentially expressed genes among rare CM cell populations. Highly expressed genes are shown as yellow/orange. (FIG. 10C) Heatmap displaying the top differentially expressed genes across all endothelial-like cells. Highly expressed genes are yellow. (FIG. 10D) Clustering and tSNE visualization of 4,183 cells implicated in valvulogenesis. (FIG. 10E) Feature expression plots of the classic, as well as some novel genes expressed during valvulogenesis. Gene expression is indicated by dark black, and the background color indicates the cluster/cellular identity shown in 10D. (FIG. 10F) Single-cell markers of cardiac valve development. The relative expression levels of each gene (column) are shown as dots for each of the 6 cardiac valve clusters identified in FIG. 10D. The size of the dot indicates the number of cells expressing the gene per cluster, and the color denotes expression levels with bright red representing the highest level of gene expression.

(FIG. 11A) Cluster FB2 feature plot of gene expression projected across the tSNE. Black indicates high gene expression, and cluster identities and boundaries are set in the background and colored according to FIG. 3B. (FIG. 11B-FIG. 11C) In addition to epicardium stained with pan-Keratin and Alcam in both control and Lats1/2 CKO hearts (white arrows), subepicardium of Lats1/2 CKO hearts exhibited ectopic expression of pan-Keratin and Alcam (yellow arrows). (FIG. 11D) Increased Spon2 expression in Lats1/2 CKO epicardium compared with wild type.

(FIG. 12B-FIG. 12C) Lats1/2 CKO exhibited significantly increased EdU labelling in GFP positive cells. Proliferating epicardial cells and EPDC were indicated as GFP$^+$ EdU$^+$ double positive cells (arrowheads). *p<0.05, Mann-Whitney U test. Data shown are means±SD. Scale bar: 50 µm.

(FIG. 13A) Mature smooth muscle cells at E15.5 were labelled with SM-MHC. Connection were established between coronary artery and aorta both in control and Lats1/2 CKO hearts (arrows). (FIG. 13B) Lineage tracing of epicardial derived coronary artery smooth muscle cell progenitors by co-labelling GFP and PDGFR-β at R14.5. (FIG. 13C) The high magnification views of the yellow boxed area in FIG. 13B. Subepicardium was highlighted with PDGFR-β (yellow arrowheads). Lats1/2 CKO hearts exhibited accumulation of PDGFR-β$^+$ cells in subepicardium. (FIG. 13D) The high magnification views of the white boxed area in FIG. 13B. Reduced epicardial derived smooth muscle progenitor cells in Lats1/2 CKO hearts.

(FIG. 14A) Numerous TEAD binding motifs were identified at the regulatory regions of genes encoding intercellular factors. (FIG. 14B-FIG. 14C) Yap-TEAD binding sites locates at the regulatory regions of Dpp4 and Dhrs3. Yap ChIP-qPCR, quantified in the bar graphs, demonstrated Yap binding at the yellow highlighted region in the corresponding gene tracks. Data are means±SD. *P<0.1 was by Mann-Whitney U test. (FIG. 14D) Cell identity of primary epicardial cell culture at 24-hour after isolation. The culture mainly contains Wt1 positive epicardial cells with minimal CTnT$^+$ CMs.

(FIG. 15A) Volcano plots displaying RNA-seq (left) and Fast-ATAC (right) differential gene expression and chromatin accessibility analysis of sorted cardiac fibroblasts (CFs) 3 days post MI (3 dPMI) and 3 days post sham, respectively. Dots indicate top 100 significantly differentially expressed genes (left) and peaks (right). (FIG. 15B) Bubble chart comparing global transcription factor motif enrichment between CFs harvested from sham and MI animals (3 days post operation) across accessible chromatin regions identified via Fast-ATAC. The expression level of each transcription factor was examined by RNA-seq. Larger bubbles are more significant (lower P-value), and smaller bubbles are less significant (higher P-value), scale for size is log 2. Dark colors indicate lowly expressed, and light highlights high transcript levels. (FIG. 15C) Fast-ATAC browser tracks from 3 dPMI and 3 days post sham CFs for representative genes Acta2, Il34, and Tead1. TEAD motifs identified via HOMER are highlighted in pink. (FIG. 15D) Representative images from cardiac tissue sections after MI or sham operations stained for GFP (green), Yap (red), and DAPI (blue). Cardiac fibroblasts (GFP, arrowheads) showed increased nuclear Yap activity at 3 dPMI compared with sham cardiac fibroblasts. Scale bar indicates 25 µm. (FIG. 15E) Genome browser tracks for CUT&RUN and Fast-ATAC. (FIG. 15F) Violin plot showing the absolute distance of Yap peaks to the nearest transcription start site (TSS). (FIG. 15G) CUT&RUN footprint analysis for Yap at TEAD motifs. (FIG. 15H) Heatmap showing Fast-ATAC signal (read depth) across all myofibroblast Yap binding sites (n=5941, p-value<1e-5) for indicated experimental conditions. (FIG. 15I) Venn diagram showing overlay of TEAD motif containing Fast-ATAC peaks from control cardiac fibroblasts 3 dPMI, and myofibroblast Yap CUT&RUN peaks. (FIG. 15J)

Figure 1A:
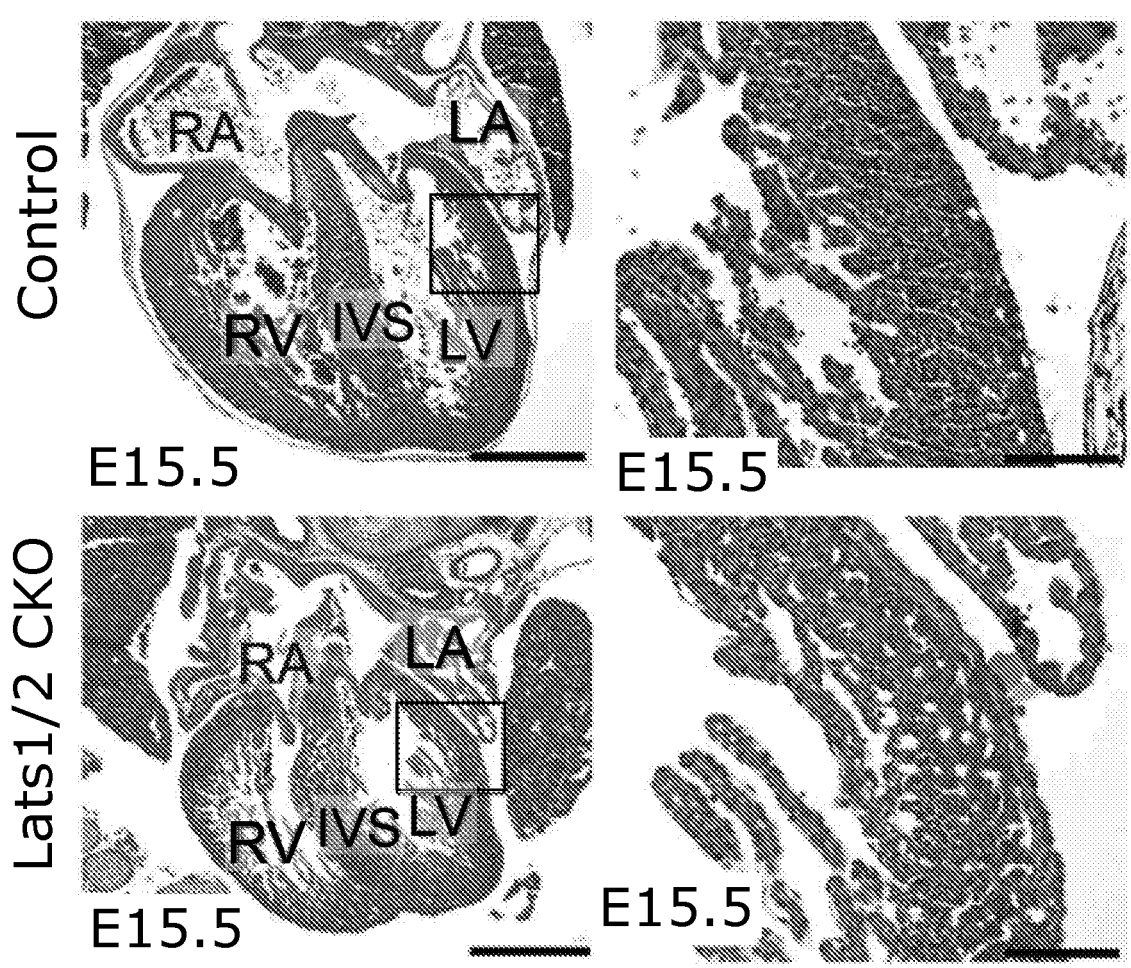
FIGS. 1A-1I. Lats1/2 deficiency results in defective heart development. See also FIG. 8 and FIG. 9.

Heatmap showing CUT&RUN signal (read depth) across all myofibroblast Yap peaks for indicated histone marks and Yap.

FIGS. 16A-16E. Yap Occupies 3D Enhancers in Myofibroblasts. (FIG. 16A) H3K27Ac HiChIP interaction maps for in vitro myofibroblasts (NIH3T3 cells). Top, Knight-Ruiz matrix-balanced HiChIP interaction maps plotted using Juicebox (Durand et al., 2016b) at 250 kb, and 5 kb resolutions. Bottom, browser tracks showing CUT&RUN, Fast-ATAC, and 3D HiChIP interaction signals. (FIG. 16B) H3K27ac interaction profile of the Vim promoter in NIH3T3 cells at 5 kb resolution. Top, virtual 4C (v4C) analysis plot. Knight-Ruiz matrix-balanced normalized (norm.) enhancer interaction signal (EIS). Bottom, genome browser tracks for indicated CUT&RUN and Fast-ATAC libraries. (FIG. 16C) Fraction of Yap CUT&RUN peaks located within H3K27Ac loop anchors. (FIG. 16D) H3K27Ac HiChIP loop interaction summary for Yap occupied loops. (FIG. 16E) Heatmap showing Fast-ATAC signal (read depth) across all Yap-associated and topologically looped promoters. Promoters (n=8,101) were identified in FIG. 16D, as being looped to enhancers. Top, schematic of enhancer-promoter H3K27Ac HiChIP loop interaction for Yap1 occupied anchors.

FIGS. 17A-17F. Lats1/2 Deletion in Adult Uninjured Cardiac Fibroblasts Results in Pervasive Myocardial Fibrosis. (FIG. 17A) Experimental strategy for cardiac fibroblast Cre activation and tissue collection. (FIG. 17B) Survival curve of control mice (Tcf21$^{iCre}$/+, Rosa26$^{mTmG}$/+) and Lats1/2 CKO (Tcf21$^{iCre}$/+; Lats1/2$^{flox/flox}$; Rosa26$^{mTmG}$/+) mice by 3 weeks after Cre activation and sham. (FIG. 17C) Representative gross heart morphology at 3 weeks after Cre activation and Lats1/2 knockout in CFs. Lats1/2 CKO heart exhibited abnormal fibrotic tissue accumulation, and atria were stiffened and enlarged (asterisks). Scale bar indicates 200 µm. (FIG. 17D) Representative Masson's trichrome serial sections of control and Lats1/2 CKO hearts. Lats1/2 CKO hearts possessed expansive and aggregated (arrows) cardiac fibrosis (stained blue) within the myocardium (stained red). Scale bar indicates 1000 µm. (FIG. 17E) Representative M-mode and B-mode echocardiographic images of control and Lats1/2 CKO mouse hearts 3 weeks after tamoxifen induction. (FIG. 17F) Echocardiography revealed impaired heart function in Lats1/2 CKO sham hearts. Percent ejection fraction, fractional shortening, and cardiac output as determined by echocardiography. Statistical significance was determined by Student t-test.

FIGS. 18A-18F. Lats1/2 Prevent the Spontaneous Differentiation of Resting Cardiac Fibroblasts to Immunostimulatory Myofibroblasts. (FIG. 18A) tSNE plot of 17,501 single cells, after graph-based clustering, captured from control and Lats1/2 CKO adult hearts 3 weeks after Cre induction via Drop-seq. MFL, myofibroblast-like cells; CF, cardiac fibroblasts; Miľ, macrophages and monocytes (myeloid cells); Epi, epicardial cells; T-cells, T lymphocyte. (FIG. 18B) Cell cycle phase analysis of single cardiac cells projected onto tSNE plot. All individual transcriptomes are scored based on their expression for S-phase genes (blue), G1 genes (red), and G2-to-M phase transition genes (green). (FIG. 18C) tSNE plot showing the genotype for each individual transcriptome. (FIG. 18D) Top, cellular composition of each cluster in control and Lats1/2 CKO hearts. Dot plot displays the relative proportion of cells from control and mutant hearts within each cluster. Dot size represents the percentage of cell origin within each cluster. The statistical difference of cell origin composition within each cluster were analyzed by Chi-square analysis (*p<10$^{-10}$). Bottom, average differential expression heat map for the top marker genes (n=784), with genes as rows and clusters as columns. Colors for each cluster match those in panel FIG. 18A. (FIG. 18E) Representative low magnification (left) and high magnification (right) immunofluorescence confocal images from control and Lats1/2 CKO hearts 3 weeks following Tcf21-iCre induction displaying lineage traced GFP+ cardiac fibroblasts (green), and Acta2 (αSMA) expression (red). Acta2 labels Lats1/2 CKO CFs (white arrow heads). Nuclei are stained with DAPI (blue). Endo, endocardium. Scale bar indicates 100 µm (left), and 25 µm (right). (FIG. 18F) Representative immunofluorescence confocal images from control and Lats1/2 CKO hearts 3 weeks following Tcf21-iCre activation showing Lyz, a myeloid cell marker, expression (red), cardiac fibroblast fate mapping (green), and nuclei labelling (blue). Scale bar indicates 25 µm.

FIGS. 19A-19L. Yap is a Cell-Nonautonomous Regulator of Cardiac Cell Composition and Inflammatory Status. (FIG. 19A) tSNE plot of cell groups. MFL, myofibroblast like cells; SubEpi, sub-epicardial-like cells; EpiC Mut, epicardial cells enriched in Lats1/2 CKO hearts; Epi WT, epicardial cells enriched in control (WT) hearts; CF WT, cardiac fibroblasts enriched in control (WT) hearts; CF Mut, cardiac fibroblasts enriched in Lats1/2 CKO hearts; Mφ WT, myeloid cells enriched in control (WT) hearts; Mφ MUT, myeloid cells enriched in Lats1/2 CKO hearts; Mφ Pro, proliferating myeloid cells; Ccr2Hi, myeloid cell cluster expressing high levels of Ccr2. (FIG. 19B) Ligand-receptor connection analysis. Left, control CF ligand-receptor interaction plot. Right, Lats1/2 CKO-specific MFL-mediated ligand-receptor interaction plot. Lines indicate significant ligand receptor pairs where ligands are expressed in top cell group and receptors are expressed by individual cells in the bottom cell group. Ligands with multiple receptors are largest. (FIG. 19C) Top, circle plots showing the strength of individual ligand-receptor interactions for each indicated group of cells (labelled and colored as in FIG. 19A). Size of arrow is proportional to the number of possible cell-cell interactions for each ligand-receptor pair. Base of arrow indicates ligand expressing group, and arrow head contacts receptor expressing cell group. Bottom, feature plots showing the expression of ligand (red), receptor (blue), and cells co-expressing both ligand and receptor (purple). (FIG. 19D) Schematic of YAP5SA-CM mouse model. The YAP5SA and Myh6-MerCreMer transgenic alleles are crossed to generate a mouse conditionally expressing YAP5SA in adult cardiomyocytes after 4 doses of tamoxifen, and cells were harvested two days following 4$^{th}$ and final dose. (FIG. 19E) tSNE plot of 24,110 single cells, after graph-based clustering, captured from control and YAP5SA-CM adult hearts following Cre induction via Drop-seq. CF, cardiac fibroblasts; Mφ macrophages and monocytes (myeloid cells); Epi, epicardial cells; SMC, smooth muscle cells; EndoC, endocardial cells; Y5SA, YAP5SA derived cardiomyocytes; CMs, cardiomyocytes (FIG. 19F) tSNE plot showing the experimental group for each individual transcriptome. Control (black), and YAP5SA-CM (orange). (FIG. 19G) Cell cycle phase analysis of single cardiac cells projected onto tSNE plot. All individual transcriptomes are scored based on their expression for S-phase genes (blue), G1 genes (red), and G2-to-M phase transition genes (green). (FIG. 19H) tSNE plot of cell groups. EpiC, epicardial cells; CF WT, cardiac fibroblasts enriched in control (WT) hearts; CF-Y5SA, cardiac fibroblasts enriched YAP5SA-CM hearts; Mφ-wt, myeloid cells enriched in control (WT) hearts; Mφ-Y5SA, myeloid cells enriched in YAP5SA-CM hearts; Pro-Mφ, proliferating myeloid cells; Ccr2Hi, myeloid cell cluster expressing high levels of Ccr2; EC, endothelial cells;

EndoC, endocardial cells; SMC, smooth muscle cells; CM, cardiomyocytes enriched in control (WT) hearts. (FIG. 19I) Ligand-receptor cell-cell connectome circle plot for YAP5SA-CM hearts, highlighting interactions with cardiac fibroblasts and myeloid cells. Plot colored according to FIG. 19H. Base of arrows indicates cells expressing ligand (Y5SA-2), and arrow heads contact cell groups expressing receptors. (FIG. 19J) Venn diagram showing overlay of all significant ligand-receptor interaction pairs shared by both Lats1/2 CKO MFLs and YAP5SA expressing CMs (Y5SA-2). (FIG. 19K) Chemokine protein expression in cardiac lysates determined by cytokine/chemokine protein array. (FIG. 19L) Relative protein expression based on densitometric analysis of FIG. 19K. Genotypes are colored according to FIG. 19K. Error bars indicate standard error of the mean.

FIGS. 20A-20E. Lats1/2 Are Required For Cardiac Scar Maturation and Compaction Following Myocardial Infarction in the Adult Heart. (FIG. 20A) Gross heart morphology 3 weeks after MI in control, Lats1/2 CKO, and Tcf21-iCre; Lats1/2 f/f; Yap/Taz f/+ animals. Suture used to ligate the left anterior descending coronary artery (LAD) shown with white arrow. Scale bar indicates 2000 µm. (FIG. 20B) Serial sections treated with Masson's trichrome stain 3 weeks after MI in control, Lats1/2 CKO, and Tcf21-iCre; Lats1/2 f/f; Yap/Taz f/+ animals. Red color tissue is muscle, and blue color is collagen (fibrotic tissue). Black arrows highlight myocardial muscle tissue. Scale bar indicates 1000 µm. (FIG. 20C) Representative images of 24 hour EdU-labelling of control and Lats1/2 CKO animals after MI. Samples were pulse-chased with EdU (white) and cardiac fibroblasts were labelled with GFP (green). Nuclei stained with DAPI (blue). Quantification shown in FIG. 26D. Scale bar indicates 25 µm. (FIG. 20C) (FIG. 20D) High magnification view of Masson's trichrome stained histological sections derived from control and Lats1/2 CKO hearts 3 weeks post-MI. Scale bar indicates 25 µm. (FIG. 20E) FACS sorted GFP+ CFs from control and Lats1/2 CKO hearts were plated on low attachment culture dishes for 24 hours. Representative images showing brightfield and GFP channels. Scale bar indicates 100 µm.

FIGS. 21A-21L. Lats1/2 Inhibit Myc Expression and Limit Homeostatic Cell Replacement To Maintain the Proper Cellular Composition of the Heart. (FIG. 21A) tSNE plot of cardiac fibroblast clusters. MFL, myofibroblast like cells; CF, resting cardiac fibroblasts; aCF, activated cardiac fibroblasts. (FIG. 21B) tSNE plot of cardiac fibroblast single-cell transcriptome experimental identities. (FIG. 21C) Differential expression analysis and cell cycle phase of cardiac fibroblasts. Top, Cell cycle phase analysis stacked bar graph of each cluster. Percentage of single-cell transcriptomes within each cluster scored for S-phase (blue), G1 (red), and G2-to-M phase transition (green) is shown. Bottom, average expression heatmap of the top differentially expressed cardiac fibroblast marker genes (n=722). (FIG. 21D) Pseudotemporal ordering of cardiac fibroblasts. Top, density plot of cluster compositions across pseudotime. Bottom, ordering of cardiac fibroblasts along a minimum spanning tree (MST). Colored by cell cluster according to FIG. 21A. (FIG. 21E) Differentiation trajectory of control and Lats1/2 CKO cardiac fibroblasts with and without injury. Top, pseudotime score for each individual transcriptome embedded on cardiac fibroblast tSNE (from FIG. 21A). Bottom, pseudotime score encoding for cardiac fibroblasts embedded on Monocle2 MST. Black denotes the beginning of pseudotime, and lighter color denotes the other extreme of pseudotime, the end. (FIG. 21F) Lats1/2 CKO cardiac fibroblasts without injury and injured control fibroblasts are transcriptionally similar. Top, density plot of experimental compositions across pseudotime. Bottom, cardiac fibroblast differentiation trajectory. Colored by cell genotype and experimental manipulation according to FIG. 21B. Green square highlights pseudotemporal overlap of control MI and LatsCKO CFs. (FIG. 21G) Dynamic cardiac fibroblast expression patterns across differentiation following myocardial infarction. Left, hierarchically clustered heatmap of gene expression dynamics (q-value<1e-5). Middle, global cluster gene expression trends across pseudotime. Right, Gene ontology analysis for cluster I (top) and cluster II (bottom). (FIG. 21H) Genome browser tracks for Fast-ATAC. All libraries scaled equally. (FIG. 21I) Principal component analysis (PCA) of Fast-ATAC signals from biological duplicates of FACS sorted GFP+ cardiac fibroblasts from control and Lats1/2 CKO hearts with and without myocardial infarction. (FIG. 21J) Differential chromatin accessibility heatmap. Left, chromatin accessibility heatmap, hierarchically clustered (n=2) showing differentially accessible peaks (n=11997, FDR=0.1) for Lats1/2 CKO hearts after myocardial infarction. Right, genome regulatory element analysis tools (GREAT) annotation of Lats1/2 CKO peaks. (FIG. 21K) Expression of Myc (red) control and Lats1/2 CKO cardiac fibroblasts (green). Nuclei stained with DAPI (blue). Endo, endocardium; Myo, myocardium. Scale bar indicates 25 µm. (FIG. 21L) Representative images of TUNEL stained control and Lats1/2 CKO hearts without injury. Cardiac fibroblasts (green), apoptotic cells (red), nuclei (blue). Scale bar indicates 100 µm.

Figure 2A:
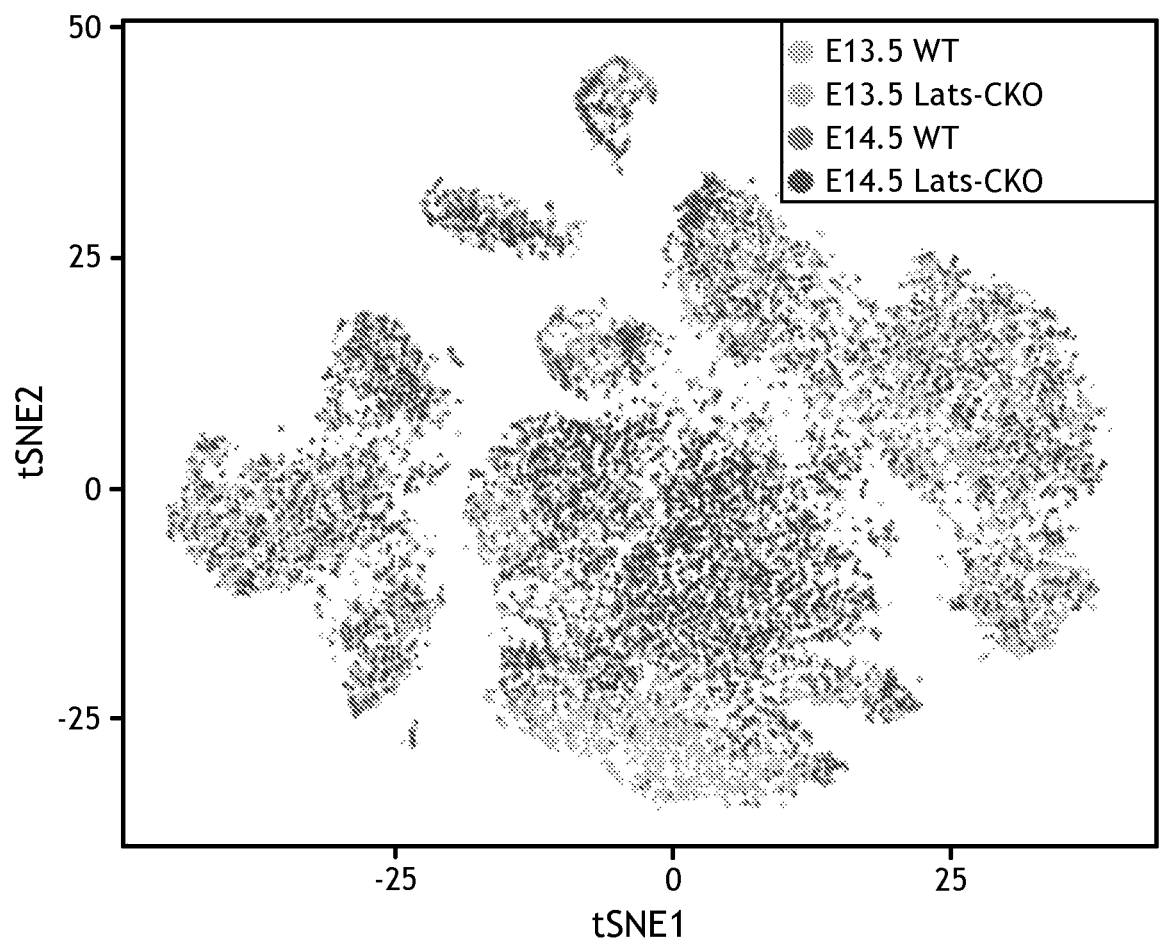
FIGS. 2A-2F. Single cell RNA-seq of embryonic cardiac tissue.
Figure 2B:
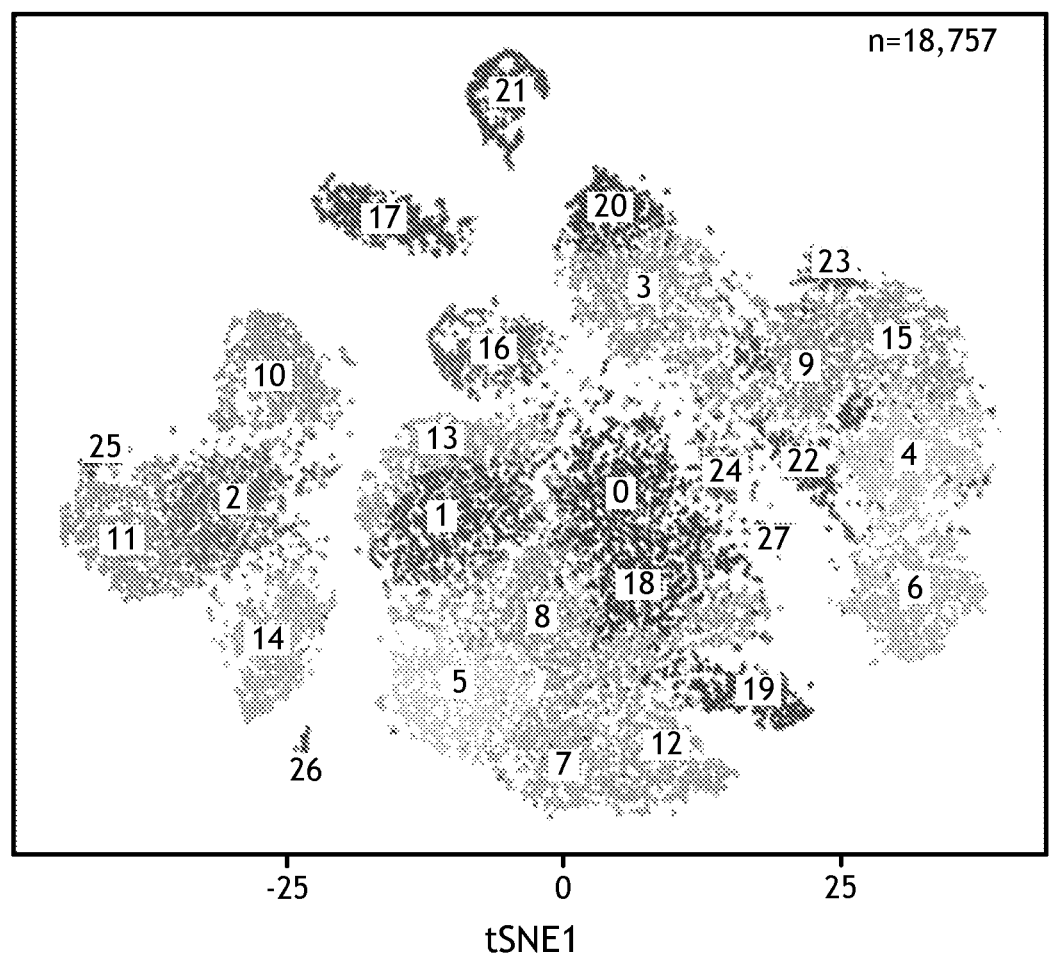
Figure 2C:
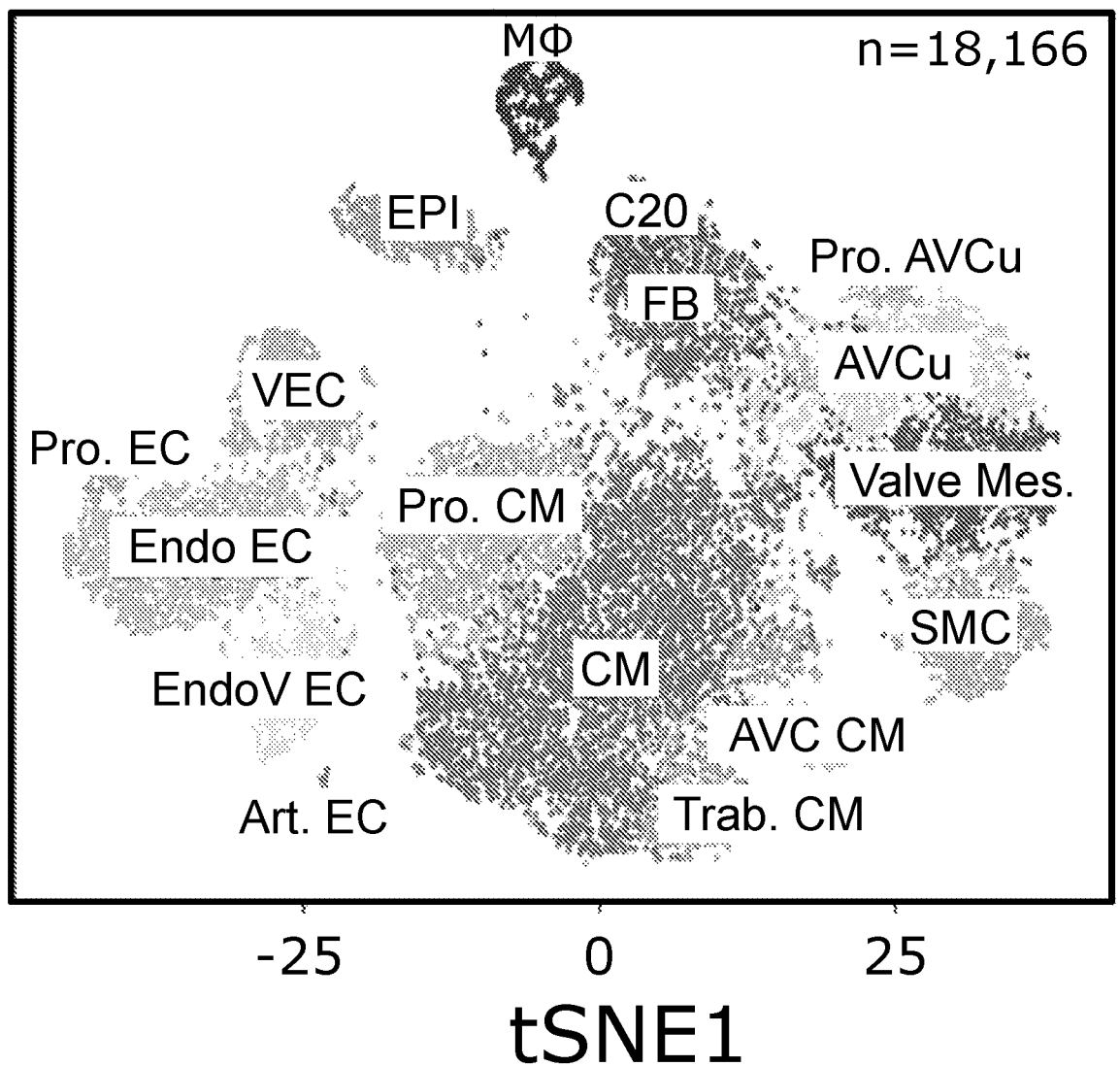
Figure 2D:
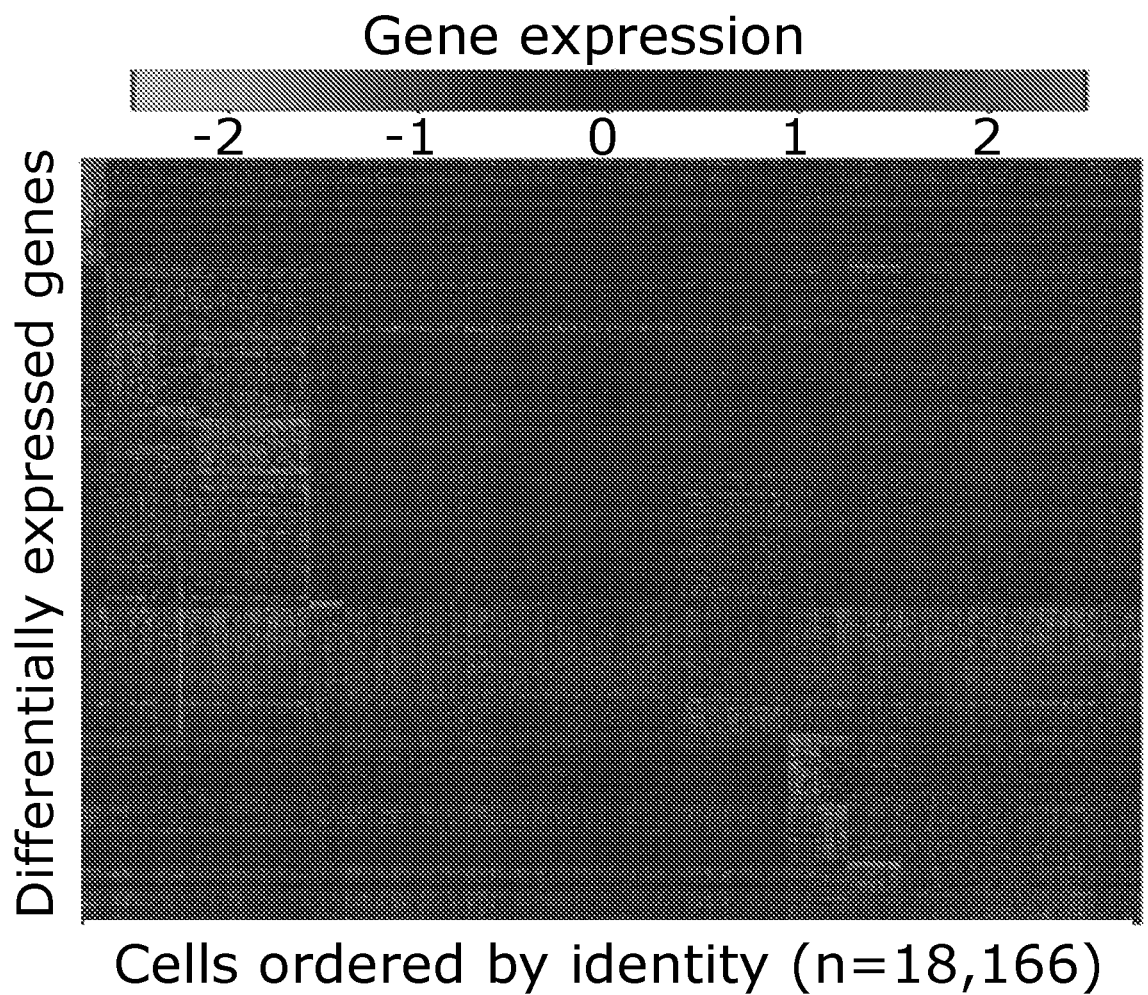
Figure 2E:
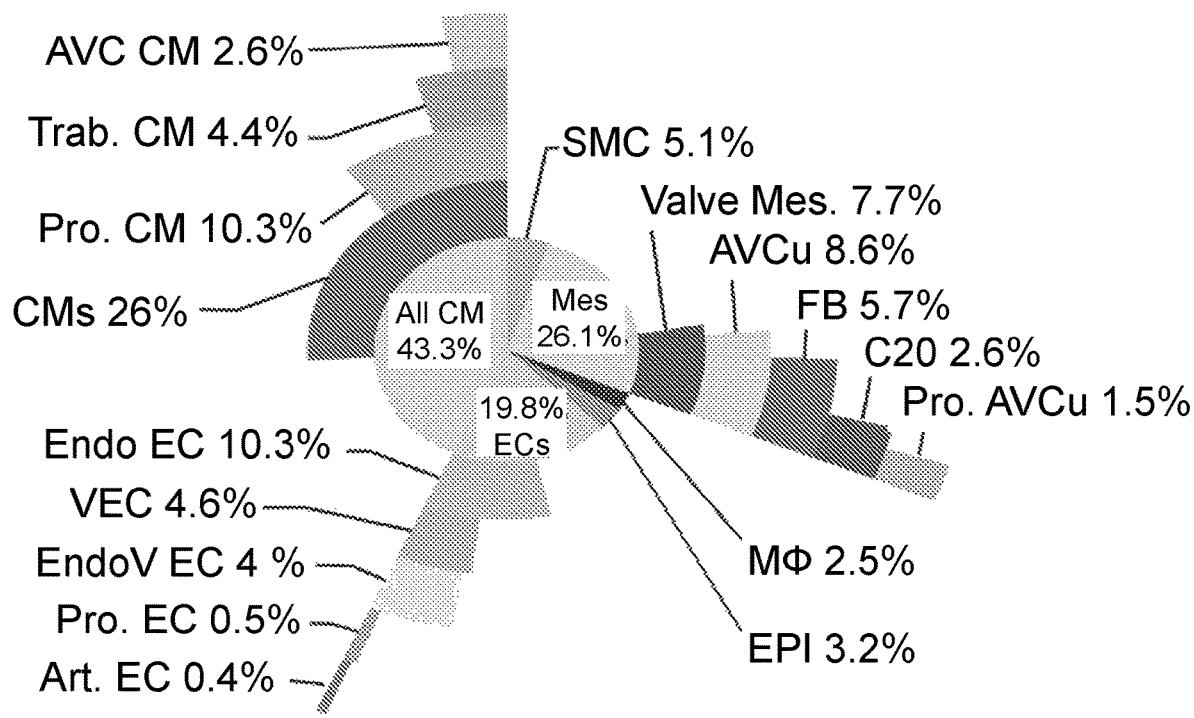
Figure 2F:
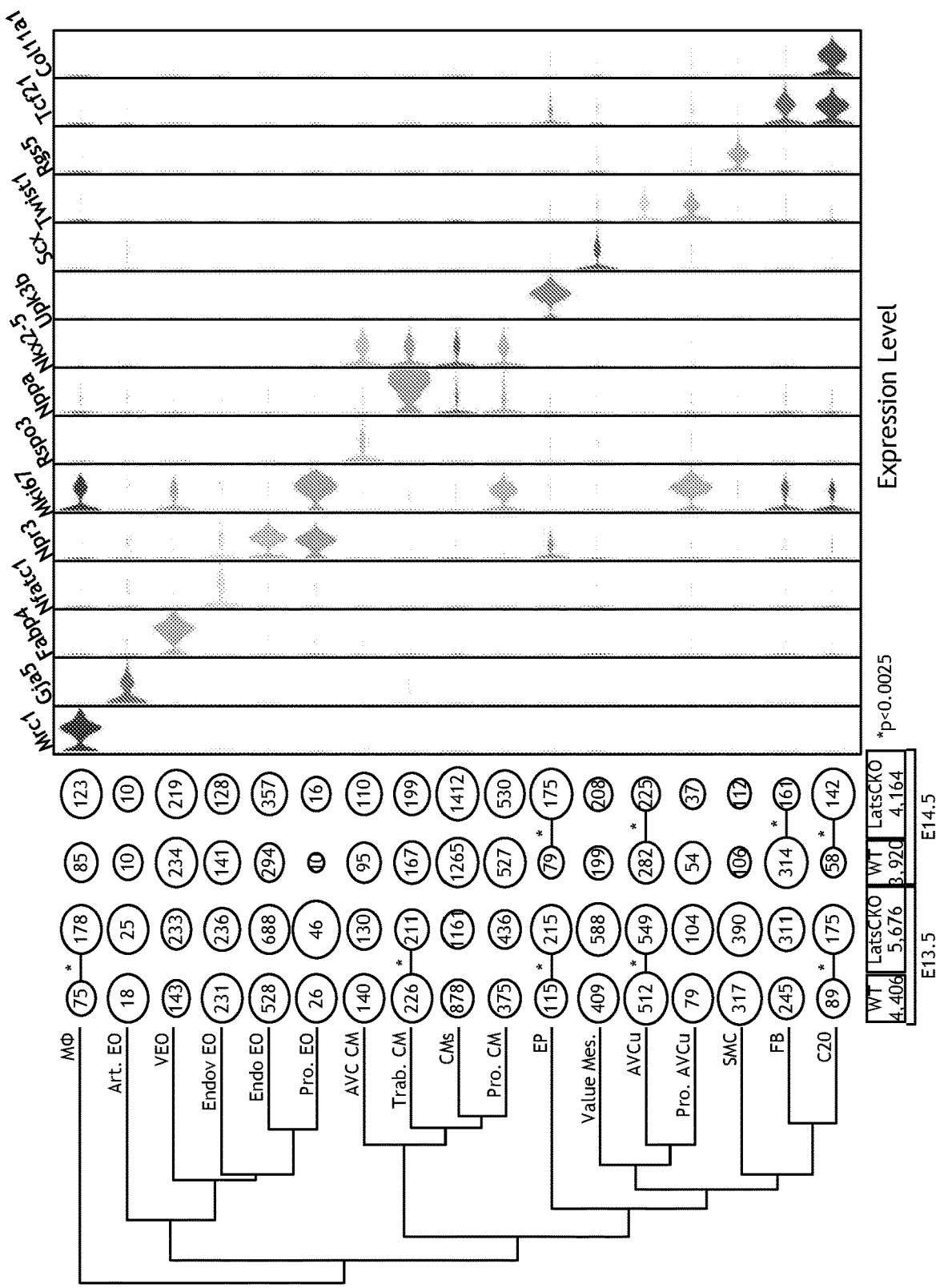
Figure 22A:
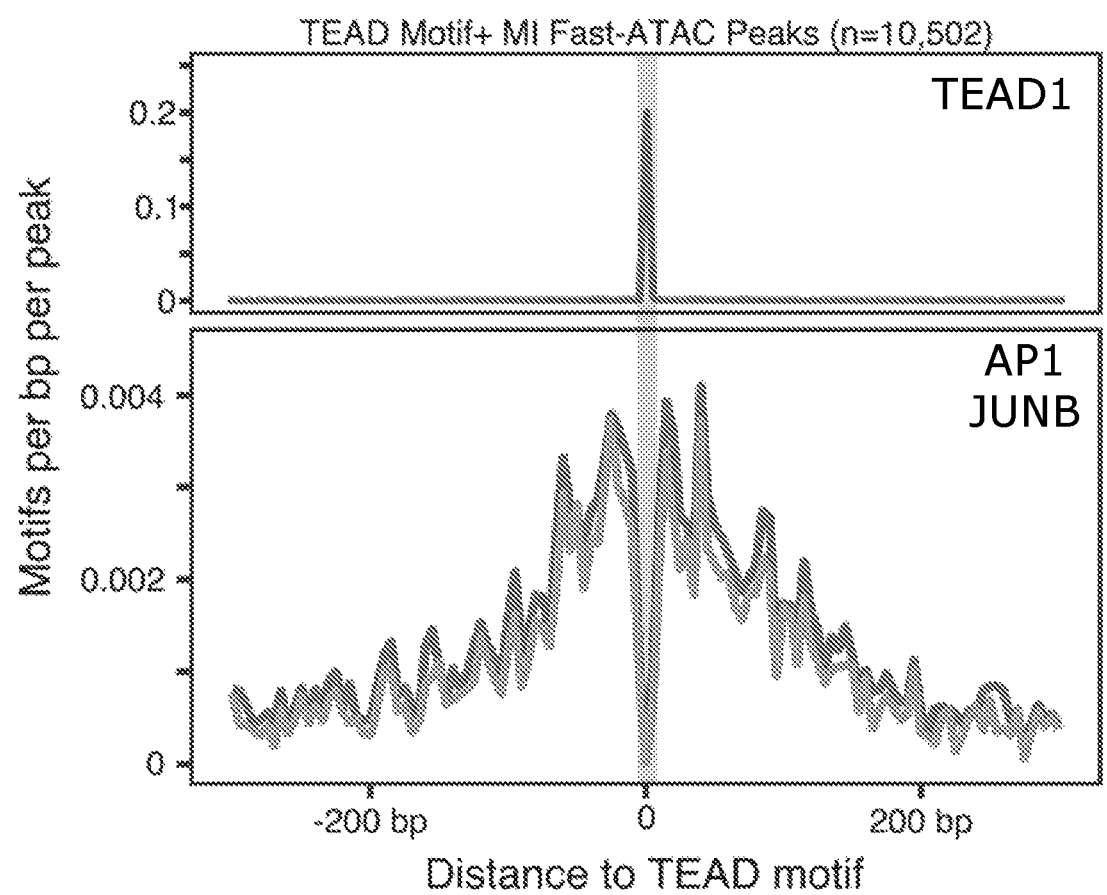

FIG. 22A-2F. Following Myocardial Infarction Chromatin Accessibility Increases at TEAD Motif Containing Genomic Elements. (FIG. 22A) TEAD motif co-enrichment plot from Fast-ATAC carried out on FACS sorted CFs 3 dPMI. Top, TEAD1 motif enrichment across all TEAD motif containing peaks derived from 3 dPMI CFs. Bottom, AP1 and JUNB motif enrichment histogram in relation to TEAD motifs within Fast-ATAC peaks. (FIG. 22B) Venn diagram showing the genes containing TEAD motifs at accessible regulatory regions detected by Fast-ATAC-seq at 3 dPMI overlaid with the differentially expressed genes detected by RNA-seq that were enriched after MI (adjusted p-value<0.05, see FIG. 15A). (FIG. 22C) Gene Ontology (GO) analysis of the 205 putative Yap target genes annotated to accessible TEAD motif containing regulatory elements identified in FIG. 22B. (FIG. 22D) Representative confocal images from cardiac tissue sections stained for cardiac troponin T (green), Yap (red), and DAPI (blue). Non-cardiomyocytes (CTnt negative, white arrowheads) and cardiomyocytes (yellow arrowheads) both exhibited enhanced nuclear Yap activity at 3 dPMI compared with sham. Scale bar indicates 25 µm. (FIG. 22E) Fraction of Yap CUT&RUN peaks annotated with each category. (FIG. 22F) CUT&RUN footprint analysis for CTCF.

FIG. 23A-23G. Single-cell RNA-seq Reveals that Hippo Signaling Inhibits the Non-Autonomous Activation of Cardiac Fibroblasts and Myeloid Cells in the Adult Heart. (FIG. 23A) Feature plot of selected signature gene expression in major cell clusters. High expression shown in purple, and cells not expressing gene are grey. tSNE plot originally shown in FIG. 18A. (FIG. 23B) Violin plot showing differential gene expression between two epicardial clusters (Epi1 and Epi2). (FIG. 23C) Feature plot of cardiac fibroblast cluster markers. Fibroblast clusters were extracted from full data set shown in FIG. 18A for detailed gene profiling. Cell clusters are outlined in same colors shown in FIG. 18A. (FIG. 23D) Feature plots of cardiac fibroblast markers enriched in non-mutant cardiac fibroblasts derived from Lats1/2 CKO hearts. (FIG. 23E) Feature plots of cardiac fibroblast markers enriched in activated cardiac fibroblasts (non-mutant) derived from Lats1/2 CKO hearts. (FIG. 23F) Feature plots of canonical Yap target genes. (FIG. 23G) Feature plots of IFNIC markers.

FIGS. 24A-24E. Tead and Endoplasmic Reticulum Stress Response-Associated Transcription Factor Gene Regulatory Networks are Active In Myofibroblasts. (FIG. 24A) Binary regulon activity matrix results from SCENIC algorithm carried out on cardiac Drop-seq data (originally shown in FIG. 18A). Shown are all correlated regulons with absolute correlation greater than 0.3 and that are in at least 1% of all single cells. Individual cells are columns, and regulons are rows. Representative transcription factor regulons are listed on right. Top, bar shows individual cell cluster identity (colored as in FIG. 18A). (FIG. 24B) Cardiac cell identity tSNE generated from the binary regulon activity matrix. Left, regulon activity density plot embedded on tSNE. Light color indicates low cumulative regulon activity, and darker color indicates high cumulative regulon activity. Right, binary regulon activity tSNE colored by individual cell cluster identity (colored the same as in FIG. 18A). (FIG. 24C) Regulon activity for individual cells embedded on the expression based tSNE (originally shown in FIG. 18A). Blue highlights active regulon for indicated transcription factor, and grey indicates that a regulon is not active. Insets show the AUCell score histogram for the regulon. (FIG. 24D) MAGIC scatterplots of gene-gene relationships for regulon components (target genes). Transcription factor expression encoded by highlighted color gradient. (FIG. 24E) Evaluation of regulon activity using Fast-ATAC. Top, global Tcf21 motif enrichment across peaks from each indicated experimental condition. Bottom, Fast-ATAC read enrichment across motif-containing peaks annotated to genes in either the Atf4 (middle) or Tead1 (bottom) regulons identified in FIG. 24A.

FIGS. 25A-25E. YAP5SA Expressing Cardiomyocytes Possess Myofibroblast Characteristics and Potently Recruit Myeloid Cells Into the Myocardium. (FIG. 25A) Average differential expression heat map for the top marker genes (n=1223), with genes as rows and clusters as columns. (FIG. 25B) Cellular composition of each cluster in control and YAP5SA-CM hearts. Dot plot displays the relative proportion of cells from control and mutant hearts within each cluster. Dot size represents the percentage of cell origin within each cluster. (FIG. 25C) Feature plot showing the expression of notable marker genes. High expression shown in red, and cells not expressing indicated gene are encoded with grey. Outlines of notable clusters are shown and colored according to cell groups shown in FIG. 19H. (FIG. 25D) Ligand-receptor circle plots showing the strength of individual ligand-receptor interactions for each indicated group of cells (labelled and colored as in FIG. 19H). Size of arrow is proportional to the number of possible cell-cell interactions for each ligand-receptor pair. Base of arrow indicates ligand expressing group, and arrow head contacts receptor expressing cell group. (FIG. 25E) Genome browser tracks showing cardiomyocyte-specific ATAC-seq and nuclear RNA-seq (nucRNA) from control and YAP5SA animals. Data from Monroe et al. (2019).

FIGS. 26A-26G. Lats1/2 Suppress Cardiac Fibroblast Proliferation, (FIG. 26A) Survival curve of control mice (Tcf21$^{iCre}$/+; Rosa26$^{mTmG}$/+) Lats1/2 CKO (Tcf21$^{iCre}$/+; Lats1/2$^{flox/flox}$; Rosa26$^{mTmG}$/+), and Tcf21$^{iCre}$/+; Lats1/2$^{flox/flox}$; Yap/Taz$^{flox/+}$ mice after myocardial infarction. (FIG. 26B) Schematic of TRAP-seq. (FIG. 26C) Gene ontology (GO) analysis of TRAP-seq results in Lats1/2 CKO animals compared to controls 1 week after myocardial infarction. (FIG. 26D) Quantification of cardiac fibroblast proliferation dynamics after myocardial infarction. Representative image of experiment shown in FIG. 20C. Statistical significance was determined by Mann-Whitney U test. (FIG. 26E) DNA content and ploidy of cardiac fibroblasts after myocardial infarction. Representative histograms from flow cytometry analysis of isolated cardiac nuclei from control and Lats1/2 CKO hearts, stained with DAPI. (FIG. 26F) Stacked bar plot showing percentage of cells within each phase of the cell cycle as determined by flow cytometry analysis. (FIG. 26G) Quantification of cardiac fibroblast proliferation after myocardial infarction. Statistical significance was determined by Chi-square test.

Figure 21A:
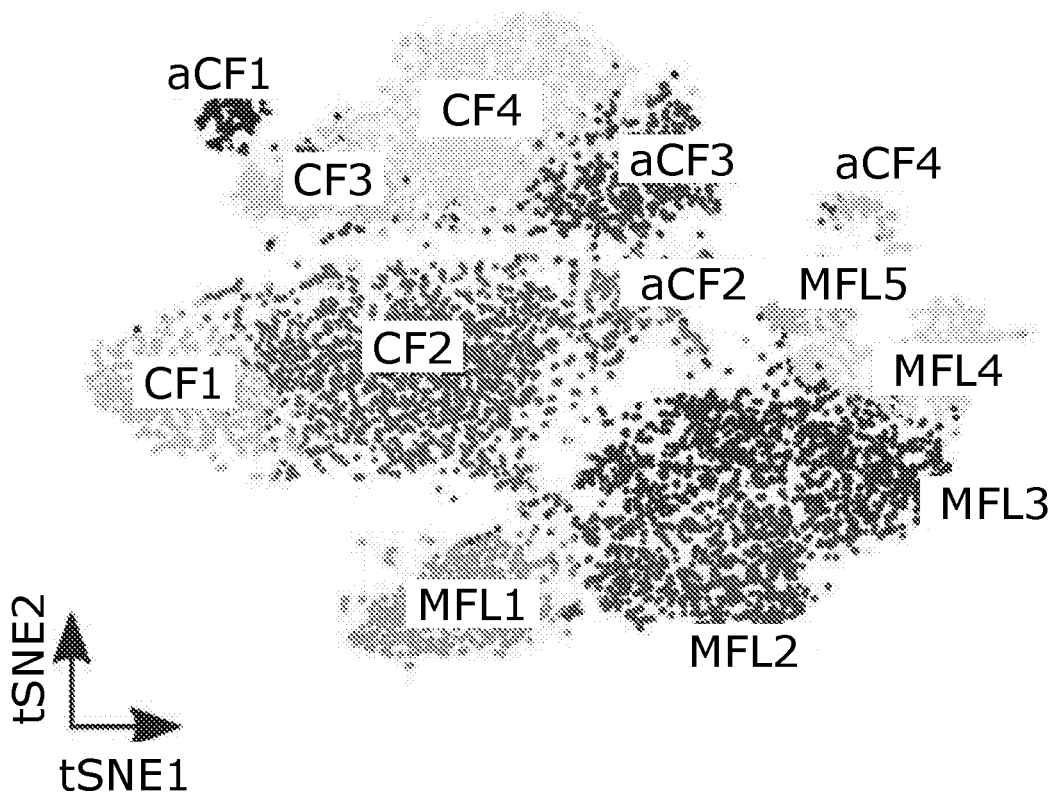

FIGS. 27A-27G. Hippo Signaling Suppresses Myc Expression to Maintain Cardiac Tissue Homeostasis, (FIG. 27A) Feature plots of markers for active fibroblasts (top), and myofibroblasts (bottom). Clusters position in tSNE from FIG. 21A is shown in colored outlines. (FIG. 27B) Dot plot of marker gene expression for each cardiac fibroblast cluster. Size of dot indicates percentage of cells within a cluster that express a given gene. (FIG. 27C) Representative in situ hybridization image of Serpina3N (red). Cardiac fibroblasts were lineage traced (green). Nuclei were stained with DAPI (blue). Epi, epicardium; Myo, myocardium. Scale bar, 100 um. (FIG. 27D) Representative in situ hybridization image of Plac8 (red). Cardiac fibroblasts were lineage traced (green). Nuclei were stained with DAPI (blue). Epi, epicardium; Myo, myocardium. Scale bar, 25 um. (FIG. 27E) Genome browser tracks showing Yap binding and enhancer interactions at the Myc Locus. (FIG. 27F) Western blot showing Myc, Lats1, and GAPDH expression in NIH3T3 myofibroblasts 48 hours after siRNA treatment with either control siNC, siLats1/2, or siMyc. (FIG. 27G) High magnification image of TUNEL (red) stained cardiac tissue from uninjured control and Lats1/2 CKO hearts shown in FIG. 21L. Lineage traced cardiac fibroblasts are GFP labelled (green). Nuclei stained with DAPI (blue). Scale bar indicates 25 µm.

DETAILED DESCRIPTION

As used herein, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "subject," as used herein, generally refers to an individual in need of a therapy for a medical condition of any kind, including at least fibrosis and inflammation. A subject can be an animal of any kind. The subject can be any organism or animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals. The subject can be a patient, e.g., have or be suspected of having a disease (that may be referred to as a medical condition), such as one or more infectious diseases, one or more genetic disorders, one or more cancers, or any combination thereof. The disease may be pathogenic. The subject may being undergoing or have undergone antibiotic treatment. The subject may be asymptomatic. The subject may be healthy individuals. The term "individual" may be used interchangeably, in at least some cases. The "subject" or "individual", as used herein, may or may not be housed in a medical facility and may be treated as an outpatient of a medical facility. The individual may be receiving one or more medical compositions via the internet. An individual may comprise any age of a human or non-human animal and therefore includes both adult and juveniles (i.e., children) and infants and includes in utero individuals. The individual may be of any race and gender. It is not intended that the term connote a need for medical treatment, therefore, an individual may voluntarily or involuntarily be part of experimentation whether clinical or in support of basic science studies.

Embodiments of the disclosure exploit information revealed in characterizing development of progenitor cells, for example in cardiac epicardium. During development, progenitors progress through poorly defined transition states. The cardiac epicardium contains progenitors of essential non-cardiomyocyte lineages. The Hippo pathway, a kinase cascade that inhibits the Yap transcriptional co-factor, controls organ size in developing hearts and inhibits adult heart regeneration. As described elsewhere herein, Hippo pathway kinases, Lats1 and Lats2 were investigated in epicardial diversification. $Wt1^{CreERT2}$; Lats1/2 mutant embryos had defective coronary vasculature remodeling. Single cell RNA-sequence revealed that Lats1/2 mutant cells failed to activate fibroblast differentiation, but remained in an intermediate cell state with characteristics of epicardium and fibroblasts. Lats1/2 mutant cells an arrested developmental trajectory with persistence of epicardial markers and expanded expression of Yap targets including Dhrs3, an inhibitor of retinoic acid synthesis, and Dpp4, a membrane-bound protease that modulates extracellular matrix. Genetic and pharmacologic manipulation revealed that Yap inhibits fibroblast differentiation, prolonging a subepicardial-like cell state, and promotes expression of matricellular factors, such as Dpp4, that define ECM characteristics.

The present disclosure also provides examples related to characterizing in vivo the importance of Hippo signaling with respect to defective cardiac tissue. That is, all organs have a well-defined cellular makeup that is essential for organ function. After myocardial infarction (MI), resting cardiac fibroblasts (CFs) differentiate into myofibroblasts and drastically expand to disrupt cardiac tissue compositional balance. As disclosed herein, the Hippo signaling pathway is a central repressor of the heart tissue's multicellular response to MI. Genetic deletion of Hippo pathway components Lats1 and Lats2 in uninjured CFs caused expansive cardiac fibrosis in addition to the influx and phenotypic expansion of myeloid cells. Single-cell transcriptomics revealed that Lats1/2 mutant CFs were fixed in a highly immunostimulatory myofibroblast cell state that prevented an adaptive wound response after MI. The inability of mutant CFs to exit the myofibroblast cell identity proved lethal, as animals perished when challenged with MI. These findings indicate that Hippo signaling acts as a molecular sensor for CF injury that dictates crucial CF cell state transitions, and preserves heart homeostasis.

Some embodiments of the present disclosure provide methods and compositions to modulate the Hippo signaling pathway to enhance transition of progenitor cells in a tissue or organ to fibroblasts, thereby also providing improvement of fibrosis and/or inflammation in at least some cases.

I. LATS1 and LATS2 Compositions

Embodiments of the disclosure encompass one or more compositions suitable for reducing or inhibiting fibrosis and/or inflammation. In specific embodiments, the fibrosis and/or inflammation are related to a cardiac condition. The compositions may be formulated for use for treatment of the fibrosis and/or inflammation, including the cardiac condition(s). In specific embodiments the compositions are comprised of certain nucleic acid(s) or polypeptide(s). Embodiments of the disclosure encompass mixtures of compositions, including mixtures of compositions of the disclosure with one or more other compositions not described herein but that are nevertheless effective for improving fibrosis and/or inflammation in an individual.

In particular embodiments, the composition(s) of the disclosure encompass LATS1/2 polynucleotides and/or LATS1/2 polypeptides for the reduction or inhibition of fibrosis and/or inflammation in a tissue or organ. The LATS1/2 composition(s) may be mammalian polynucleotides and/or polypeptides, for example, including human (or, in some cases murine or rat but for the treatment of a human), in at least some cases.

In particular embodiments, there are one or more nucleic acids that express LATS1/2 such that upon delivery to an individual the levels of LATS1/2 polynucleotides and/or polypeptides at the site of delivery are detectably increased compared to in the absence of providing of the nucleic acids. The nucleic acids may be DNA or RNA, for example. Upon administration of LATS1/2 polypeptide(s) to the tissue or organ, the level of LATS1/2 polypeptides may detectably increase at the site of delivery.

Embodiments of the disclosure include use of LATS1/2 polypeptides and LATS1/2 polynucleotides and functional derivatives or functional fragments thereof, and the derivative or fragment may be considered functional if it has the ability to improve at least one symptom of fibrosis and/or inflammation when provided in an effective amount, for example. Such an activity may be measured by any suitable means. In particular embodiments, one can assess functional activity by assaying for reduction in the severity of a symptom, for example. In specific embodiments, the LATS1/2 or functional fragment or functional derivative is soluble. The LATS1/2 or functional fragment or functional derivative may be comprised in a fusion protein, for example with a tag or label.

When the agent is proteinaceous, the LATS1/2 proteinaceous composition(s) may be made by any technique known to those of skill in the art, including, for example, the expression of proteins, polypeptides or peptides through standard molecular biological techniques, the isolation of proteinaceous compounds from natural sources, or the chemical synthesis of proteinaceous materials. A LATS1/2 coding region may be amplified and/or expressed using the techniques disclosed herein or as would be known to those of ordinary skill in the art. Alternatively, various commercial preparations of proteins, polypeptides and peptides are known to those of skill in the art.

In certain embodiments a LATS1/2 (or functional fragment or derivative thereof) proteinaceous compound may be purified. Generally, "purified" will refer to a specific protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide. Biological functional equivalents of LATS1/2, including such functional derivatives and fragments, may be employed. As modifications and/or changes may be made in the structure of LATS1/2 polynucleotides and and/or proteins according to the present disclosure, while obtaining molecules having similar or improved characteristics, such biologically functional equivalents are also encompassed within embodiments of the present disclosure.

In particular embodiments, LATS1/2 (or functional fragment or derivative thereof) polynucleotides are utilized, including DNA or RNA. The polynucleotides may be synthetic, such as produced by standard recombination techniques utilized in the art. Part or all of the LATS1/2 polynucletoide may be amplified prior to delivery, such as using an amplification process including PCR. In other cases, LATS1/2 polynucleotides are equipped to be amplified following delivery into the individual, such as being expressed from a vector having elements for regulation of expression of the LATS1/2 polynucleotides.

An example of LATS1 nucleic acid is in the NCBI GenBank® database at Accession No. NM_004690 (SEQ ID NO:1).

An example of LATS1 amino acid sequence is in the NCBI GenBank® database at Accession No. NP_004681.1 (SEQ ID NO:2).

An example of LATS2 nucleic acid sequence is in the NCBI GenBank® database at Accession No. NM_014572 (SEQ ID NO:3).

An example of LATS2 amino acid sequence is in the NCBI GenBank® database at Accession No. NP_055387.2 (SEQ ID NO:4).

These sequences are merely examples, and the skilled artisan recognizes that they may be utilized as agents for treatment or functional derivatives and/or functional fragments of them may also be utilized.

As an example, a LATS1 functional derivative or fragment thereof may comprise 1, 2, 3, 4, 5, 6, 7, 8, 9, 10, 11, 12, 13, 14, 15, 16, 17, 18, 19, or 20 or more amino acid alterations compared to SEQ ID NO:2. A LATS2 functional derivative or fragment thereof may comprise 1, 2, 3, 4, 5, 6, 7, 8, 9, 10, 11, 12, 13, 14, 15, 16, 17, 18, 19, or 20 or more amino acid alterations compared to SEQ ID NO:4.

The LATS1 functional derivative or fragment thereof may comprise an N-terminal truncation of SEQ ID NO:2, for example wherein the truncation is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or wherein the truncation is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids. The LATS1 functional derivative or fragment thereof may comprise a C-terminal truncation of SEQ ID NO: 2, such as wherein the truncation is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids. The LATS1 functional derivative or fragment thereof may comprise an internal deletion in SEQ ID NO: 2, such as wherein the internal deletion is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids. In specific embodiments, a LATS1 functional derivative or fragment thereof may comprise sequence that is at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identical to SEQ ID NO:2.

The LATS2 functional derivative or fragment thereof may comprise an N-terminal truncation of SEQ ID NO:4, for example wherein the truncation is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or wherein the truncation is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids. The LATS2 functional derivative or fragment thereof may comprise a C-terminal truncation of SEQ ID NO:4, such as wherein the truncation is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids. The LATS2 functional derivative or fragment thereof may comprise an internal deletion in SEQ ID NO:4, such as wherein the internal deletion is no more than 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids or is at least 1, 2, 3, 4, 5, 6, 7, 8, 9, 10, 12, 15, 20, 25, 30, 35, 40, 45, 50, 55, 60, 65, 70, 75, 80, 85, 90, 95, or 100 amino acids. In specific embodiments, a LATS2 functional derivative or fragment thereof may comprise sequence that is at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identical to SEQ ID NO:4.

A biological functional equivalent of LATS1/2 may be produced from a polynucleotide that has been engineered to contain distinct sequences while at the same time retaining the capacity to encode the "wild-type" or standard protein. This can be accomplished to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein.

In another example, a LATS1/2 polynucleotide made be (and encode) a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and so forth. So-called "conservative" changes do not disrupt the biological activity of the protein, as the structural change is not one that impinges on the protein's ability to carry out its designed function. It is thus contemplated by the inventors that various changes may be made in the sequence of genes and proteins disclosed herein, while still fulfilling the goals of the embodiments of the present disclosure.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those proteins (and polynucleotides) in selected amino acids (or codons) that may be substituted.

In general, the shorter the length of the molecule, the fewer changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents.

To effect more quantitative changes, the hydropathic index of amino acids may be considered. Each amino acid has been assigned a hydropathy index on the basis of their hydrophobicity and/or charge characteristics, and these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5).

The importance of the hydropathy amino acid index in conferring interactive biological function on a protein is generally understood in the art (Kyte & Doolittle, 1982, incorporated herein by reference). It is known that certain amino acids may be substituted for other amino acids having a similar hydropathy index and/or score and/or still retain a similar biological activity. In making changes based upon the hydropathy index, the substitution of amino acids whose hydropathy indices are within ±2 is preferred, those which are within ±1 are particularly preferred, and/or those within ±0.5 are even more particularly preferred.

It also is understood in the art that the substitution of like amino acids can be made effectively on the basis of hydrophilicity, particularly where the biological functional equivalent protein and/or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

The present disclosure, in many aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified and/or unusual amino acids. Exemplary, but not limiting, modified and/or unusual amino acids are known in the art.

In addition to the biological functional equivalents discussed above, the present inventors also contemplate that structurally or functionally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule. Such peptidomimetics include compounds that do not incorporate any natural amino acids or amino acid side chains, but are instead designed based on a LATS1/2 peptide sequence and have the ability to functionally replace LATS1/2.

In some respects, a particular LATS1 polynucleotide is utilized in compositions and methods of the embodiments of the disclosure. In some cases, the LATS1 polynucleotide comprises, consists of, or consists essentially of part or all of a sequence of SEQ ID NO:1. The LATS1 polynucleotide may comprise, consists of, or consist essentially of SEQ ID NO:1.

The LATS1 nucleotide sequence may have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to the sequence of SEQ ID NO. 1. The LATS1 nucleotide sequence may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more alterations with respect to SEQ ID NO:1. The LATS1 polynucleotide sequence may be at least about 7300, 7200, 7100, 7000, 6750, 6500, 6250, 6000, 5750, 5500, 5250, 5000, 4750, 4500, 4250, 4000, 3750, 3500, 3250, 3000, 2750, 2500, 2250, 2000, 1000, or 500 nucleotides of SEQ ID NO:1, including contiguous nucleotides of SEQ ID NO:1. Any effective fragment of SEQ ID NO:1 may be utilized. In specific embodiments, any region of SEQ ID NO:1 that imparts improvement of fibrosis may be included in the polynucleotide to be given to the individual in need.

In some respects, a particular LATS2 polynucleotide is utilized in compositions and methods of the embodiments of the disclosure. In some cases, the LATS2 polynucleotide comprises, consists of, or consists essentially of part or all of a sequence of SEQ ID NO:3. The LATS2 polynucleotide may comprise, consists of, or consist essentially of SEQ ID NO:3.

The LATS2 nucleotide sequence may have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to the sequence of SEQ ID NO:3. The LATS2 nucleotide sequence may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more alterations with respect to SEQ ID NO:3. The LATS2 polynucleotide sequence may be at least about 5500, 5250, 5000, 4750, 4500, 4250, 4000, 3750, 3500, 3250, 3000, 2750, 2500, 2250, 2000, 1750, 1500, 1250, 1000, 750, or 500 nucleotides of SEQ ID NO:3, including contiguous nucleotides of SEQ ID NO:3. Any effective fragment of SEQ ID NO:3 may be utilized. In specific embodiments, any region of SEQ ID NO:1 that imparts improvement of fibrosis may be included in the polynucleotide to be given to the tissue or organ in need.

II. Methods of Use

Methods of embodiments of the disclosure encompass reduction or inhibition of a fibrotic and/or inflammatory condition. The methods may treat, delay onset of at least one symptom, and/or reduce severity of at least one symptom related to a fibrotic and/or inflammatory condition. The methods may treat or reduce the severity or delay the onset of one or more fibrotic and/or inflammatory conditions, and the methods may reduce the chance of mortality with a fibrotic and/or inflammatory condition.

In specific embodiments, the fibrotic and/or inflammatory is related to a cardiac condition. Methods of embodiments of the disclosure encompass treatment or prophylactic activity for a cardiac condition. The methods may treat, delay onset of at least one symptom, and/or reduce severity of at least one symptom related to a cardiac condition. The methods may treat or reduce the severity or delay the onset of one or more cardiac conditions, and the methods may reduce the chance of mortality with a cardiac condition. The cardiac condition may be, for example, coronary heart disease, heart failure, hypertensive heart disease, inflammatory heart disease, rheumatic heart disease, coronary heart disease, and so forth.

In some embodiments of the disclosure, methods of reducing or inhibiting a fibrotic and/or inflammatory (including cardiac condition (or susceptible to or at risk for a cardiac condition)) using one or more nucleic acids that express part or all of a LATS1 and/or LATS2 polynucleotide are disclosed and described.

In specific embodiments, there is diseased and/or damaged heart tissue. The individual may have damaged heart because of a prior or current event, such as, for example, an infarct or ischemia. In specific embodiments, the individual may have, for example, heart failure, fibrosis of the heart, cardiomyopathy, ischemic cardiomyopathy, myocardial necrosis, dilated cardiomyopathy, degeneration of skeletal and/or cardiac muscle fibers, diabetic cardiomyopathy, age-related cardiomyopathy, and so forth. The individual may be in need of improved cardiac function for any reason, including, for example, because of age, disease, trauma, a combination thereof, and so forth.

The tissue or organ may be from an individual of any age, race, gender, and so forth. The tissue or organ may be in need of preventing or delaying onset of fibrosis or inflammation because of personal or family history and/or because of one or more risk factors.

In particular embodiments, the tissue or organ is provided a therapeutically effective amount of nucleic acid that expresses LATS1/2 and/or LATS1/2 polypeptides, wherein the tissue or organ is damaged from a myocardial infarction.

In some embodiments, the tissue or organ is provided nucleic acids that express LATS1 and/or LATS2 wherein the nucleic acids are already present in any kind of cell at the time of delivery of the cells, including a cardiomyocyte or stem cell, for example. An individual may be provided an effective amount of one or more LATS1 and/or LATS2 polypeptides in lieu of or in addition to gene therapy with one or more LATS1 and/or LATS2 polynucleotides.

The nucleic acid compositions of the embodiments of the disclosure may be provided to the tissue or organ once or more than once. The delivery may occur upon the determination of a need for improving the tissue or organ. Delivery may occur to tissue from an individual who is susceptible to a cardiac condition, such as, for example, an individual having a personal or family history of cardiac condition(s), being overweight, having high cholesterol, and/or a smoker. The delivery may cease or continue once it is determined that a cardiac symptom is improved.

In particular embodiments, cardiac tissue or a heart subject to a MI is provided an effective amount of one or more agents that increase LATS1/2 in cells of the tissue or heart (including progenitor cells or other cells) so that the extent of fibrosis and/or inflammation will be non-existent or reduced following the MI. One or more agents that increase LATS1/2 in cells of the cardiac tissue or heart (including progenitor cells or other cells) may be provided so that the extent of fibrosis is reduced following damage. In at least some cases, the damage following an MI is reduced in intensity compared to damage that would have occurred in the absence of use of the one or more agents that increase LATS1/2.

III. Kits of the Disclosure

Any of the compositions described herein may be comprised in a kit. In a non-limiting example, LATS1/2 compositions (or functional fragments and/or functional derivatives), whether they be polynucleotides or polypeptides or a combination thereof, may be comprised in a kit. The kits will thus comprise, in suitable container means, LATS1/2 composition(s) (or functional fragment or functional derivative).

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the LATS1/2 compositions (or functional fragment or functional derivative) in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The LATS1/2 compositions (or functional fragment or functional derivative) may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The kits of the present disclosure will also typically include a means for containing the vials in close confinement for commercial sale, such as, e.g., injection and/or blow-molded plastic containers into which the desired vials are retained.

The kit may comprise LATS1/2 composition(s) (or functional fragment or functional derivative) formulated as a cardiac therapy.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 8B:
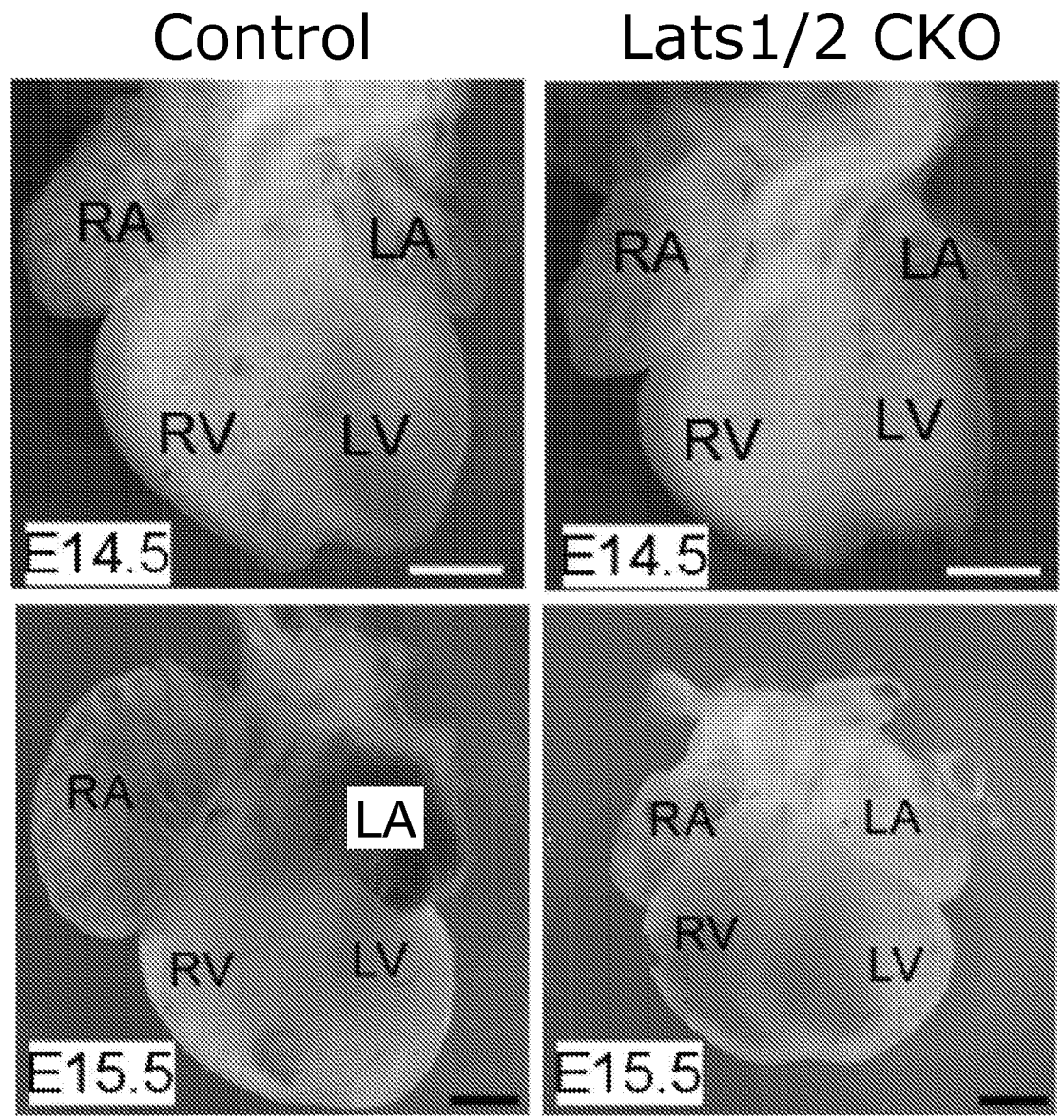
Figure 8C:
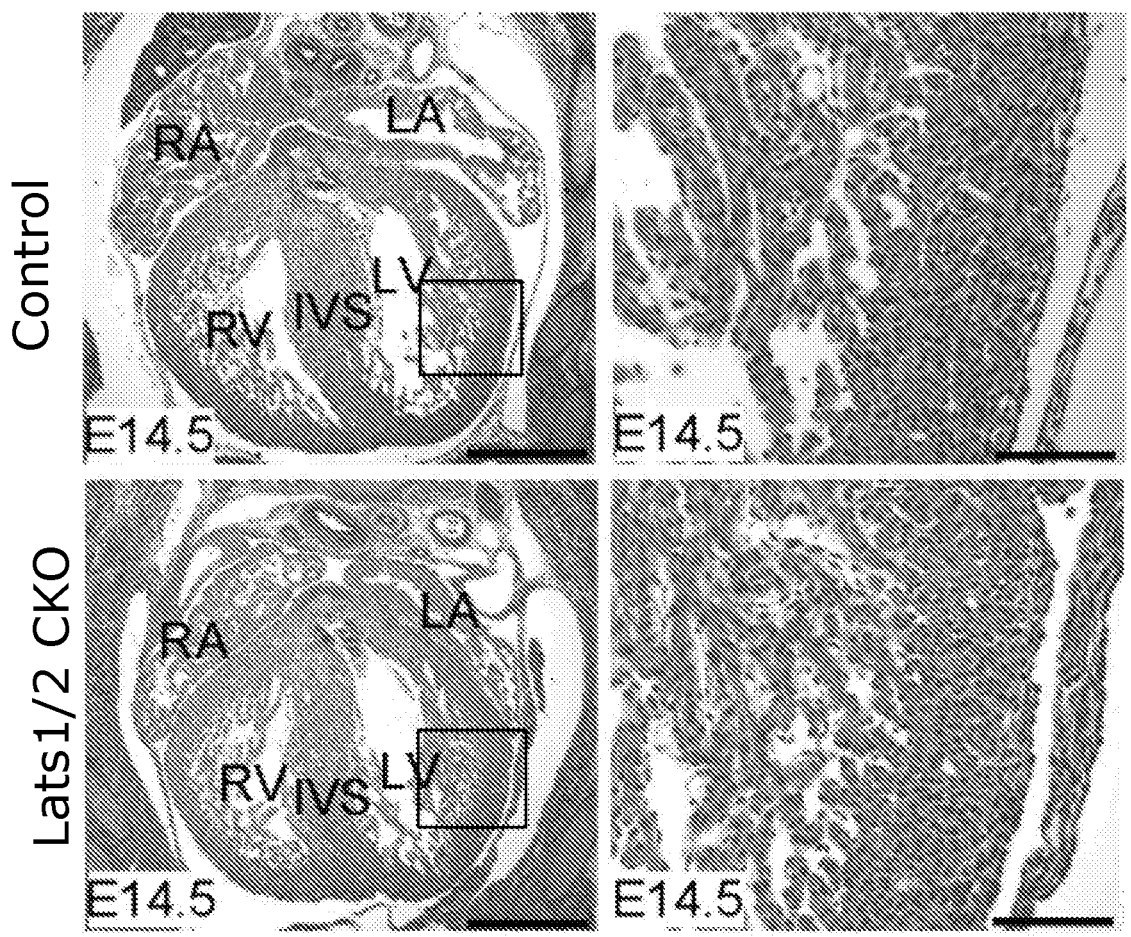
Figure 8D:
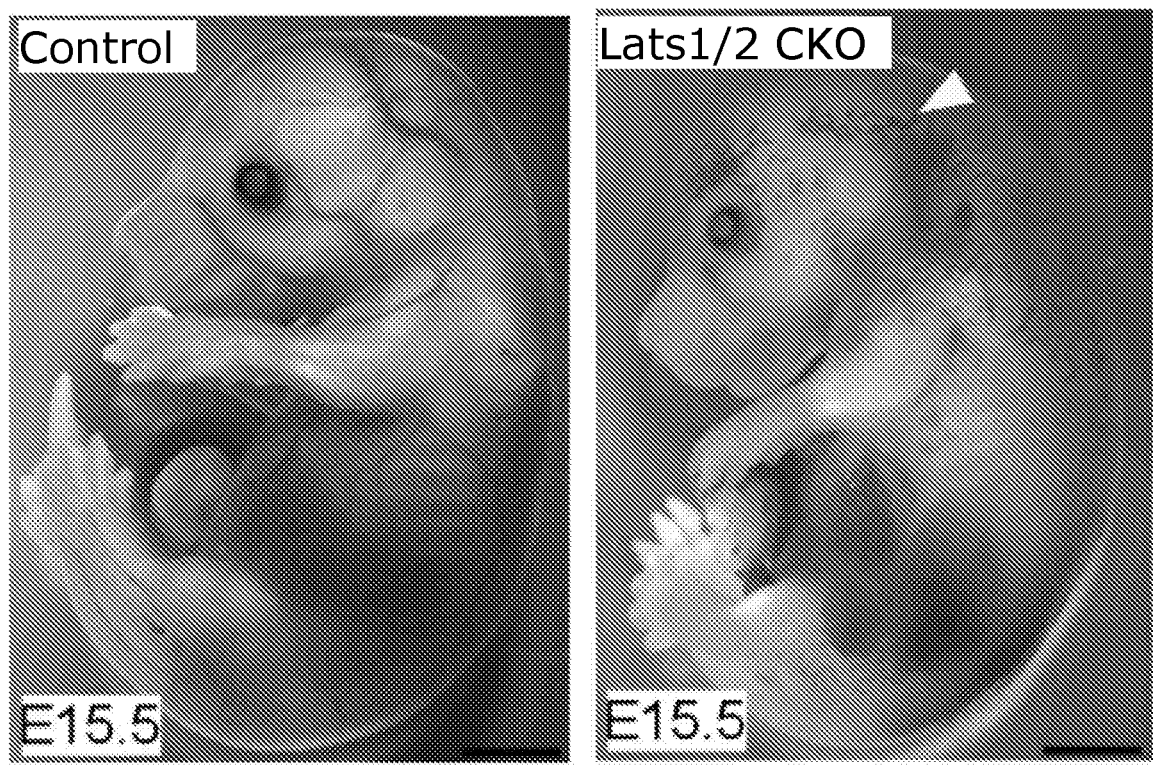
Figure 8E:
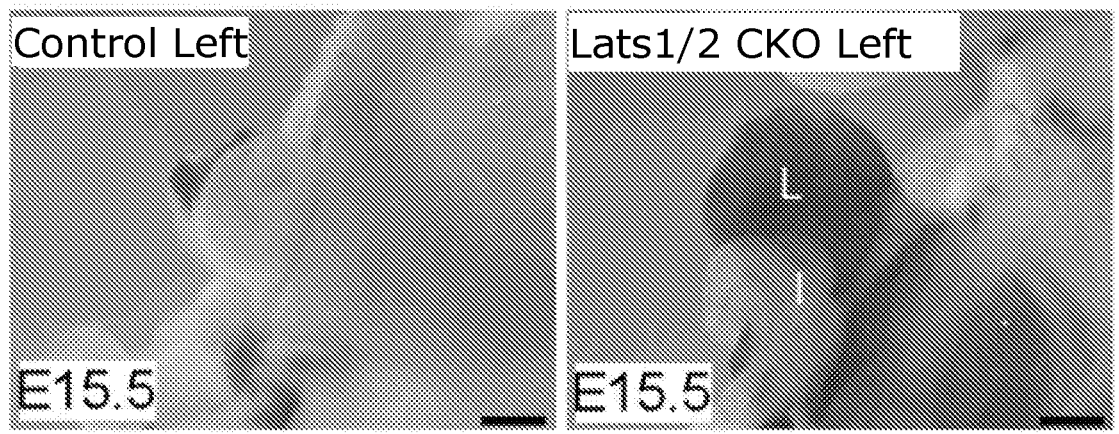
Figure 8F:
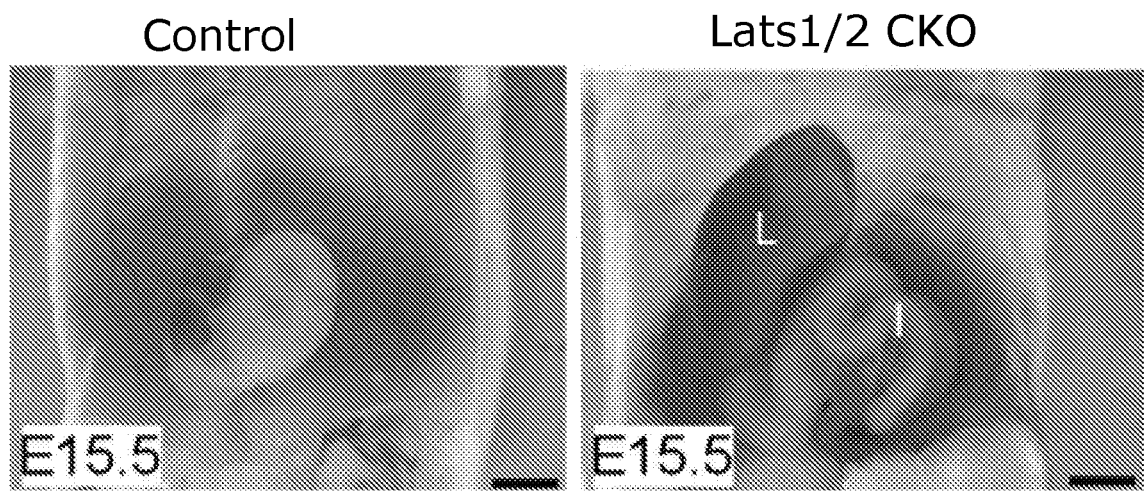

Single Cell Transcriptomics Reveal an Essential Role for Hippo Signaling in Cell State Transitions During Cardiac Fibroblast Development Epicardial Deletion of Lats1/2 Results in Defective Coronary Vessel Development Lats1/2 was deleted in E11.5 epicardium using the Wt1$^{CreERT2}$ allele (Zhou et al., 2008). Lats1/2 conditional knock out (CKO) embryos failed to survive past E15.5 (FIG. 8A). Lats1/2 CKO E14.5 hearts appeared normal (FIG. 8B,8C), but E15.5 mutant hearts were smaller, with less compacted myocardium (FIG. 1A, FIG. 8B). Lats1/2 CKO embryos also displayed skin hemorrhages, as well as, herniated livers and intestines (FIG. 8D-8F).

Figure 1B:
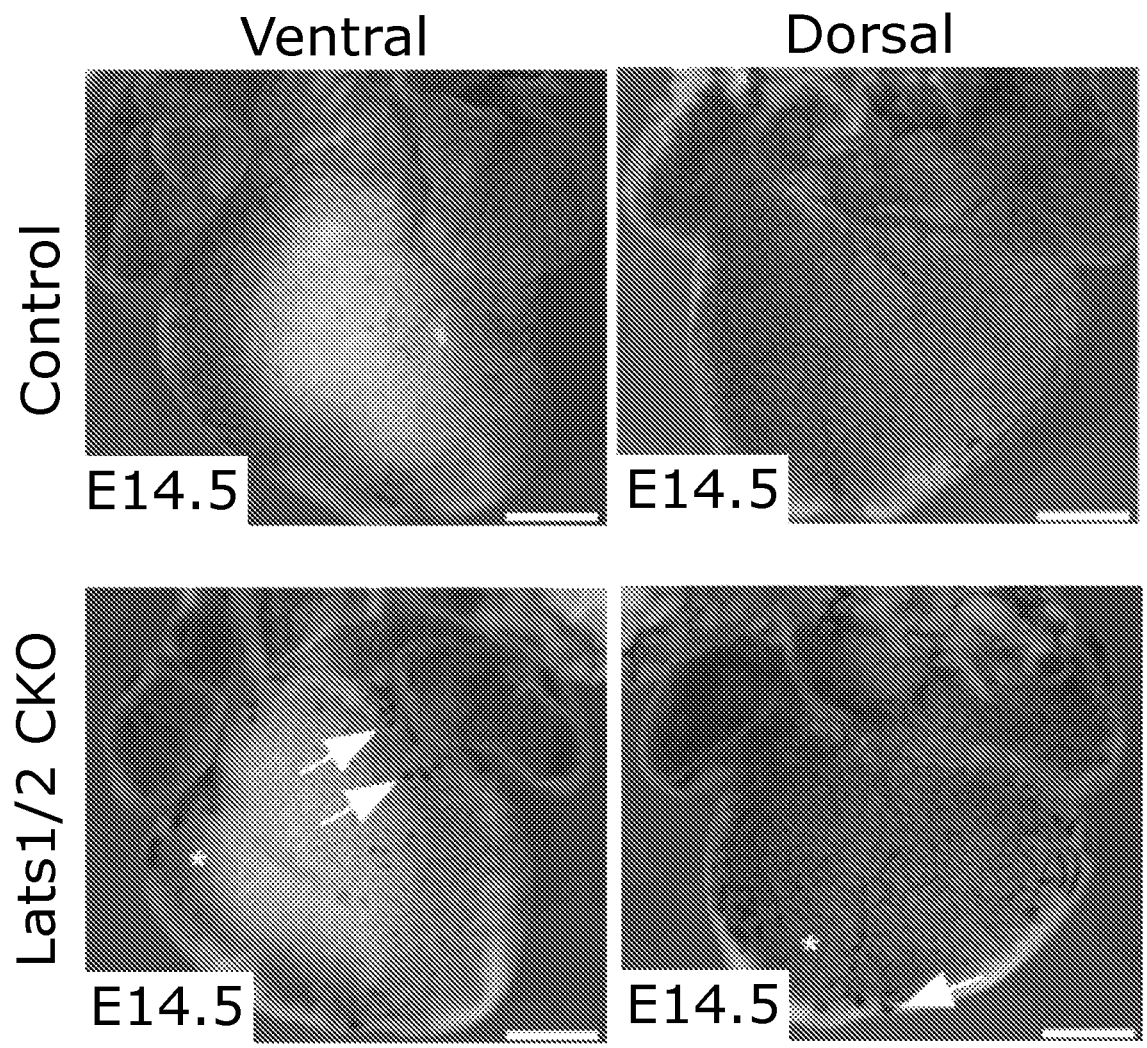
Figure 1C:
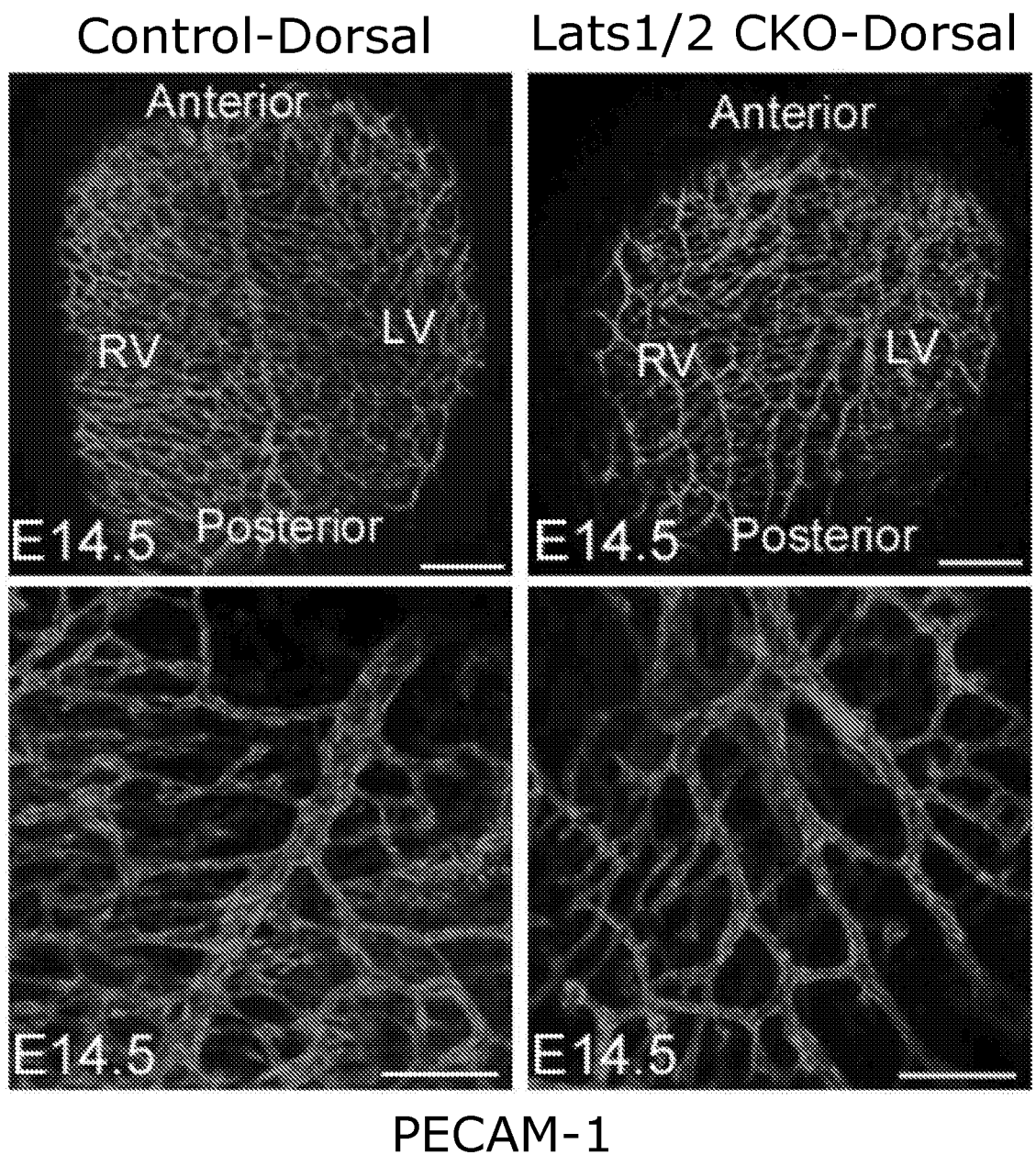
Figure 1D:
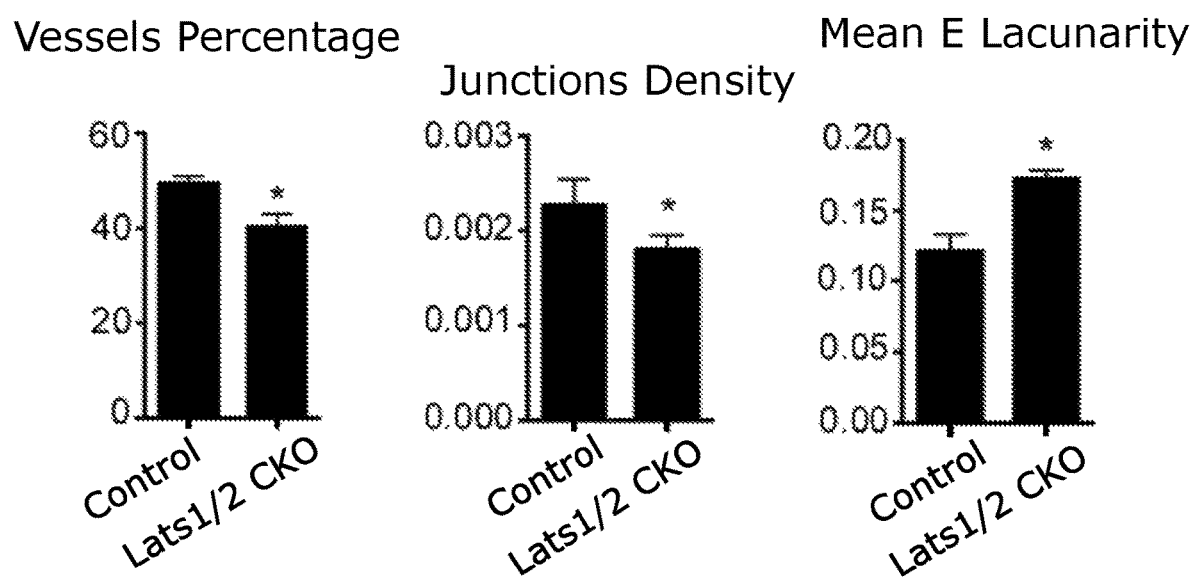
Figure 9A:
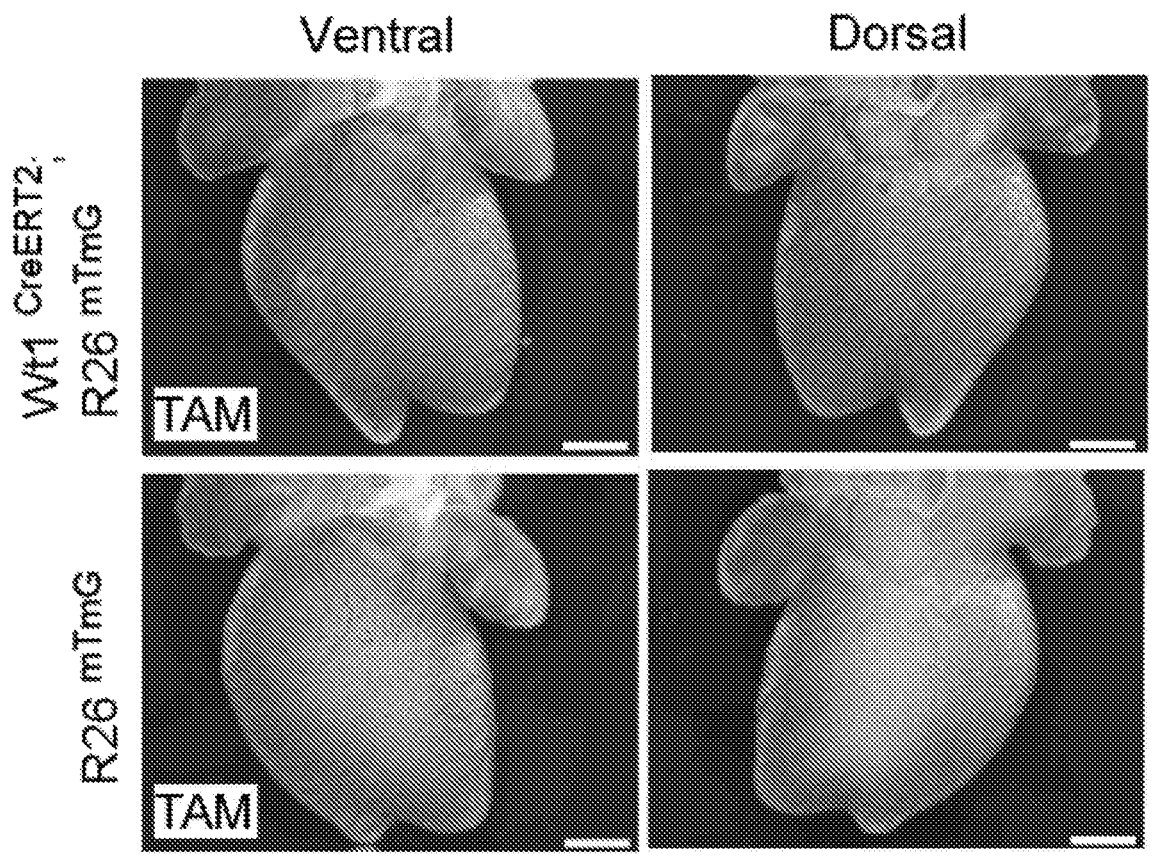
Figure 9B:
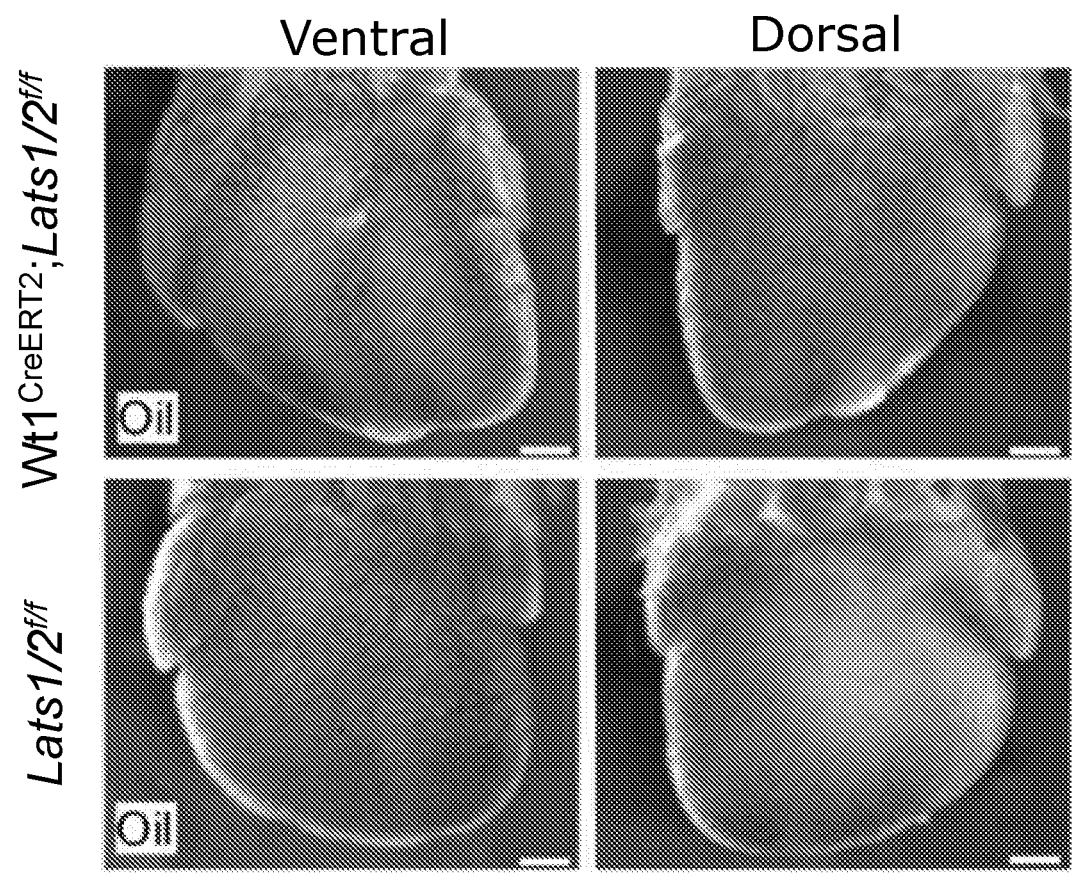

E14.5 to E15.5 is a critical stage for coronary vessel morphogenesis when the vascular plexus remodels to meet increased oxygen demands (Red-Horse et al., 2010; Viragh and Challice, 1981). Pecam-1 immunostaining in E14.5 Lats1/2 CKO hearts revealed reduced vessel coverage and density with blood island-like structures (FIG. 1B). Pecam-1 immunofluorescence (IF) staining with confocal microscopy and automated quantification revealed dorsal vasculature had decreased branching and reduced vessel coverage with fewer junctions and increased lacunarity (FIG. 1C,D). As controls, tamoxifen was injected into wt1$^{CreERT2}$/+ embryos and Cre negative littermates and vehicle (peanut oil) was injected into Wt1$^{CreERT2}$; Lats1/2$^{f/f}$ and Cre negative littermates. Coronary vessel development in controls was normal (FIG. 9A,9B).

Figure 1E:
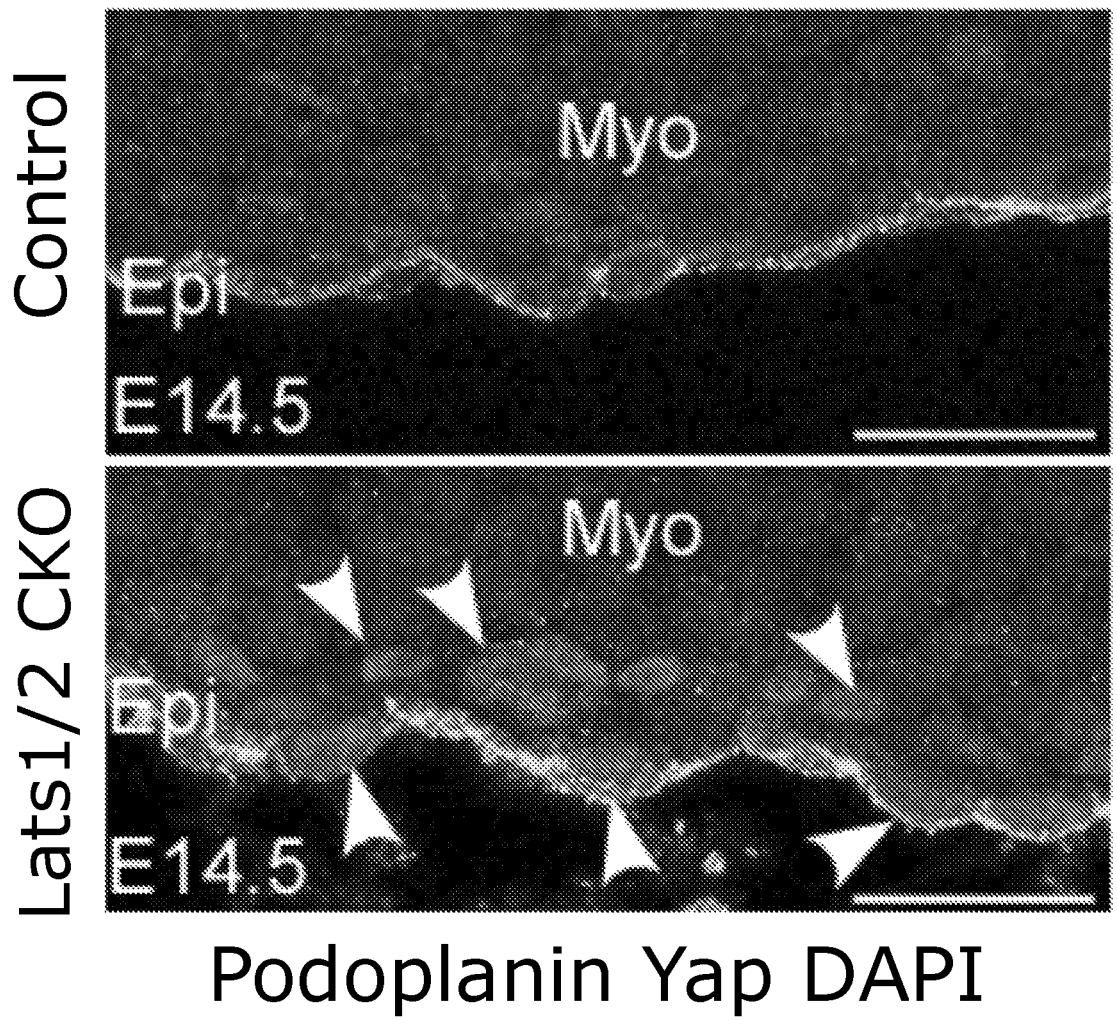
Figure 1F:
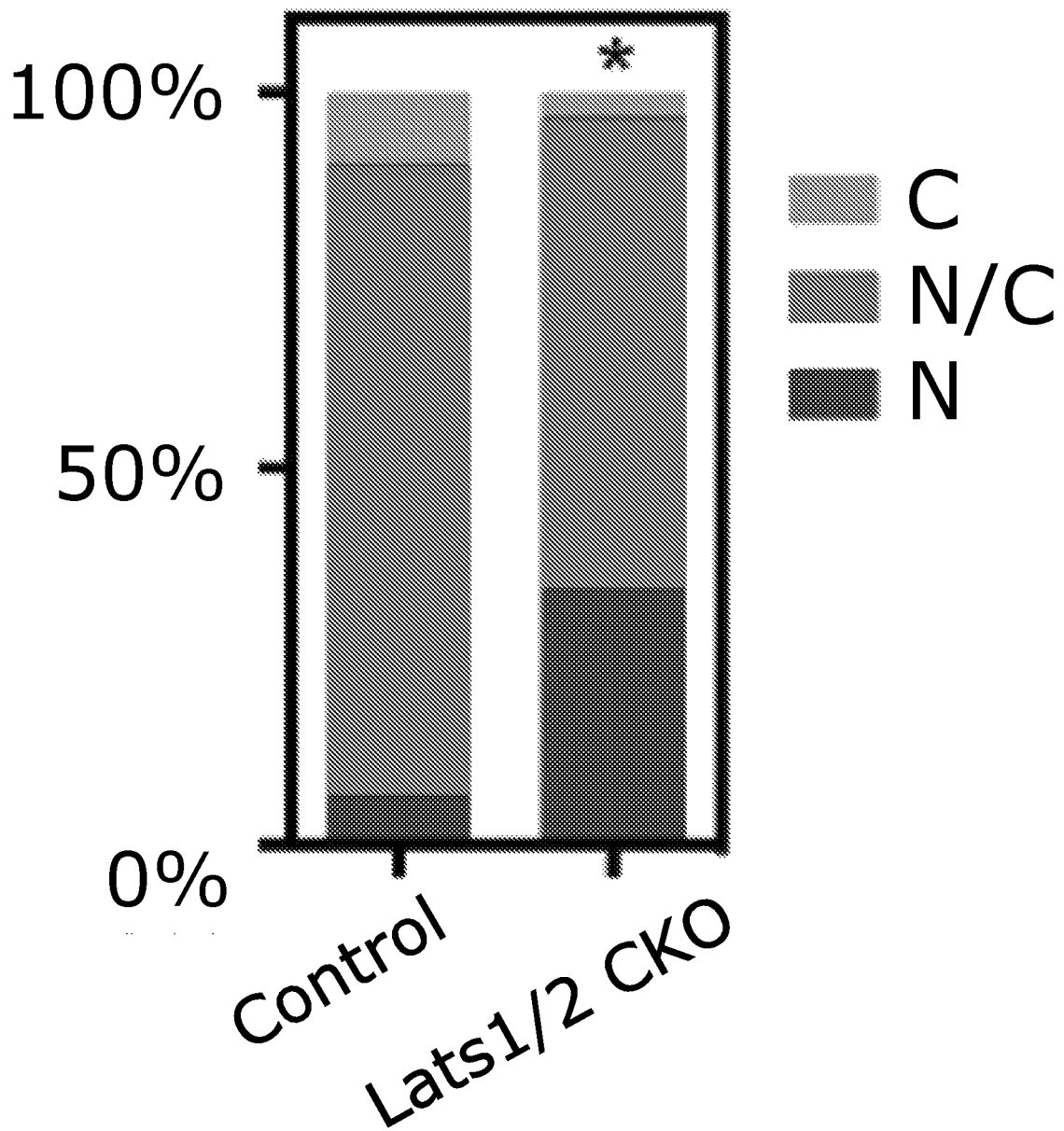
Figure 1G:
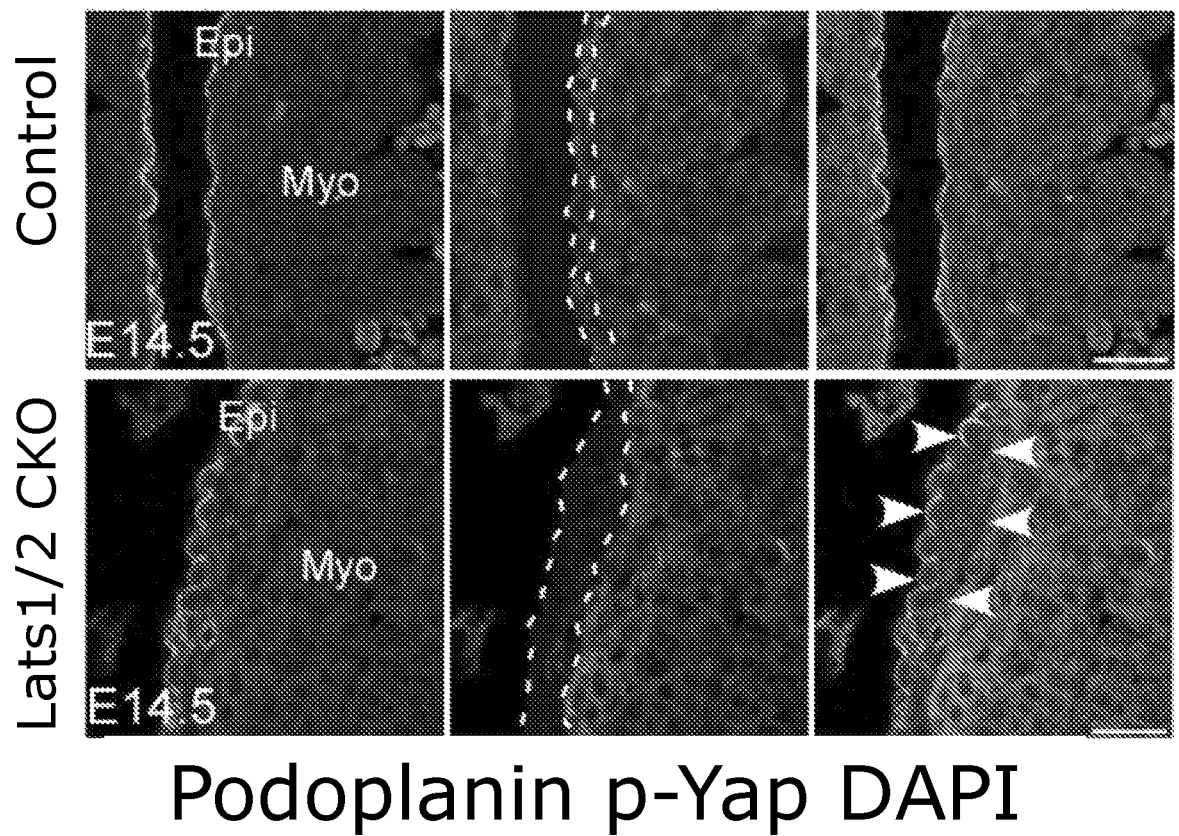

Yap sub-cellular localization and Yap phosphorylation (p-Yap) was examined as a readout of Lats kinase activity. Yap localization in Lats1/2 CKO hearts, detected by total Yap and Podoplanin IF, revealed increased nuclear Yap in both epicardium and subepicardium (FIG. 1E,1F). IF revealed decreased p-Yap in Lats1/2 CKO epicardium and subepicardium but no change in CMs since Lats 1/2 was inactivated in the epicardial lineage (FIG. 1G). Podoplanin, restricted to the epicardium in control embryos, was also expressed in Lats1/2 CKO subepicardium suggesting that EMT occurred prior to repression of the epicardial program (FIG. 1G).

Figure 9C:
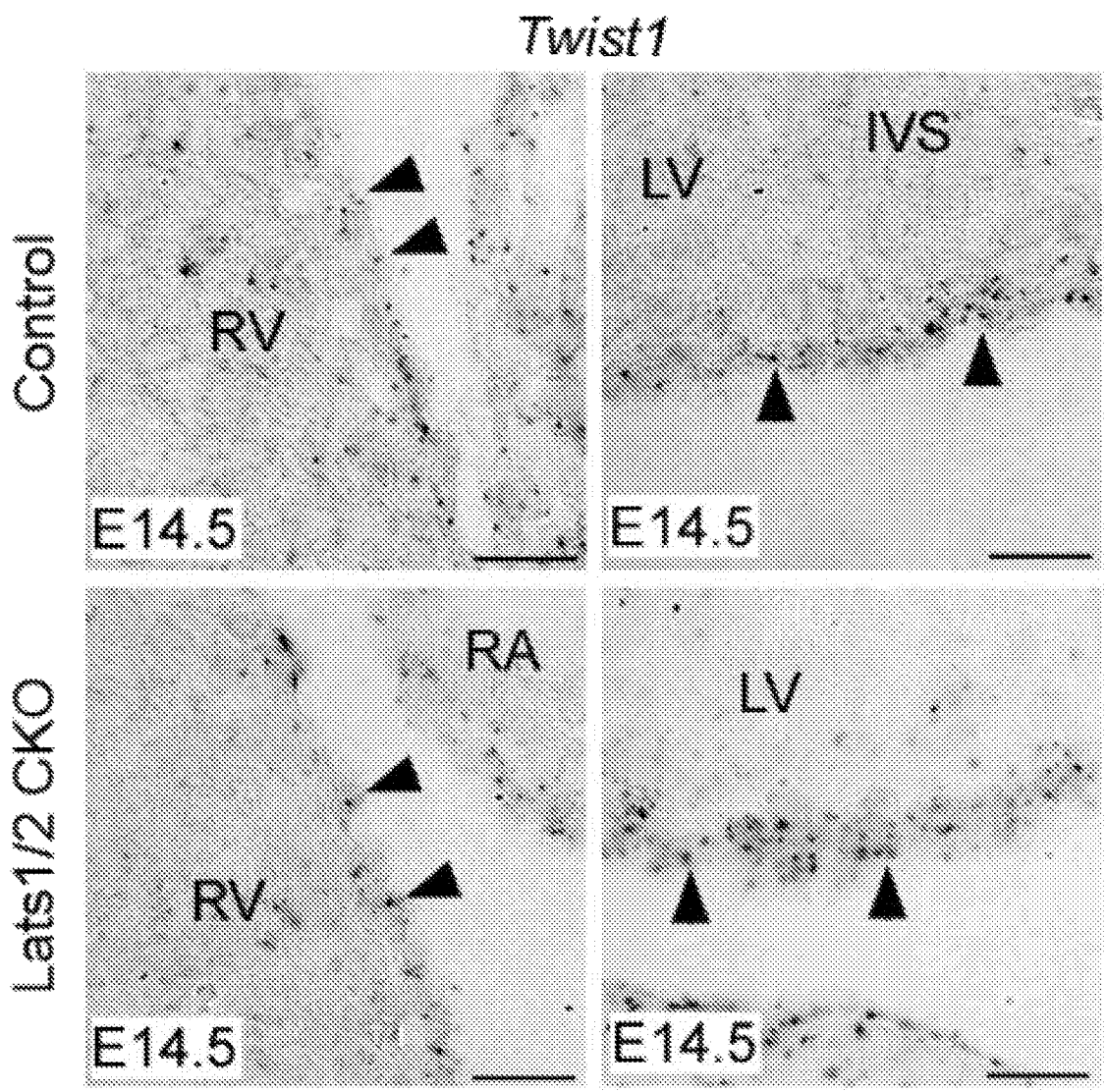
Figure 9D:
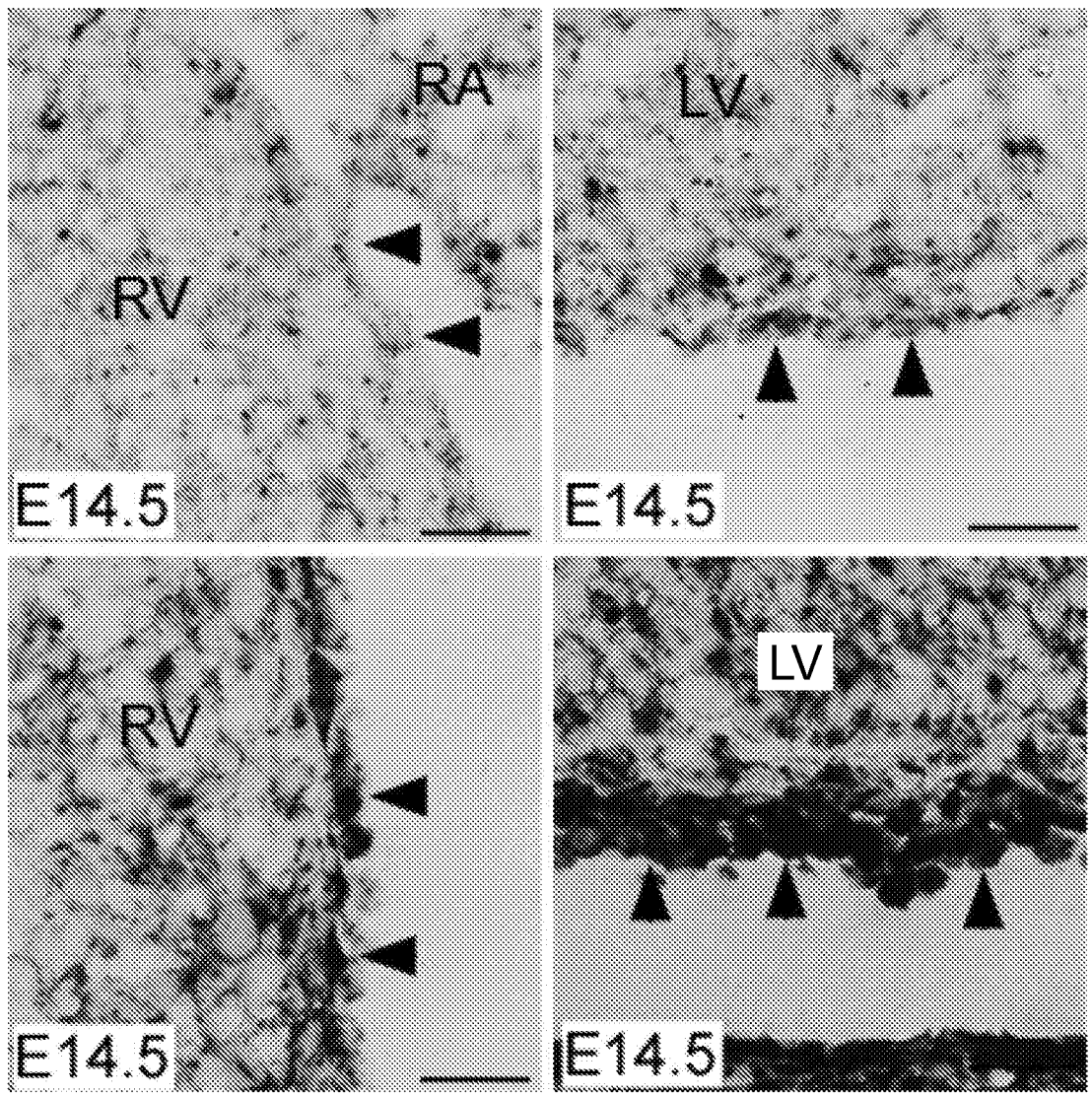
Figure 9E:
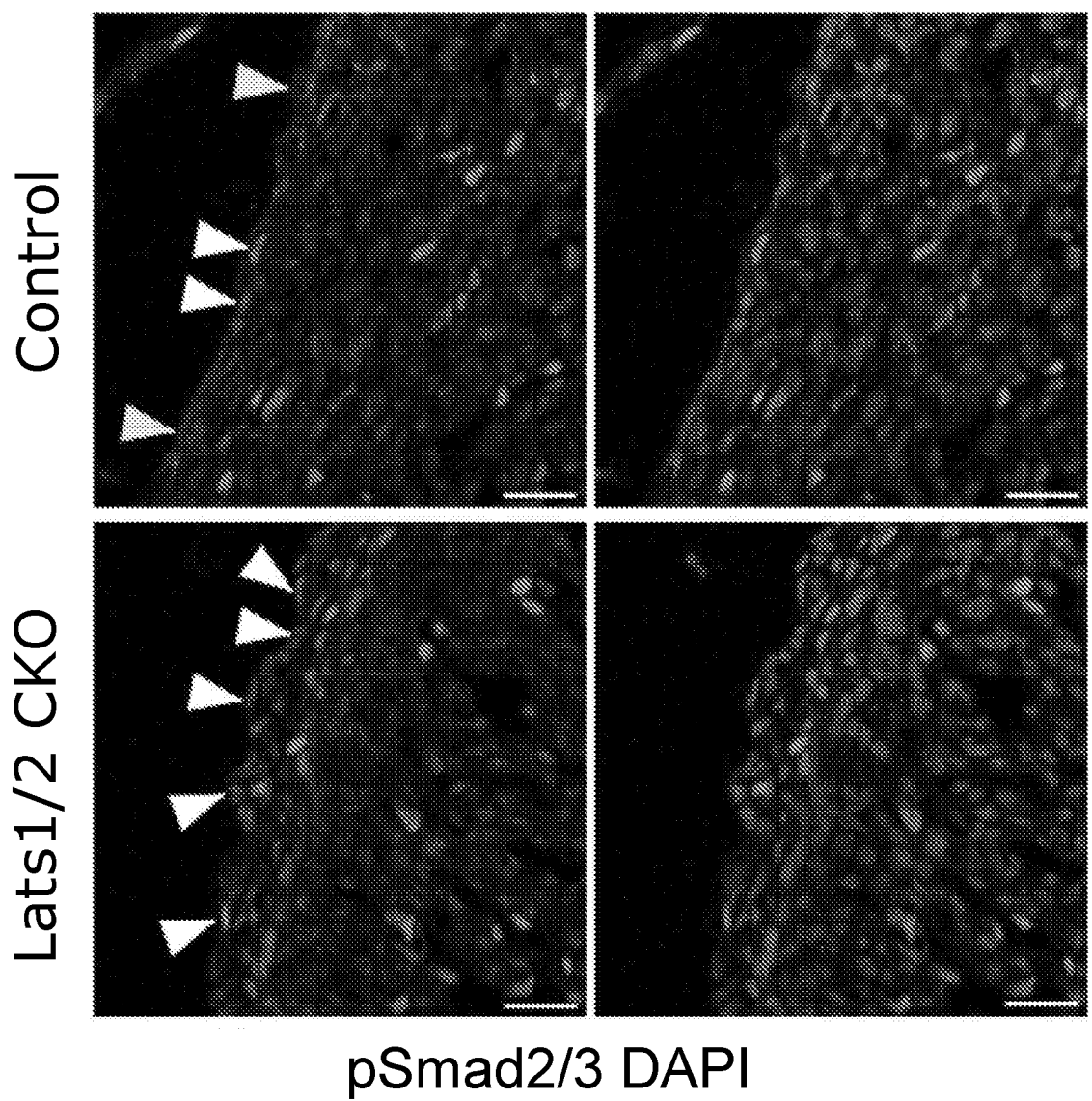

Recent work indicated that epicardial deletion of Yap and Taz led to defective EMT (Singh et al., 2016). In situ hybridization with EMT markers revealed that Snai2 was elevated in Lats1/2 CKO hearts, while Twist1 was unchanged (FIG. 9C,9D). Tgfβ-signaling that promotes epicardial EMT (Sridurongrit et al., 2008) was elevated in Lats1/2 CKO epicardium as determined by increased nuclear p-Smad2/3, a readout of Tgfβ-signaling (FIG. 9E,9F).

Figure 1H:
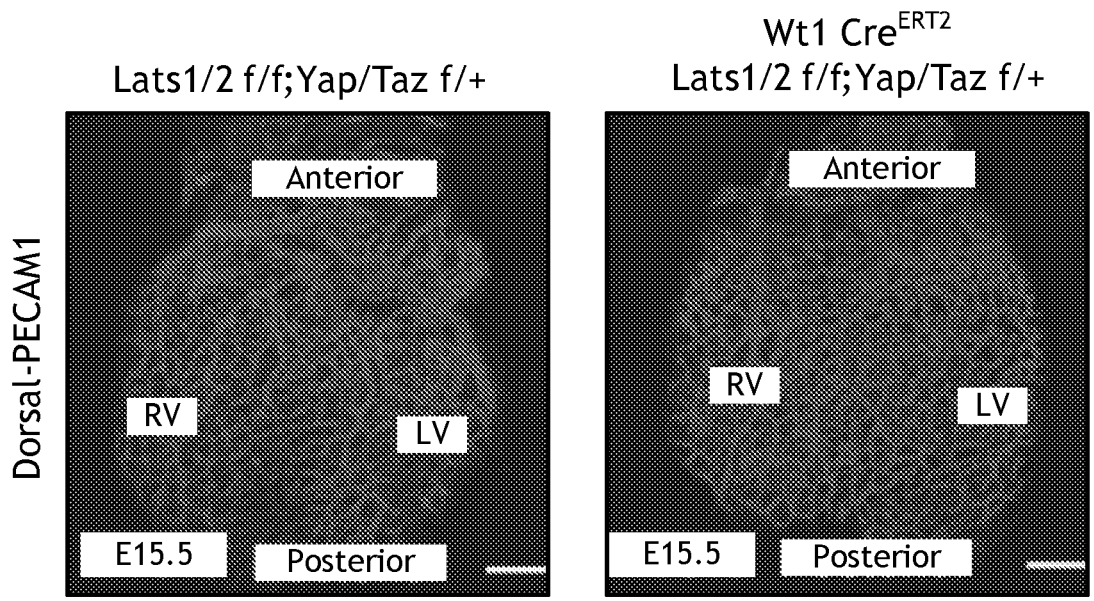
Figure 1I:
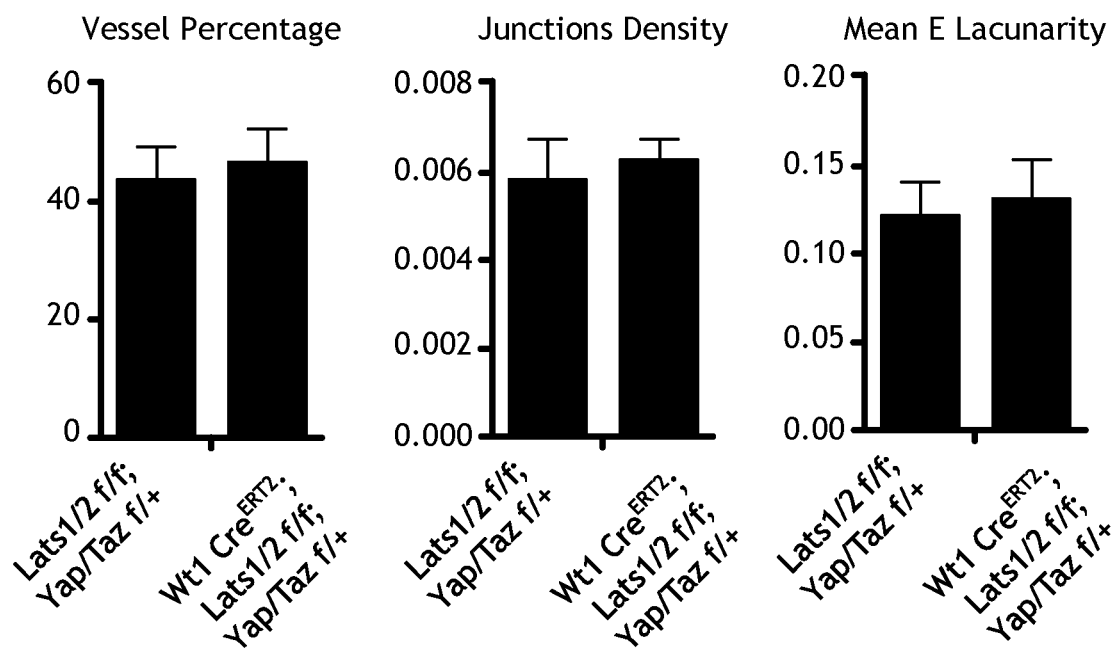

To determine if Yap function was required for Lats1/2 CKO phenotype, endogenous Yap and Taz was genetically reduced in Lats1/2 CKO embryos by generating Wt1$^{CreERT2}$; Lats1/2$^{f/f}$; Yap/Taz$^{f/+}$ embryos and induced Cre activity at E11.5. The Wt1$^{CreERT2}$; Lats1/2$^{f/f}$; Yap/Taz$^{f/+}$ embryos were viable at E15.5 without major coronary vasculature defects indicating that Lats1/2 kinases are required for normal coronary vessel development by restricting Yap activity (FIG. 1H,1I).

Unbiased Single-Cell Transcriptomics of E13.5 and E14.5 Embryonic Hearts

Drop-seq was used to profile cardiac tissue from control and Lats1/2 CKO E13.5 and E14.5 embryos, the stages preceding the Lats1/2 CKO cardiac phenotype. Graph based clustering was performed on significant principle components and visualized results through non-linear dimensional reduction algorithm, t-Distributed Stochastic Neighbor Embedding (tSNE) (Maaten and Hinton, 2008; Macosko et al., 2015). There was acquired 18,757 cells in total across two time points and two genotypes that was reduced to 18,166 single cells, after subtracting red blood cells and platelets (cluster 16), in 27 distinct clusters (FIG. 2A-2C). Differential expression analysis on spatially proximal clusters revealed transcriptionally well-defined clusters. Clusters without transcriptional distinctions were merged and classified based on expression of known markers (FIG. 2C-2F).

Transcriptional Characteristics of Cardiomyocytes, Endothelial Cells, and Valve Development CMs, endothelial cells, smooth muscle cells, mesenchymal cells, macrophages, and epicardial cells had cluster sizes that ranged from 63 to 4,716 cells (FIG. 2E,2F). Non-epicardial-derived lineages were evaluated, specifically CMs and endothelial cells. Analysis of E13.5-E14.5 heart tissue, excluding the atria, revealed a cellular composition that was distinct from adult murine cardiac tissue that is made up of approximately 31% CMs and 43% endothelial cells (Pinto et al., 2016). The results indicated that E13.5-E14.5 murine heart contains 43% CMs and only 19% endothelial cells (FIG. 2E).

Figure 10A:
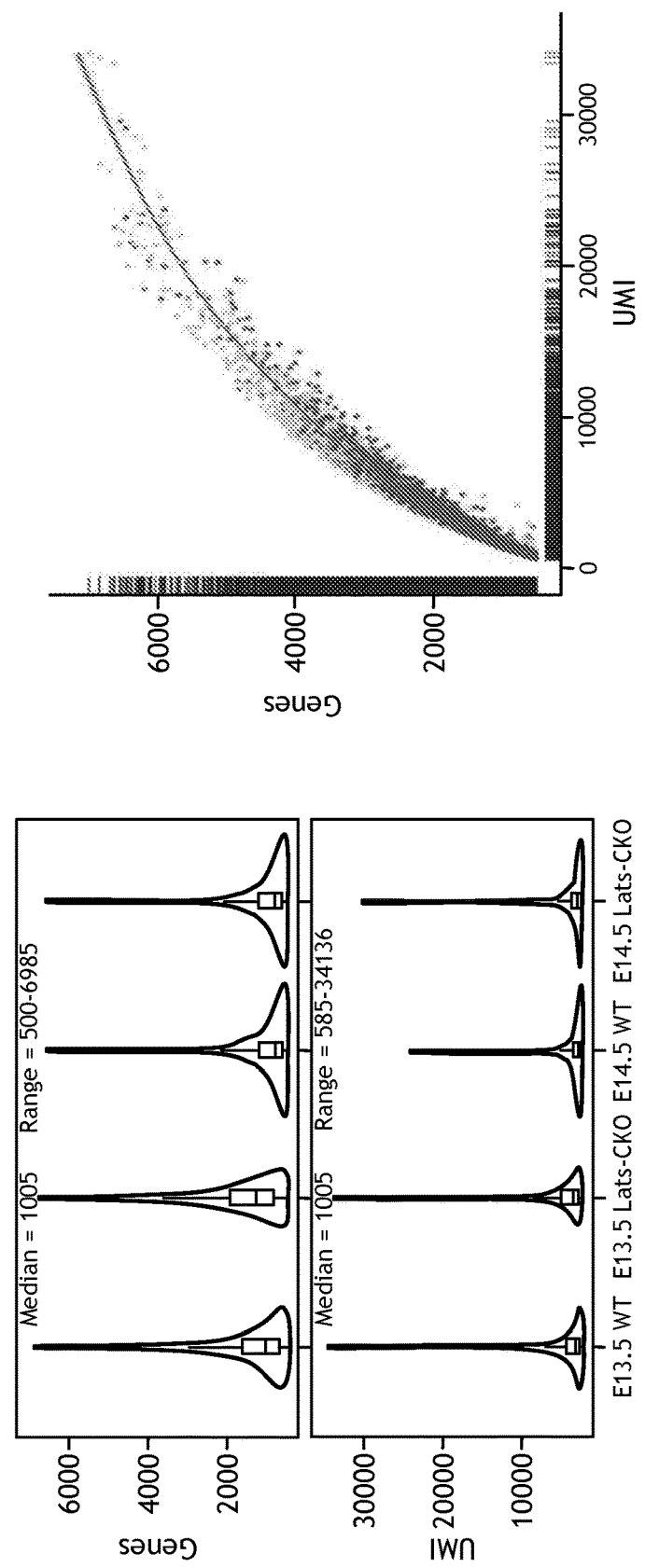
FIGS. 10A-10F. Drop-seq library quality control, cardiomyocyte sub-population expression, endothelial cell markers, and valvulogenesis signatures.
Figure 10B:
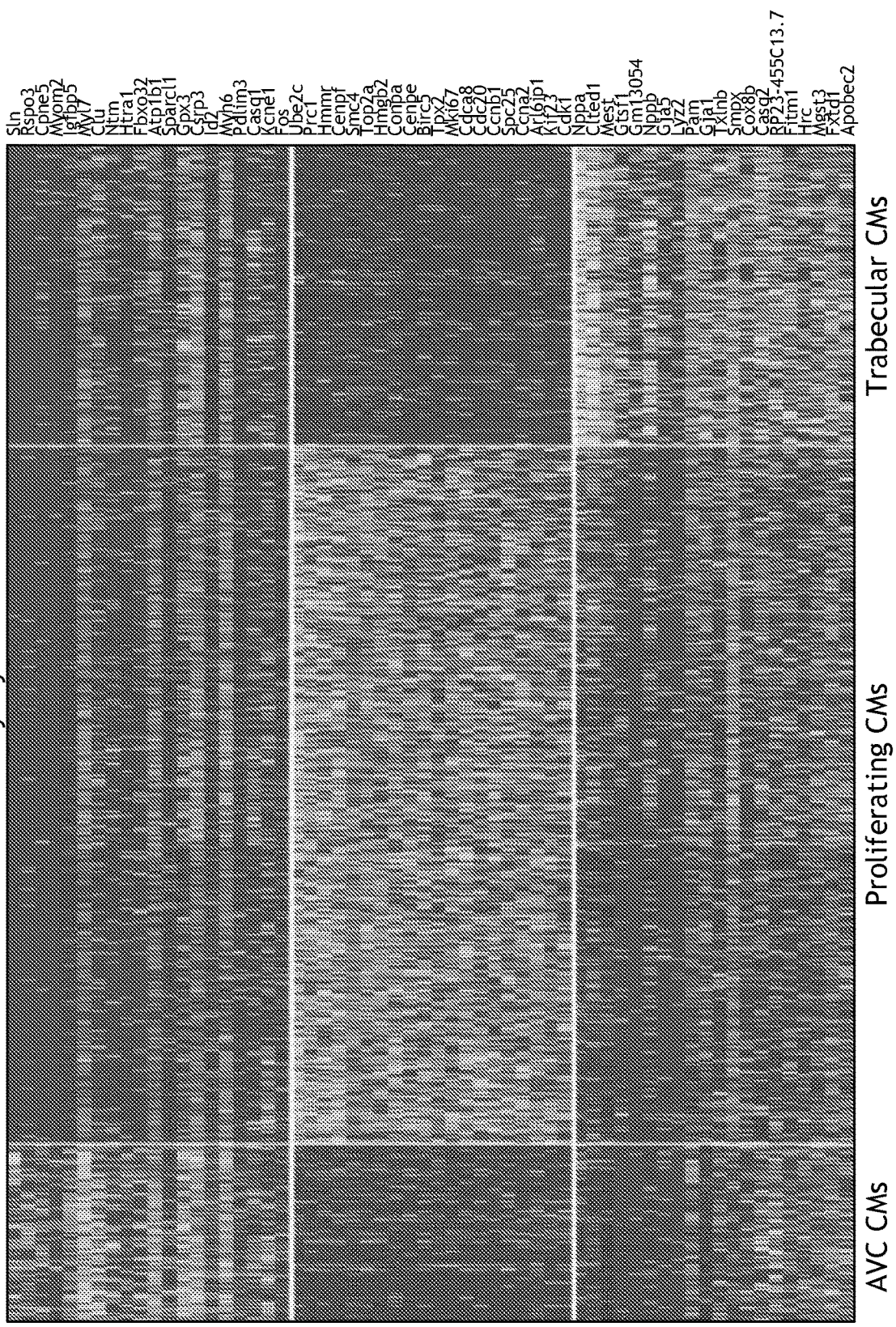

CMs and endothelial cells were heterogeneous and were further sub-categorized (FIG. 2E,F). The two rarest CM populations were atrioventricular canal (AVC) and trabecular CMs. AVC CMs were identified based on a molecular signature that included the Wnt-pathway gene Rspo3 and the Bmp-pathway gene Bmp2 (FIG. 2F, FIG. 10A,10B) (Cambier et al., 2014; Ma et al., 2005). In addition to Rspo3 and Bmp2, other AVC CM markers were detected, including Pitx2, Shox2, Wisp1, Tbx2, Tbx3, Tbx5, and Bmp7 (Campione et al., 2001; Habets et al., 2002) (FIG. 10B). Trabecular CMs were identified by a signature that included Nppa and Gja5 (FIG. 2F, FIG. 10B) (Jensen et al., 2012). Further clustering revealed several known and novel CM markers, as well as, proliferating CM signatures (FIG. 10B) (Li et al., 2016).

Figure 10C:
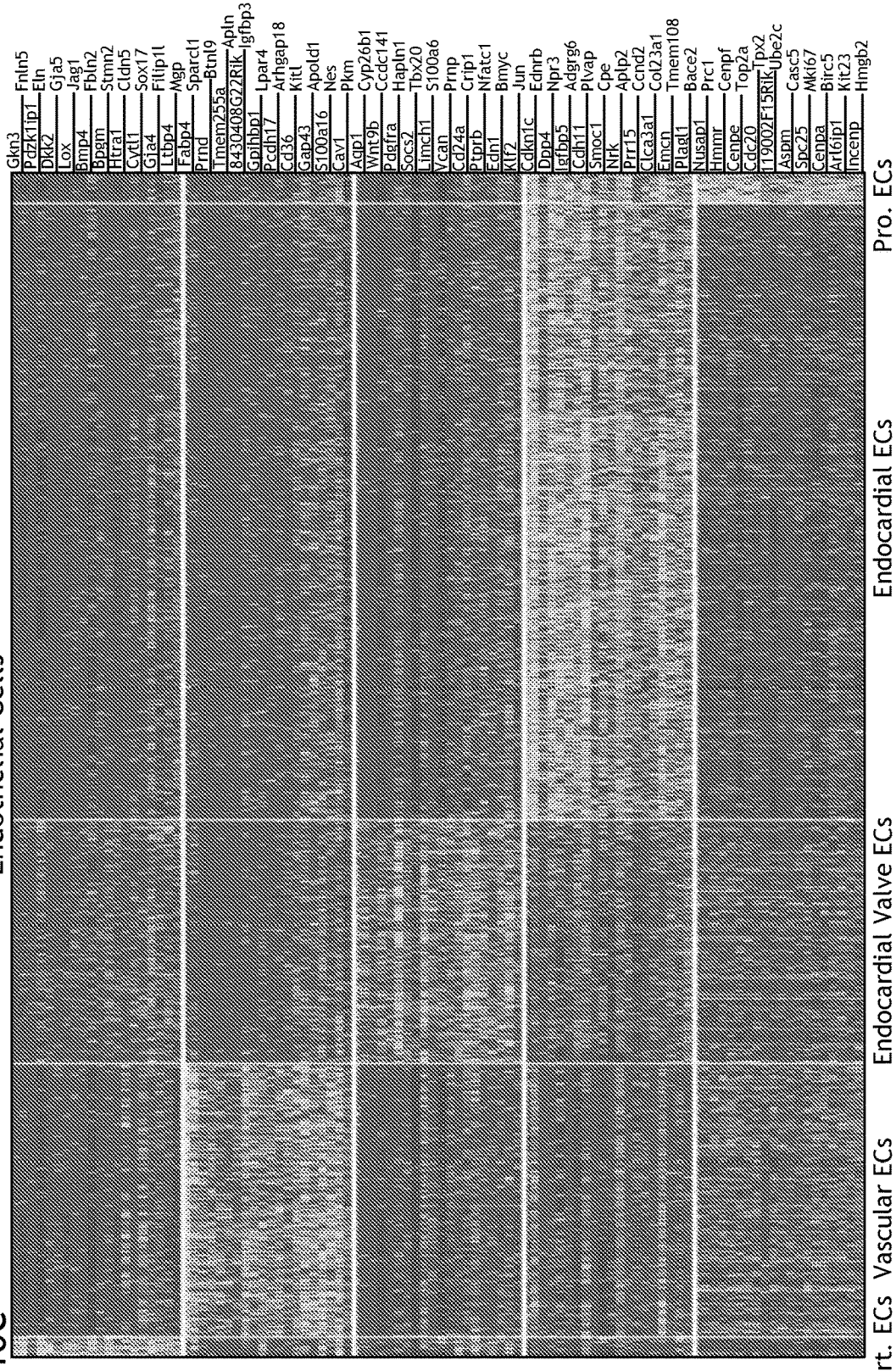
Figure 10D:
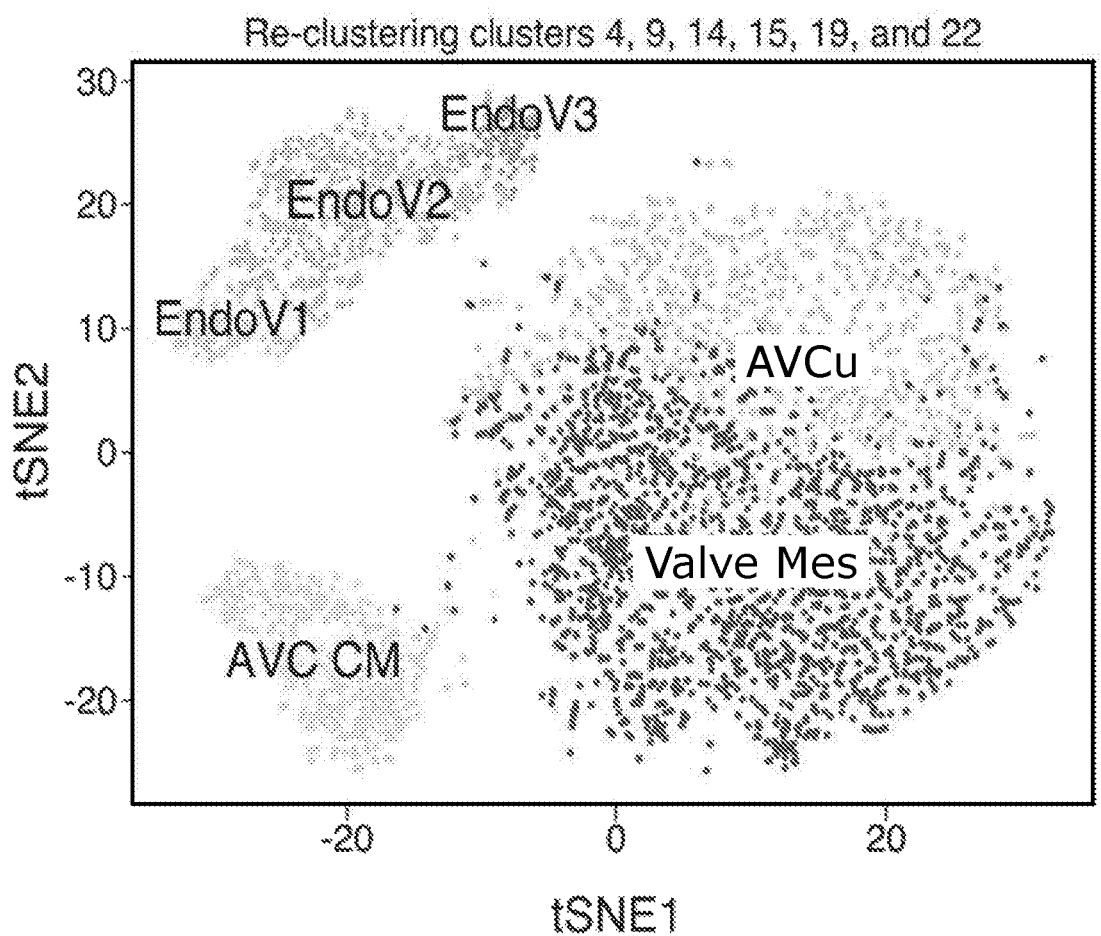

Endothelial cell subcategories included vascular endothelial cells that were distinguishable by Fabp4 and Apln expression (FIG. 10C) (He et al., 2014; Liu et al., 2015). Arterial endothelial cells were identified by markers, including Gja5, Fbln2, Fbln5, and Sox17 (FIG. 2F and FIG. 10C) (Liu et al., 2015). Endocardial cells were characterized by high levels of Npr3 (Zhang et al., 2016) in addition to markers not previously associated with endocardium including Ednrb, Adgrg6, Plvap, and Smoc1 (FIG. 2F and FIG. 10C). In valvular endocardium, there were three distinct clusters of Nfatc1-positive cells (EndoV1-EndoV3) revealing an unappreciated heterogeneity (FIG. 10D). The EndoV3 cluster displayed high expression of endocardial-to-mesenchymal transition (EndoMT) associated genes Enpp2, Prox1, and Fzd10 (FIG. 10C-10F) suggesting that dynamic phenotypic changes that characterize EndoMT may add to valvular endocardial heterogeneity (Gong et al., 2014; Lu et al., 2012; Shaul et al., 2014).

Figure 10E:
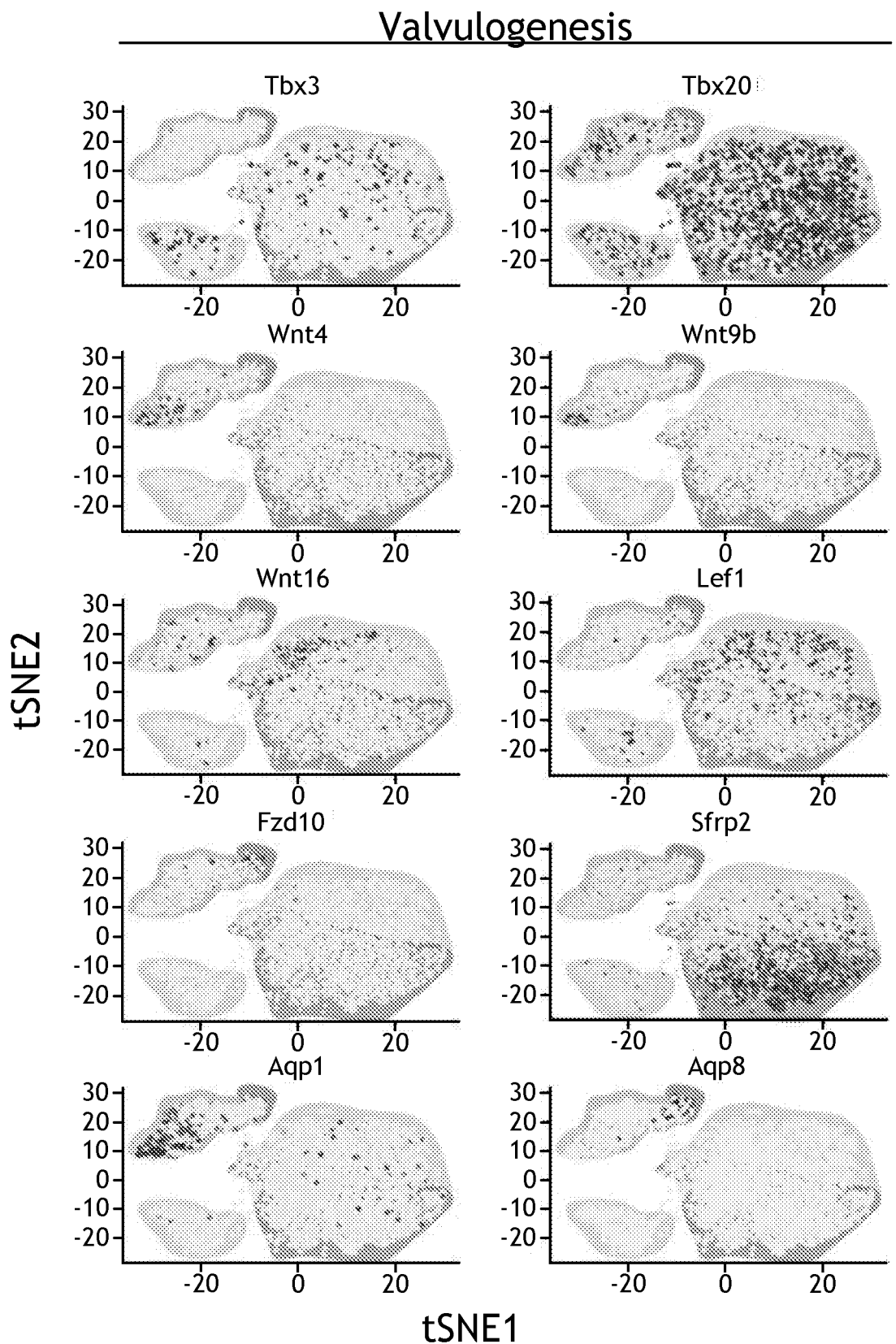
Figure 10F:
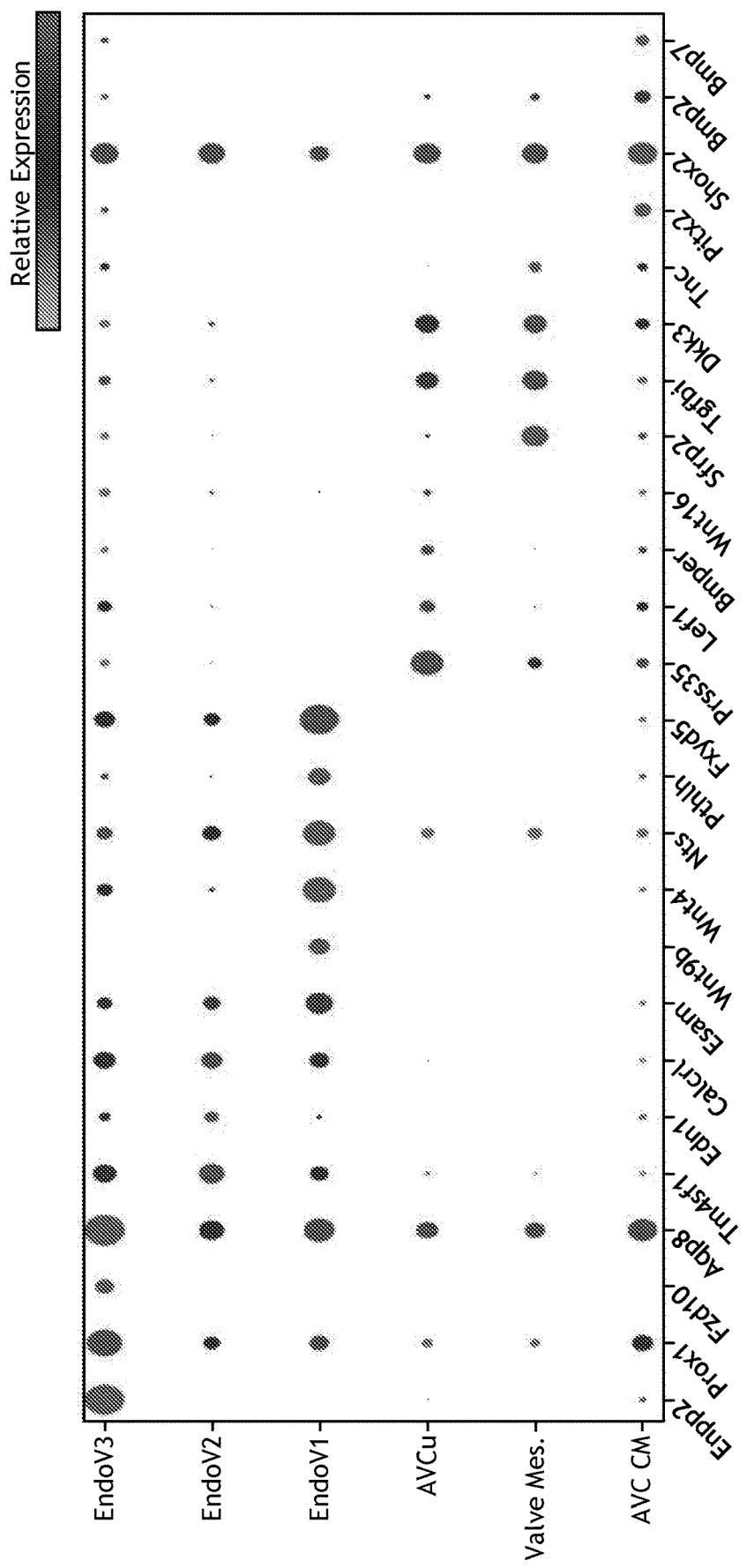

The data indicate about Wnt-signaling between tissues during valve development. Endo V1 and V2 valvular endothelial cells express Wnt genes Wnt4, Wnt9b, and Wnt16 while the gene encoding Wnt receptor Fzd10 is expressed predominantly in EndoV3 endothelial cells suggesting paracrine signaling between valvular endothelial cells that may promote EndoMT (FIG. 10E,10F)(Liebner et al., 2004) (Bosada et al., 2016). Valve mesenchyme expresses Sfrp2, a Wnt inhibitor (Cruciat and Niehrs, 2013), suggesting a mechanism to downregulate Wnt in mesenchymal cell maturation (FIG. 10E,10F). There was heterogeneous expression across valve endocardial clusters of aquaporin (AQPs) genes (e.g. Aqp8 and Aqp1) that encode water channel proteins and control cellular osmotic balance. AQPs have not been implicated in valve development (FIG. 10E, 10F)(Rutkovskiy et al., 2013).

An Epicardial-Derived Population Composed Primarily of Lats1/2 Deficient Cells

Relative proportions were compared of cell types in control and Lats1/2 CKO hearts (FIG. 2F). Although there were differences in a few non-epicardial-derived cell types, such as macrophages and trabeculated myocardium, the epicardial lineage was focused upon. Two clusters showed statistically significant enrichment in Lats1/2 CKO hearts compared to control (chi-squared test, $p<0.0025$). One of these was the epicardial cluster, which suggests increased proliferation and self-renewal or defective differentiation of Lats1/2 CKO epicardium. The second predominantly Lats 1/2 mutant cluster, designated Cluster 20 (C20), possessed a gene signature intermediate between that of fibroblasts and epicardium. C20 cells expressed Tcf21, a marker of epicardial cells and resting fibroblasts and Col11a1 (FIG. 2F) (Acharya et al., 2012). Cells that had a transcriptional signature similar to C20 cells were also observed in control hearts at lower frequency than Lats1/2 CKO hearts and IF data revealed that these cells, localized to the subepicardial space, represent subepicardial mesenchyme (see below). Because IF experiments uncovered important differences in protein expression between control and Lats 1/2 CKO subepicardial cells (see below), the disclosure will refer to the subepicardial-like cells in Lats 1/2 CKO hearts as C20 cells and in control as subepicardial mesenchyme cells. There was a reduction in cardiac fibroblasts in E14.5 Lats1/2 CKO hearts, suggesting a defect in epicardial to fibroblast transition (FIG. 2F).

Figure 3A:
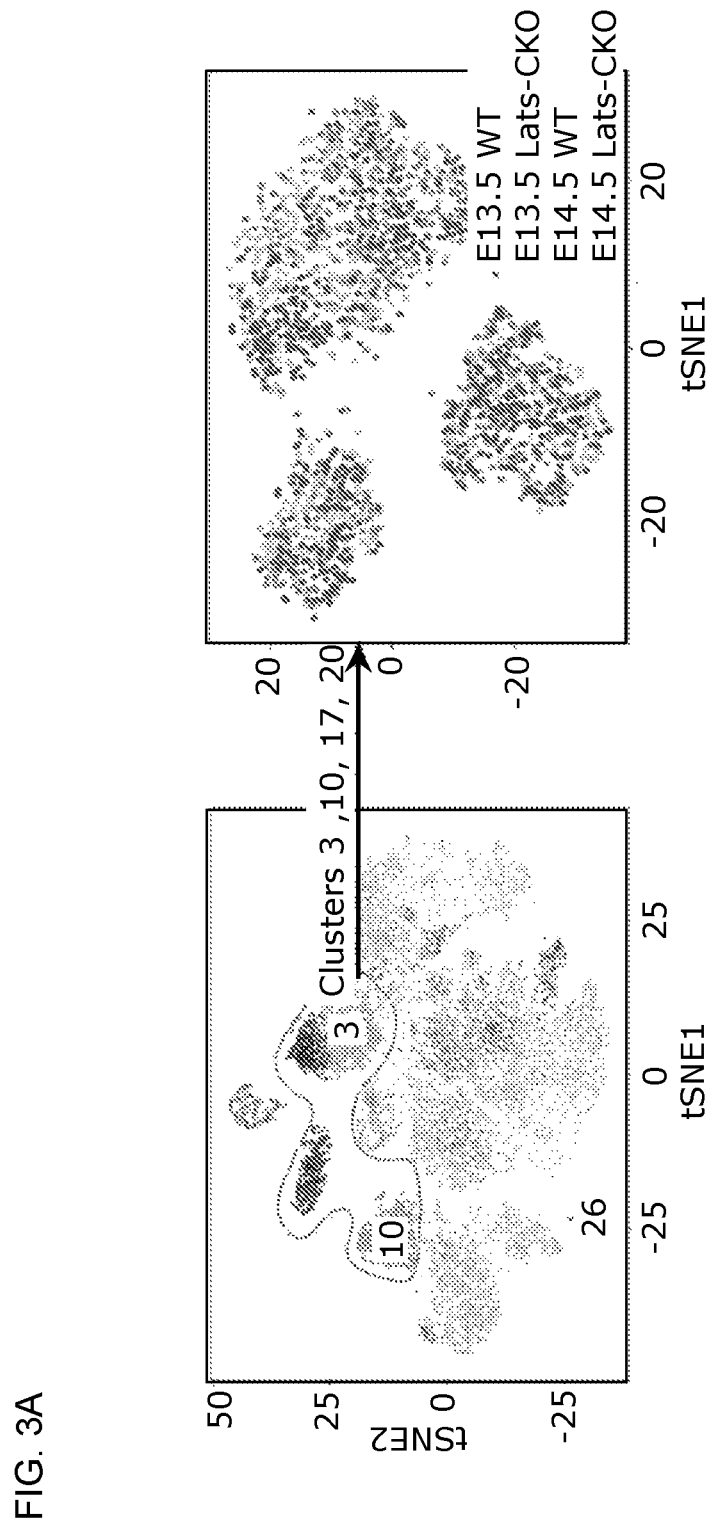
FIGS. 3A-3K. Fibroblast-specified Lats1/2 CKO epicardial cells are arrested along a common differentiation trajectory. See also FIG. 10 and FIG. 11.
Figure 3B:
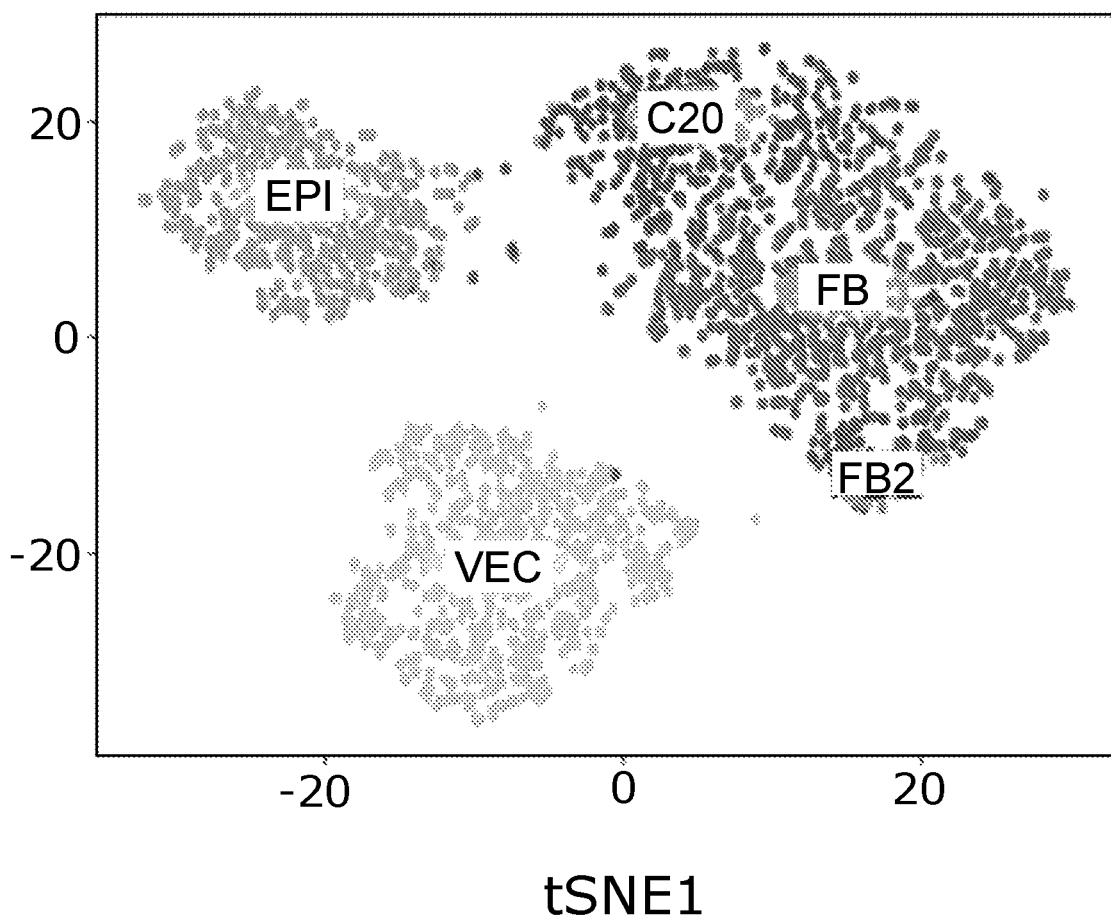
Figure 3C:
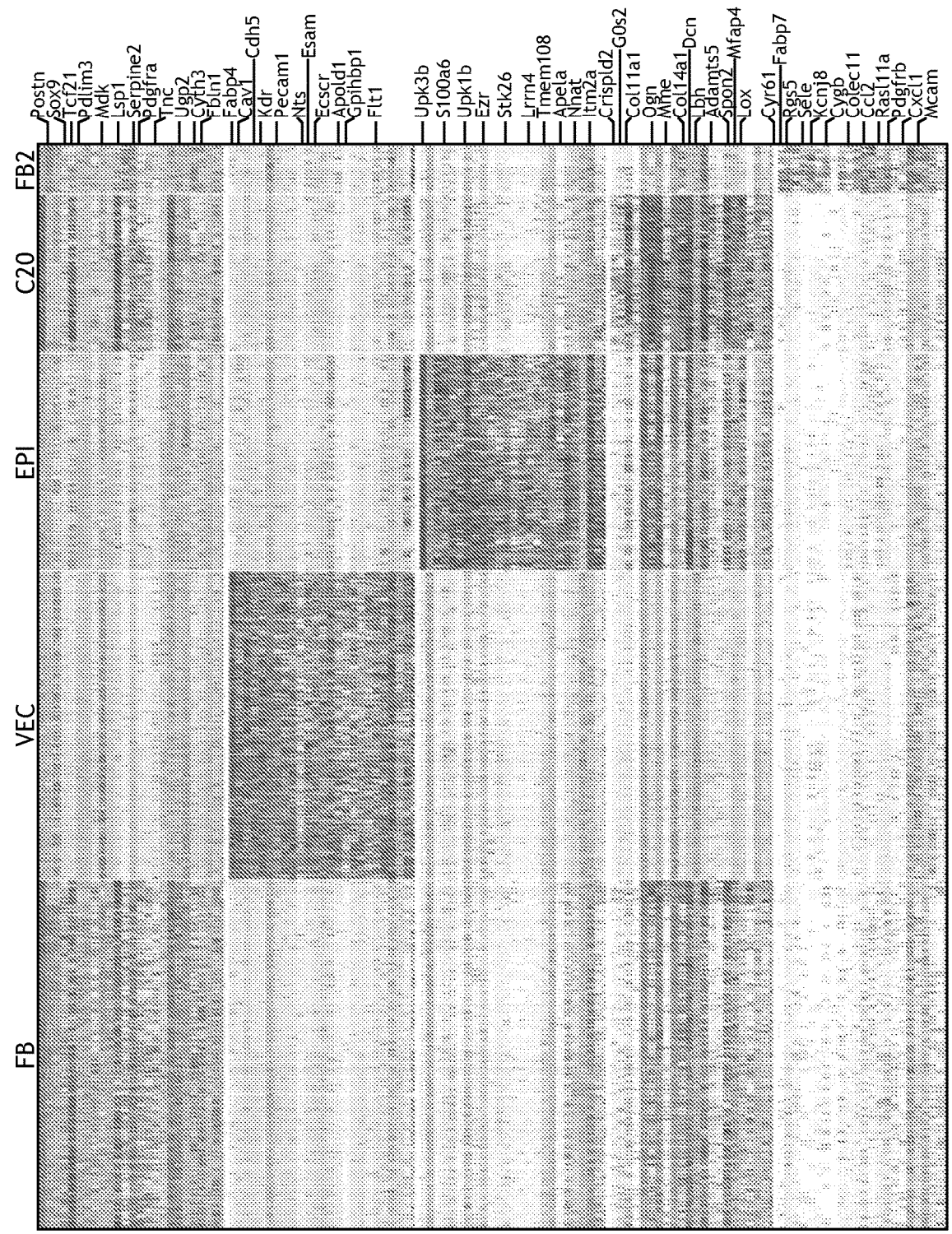
Figure 3D:
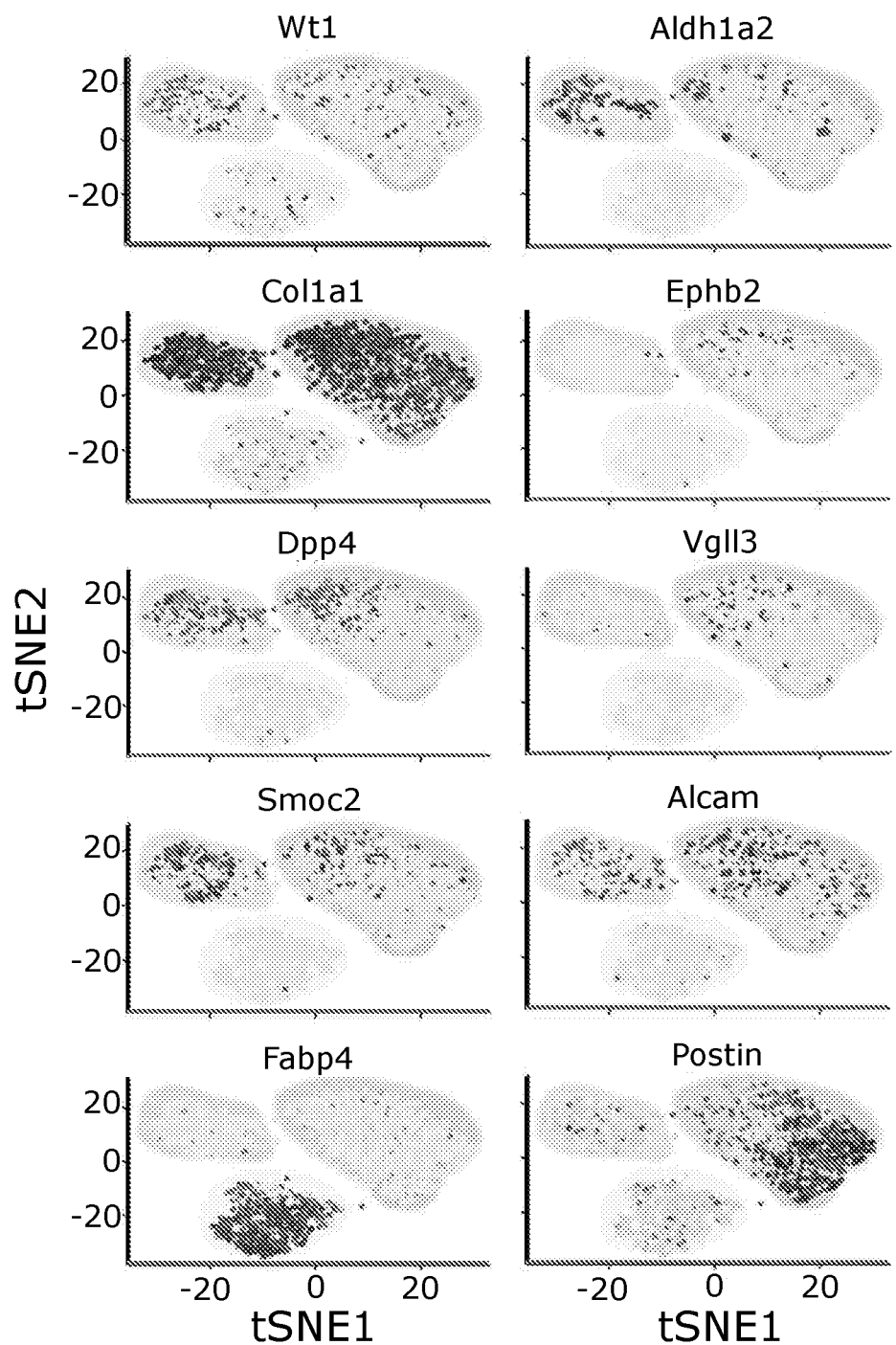
Figure 11A:
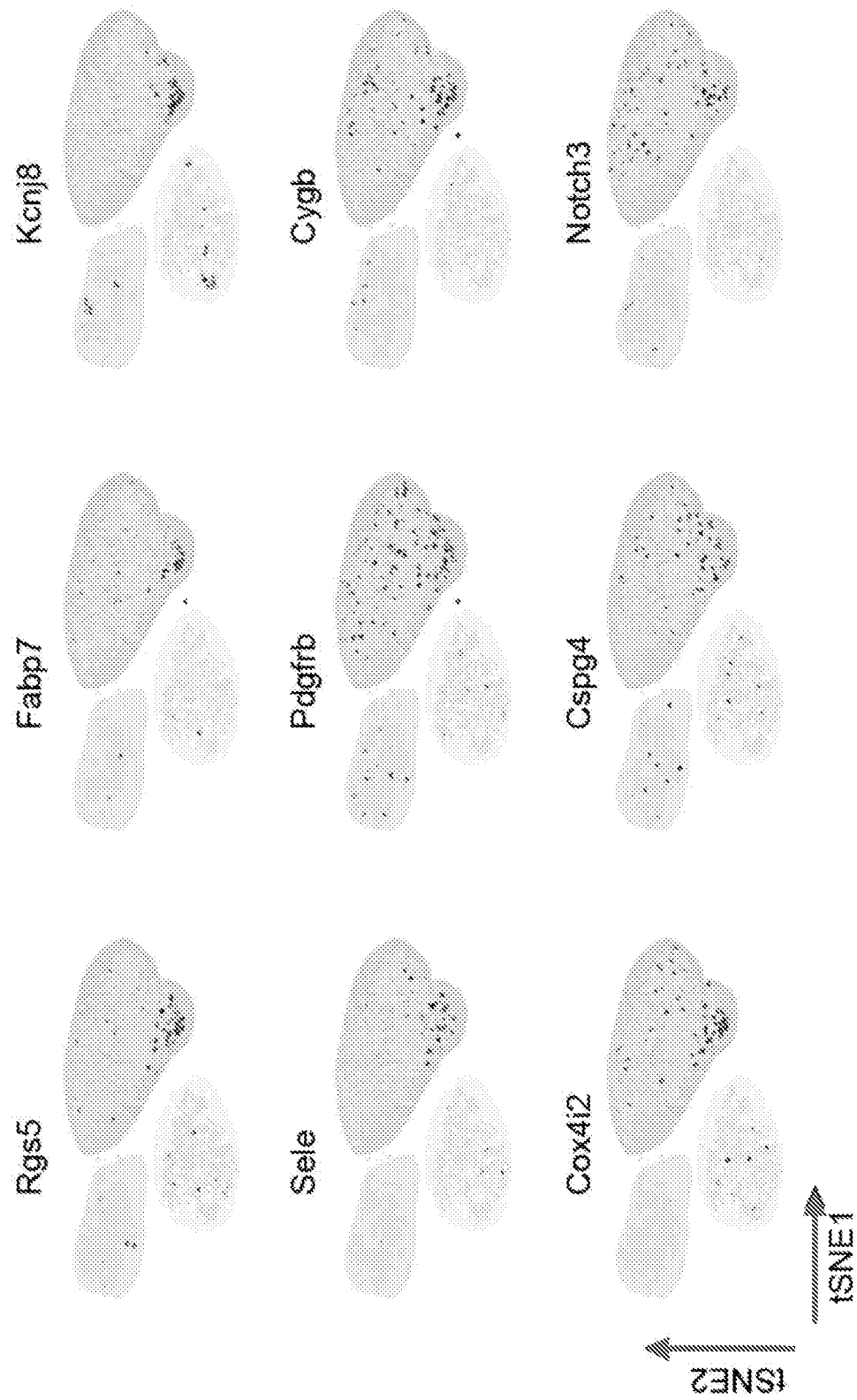
FIGS. 11A-11D. Gene expression of FB2 and validation of epicardial/subepicardial cell identity.

Iterative clustering was used to investigate the transcriptional distinctions between cell populations in more depth. Vascular endothelial cells (VECs) were used in the analysis given the Lats 1/2 CKO defective coronary vessel phenotype (FIG. 3A-3C). There was an additional fibroblast-like subtype, FB2, expressing multiple pericyte markers including Rgs5, Cspg4 (Ng2), Kcnj8, and Pdgfr β (FIG. 3C and FIG. 11A) (Armulik et al., 2011). Pericytes are precursors of epicardial-derived smooth muscle (Volz et al., 2015). Importantly, the C20 and subepicardial mesenchyme transcriptional signature resembled that of fibroblasts with epicardial features, but was distinct from Fabp4 expressing VECs (FIG. 3C,3D). C20 cells and subepicardial mesenchyme expressed a subset of fibroblast markers such as Col1a1 and Spon2, but were deficient for mature fibroblast markers, such as Postn and Sox9 (FIG. 3C,3D). C20 and subepicardial mesenchyme also expressed epicardial genes such as Wt1 and Aldh1a2, Dpp4, Smoc2, and Alcam, but failed to express Upk3a and Upk3b that mark mesothelium (FIG. 3C,3D)(Rudat et al., 2014). Other genes, not normally expressed in epicardium or fibroblasts, were uniquely enriched in C20 and subepicardial mesenchyme, such as Ephb2 and Vgll3, indicating that C20 and subepicardial mesenchyme have a distinctive signature, while sharing similarity with epicardium and cardiac fibroblasts. The subclustering also revealed that C20 and subepicardial mesenchyme were homogenous and represented an intermediate population between epicardium and fibroblasts (FIG. 3B). Together, the Drop-seq data showed accumulation of epicardial and C20 cells in Lats 1/2 CKO hearts, with a concomitant reduction in differentiated cardiac fibroblasts suggesting that Lats1/2 are required for progression of the normal developmental transition from epicardium to fibroblasts.

Figure 3E:
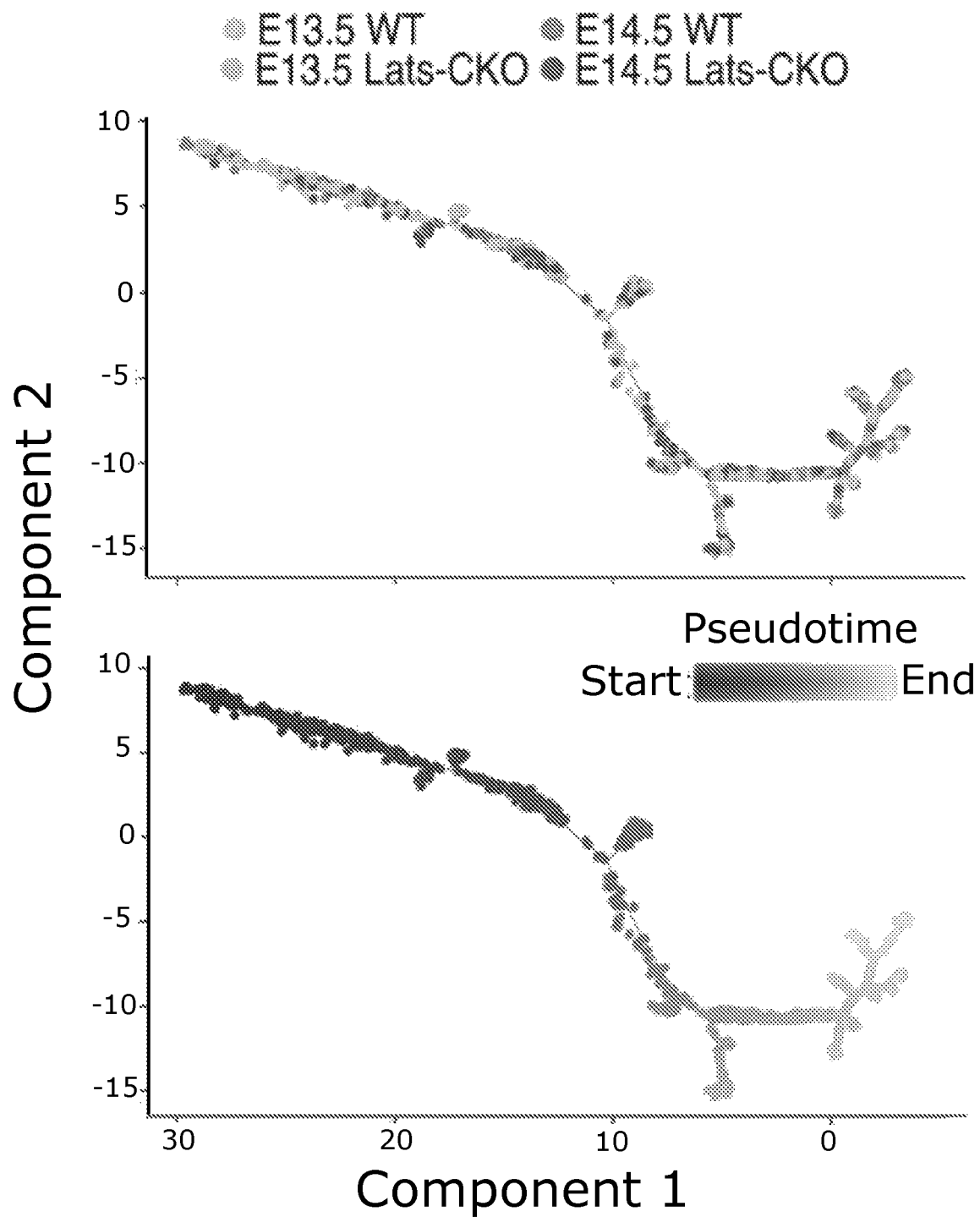
Figure 3F:
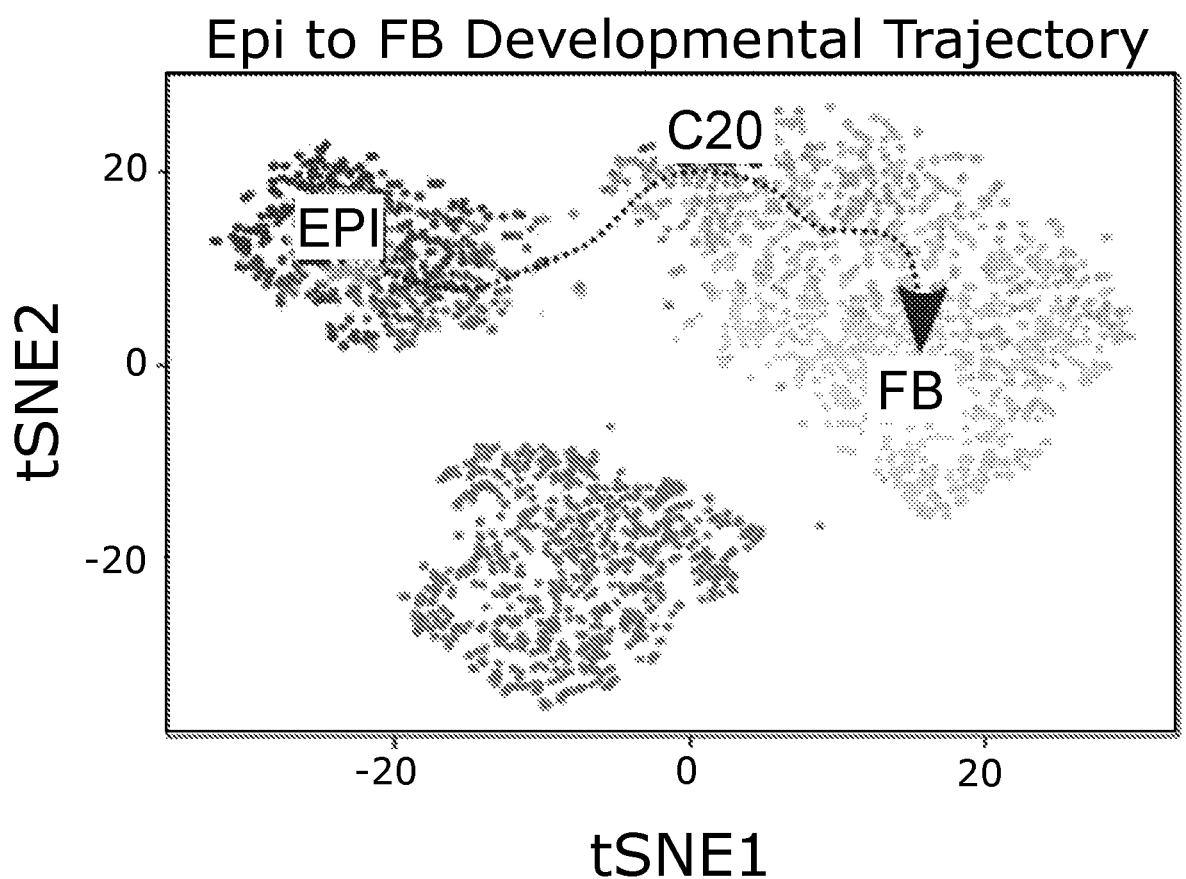
Figure 3G:
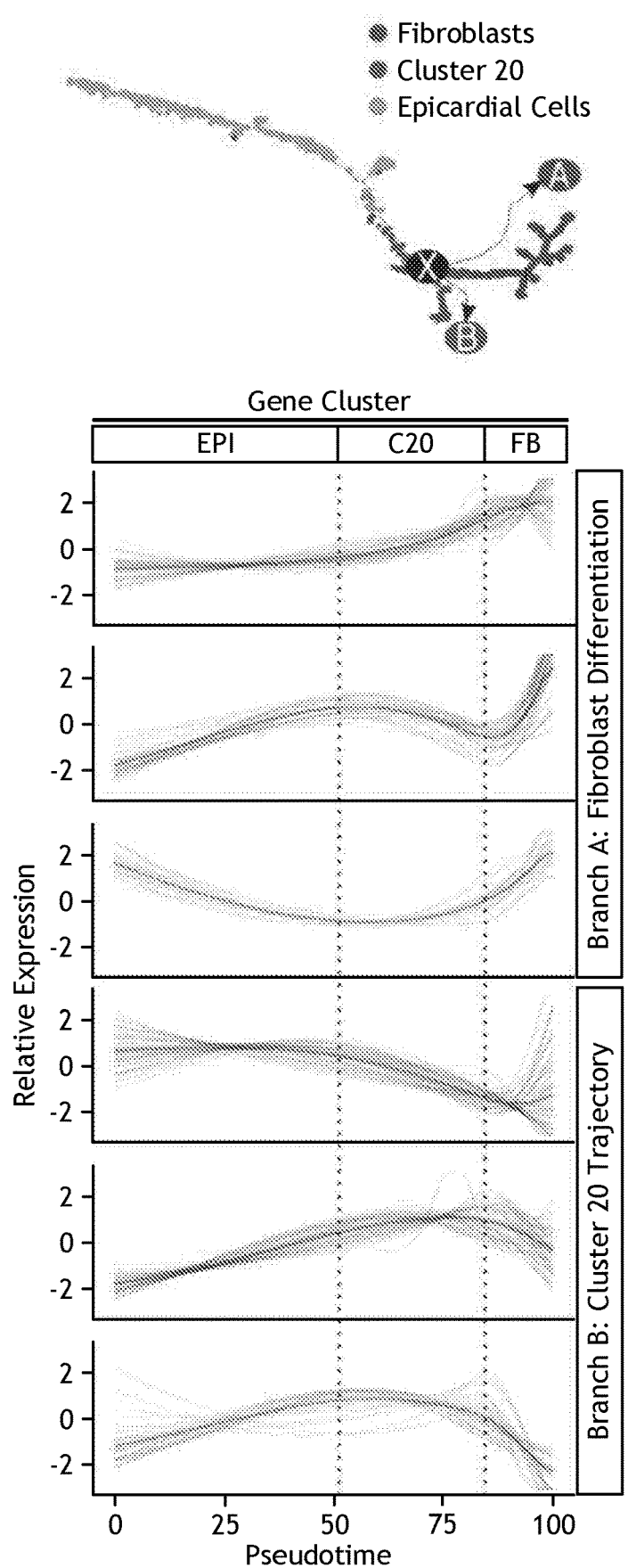

Pseudo-Time Analysis Revealed Defective Epicardial Cell Transitions in Lats 1/2 CKO Hearts To investigate epicardial cell developmental trajectory, Monocle2 was used to order cells along a developmental axis progressing from epicardial cells to cardiac fibroblasts (Qiu et al., 2017). Importantly, pseudo-time ordering matched closely with graph-based clustering results, especially when projected across tSNE (FIG. 3E (top panel), 3F). The left most portion of the epicardial cluster represents the most primitive cellular state and the bottom right section the most differentiated cellular state (FIG. 3E, bottom panel). C20, and a few control subepicardial mesenchyme cells, were isolated centrally along this differentiation axis supporting the notion that C20 is a transition state intermediate between epicardial progenitors and differentiated fibroblasts (FIG. 3G, top panel).

Cells diverging from the Monocle Minimum Spanning Tree (MST) were captured as alternative trajectories by their connection to the full MST path through nodes that represent developmental junctions where cell-fate decisions are made (Trapnell et al., 2014). There was a node (FIG. 3G, top panel, Node X) proximal to final bifurcation of cardiac fibroblasts (FIG. 3G, top panel, Branch A) and C20 population (FIG. 3G, top panel, Branch B) revealing two distinct EPDC differentiation paths. The "Branch A" trace, composed primarily of control cells (FIG. 3E, top panel), revealed normal EPDC to fibroblast differentiation trajectory and cellular transition from epicardial cells to mature fibroblasts. In contrast, the "Branch B" trace, comprised predominantly of Lats1/2 CKO mutant C20 cells (FIG. 3E top panel), revealed a cell type that was intermediate between epicardial cells and fibroblasts, indicating that most Lats1/2 CKO cells failed to progress to fully differentiated cardiac fibroblasts.

Figure 3H:
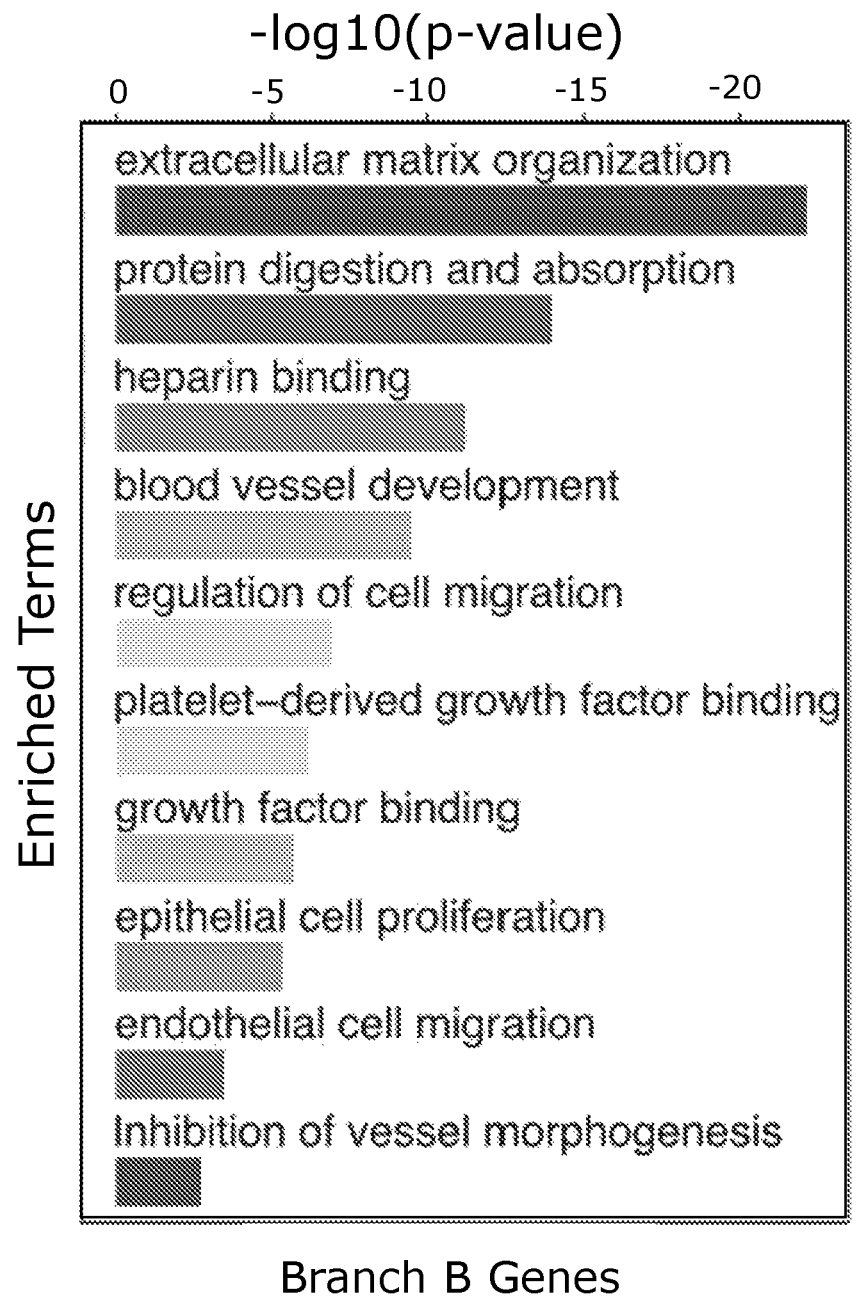

To identify genes expressed in the Node X bifurcation, gene expression patterns were examined across pseudotime and there were several co-varying expression patterns. The first expression pattern, characteristic of Branch A fibroblast differentiation, had a higher expression level in differentiated fibroblasts (FIG. 3G bottom panel, top three tracks-Branch A). The second expression pattern was typical of C20 population found in Branch B (FIG. 3G bottom panel, bottom three tracks-Branch B). Gene ontology (GO) analysis on Branch B genes revealed GO terms including extracellular matrix (ECM) and blood vessel development, suggesting that genes expressed by C20 cells contributed to the coronary vessel remodeling defects observed in Lats1/2 CKO hearts (FIG. 3H).

Figure 3I:
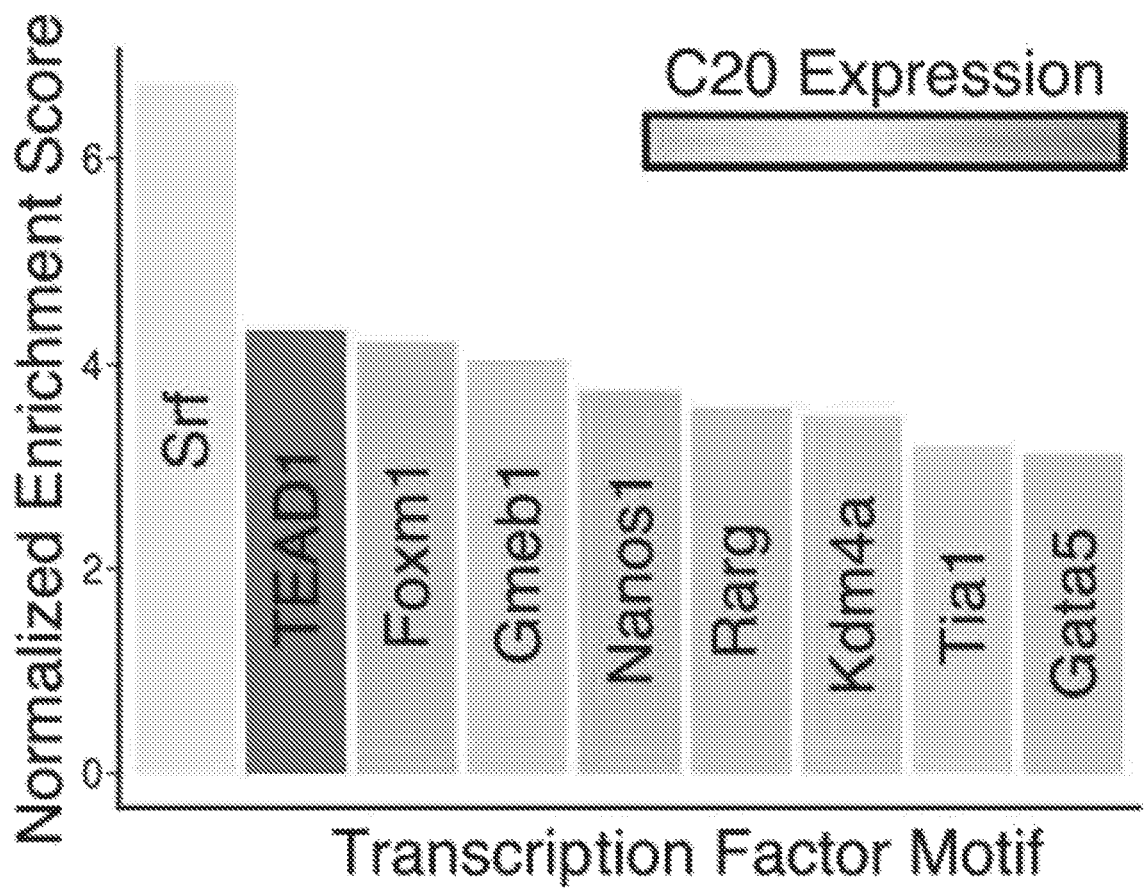
Figure 3J:
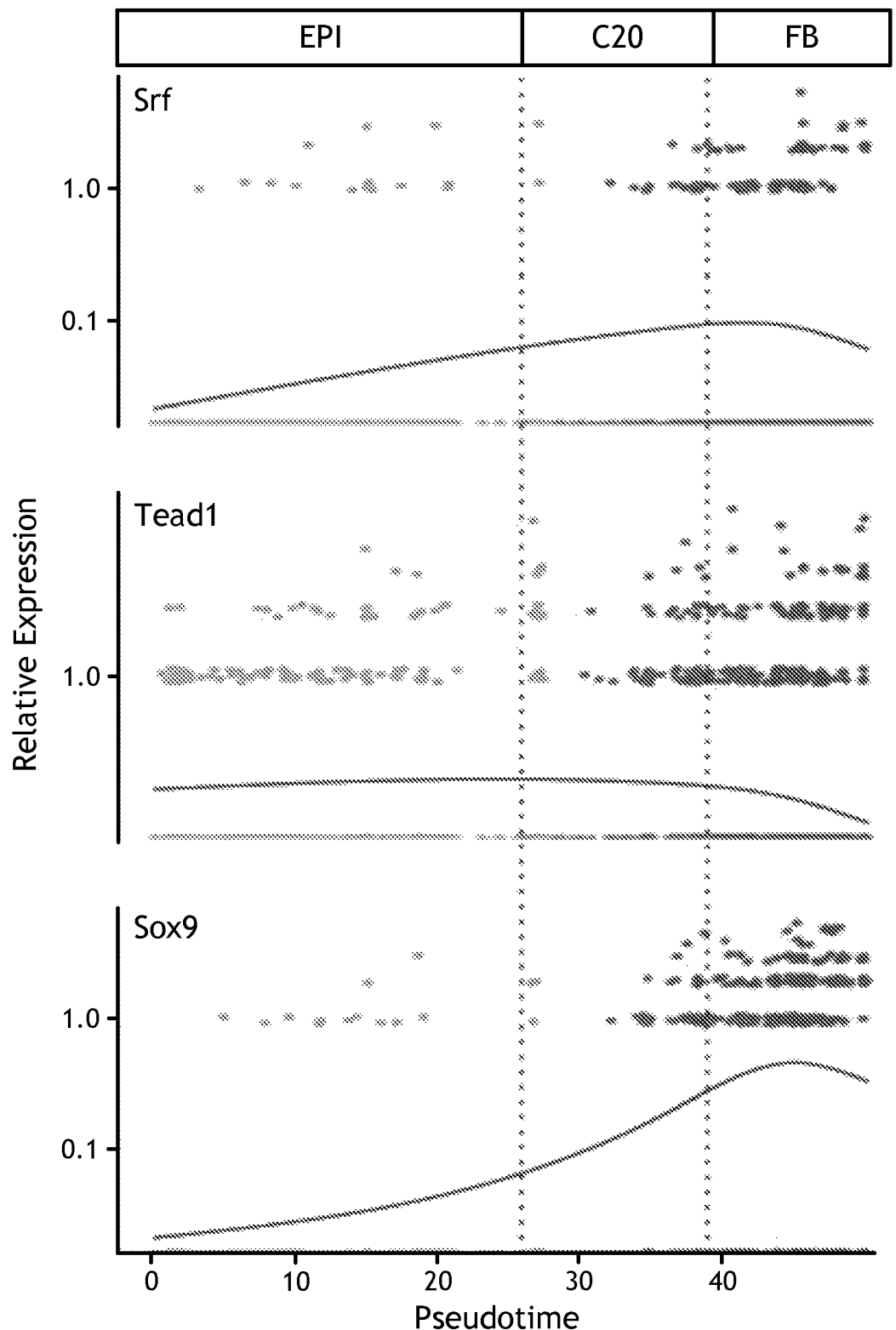
Figure 3K:
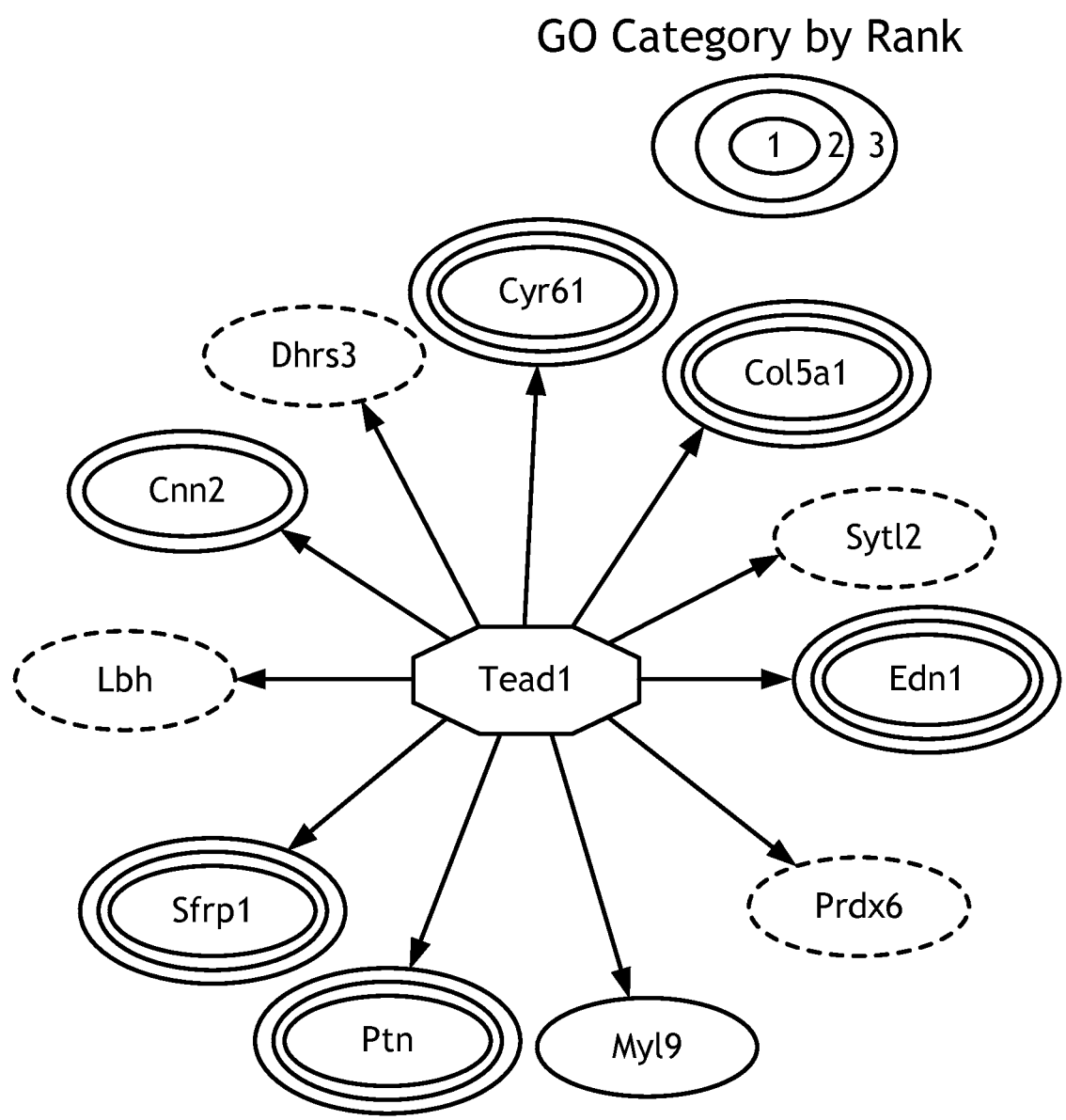

The enriched GO term, ECM, included collagen genes and genes that are essential for collagen processing including SerpinH1 and Plod2 that have also been implicated in human osteogenesis imperfecta syndromes (Ito and Nagata, 2017; Puig-Hervas et al., 2012). In addition, genes encoding growth factors, such as Bmp4 and Edn1 that modulate ECM composition in multiple contexts were also in the Branch B category (Hathaway et al., 2015; Salazar et al., 2016) (FIG. 3K). It has been shown that collagen density regulates proper angiogenesis by modulating the balance between endothelial cell migration and proliferation. An excessive amount of collagen suppresses vessel sprouting (Shamloo et al., 2016). Other ECM genes in Branch B, such as Cyr61 and Ptn (FIG. 3K), are matricellular proteins that promote endothelial cell proliferation (Fang et al., 1992; Hanna et al., 2009; Hinkel et al., 2014). Dpp4, encoding a membrane bound protease, is another ECM gene that is also in "Protein digestion and absorption" GO category. Dpp4 proteolyzes both ECM and matrix embedded growth factors to modulate endothelial cell migration (Ghersi et al., 2006). Taken together, Hippo inhibits a gene program that controls multiple aspects of ECM composition, which affects vessel development including endothelial cell proliferation, migration and vessel branching.

Cluster 20-Enriched Genes are Direct Yap-Tead Targets

To determine whether C20 and subepicardial mesenchyme expressed genes were direct Yap-Tead targets, unbiased transcription factor DNA-binding motif enrichment analysis was performed across a 20 kb region centered on Transcription Start Site (TSS) of each Branch B gene. Srf and Tead elements were most enriched motifs in Branch B (FIG. 3I). While Tead was highly expressed in C20 and subepicardial mesenchyme, Srf was lowly expressed, suggesting that most Branch B genes were directly regulated by Yap-Tead (FIG. 3I). Tead1 expression was enriched throughout C20 and subepicardial mesenchyme and its expression level decreased moving across pseudotime from C20 and subepicardial mesenchyme toward differentiated fibroblasts (FIG. 3J). Conversely, Sox9 was low in epicardial cells and C20 and subepicardial mesenchyme but high in cardiac fibroblasts (FIG. 3J). Tead1 motif enriched Branch B genes, and GO analysis was performed specifically on these Yap-Tead target genes. Enriched GO terms among Branch B Yap-Tead direct target genes were similar to total Branch B enriched GO terms defined above and included ECM organization, regulation of cell migration, and blood vessel development (FIG. 3H,3K). Other direct Yap-Tead target genes in C20 and subepicardial mesenchyme were not included in a specific GO category such as Dhrs3, encoding an enzyme that reduces retinoic acid levels (FIG. 3K) (Billings et al., 2013). Other Yap-Tead targets expressed in C20 and subepicardial mesenchyme included Sfrp1, encoding a Wnt antagonist, Lbh, implicated in human congenital heart disease, and Cnn2 encoding an actin binding protein that regulates directed cell migration (McKean et al., 2016; Nusse and Clevers, 2017; Ulmer et al., 2013).

The C20 Cluster Resides in Subepicardial Space

Figure 4A:
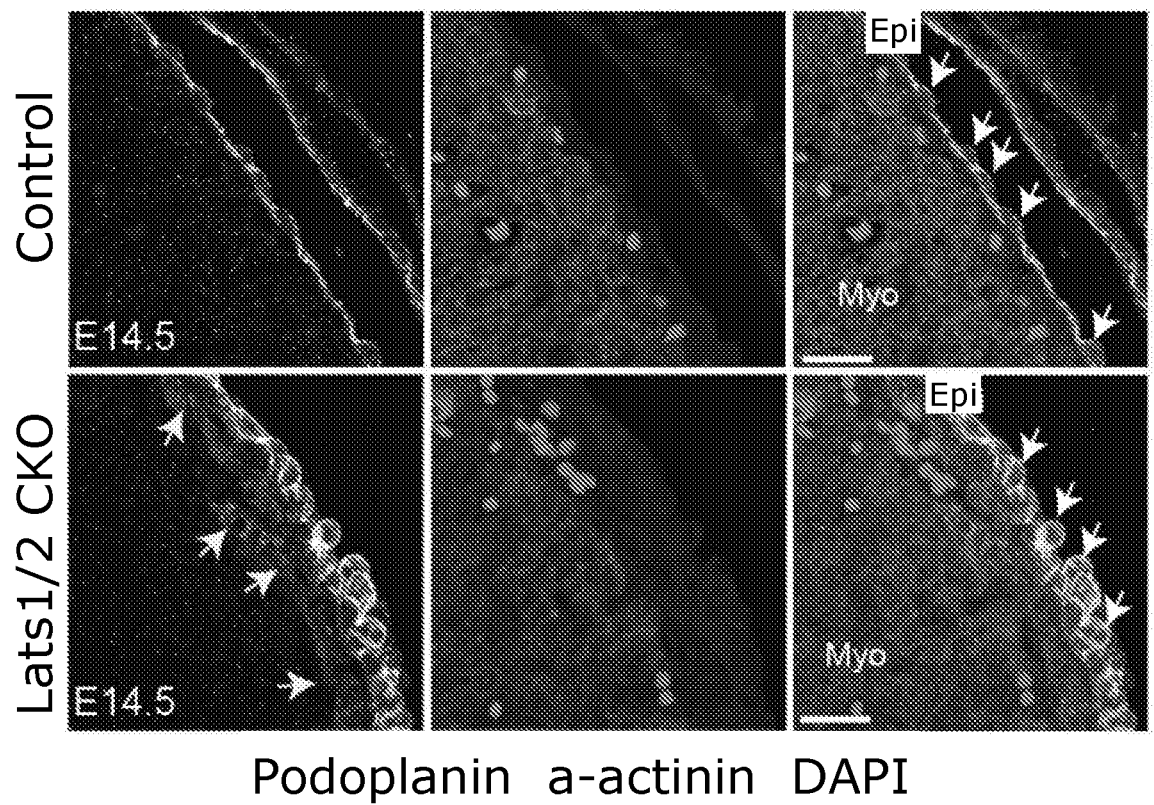
Figure 4B:
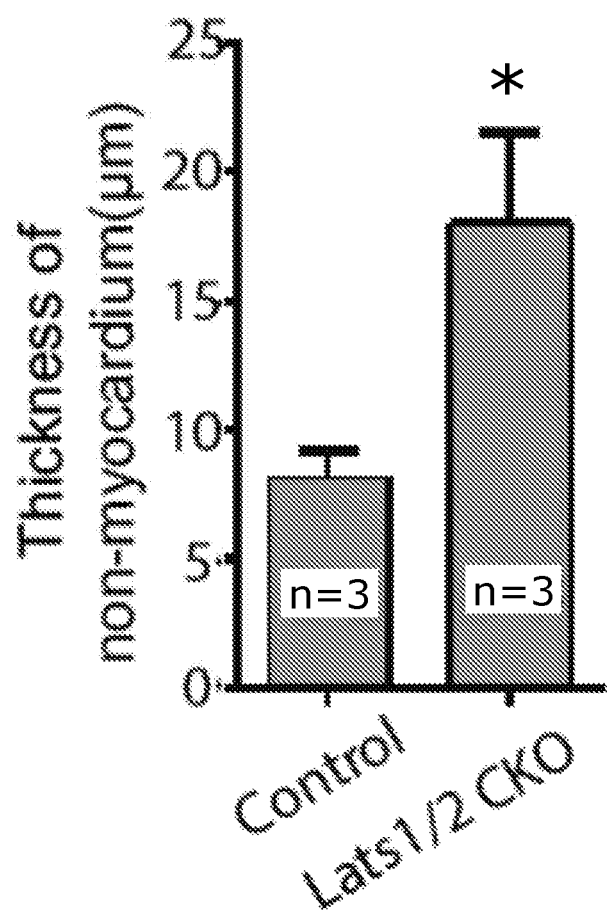
Figure 4E:
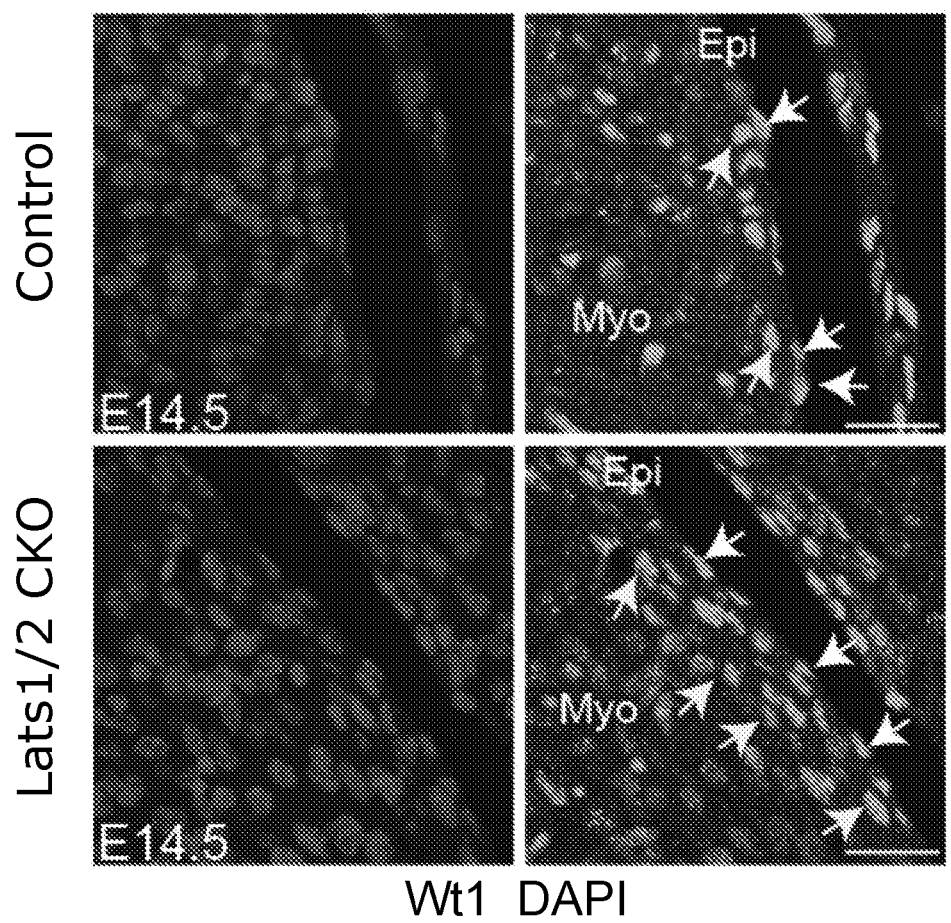
Figure 4F:
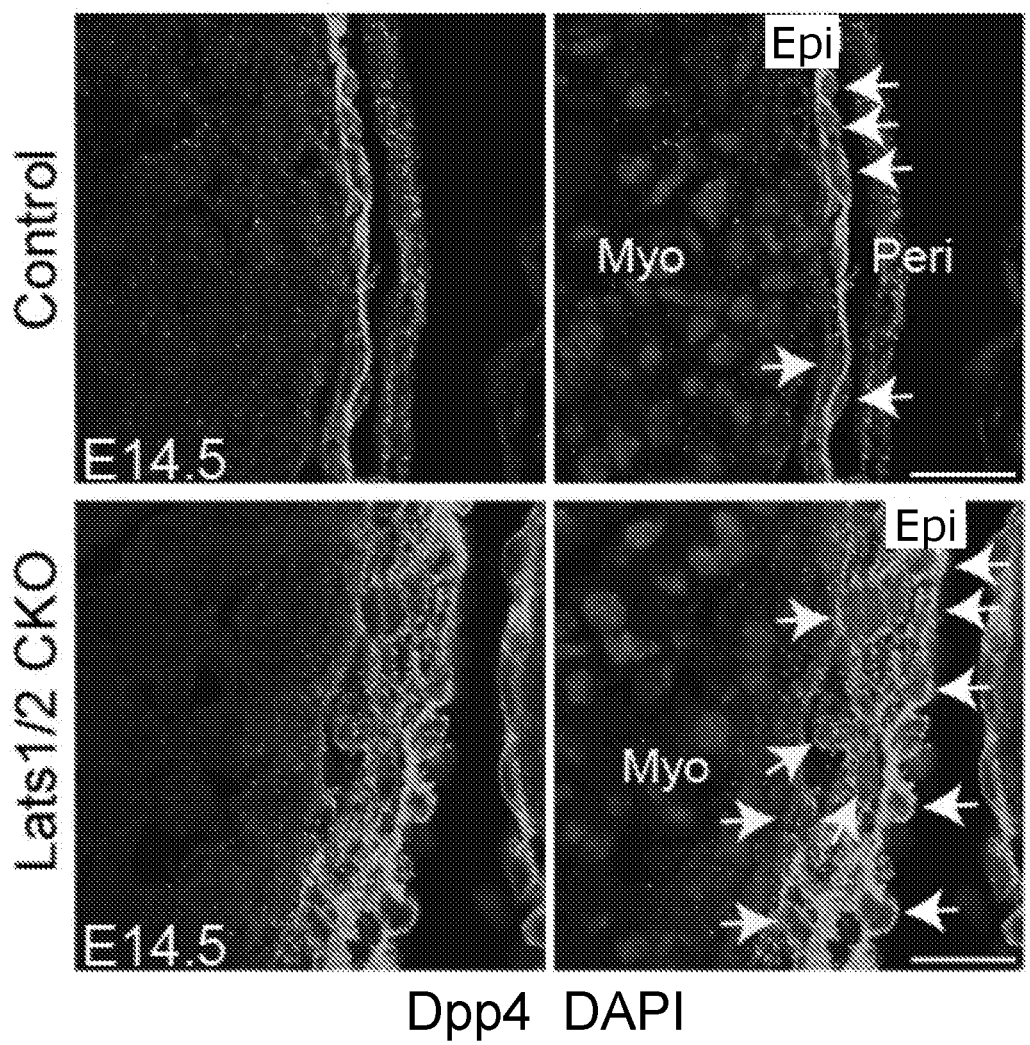
Figure 4G:
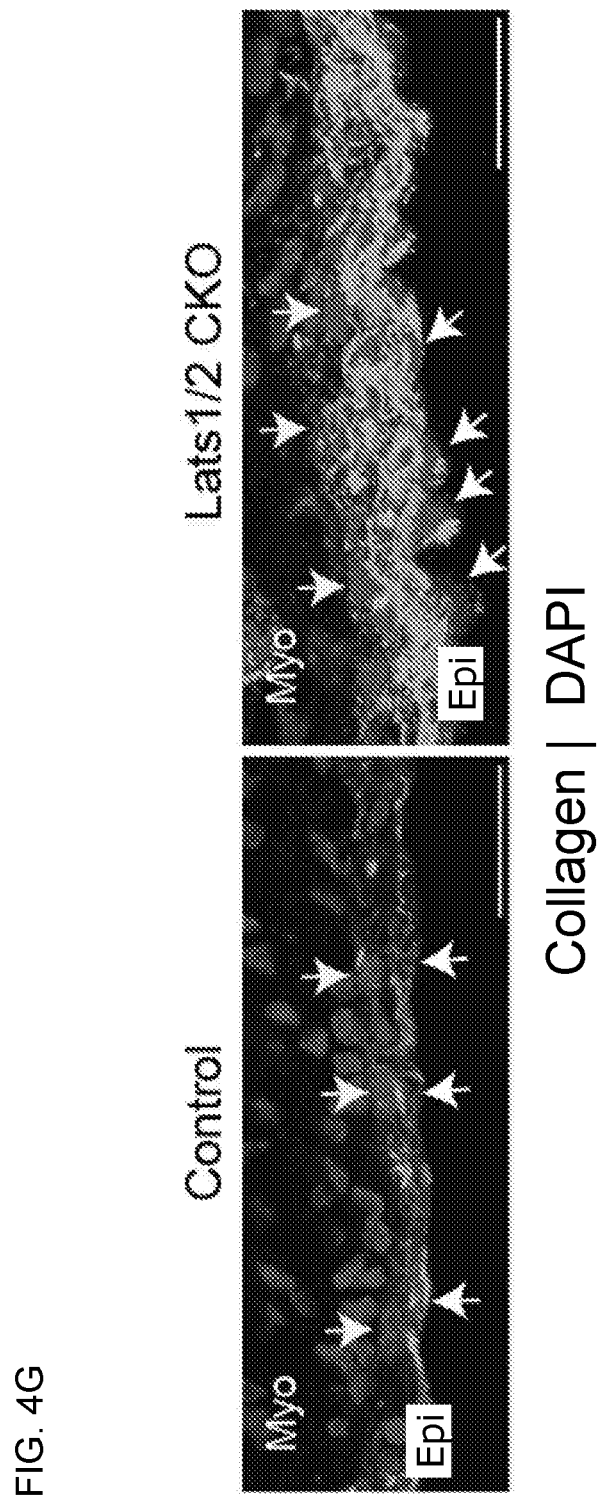
Figure 4H:
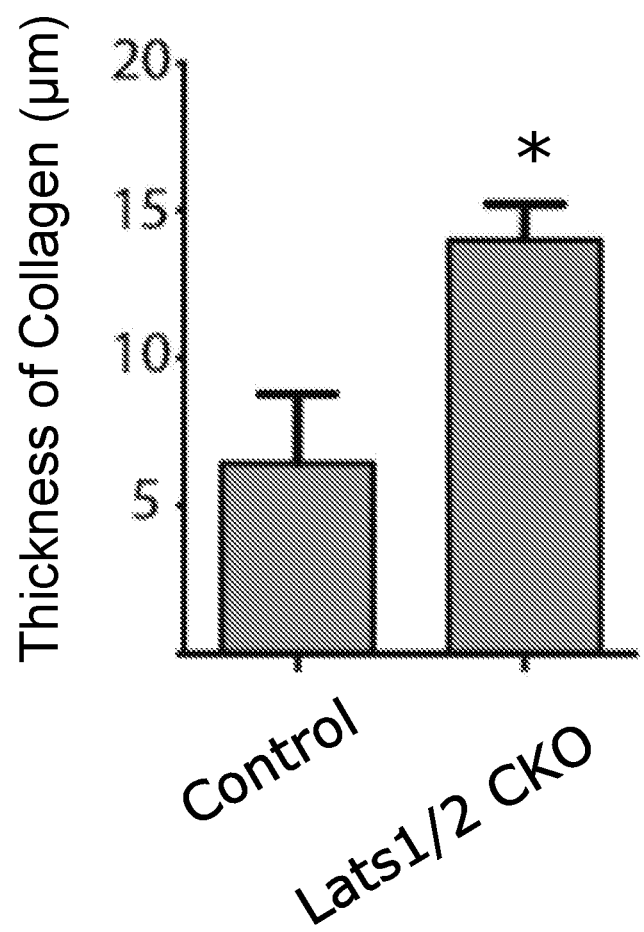

To validate the Drop-seq findings and gain spatial information about C20, IF experiments were performed based on known epicardial markers and newly identified genes expressed in C20. Podoplanin and Keratin expression, markers of the single cell layer epicardium, both expanded into Lats1/2 CKO subepicardium indicating that the Lats1/2 CKO mutant C20 cells still maintained epicardial characteristics that were not observed in control subepicardial mesenchyme (FIG. 4A, FIG. 4B, and FIG. 11B) (Acharya et al., 2012). Pdgfr-α, a marker of fibroblasts and subepicardial mesenchyme, was expressed in a single cell layer within E14.5 control subepicardium, while in Lats1/2 CKO embryos Pdgfr-α was expressed in a several layer thick subepicardium containing C20 cells (FIG. 4C,D). Likewise, Wt1, a marker for epicardium and subepicardium, was expressed in Lats1/2 CKO epicardium and C20 cells within the subepicardial space (FIG. 4E) (Rudat and Kispert, 2012). Similarly, Dpp4, Col1a1, and Alcam, expressed in both epicardium and subepicardium in control embryos, were expressed in epicardium and C20 cells in Lats1/2 CKO hearts (FIG. 4F-4H and FIG. 11C). Spon2 displayed a different expression pattern by IF (FIG. S4D) compared to its transcriptional expression (FIG. 3C). In Lats 1/2 CKO epicardium, Spon2 was restricted to Lats 1/2 CKO epicardium suggesting posttranscriptional mechanisms inhibit Spon2 protein expression in C20 and subepicardial mesenchyme. Together, the IF data support the conclusion that the C20 population normally resides in subepicardium and that Lats1/2 deficiency results in increased numbers of C20 cells in the subepicardial space.

Figure 5A:
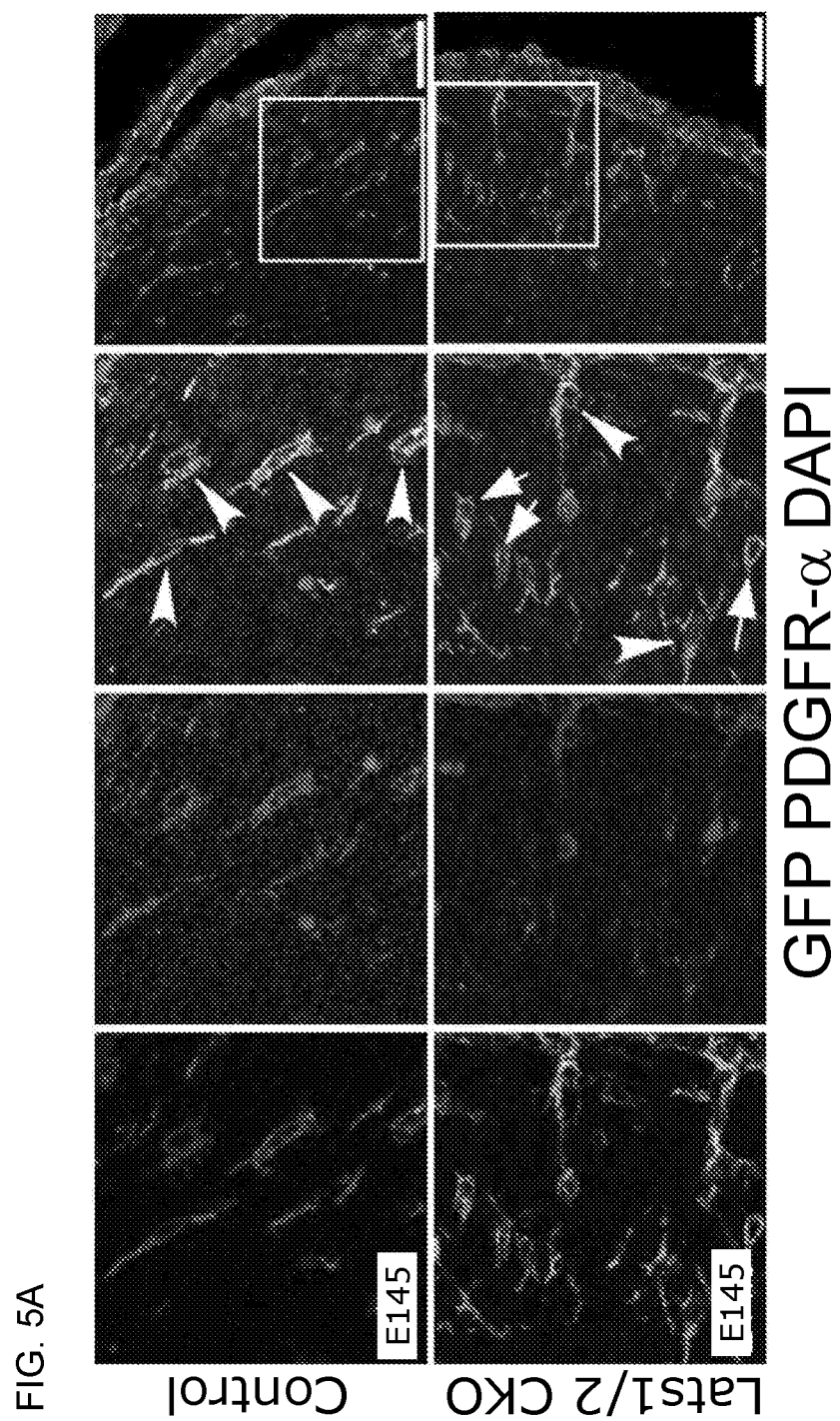
FIGS. 5A-5E. Lats1/2 epicardial deletion leads to reduction of epicardial-derived fibroblast. See also FIG. 12.
Figure 5B:
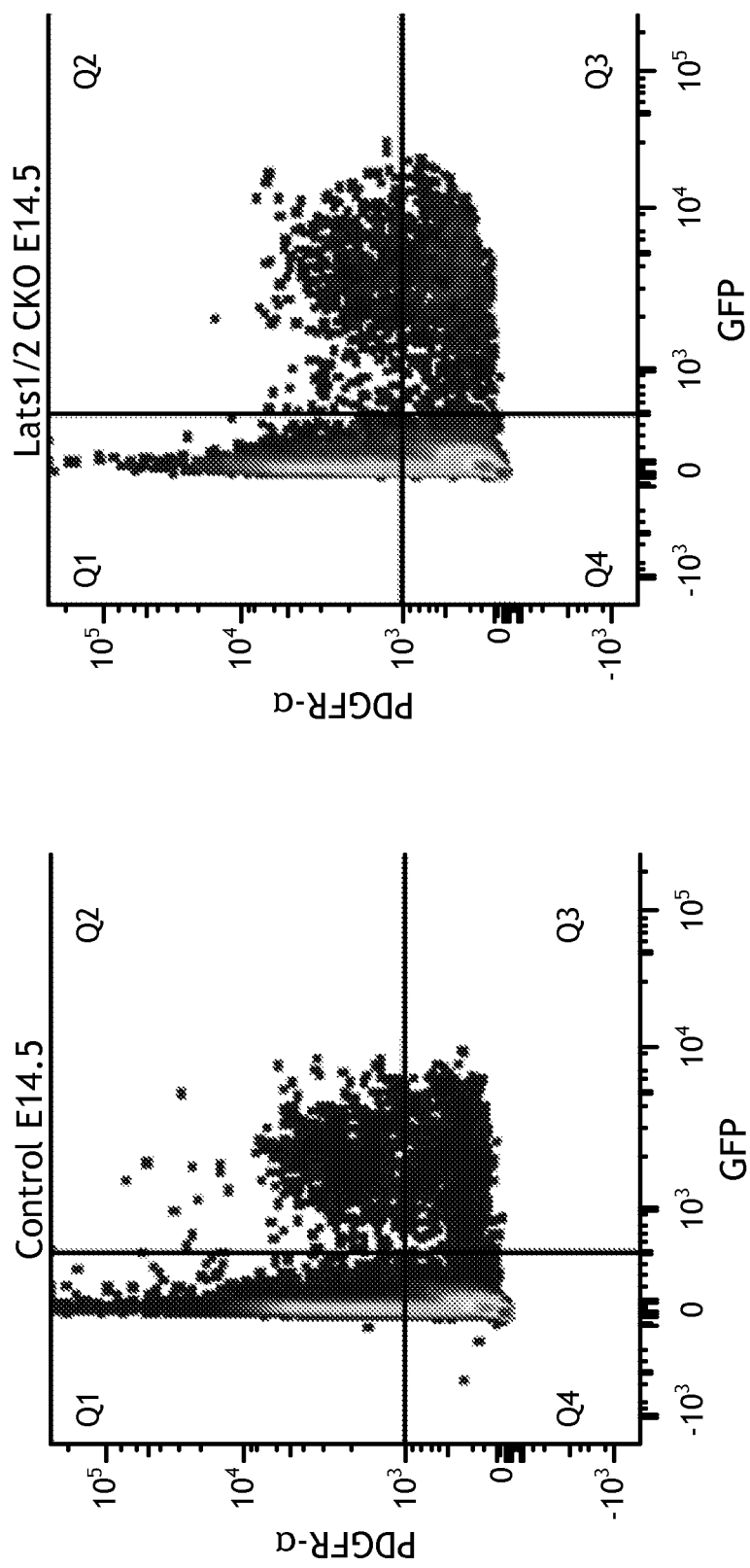
Figures 5C, 5D:
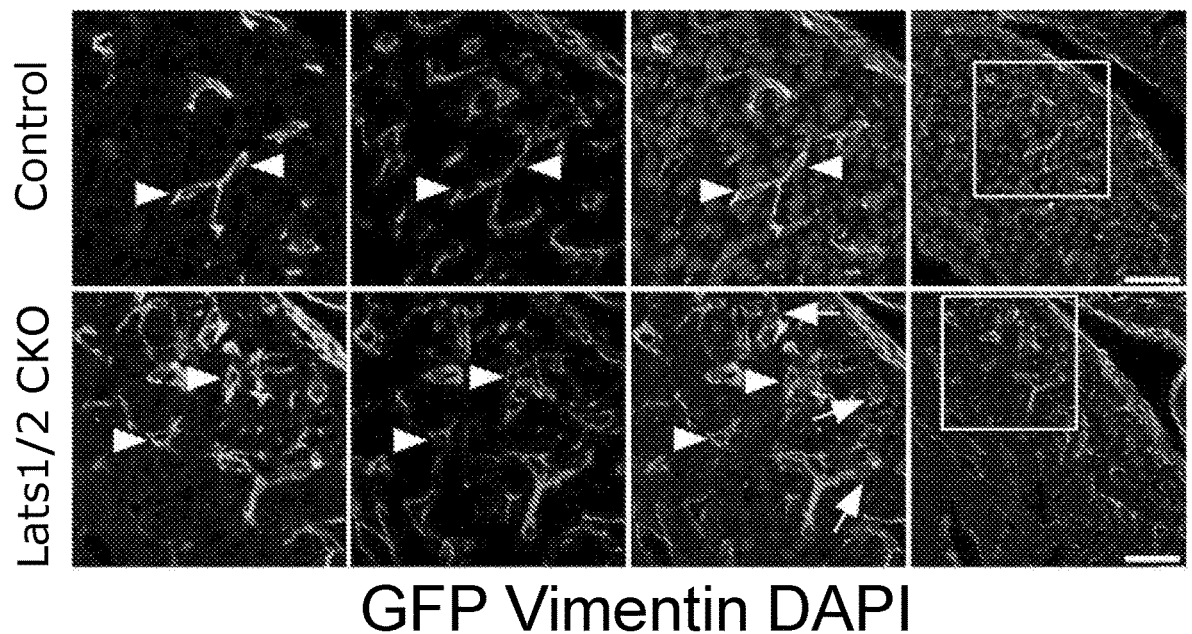
Figure 5E:
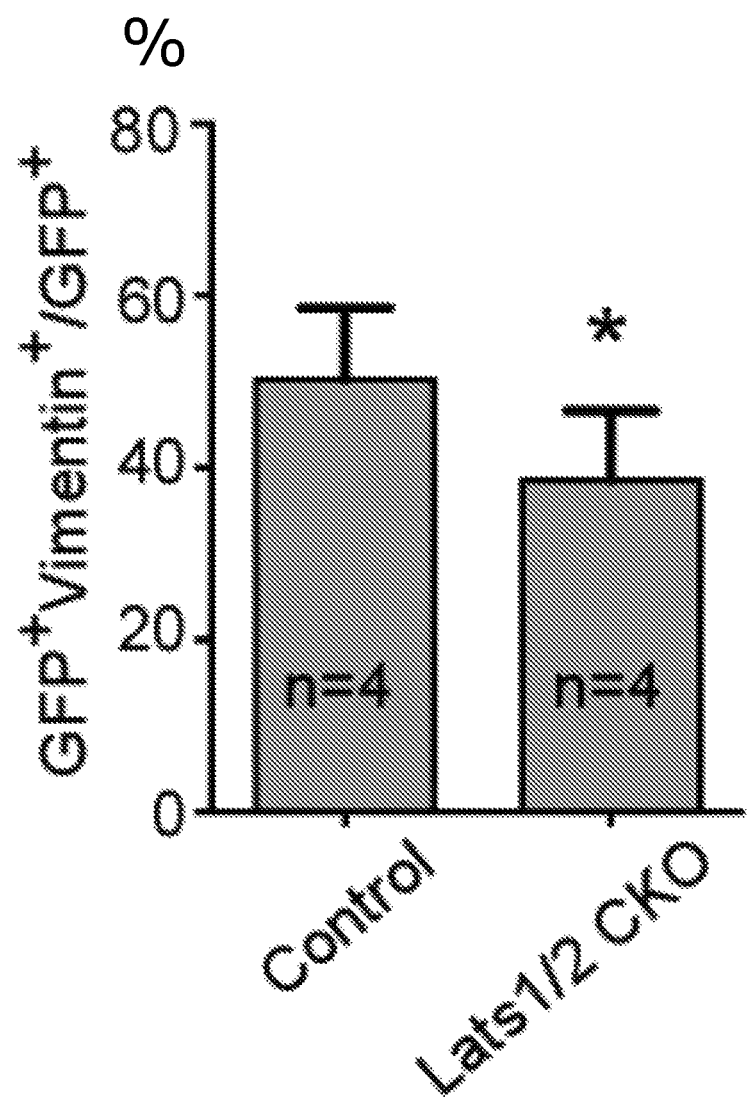
Figure 12A:
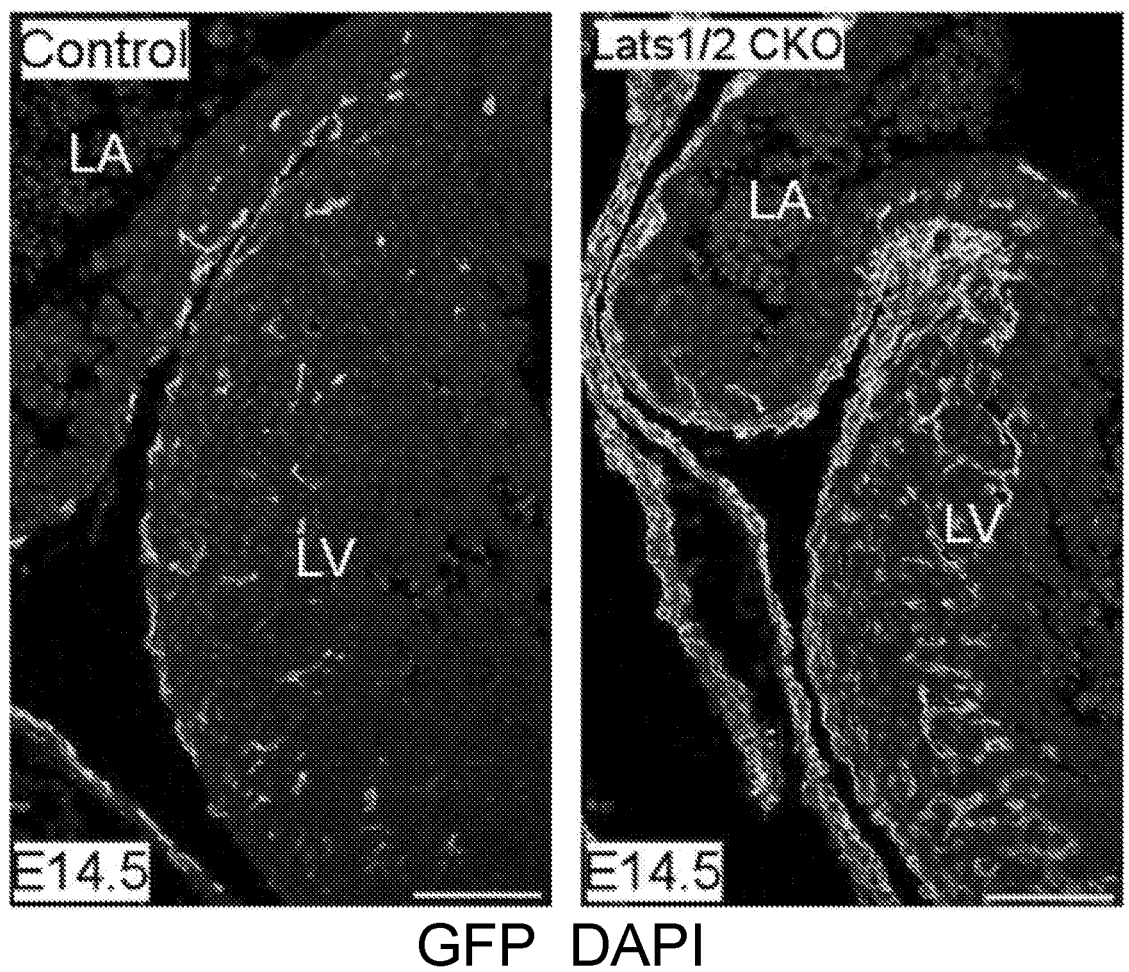
FIGS. 12A-12C. Increased epicardium and EPDC proliferation in Lats1/2 CKO hearts (FIG. 12A) The Wt1 lineage was traced by GFP expression, which includes epicardium and EPDC. An increased number of epicardium and EPDCs were observed in Lats1/2 CKO hearts.
Figure 12B:
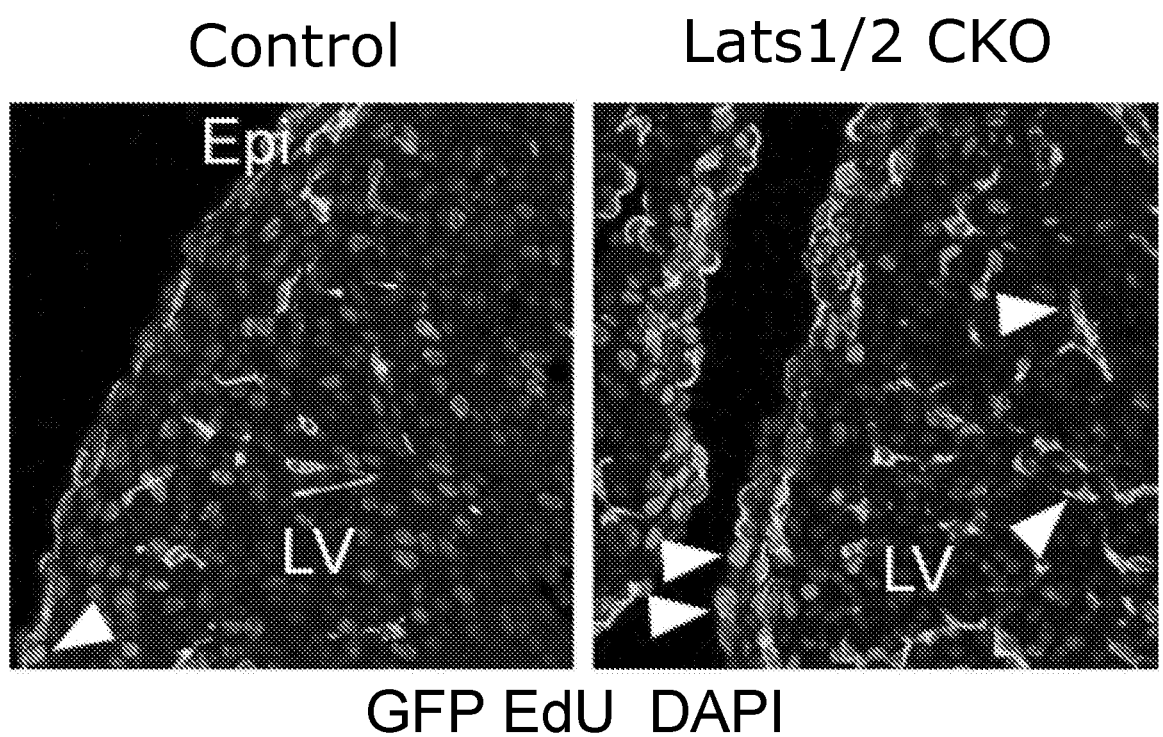
Figure 12C:
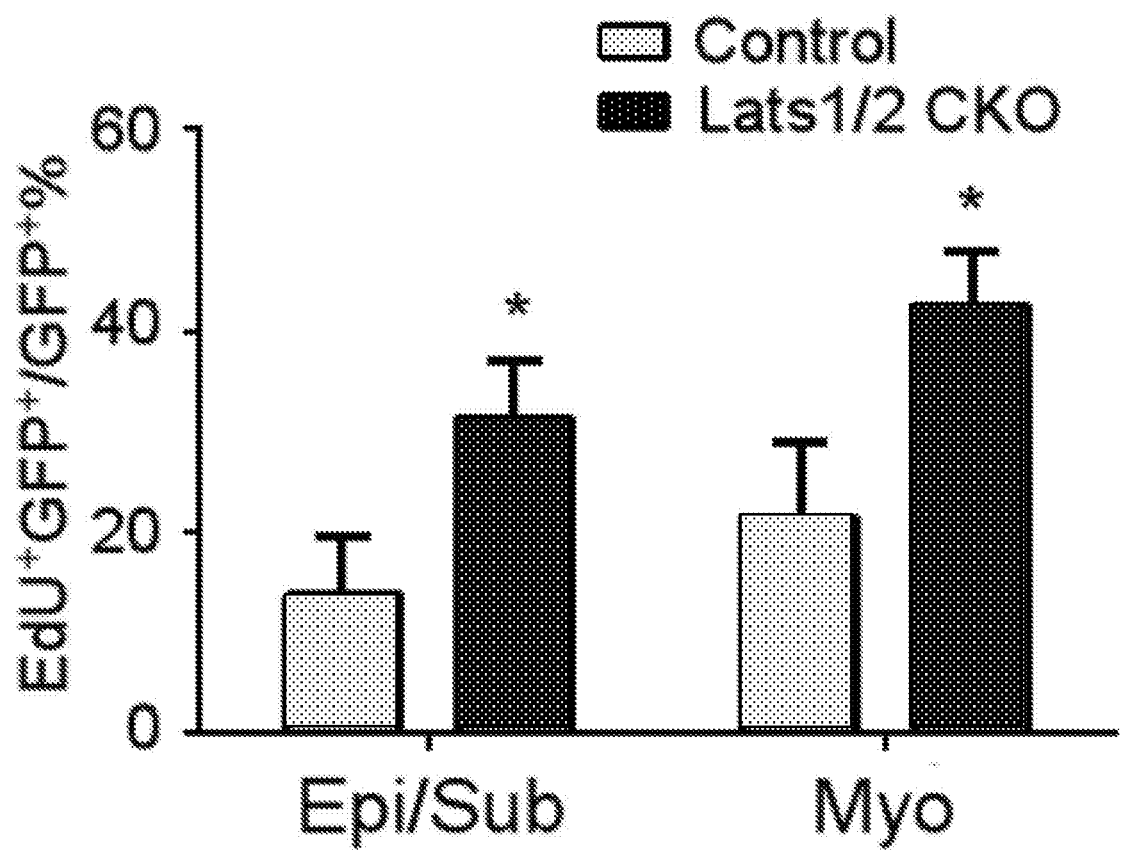

Lats1/2 Epicardial Deficiency Results in Diminished Cardiac Fibroblast Differentiation Experiments using Rosa26$^{mTmG}$ reporter to lineage trace epicardial-derived lineages revealed that Lats1/2 CKO hearts showed abundant GFP positive cells in myocardium indicating that EPDC entered the myocardium (FIG. 12A). EdU labeling indicated that Wt1$^{CreERT2}$ lineage-derived epicardial cells and EPDCs were more proliferative in Lats1/2 CKO embryos than controls (FIG. 12B,12C). Proliferation genes were not enriched on the Branch B GO analysis suggesting that proliferation was not the main distinguishing feature between C20 and cardiac fibroblasts (FIG. 3H). Concurrent labeling of the Wt1$^{CreERT2}$ lineage with Rosa26$^{mTmG}$ and PDGFRα to mark cardiac fibroblasts, revealed by both IF and FACS a reduction in epicardial-derived fibroblasts from 44% to 32% in Lats1/2 CKO mutants compared to controls (FIG. 5A-5C). IF with Vimentin, another cardiac fibroblast marker, confirmed the reduction of epicardial-derived fibroblasts (FIG. 5D,5E). Together, the lineage tracing data further supported the Drop-seq results, demonstrating that inactivation of Lats1/2 led to defective epicardial differentiation into mature cardiac fibroblasts.

Figure 13A:
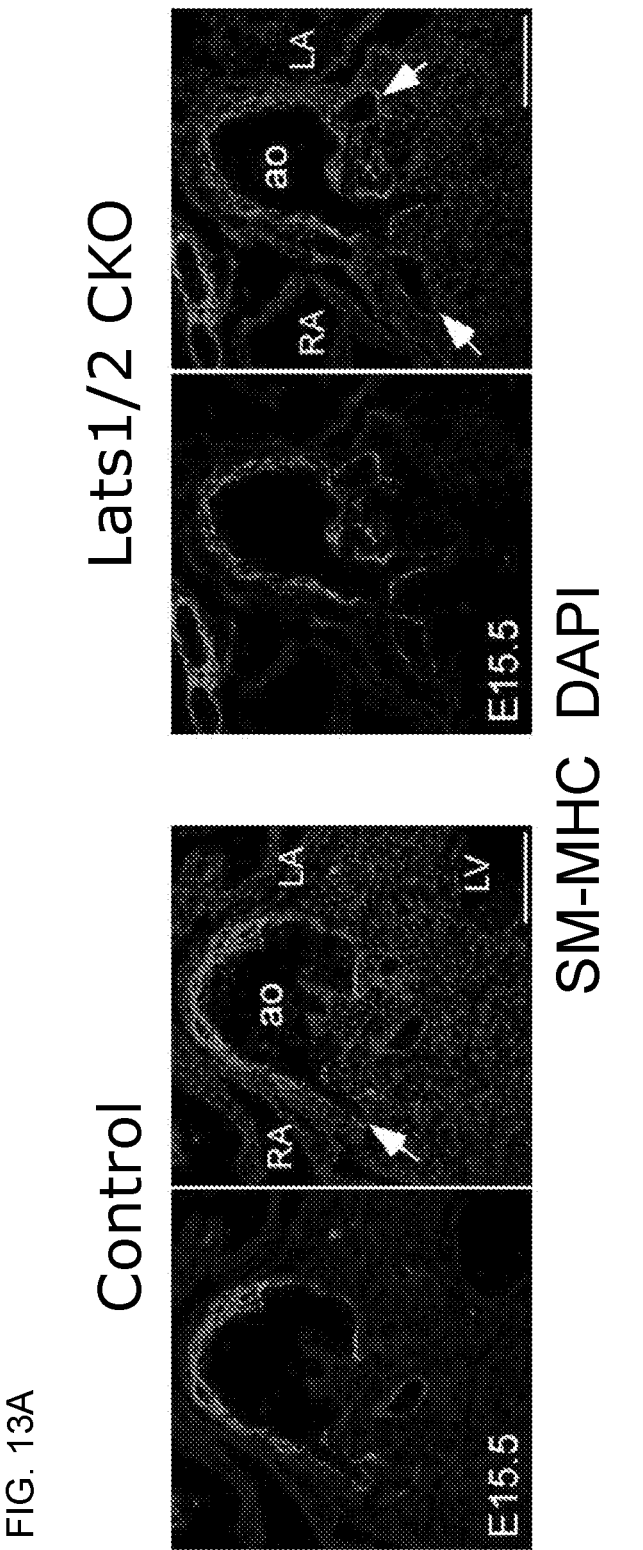
FIGS. 13A-13D. Reduction of epicardial derived coronary artery smooth muscle cells in Lats1/2 CKO hearts.
Figure 13B:
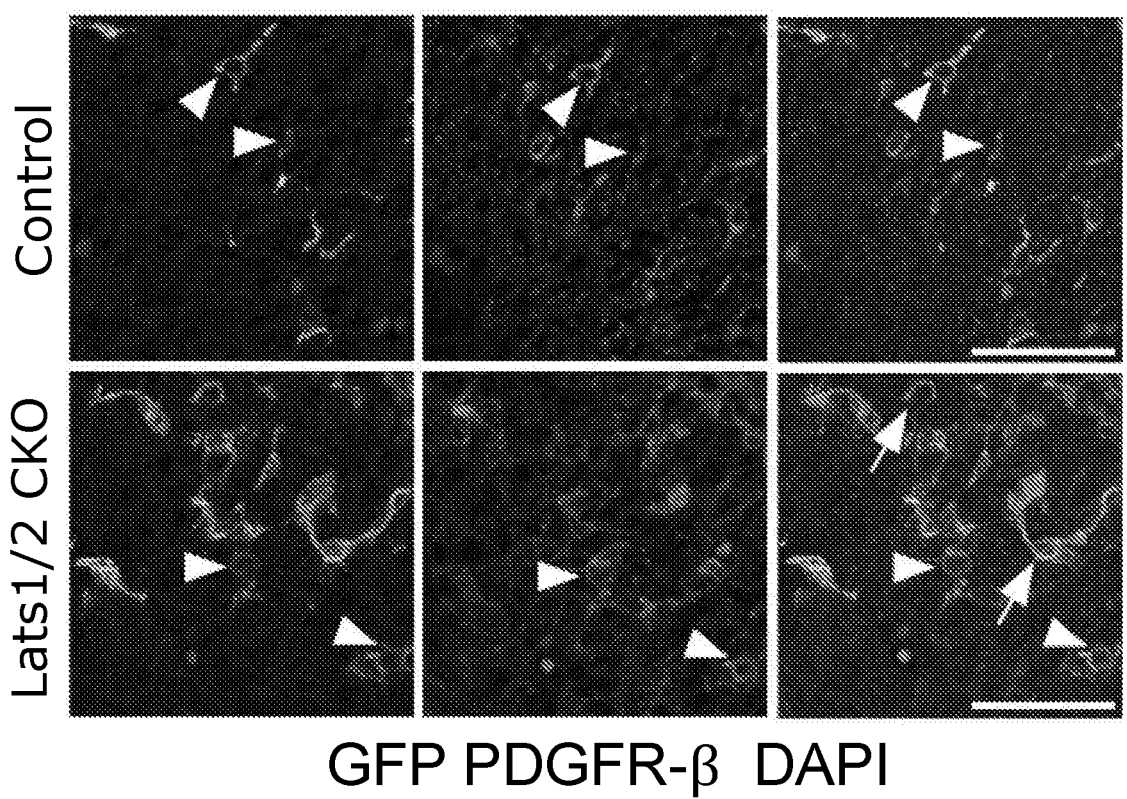
Figure 13C:
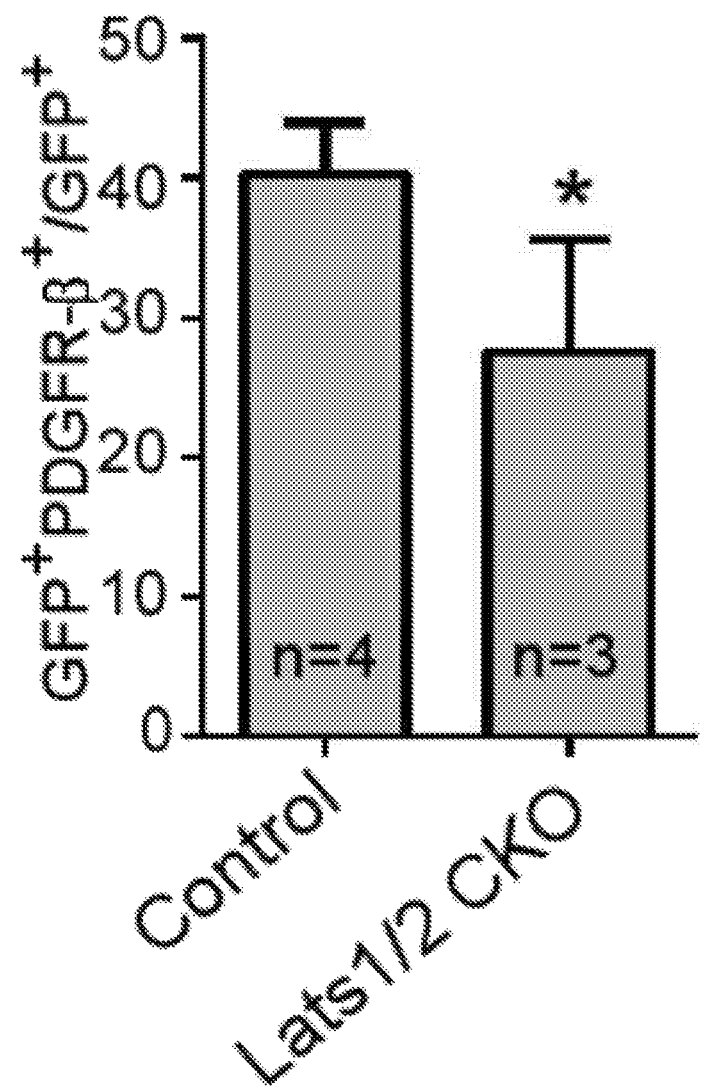
Figure 13D:
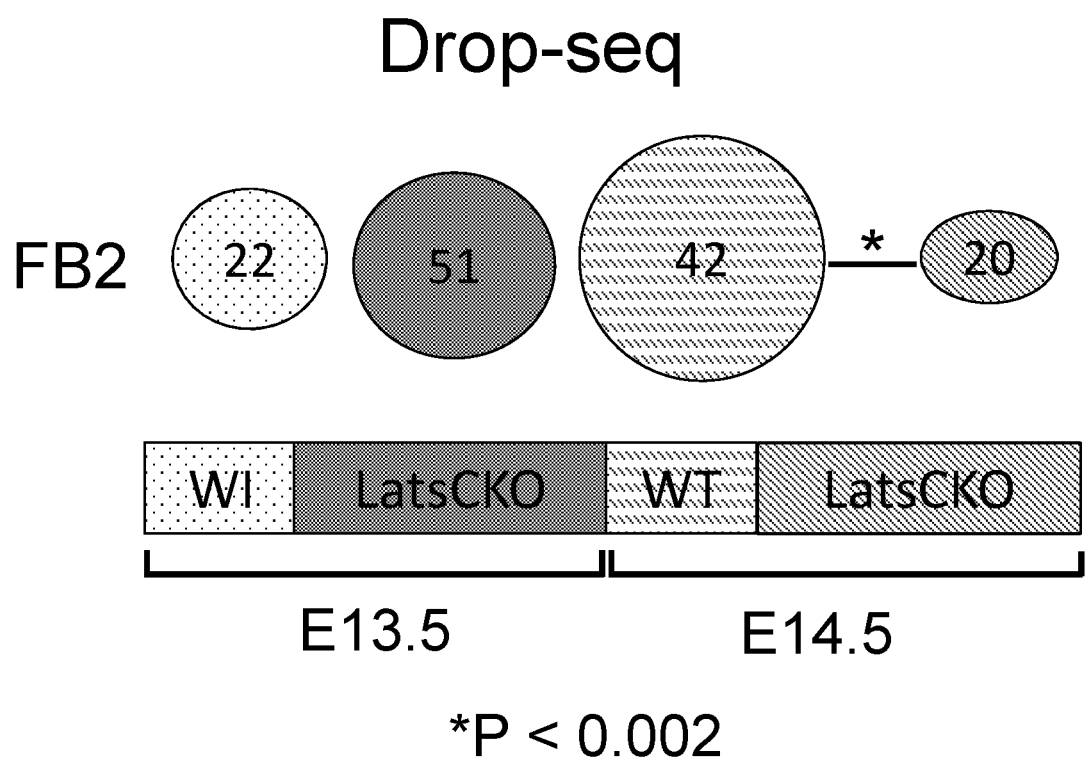

Coronary artery smooth muscle differentiation was examined. Smooth muscle myosin heavy chain IF in E15.5 Lats1/2 CKO embryos revealed that coronary arteries established an aortic connection in Lats1/2 CKO embryos and were invested with neural crest-derived smooth muscle (FIG. 13A) (Jiang et al., 2000). PDGFR-β IF combined with lineage tracing uncovered a reduction of E14.5 epicardial-derived smooth muscle cell progenitors suggesting that the smooth muscle lineage differentiation from epicardium was diminished in Lats1/2 CKO hearts. The IF data were consistent with reduction in FB2 pericyte smooth muscle progenitors observed in Drop-seq data (FIG. 13B-13D)(Volz et al., 2015).

Figure 14A:
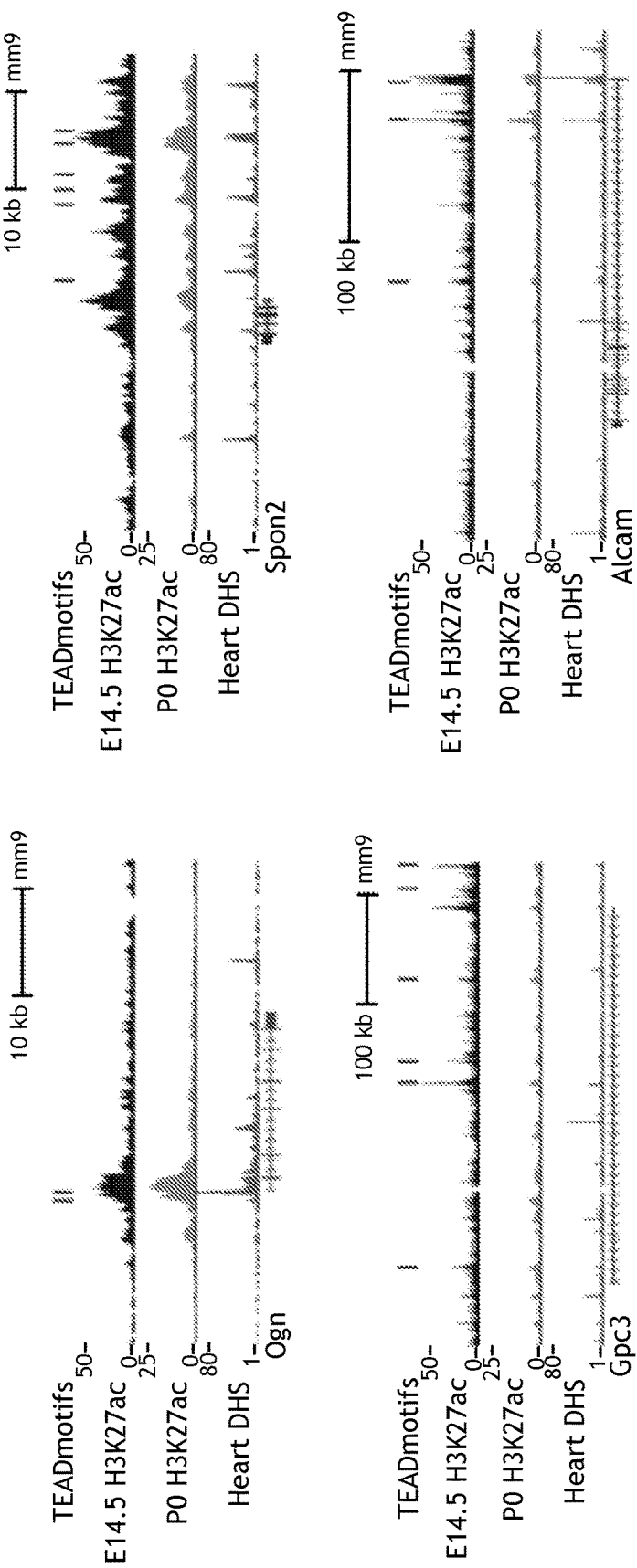
FIGS. 14A-14D. Direct Yap binding to the regulatory regions of the factors regulating extracellular milieu and cell differentiation in Lats1/2 CKO hearts and cell identity of primary epicardial cell culture.
Figure 14B:
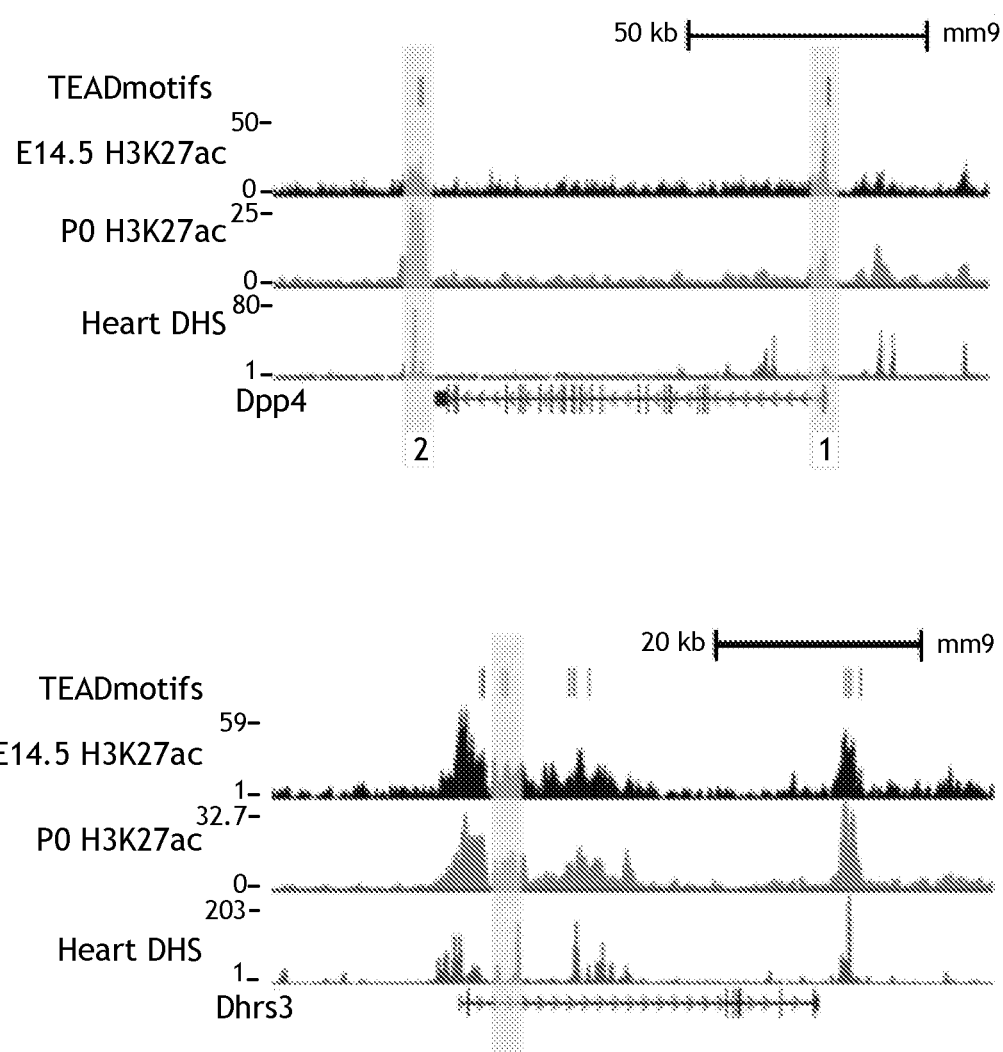
Figure 14C:
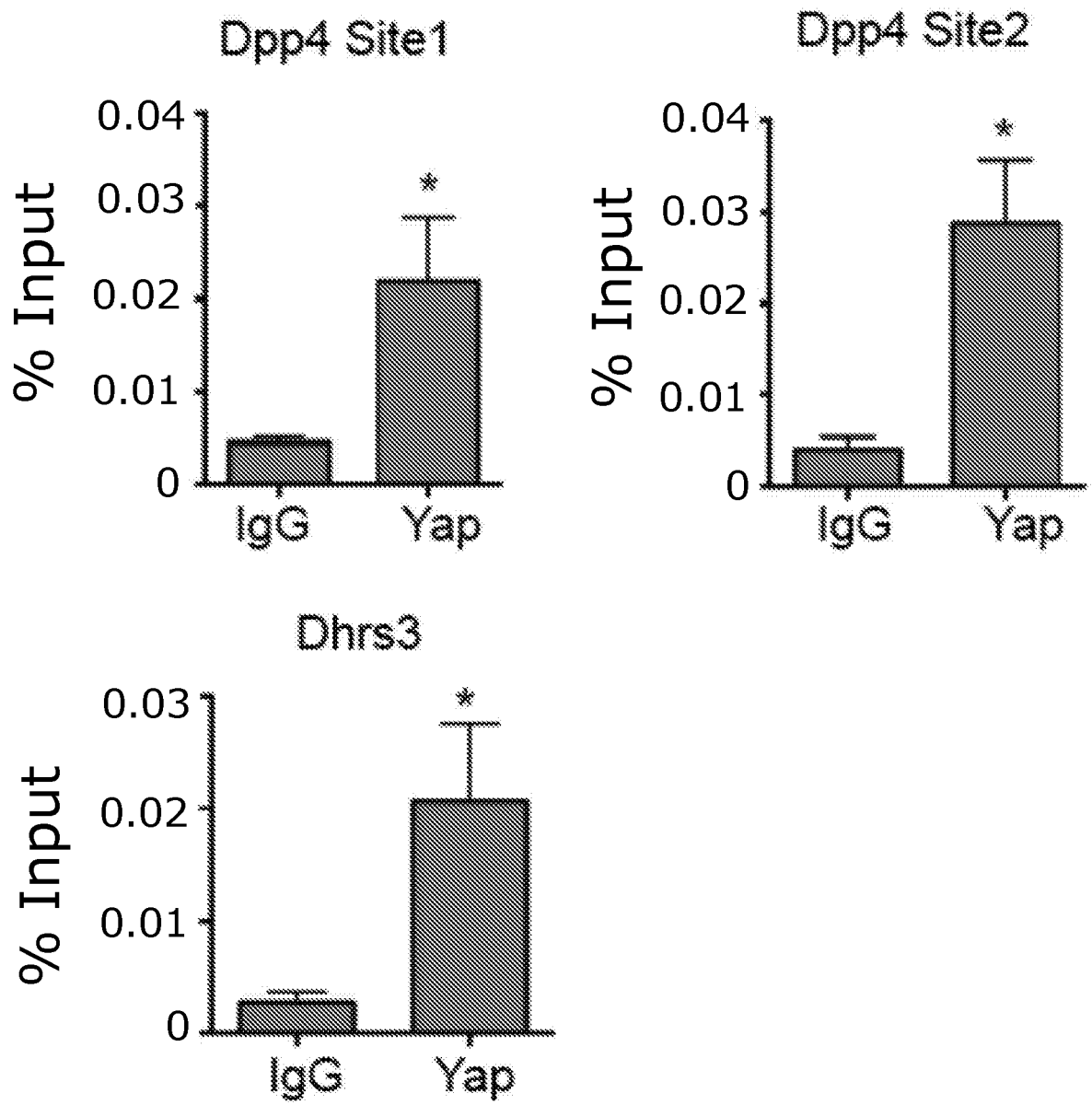

Yap Coordinately Regulates Fibroblast Differentiation and Coronary Vessel Remodeling To investigate in more depth if genes expressed in C20 and subepicardial mesenchyme are direct Yap target genes, embryonic heart H3K27ac data were compared with cardiac DNase-seq (DNase I hypersensitive site (DHS)) data and TEAD motifs were extracted from the E14.5 H3K27ac peaks (GSE52386). Several consensus TEAD motifs, Yap binding sites, were identified at enhancer and promoter regions of genes enriched in Branch B, such as Ogn, Spon2, Gpc3, and Alcam (FIG. 14A,14B). Consensus Tead motifs were also found in Dpp4 and Dhrs3. Yap ChIP-qPCR at Tead motifs contained within H3K27ac and DHS peaks was performed using the MEC1 epicardial cell line (Li et al., 2011) to determine if Yap directly bound to these loci. In the Dpp4 and Dhrs3 loci, Yap showed specific binding (FIG. 14B,14C).

Figure 6A:
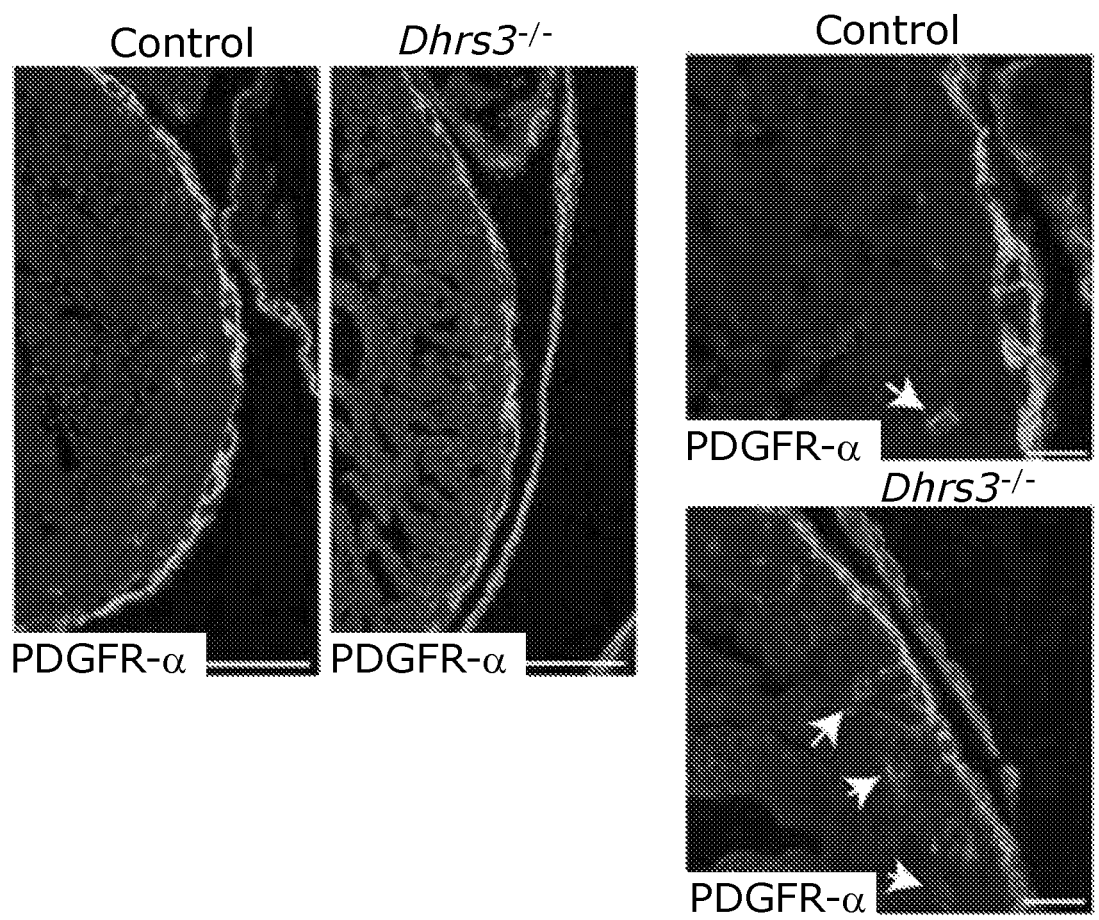
FIGS. 6A-6H. Hippo/Yap signaling controls fibroblast differentiation and coronary vessel patterning. See also FIG. 14.
Figure 6B:
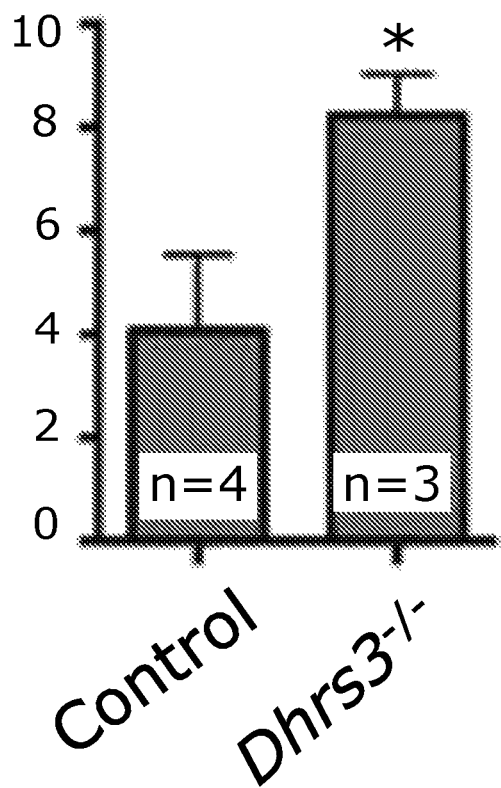

Dhrs3 was up-regulated in Lats 1/2 CKO hearts, which may contribute to impaired fibroblast differentiation by reducing retinoic acid formation and signaling (Billings et al., 2013). Retinoic acid was suggested to play a role in EPDC differentiation into fibroblasts (Braitsch et al., 2012). A Dhrs3$^{-/-}$ mouse model was used that had elevated retinoic acid signaling to examine cardiac fibroblast differentiation using PDGFRα$^+$ IF (Billings et al., 2013). There were more PDGFR-α expressing fibroblasts in Dhrs3$^{-/-}$ myocardium compared with controls supporting the hypothesis that Dhrs3 upregulation, as a downstream Yap target, led to reduction in retinoic acid signaling and promoted fibroblast differentiation arrest in Lat1/2 CKO hearts (FIG. 6A,6B).

Figure 6C:
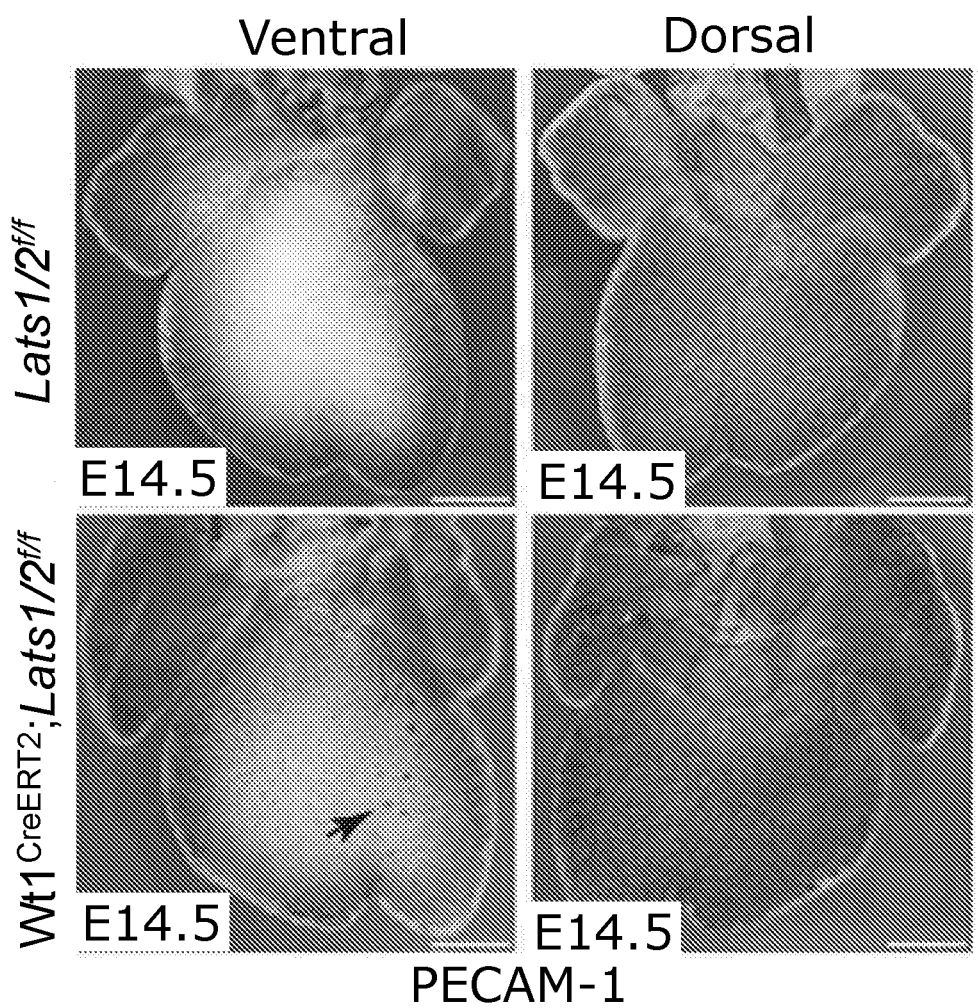
Figure 6D:
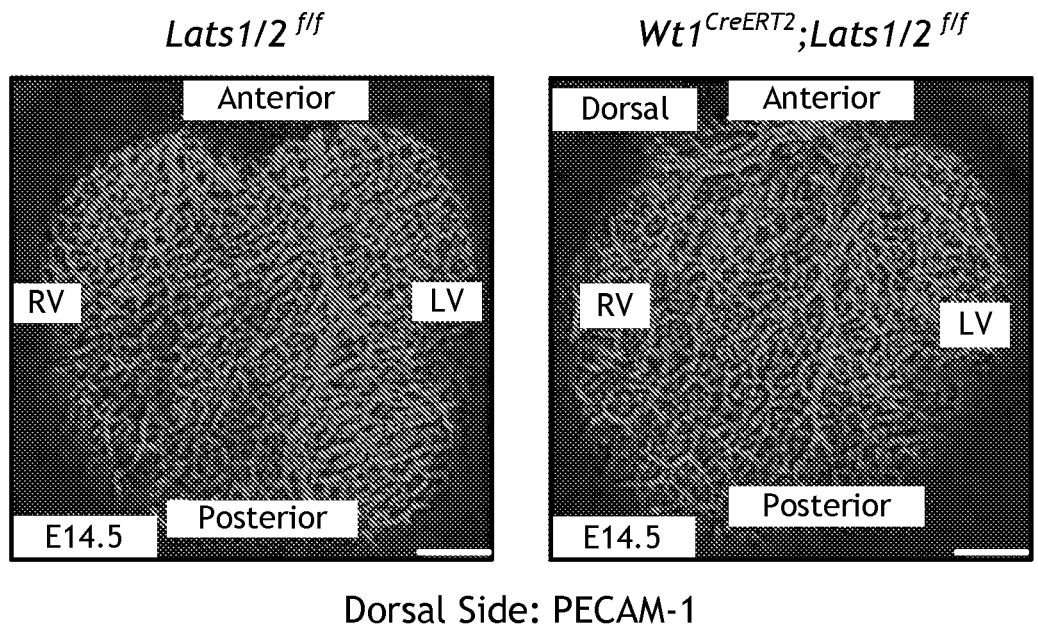
Figure 6E:
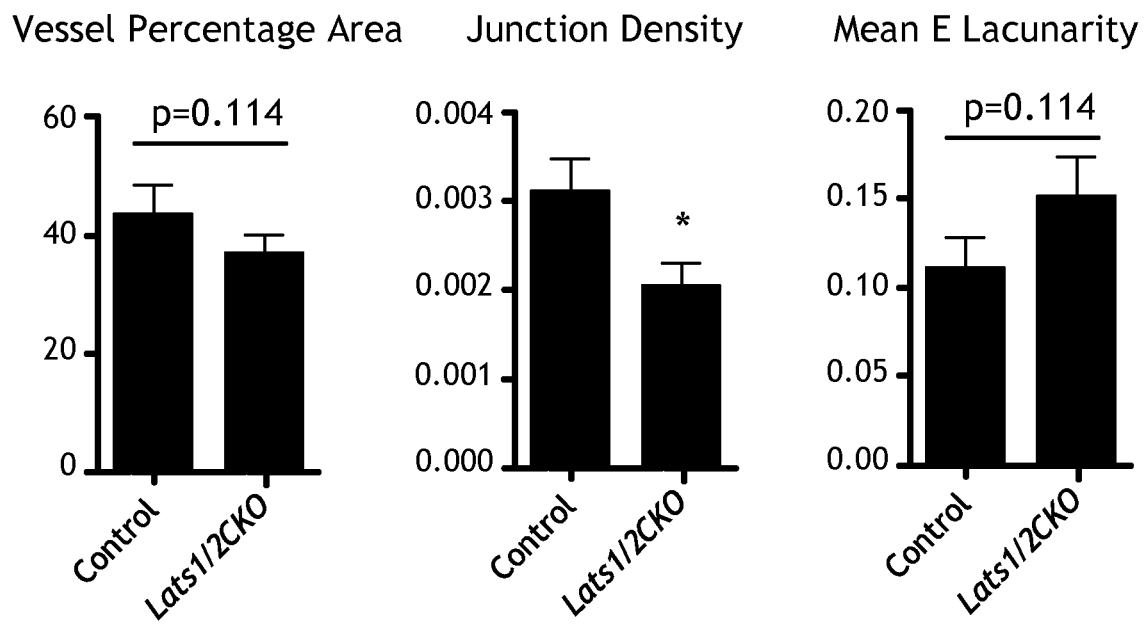

Lats1/2 CKO embryos and controls were treated with the Dpp4 inhibitor Sitagliptin (Choy and Lam, 2007). Pecam IF and automated quantification revealed that Sitaglipin treatment partially suppressed the disorganized coronary vessel in Lats1/2 CKO hearts (FIG. 6C-E). While some blood islands still appeared on the ventral side of Sitaglipin treated Lats1/2 CKO hearts, the dorsal side lacked blood islands (FIG. 6C). Moreover, the dorsal side vessel coverage phenotype was also suppressed in Sitaglipin treated Lats1/2 CKO hearts when compared to untreated Lats1/2 CKO hearts (compare FIG. 1B,1C to FIG. 6C,6D). Pecam-1 IF also revealed that defects of vessel percentage area and mean lacunarity were suppressed by Dpp4 inhibition (FIG. 6D,E), supporting the embodiment that Lat1/2 CKO coronary vessel defects were partially caused by elevated Dpp4 activity.

Mechanical Signaling Regulates Hippo Activity in Epicardial Cells

Figure 6F:
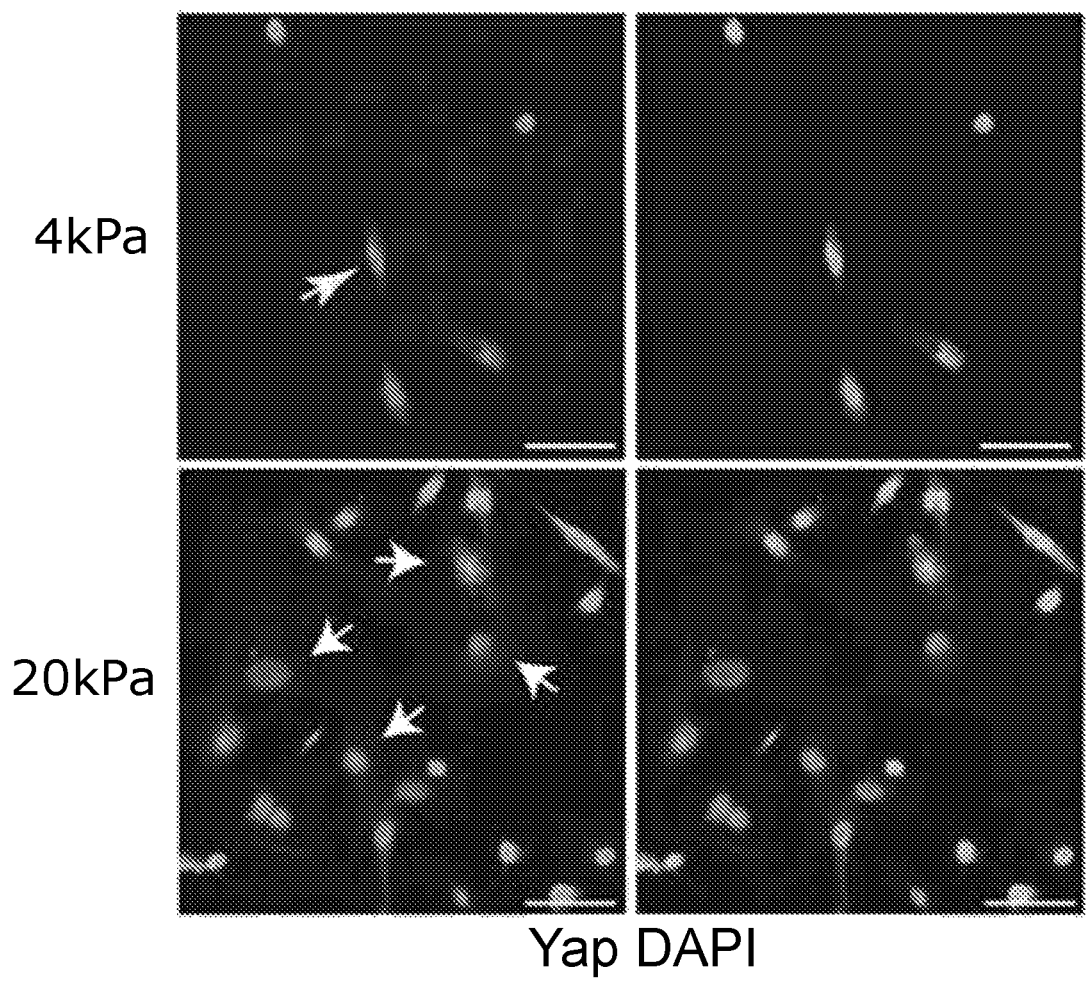
Figure 6G:
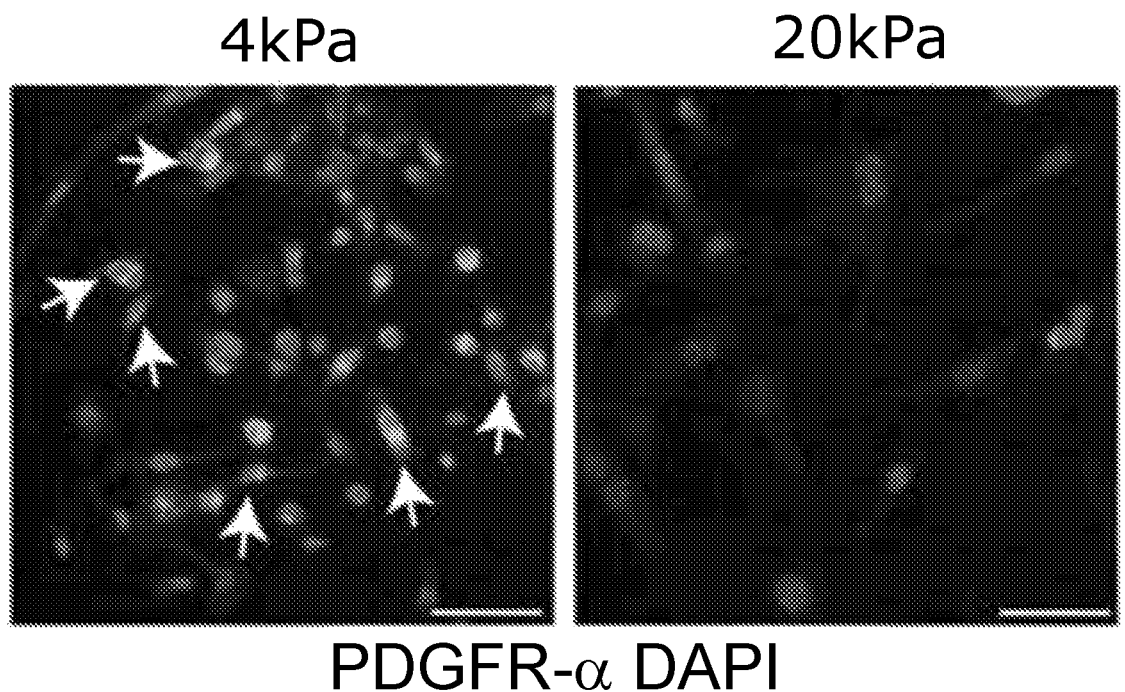
Figure 6H:
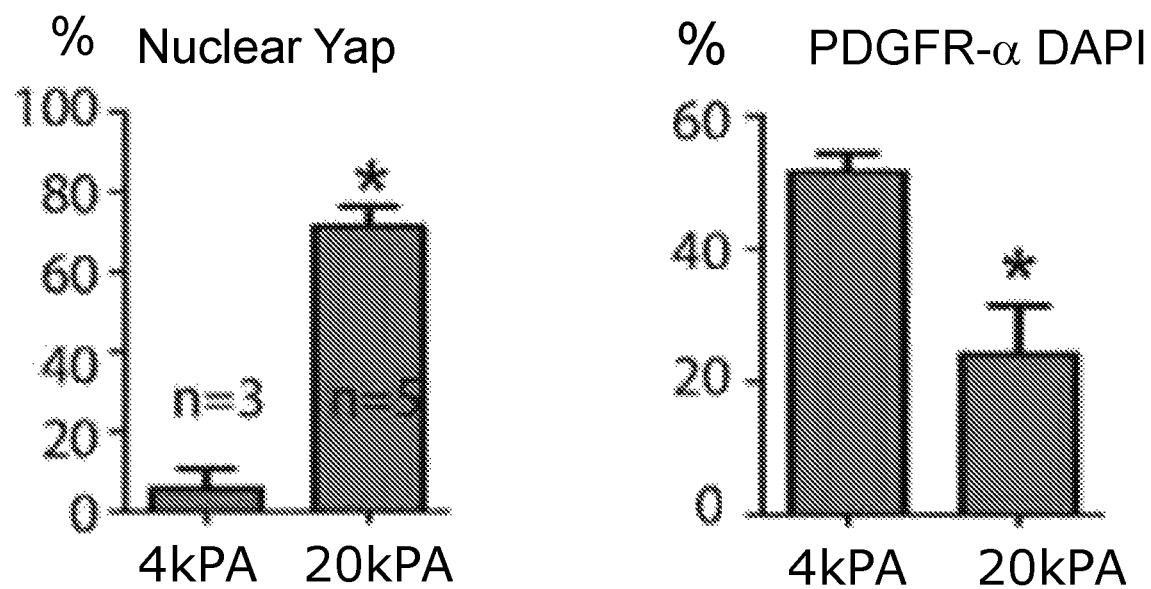
Figure 14D:
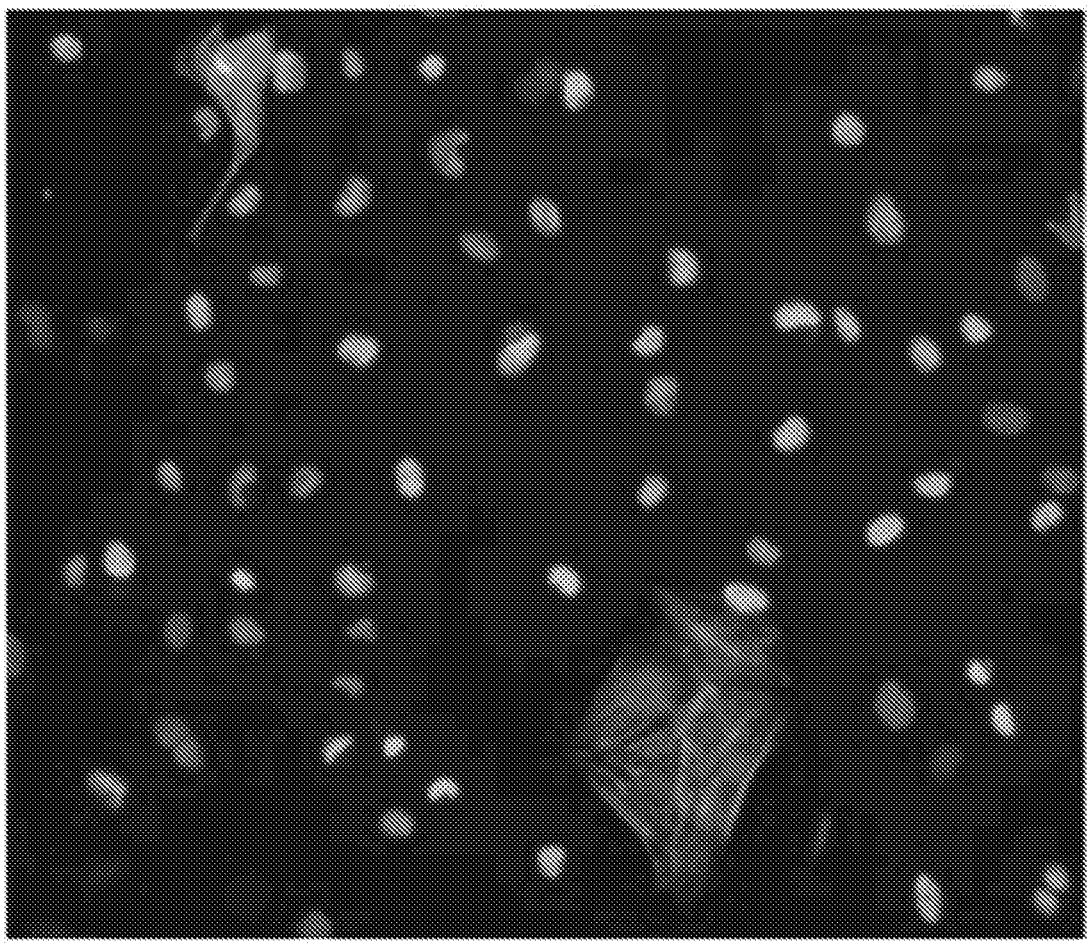

Mechanical tension is an upstream physiologic regulator of Hippo/Yap activity (Dupont et al., 2011). To examine mechanical tension in epicardial differentiation, Wt1-expressing primary epicardial cells were cultured on hydrogels of different stiffness (FIG. 14D). Primary epicardial cells cultured on 4 kPa matrix, approximating embryonic heart stiffness (Majkut et al., 2013), exhibited a spindle shape with Yap distributing equally to nucleus and cytoplasm (FIG. 6F). In contrast, epicardial cells grown on a stiffer 20 kPa matrix had a flat shape with increased nuclear Yap localization (FIG. 6F). Interestingly, spindle-shape cells strongly expressed fibroblast marker PDGFRα while flat-shape cells were weakly positive for PDGFRα (FIG. 6G,H). These data indicate that mechanical tension is an upstream physiologic signal controlling Hippo/Yap activity in epicardial cells and that increased nuclear Yap, perhaps resulting from elevated mechanical tension, impedes epicardial cell to fibroblast transition.

Significance of Certain Embodiments

Figure 7:
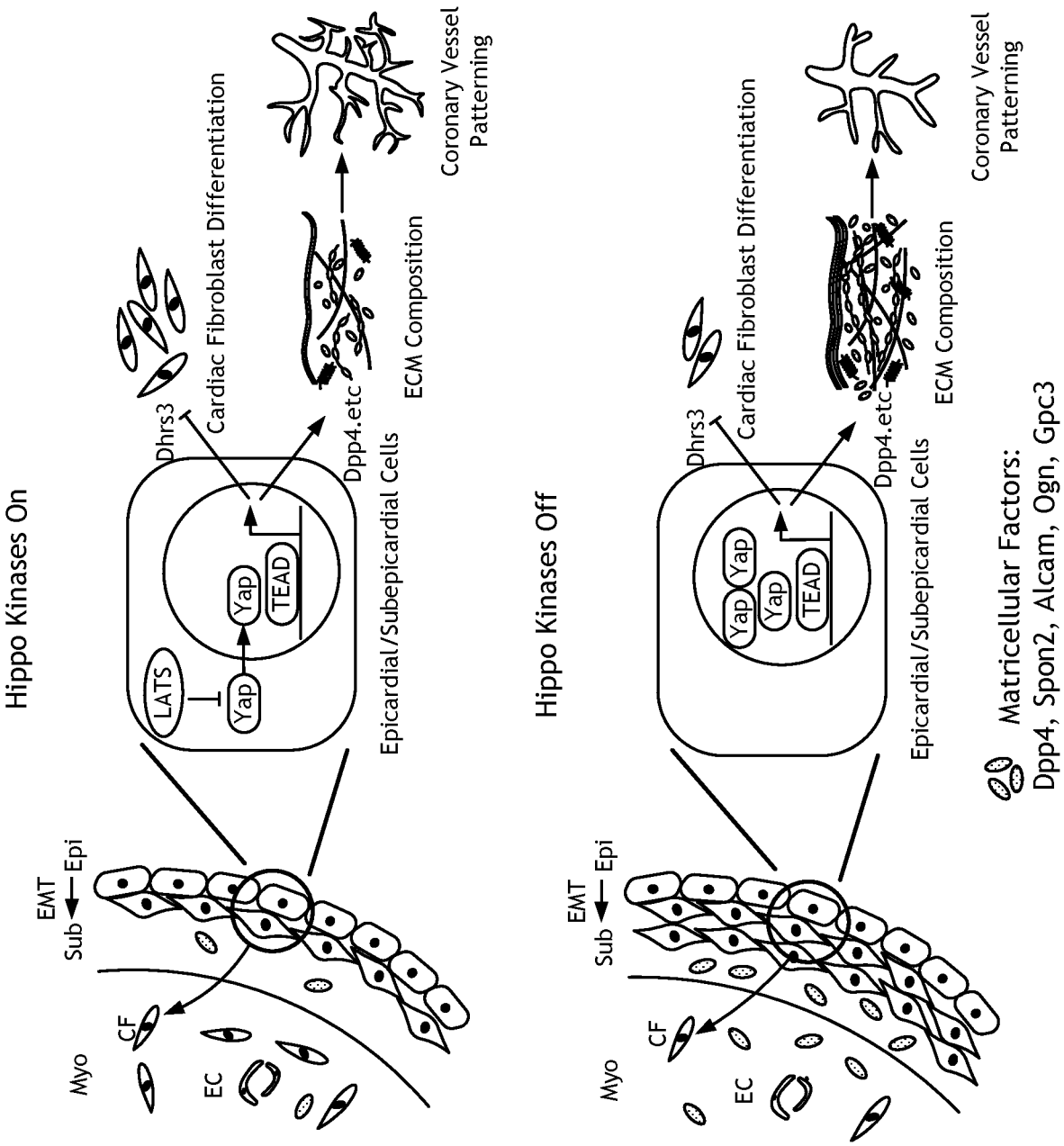
FIG. 7. Model of Lats kinase regulation of subepicardial cell differentiation and coronary vessel patterning. In presence of Lats (Hippo kinases on), epicardial cells undergo EMT and transform into subepicardial mesenchyme. Subepicardial mesenchymal cells migrate and differentiate into cardiac fibroblasts (upper left). In absence of Lats (Hippo kinases off), epicardial cells undergo EMT and transform into subepicardium. Differentiation from subepicardium to cardiac fibroblasts is impaired (bottom left). In epicardial and subepicardial cells (middle and right), Lats1/2 kinases restrict nuclear Yap that is required for proper Dhrs3 activity. Nuclear Yap controls ECM composition and coronary patterning by matricellular factor regulation.

An essential role was uncovered for the Hippo pathway kinases, Lats1/2, in promoting the transition from epicardial progenitors into differentiated cardiac fibroblasts while concurrently controlling ECM composition and vascular remodeling (FIG. 7). Hippo signaling promotes retinoid signaling by inhibiting a negative regulator of retinoid signaling, Dhrs3, enhancing subepicardial mesenchyme to cardiac fibroblast differentiation. The data suggest that the subepicardial transition state may be responsive to specific physiologic cues, mediated through the Hippo pathway, that modulate genes encoding matricellular factors such as Dpp4 that control ECM characteristics and vascular remodeling (FIG. 7). The data represent the first in vivo characterization of a transition state at the single cell level in the heart.

Lats1/2 Regulate Epicardial Progenitor Differentiation into Cardiac Fibroblasts There was an autonomous function for Hippo signaling in promoting differentiation of cardiac fibroblasts. Lats1/2 inhibit Dhrs3, a Yap target gene and a negative modulator of retinoic acid signaling, as subepicardial cells differentiate into cardiac fibroblasts. The data are consistent with previous findings showing that retinoid signaling is required for cardiac fibroblast differentiation and epicardial EMT (Braitsch et al., 2012; Wang et al., 2018). Dhrs3 mutant embryos had more cardiac fibroblasts. Little is known about the interaction of retinoic acid signaling with the Hippo pathway. In an in vitro model of neural crest development, in contrast to the findings Yap synergizes with retinoids to promote the neural crest phenotype suggesting context dependent modifiers of Yap and retinoid interactions (Hindley et al., 2016).

Cluster 20, a Cell Intermediate Between Epicardium and Cardiac Fibroblasts

Figure 11B:
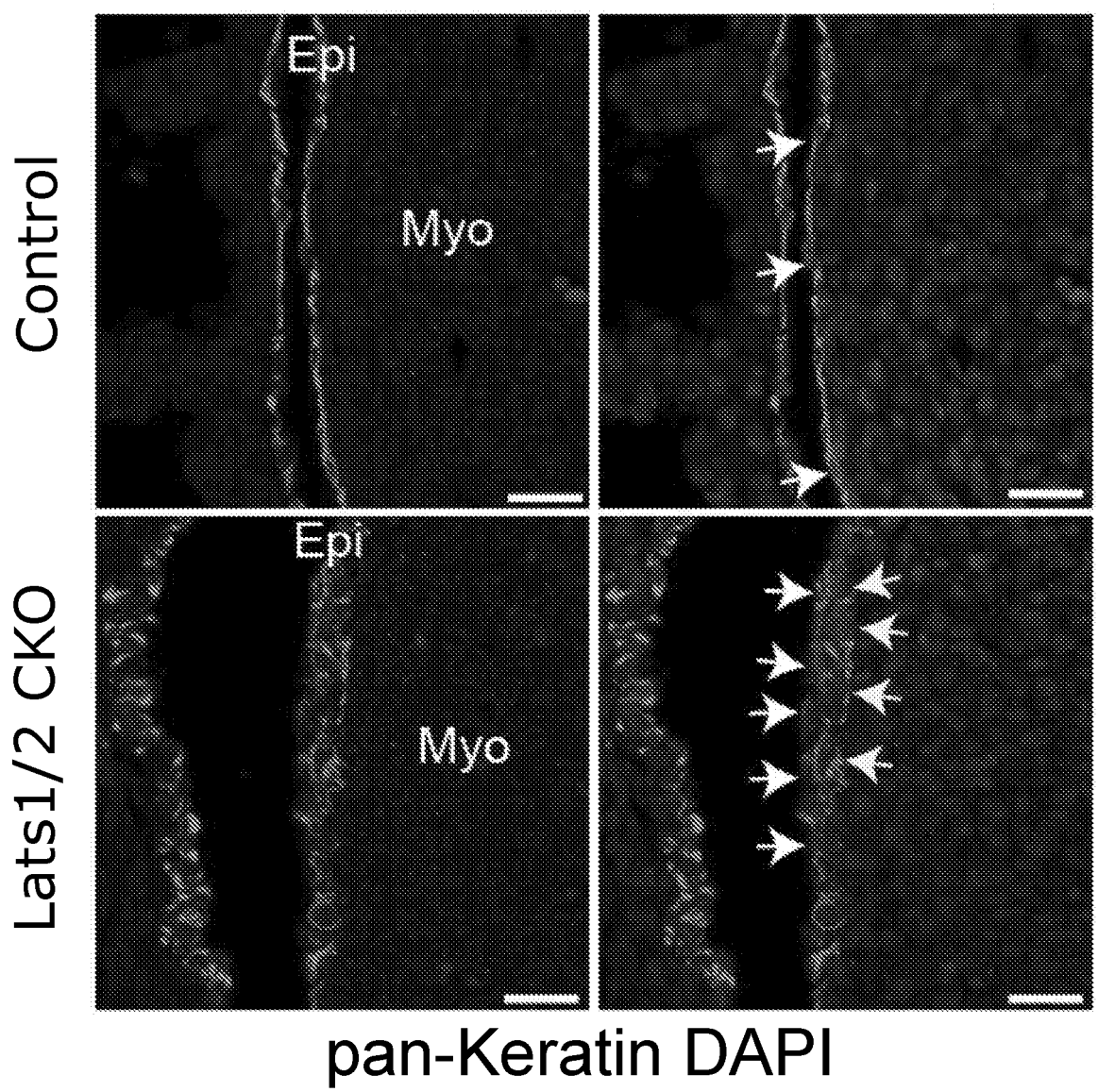
Figure 11C:
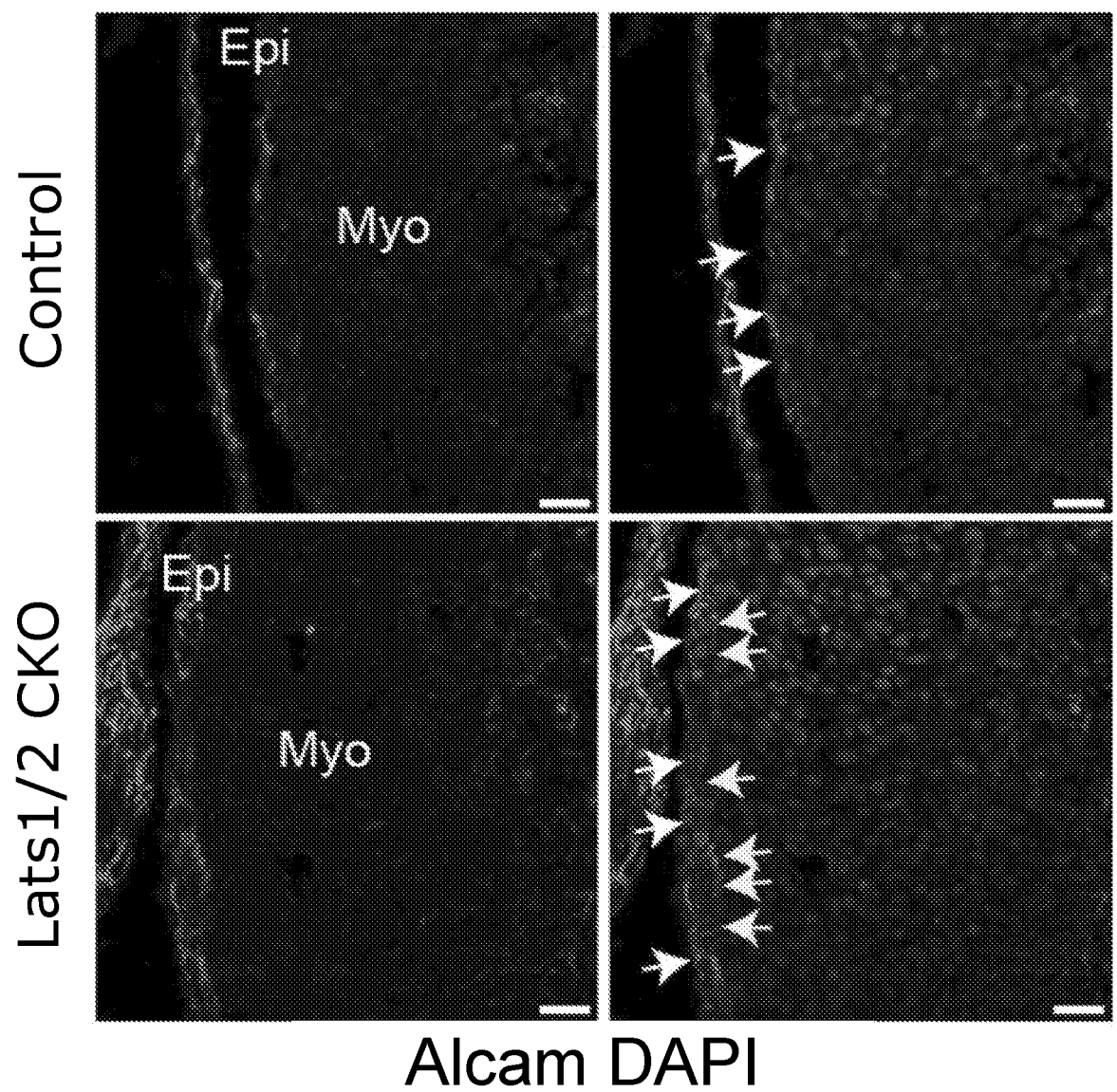
Figure 11D:
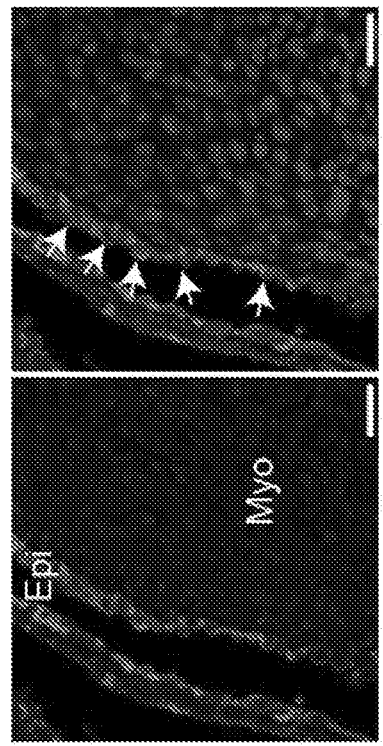
Figure 11D:
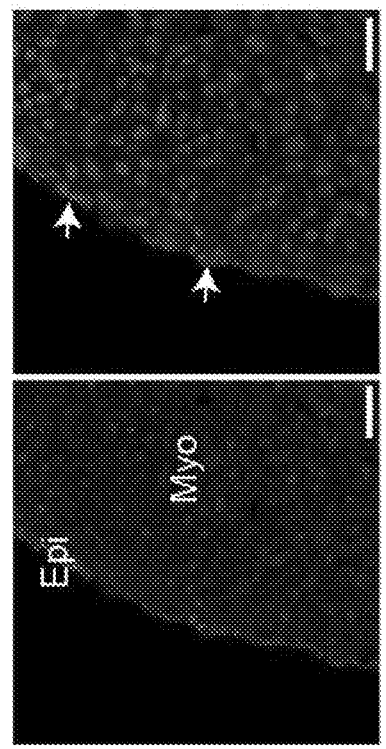

In Lats1/2 CKO hearts, there was an expansion of C20, a cell type with characteristics of both epicardium and primitive cardiac fibroblasts. Importantly, Drop-seq revealed that C20 was found in both wild type and mutant hearts, indicating that C20 is a transition cell, related to subepicardial mesenchyme, that exists during normal epicardial diversification. Furthermore, IF validation revealed that C20 was located in the subepicardial space supporting the hypothesis that C20 is closely related to subepicardial cells. IF experiments also revealed that cells in the Lats 1/2 CKO subepicardial space, containing C20 cells, expressed Podoplanin and Keratin that are restricted epicardial markers indicating that C20, while closely related to control subepicardial cells, also had distinct epicardial characteristics (Acharya et al., 2012) (FIG. 4A and FIG. 11B). The distinct Podoplanin and Keratin expression between Lats1/2 CKO C20 cells and control subepicardial cells was not detected by Drop-seq suggesting that Podoplanin and Keratin expression was regulated post transcriptionally or their transcripts were below the level of detection for Drop-seq.

Hippo Signaling Coordinates Vascular Development with Fibroblast Differentiation An important insight from the disclosure, not previously appreciated, is the non-autonomous connection between cardiac fibroblast differentiation and vascular patterning. The data suggest that the disorganized coronary vessel patterning in Lats1/2 CKO hearts is due to aberrant signaling from Lats1/2 mutant C20 cells. Importantly, Dpp4 was validated as a direct Yap target and found that Dpp4 inhibition partially suppressed the coronary vessel remodeling defect in Lats1/2 CKO hearts. Cross talk, mediated by growth factors, between epicardium and myocardium is critical for coronary vessel angiogenesis and myocardium growth during heart development (Smart et al., 2011; Zhou et al., 2011). The data reveal a new interaction between developing fibroblasts that express matricellular factors that modulate ECM composition and control signaling to developing vasculature.

The cell surface serine protease, Dpp4, and its direct inhibitor Gpc3 regulate multiple, essential signaling events in coronary vascular development (Khurana et al., 2013; Ou et al., 2013). Dpp4 controls the functional activity of chemokines and cytokines that contain Dpp4 proteolytic motifs. In the context of human cord blood, the chemokine Cxcl12 is cleaved by Dpp4 and inhibits the function of uncleaved Cxcl12 (Christopherson et al., 2002). Recent data reveal that Cxcl12, signaling through Cxcr4, promotes endothelial cell migration and coronary plexus pruning and maturation (Cavallero et al., 2015; Harrison et al., 2015). The Dpp4 inhibitor findings also suggest that a prolonged C20 transition state results in more Dpp4 activity resulting in endothelial remodeling defects.

Mechanical Tension Determines Cardiac Fibroblast Differentiation by Controlling Yap Activity During heart development, organ vascularization is coordinated with overall heart size to meet growing cardiac metabolic needs. The data indicate that the epicardium and subepicardium are important for coordinating organ vascularity with organ size. In other contexts, it has been shown that in addition to Hippo pathway kinases, mechanical tension acts as another mode of regulation of nuclear Yap activity (Dupont et al., 2011). The data, using primary epicardial cells, further reveal the importance of mechanical signaling in regulating Yap. In one embodiment, with heart growth, a gradual tension increase in epicardium and subepicardium may transiently promote nuclear Yap activity and EMT with subepicardial cell proliferation and activation of Yap target genes. In this scenario, Hippo kinase activity may modify the influence of mechanical tension on EMT, proliferation, and differentiation so that the correct number of subepicardial cells and EPDCs are formed.

In addition to new insights into Hippo signaling in epicardial diversification, the data provide important insight into all developing cardiac cell types at E13.5-E14.5, including rare cell types like macrophages and arterial endothelial cells.

Example 2

Experimental Model and Subject Details for Example 1

Mice Strain

Wt1$^{CreERT2}$ (Zhou et al., 2008), Lats1/2$^{f/f}$ (Heallen et al., 2011), Yap/Taz$^{f/f}$ (Xin et al., 2011), Rosa26$^{mTmG}$ (Muzumdar et al., 2007), Dhrs3$^{-/-}$(Billings et al., 2013) alleles have been described previously. Mice were on a mixed genetic background of C57BL/6 and 129SV. All animals were maintained in pathogen-free BCM Transgenic Mouse Facility (TMF). All animal protocols and procedures were approved by the Institutional Animal Care and Use Committee (IACUC) of Baylor College of Medicine in Houston, Texas.

Method Details

Cre Activity Induction

Tamoxifen was dissolved in peanut oil with 5% ethanol at 10 mg/ml. For Wt1$^{CreERT2}$, 0.1 mg/g body weight tamoxifen was administrated to plugged female by intraperitoneal injection at embryonic (E) day 11.5.

Cell Preparation and Drop-Sea Workflow

Atria were removed prior to single cell suspension preparation, droplet generation, cDNA amplification, and library preparation. Following sequencing of Drop-seq libraries, a minimum gene per cell threshold of 500 was set for inclusion into the data set resulting in a final digital gene expression matrix with a median of 1,005 genes per cell and 1,500 Unique Molecular Identifiers (UMI) per cell (FIG. 9A). Batch effects were corrected for and principle components analysis was carried out. Cells were dissociated as previously described (Dyer and Patterson, 2013). Hearts were chopped into several pieces and digested by 1 mg/ml collagenase I for 20 min at 37° C. Every 10 min, the sample was gently pipetted sample up and down to mechanically dissociate the cells. 10% FBS in DMEM was applied to quench the protease, and samples were passed through a 100 μm strainer. Following tissue dissociation cells were diluted to a concentration of 150,000 cells/mL in PBS with 0.1% BSA. Next, Drop-seq was performed according to Macosko et. al (Macosko et al., 2015). Briefly, cells were co-encapsulated into nano-liter sized droplets containing barcoded microparticles and lysis buffer using a Drop-seq specific microfluidics device (custom made by FlowJEM, Toronto, Canada). After droplet breakage, reverse transcription, and exonuclease treatment, total cDNA was amplified, pooled, and purified with Ampure XP beads and then quality control, quantification and size determination was performed using a Fragment analyzer (Advanced Analytical Technologies, Inc.) for quality control, quantification, and size determination. Tagmentation and library preparation was performed with the Illumina Nextera XT kit. Final libraries were triple purified with a successive Ampure XP based protocol, whereby two successive 0.6× (beads to sample ratio) purifications were performed, followed by a final 1× purification step. All libraries were sequenced on an Illumina Nextseq500 instrument.

Drop-Sea Data Analysis

Sequencing data was processed as described in Shekhar et. al. (2016)(Macosko et al., 2015; Shekhar et al., 2016). Briefly, raw fastq files were converted to BAMS with Picard tools (MergeSamFiles) and then used as input for STAR alignment (Dobin et al., 2013), cell barcode correction, and digital gene expression (DGE) matrix generation via the Drop-seq tools software package (available at the Drop-seq website maintained by the McCarroll Lab). Next, DGEs from each experiment were merged. The comprehensive DGE was imported into Seurat (version 1.4.0.5) where normalization was performed according to package default settings (Satija et al., 2015). Batch effects were corrected for with the application of Combat, from the R SVA package (version 3.18.0), and by further regressing out the number of molecules per cell and the percentage of mapped mitochondrial reads with the RegressOut function (Seurat package) (Leek et al., 2012). Next, principle components analysis was performed and significant PCs were used as input for graph-based clustering. Finally, 2-dimesnsional visualization of the multi-dimensional data set was done with tSNE (Maaten and Hinton, 2008). Differential expression of the various clusters was also performed with Seurat, using the likelihood-ratio test for single cell gene expression (McDavid et al., 2013). For iterative clustering, cell barcodes were selected from each cell type and deposited into a new digital expression matrix prior to principle component analysis (PCA), graph based clustering, and tSNE visualization. These cell types were evaluated and differential expression analysis was performed (likelihood-ratio test for single cell gene expression (McDavid et al., 2013). For pseudotime analysis, the normalized data from the indicated clusters calculated in Seurat was then passed directly into Monocle2 (Qiu et al., 2017b). The Monocle2 branched expression analysis modeling (BEAM) statistical test was utilized to isolate the branch-specific gene expression patterns (256 genes with qval<0.1). Motif enrichment analysis was carried out with the Cytoscape plug-in iRegulon using the mouse genome's default parameters (Janky et al., 2014). All gene ontology (GO) analysis was performed with the Metascape tool (available on the Metascape website) (Tripathi et al., 2015).

Histology and Immunofluorescence

Epicardium-restricted-Lats1/2 mutant embryos (Lats1/2 CKO) were generated by crossing Wt1$^{CreERT2}$ with Lats1/2$^{f/f}$ or Lats1/2$^{f/f}$; Rosa26$^{mTmG}$. Control embryos were generated by crossing Wt1$^{CreERT2}$ with Rosa26$^{mTmG}$ or Cre negative littermate control. For H&E staining and immunofluorescence staining, hearts were fixed in 4% PFA overnight at 4° C. and dehydrated in a serial ethanol, xylene and embedded in paraffin. Sections of 7 μm thick sections were stained with H&E for histological analyses (Singhal and Martin, 2015). For some immunofluorescence staining, cryosections were used. Antibodies used for immunofluorescence staining were as follows: GFP(1:200, Abcam ab290, ab6673), phospho-YAP (1:200, Cell signaling technology, 4911), Yap (1:200, Novus NB110-583538), PECAM-1(1:100-1:200, BD Pharmingen 550274), Vimentin (1:200, Abcam, ab92547), Wt1(1:200, Abcam ab89901), Podoplanin (1:200, Developmental Studies Hybridoma Bank 8.1.1), α-actinin (1:200, Abcam ab68687), Collagen I (1:200, Abcam ab21286), Dpp4 (1:100, Biolegend H194-112), pan-Keratin (1:200, Abcam ab9377), pSmad2/3(1:200, Abcam ab52903), PDGFRα(1:100, Cell signaling technology 3174), PDGFRβ (1:100, Cell signaling technology 3169), SM-MHC (1:200, Alfa Aesar BT-562), Spon2(1:200, Thermo Fisher Scientific PAS-59087), Alcam (1:200, Abcam ab109215). To visualize some antigens, Alexa-647 was employed. When applications required green and red co-staining, sections were pre-treated with 0.3% $H_2O_2$ in PBS for 20 min at room temperature to quench the endogenous GFP and Tomato signals, which come from the Rosa26$^{mTmG}$ reporter line. In some cases, Tyramide Signal Amplification Systems (1:100, Perkin Elmer) were used to amplify signal. PECAM-1 whole mount staining was performed as previously described (Mukouyama et al., 2012). PECAM-1(1:100) staining was followed either by anti-rat-HRP (1:200, Life Technologies, 62-9520) and a DAB kit (Vector lab) for color development or anti-rat-Alexa-647 for immunofluorescence staining. The vessel pattern was quantified by Angiotool.

RNA In Situ Hybridization

The tissues for RNA in-situ hybridization were prepared as described above except adding Diethylpyrocarbonate (DEPC) was added to avoid RNAse contamination. RNA in-situ hybridization was performed by the RNA In Situ Hybridization Core at Baylor College of Medicine. The Twist1 (Ma et al., 2005) and Snai2 (Jiang et al., 1998) probes were previously described.

Gross heart images were captured by Zeiss SteREO Discovery. V12 microscope. Histology and RNA in situ images were captured by Nikon Eclipse 80i microscope. Immunofluorescence images were captured on a Leica TCS SP5 confocal microscope, a Zeiss LSM 780 confocal microscope or Nikon A1-Rs inverted laser scanning microscope.

EdU Incorporation Assay

To study cell proliferation, pregnant females were injected with 0.08 mg/g body weight EdU 2 hr before harvesting embryos. Hearts were processed as described above. EdU incorporation was assayed using the Click-it EdU imaging kit.

FACS Analysis

Cells were dissociated as previously described in the method section of "Cell preparation and Drop-seq workflow". BV421 Rat Anti-Mouse CD140A antibody (BD Biosciences 562774) was used to detect PDGFR-α and BV421 Rat IgG2α, κ Isotype (BD Biosciences 562602) was used for gating control. Cells were analyzed using BD Biosciences CORP Aria I and BD Biosciences LSRII and images were processed with FlowJo software.

Motif Analysis and ChIP-q-PCR

Gene regulatory region information was extracted from GEO database: E14.5 H3K27ac (GSE52386), P0 H3K27ac (GSE52386) and Adult Heart DHS (GSE37074). TEAD motif was analyzed by Homer. Chromatin immunoprecipitation was performed with an anti-Yap antibody (Novus NB110-58358) in the MEC1 epicardial cell line (Li et al., 2011). Three biological replicates were included in each group. The primers used for detecting TEAD binding region at Dhrs3 and Dpp4 are as follows:

```
Dpp4 site1-Forward
                                (SEQ ID NO: 5)
5'-GGAGGAAGATTATGCACAACAAC-3';

Dpp4 site1-Reserve
                                (SEQ ID NO: 6)
5'-TGTGGAGACATGAAAGACTAAGG-3';

Dpp4 site2-Forward
                                (SEQ ID NO: 7)
5'-GGAGCTCATGAATGCCTGATT-3';

Dpp4 site2-Reserve
                                (SEQ ID NO: 8)
5'-CTGCAGAAGAACTGTGCTCTTA-3';

Dhrs3-Forward
                                (SEQ ID NO: 9)
5'-CCTACCCACACAAGACATCAA-3';

Dhrs3-Reserve
                                (SEQ ID NO: 10)
5'-CTCAGGAGATGATCCAACAAGAA-3'.
```

Primary Epicardial Cell Culture

Embryonic hearts were isolated from embryos from ICR (CD-1) at E11.5. One litter of the hearts were pooled and digested with 1mg/ml Collagenase I (Worthington). The hearts were maintained intact to expose epicardium only to the digestion buffer. The hearts were digested twice with 500 μl Collagenase I at 37 degree with agitation (~100 rpm). After every 5 min digestion, pipet hearts up and down for about ten times using disposable dropper. Cell suspension was collected and new digestions buffer was added to the tissue. Next, cell suspension was collected in an equal volume of 10% FBS DMEM and kept on ice. Cell suspension with 10% FBS DMEM from two-time digestion were pooled and filtered through 100-micron tissue strainer (Falcon). Spin down cells at 400 g for 5 min and re-suspend cells in 10% FBS DMEM number for culturing on stiffness hydrogel. About 2000-3000 cells/well were plated in 24 well plate with stiffness hydrogel made on 12 mm round coverslide. After one-day culture, cell identity was detected by IF and >90% cells express epicardial cell marker Wt1. To examine the effect of stiffness on epicardial-fibroblast differentiation, cells were continuously cultured in 10% FBS DMEM supplemented with 100 ng/ml b-Fgf (R&D Systems) for 10 days and medium was changed every day.

Stiffness Hydrogel Preparation

Tunable stiffness hydrogels were prepared as previously described (Tse and Engler, 2010). 12 mm round coverslips were used for making hydrogel. Coverslips were pre-treated with 0.1M NaOH and (3-Aminopropyl) trimethoxysilane (Sigma) for 5 and 10 mins respectively. After rinsed with water, coverslips were covered with 0.5% Glutaraldehyde (Sigma) solution for 30 mins. Another same number of coverslips were coated with Dichlorodimethylsilane (Sigma) and let them air dry. Stiffness was adjusted based on the relative concentration of acrylamide and bis-acrylamide. For 4 kPa, 5% acrylamide and 0.15% bis-acrylamide were mixed with ammonium persulfate and TEMED; for 20 kPa, 8% acrylamide and 0.264% bis-acrylamide were mixed with ammonium persulfate and TEMED On the day for cell culture, 1 ml of 50 mM HEPES Ph8.5 was mixed with 10 ul 50 mg/ml Sulfo-SANPAH (sulfosuccinimidyl 6-(4'-azido-2'-nitrophenylamino) hexanoate) (Thermo Fisher Scientific) and was applied to hydrogel under 375 nm, 15W UV light for 5 mins twice. Hydrogel were rinsed with 50 mM HEPES PH8.5 several times and were freshly coated with type I rat tail collagen (0.5 mg/ml in 0.2% acetic acid) for 2 hours. After this, hydrogels were washed three times by sterile PBS and sterilized under UV in cell culture hood for 30 min. Hydrogels were ready to use.

Fibroblast Detection on Hydrogel

After 10-day culture, only the region with less than 50% confluency were studied. Cells were stained with Yap to visualize Yap cellular localization and PDGFR-α for fibroblast.

Sitagliptin Treatment

Dpp4 inhibitor Sitagliptin (Sitagliptin phosphate, Sigma, 1612903) was dissolved in saline. 0.01 mg/g body weight Sitagliptin was administrated to plugged female by gavage at E11.5, E12.5 and E13.5.

Quantification and Statistical Analysis

Images taken by Nikon A1-Rs inverted laser scanning microscope were process with FIJI software. Contrast and image size of IF images were adjusted with Adobe photoshop CC or GIMP. Images of Drop-seq were produced in R. Flow cytometry graphs were generated by FlowJo. Bar graphs were generated by GraphPad Prism 6. All figures were made in Adobe Illustrator CC 2015 or Canvas X or Inkscape.

Coronary vessel pattern was analyzed by AngioTool. Statistical analyses were performed in SPSS 21.0. Sample size was labelled on the corresponding bar graph, otherwise n=3 in all groups, which represent the number of hearts were analyzed in each experimental group. N number of cell composition in Drop-seq (FIG. 2F) and FACS analysis (FIG. 5C) indicated number of cells were analyzed. For IF images, three fields of views were analyzed in each heart. For quantification of PDGFR-α cells FIG. 6A, percentage of PDGFR-α was calculated by PDGFR-α$^+$ cell number was divided by total cell number in compact myocardium. For quantification of pSmad2/3$^{high}$ in FIG. 9E and FIG. 6F, in each experimental group, epicardial cells from 2-4 different hearts were analyzed and counted as total observation number. Mann-Whitney U test were used for most studies, except the cell composition in Drop-seq (FIG. 2F), FACS analysis (FIG. 5C), and pSmad2/3$^{high}$ cells in epicardium, in which Chi-square were used. The cut-off value for statistical significance were indicated in corresponding figure legend.

Data and Software Availability

The Drop-seq dataset has been deposited in Gene Expression Omnibus (GEO) with accession number GSE100861.

Example 3

Hippo Signaling Prevents Spontaneous Activation of the Cardiac Wound Response

Derangements of tissue composition, often initiated by injury, is the primary cause of a multitude of illnesses. In adult mammals suffering from an infarct, the cardiac muscle cells, cardiomyocytes (CMs), are permanently lost and replaced with collagenous scar tissue. Scar tissue deposition is essential to prevent catastrophic ventricular rupture, as genetic studies on key fibrotic genes and molecular scar components have shown (Ichihara et al., 2002; Oka et al., 2007). However, scar tissue severely obstructs the cardiac contractile function and contributes to heart failure. Chronic cardiac fibrosis is associated with the vast majority of heart disease, currently the predominant cause of death in the United States. Therapies aimed at reducing detrimental cardiac fibrosis must avoid affecting the acute wound-healing capacity of CFs. However, little information exists on the cellular constituents of the cardiac scar.

Only recently have the genetic reagents been developed for interrogating CFs and their cellular origins (Fu et al., 2018; Kanisicak et al., 2016; Moore-Morris et al., 2018). Importantly, these studies have found that immediately following MI, resting CFs perish within the ischemic region along with CMs, vascular endothelial cells, and immune cells (Fu et al., 2018). The CFs located on the periphery of the wound are activated within two to four days after MI and localize to the infarct zone where they then differentiate into proliferative and contractile α-smooth muscle actin (Acta2) expressing myofibroblasts, which persist until approximately ten days post-MI when they differentiate into matrifibrocytes, the most highly differentiated CF state. Thus, after ischemic injury CFs dynamically progress through at least three discrete cellular states in order to ultimately generate a stable scar.

Traditionally, the focus on fibroblast cell identity after wounding has concentrated primarily on Acta2 expressing myofibroblasts, which are often considered the primary cellular source for cardiac fibrosis and also the principal depositors of the extracellular matrix (ECM), along with other matricellular components and proteoglycans that make up the post-infarct scar. To date, several signaling pathways have been implicated in myofibroblast differentiation in various tissues, including transforming growth factor β (TGF-β) signaling (Desmouliére et al., 1993; Khalil et al., 2017; Tallquist and Molkentin, 2017), Interleukin-mediated signaling (Hashimoto et al., 2001; Mattey et al., 1997), and platelet derived growth factor (PDGF) signaling (Borthwick et al., 2013; Oh et al., 1998). Despite progress, a comprehensive understanding of the molecular pathways, epigenomic landscapes, regulatory factors, secreted proteins, and biomarkers present during injury-induced CF differentiation is lacking.

In addition to fibroblasts, the infarct region is rapidly colonized by myeloid cells, including macrophages and monocytes. Myeloid cells also reside in the normal heart and play an important role in cardiac development (Leid et al., 2016), physiology (Hulsmans et al., 2018), conduction (Hulsmans et al., 2017), regeneration (Aurora et al., 2014), and the adult wound response (Nahrendorf, 2018; Nahrendorf et al., 2007). Importantly, myeloid cells have also been implicated as regulators of organ fibrosis (Duffield et al., 2005). Consistent with the idea that myeloid cells functionally interact with CFs in the heart to regulate fibrosis, an in vitro system revealed that bone marrow-derived macrophages and murine embryonic fibroblasts constitute a stable two-cell circuit connected by reciprocal growth factor exchange (Zhou et al., 2018). This cell-cell communication maintains proper cellular composition during homeostasis and is regulated in-part by the "carrying capacity" of fibroblasts, or the maximum CF population that can be supported by the extrinsic tissue environment (Hart et al., 2014; Zhou et al., 2018). The massive tissue loss following ischemic injury represents a dramatic shift in carrying capacity within the heart, and thus represents a model for studying CF tissue composition at homeostasis and after injury. The molecular mechanisms that are responsible for sensing CF carrying capacity after injury and then communicating this information to the other cardiac tissue constituents and the immune system are unknown.

The Hippo pathway, a kinase cascade, is highly conserved organ size control pathway. The core Hippo pathway components include the Mst and Lats family kinases that are activated by physiologic inputs, such as cell density. When activated, Lats1 and Lats2 phosphorylate the downstream effector Yap. Yap is a transcriptional coactivator that is excluded from the nucleus when phosphorylated by the Lats kinases. Inactivation of Hippo pathway components, Lats1 and Lats2, in CFs results in a cell state transition to myofibroblasts that mimics the cell state transition observed following MI. Single-cell transcriptomic analysis revealed that Lats1 and Lats2 (Lats 1/2) mutant CFs differentiated into myofibroblasts and concurrently promoted myeloid cell influx into the heart. Mutant CFs engaged both myeloid and non-mutant CFs via an expansive inflammatory cellular connectome of direct Yap target genes. Following MI, Lats1/2 mutant CFs failed to transition to matrifibrocytes that normally promote cardiac scar maturation. Thus, Hippo signaling inhibits activation of the cardiac wound response and dictates CF cell state, cardiac tissue composition, scar formation, and myocardial myeloid cell influx.

Yap Activity is Increased in Cardiac Fibroblasts after Myocardial Infarction

Figure 15A:
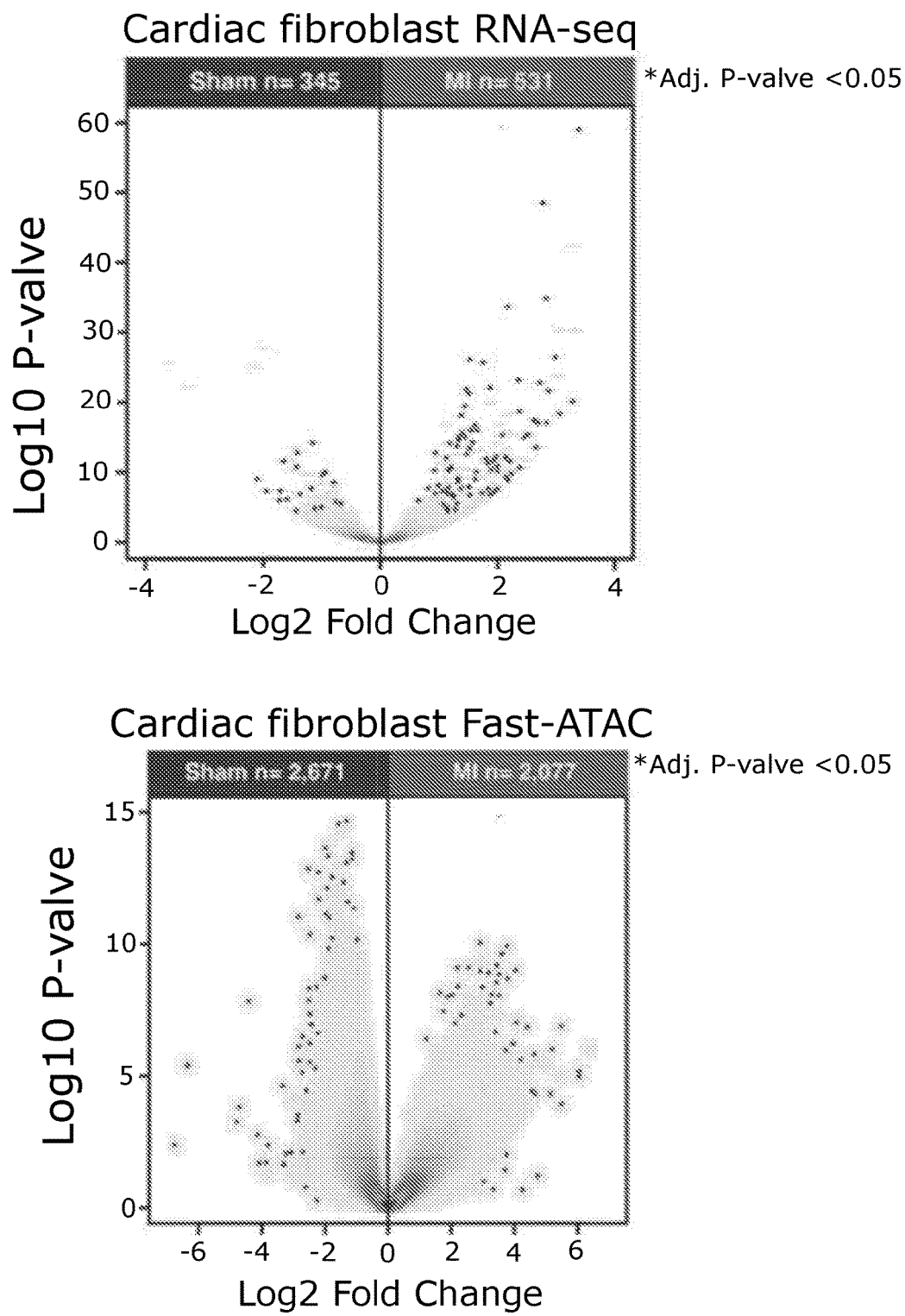
FIGS. 15A-15J. Yap is Activated in Cardiac Fibroblasts After Acute Myocardial Infarction in the Adult Heart.

To investigate the molecular regulation of CF cell fate transitions post MI, the global transcriptomic and epigenomic landscapes present during the differentiation of resting CFs to myofibroblasts was characterized. To label CFs, a CF lineage tracing model was employed with Tcf21-iCre; mTmG mice which possess a tamoxifen inducible Cre recombinase (MerCreMer) knocked into the endogenous transcription factor 21 (Tcf21) locus (Acharya et al., 2011), as well as the mTmG double-fluorescent Cre reporter (Muzumdar et al., 2007). With the Tcf21-iCre; mTmG mouse, resting CFs are labelled with GFP. RNA-seq and Fast-Assay were performed for Transposase Accessible Chromatin (ATAC)(Corces et al., 2016) on FACS sorted GFP positive CFs from sham and 3-day-post-MI (3dPMI) adult murine hearts to examine gene expression and chromatin accessibility dynamics following injury. Global transcriptomic analysis revealed that 531 genes were significantly up-regulated and 345 genes were down-regulated in CF 3dPMI (adjusted p-value<0.05) (FIG. 15A). And, global differential chromatin accessibility analysis showed that 2077 peaks had increased accessibility while 2671 peaks reduced accessibility in CFs 3d PMI (adjusted p-value<0.05) (FIG. 15A).

Figure 15B:
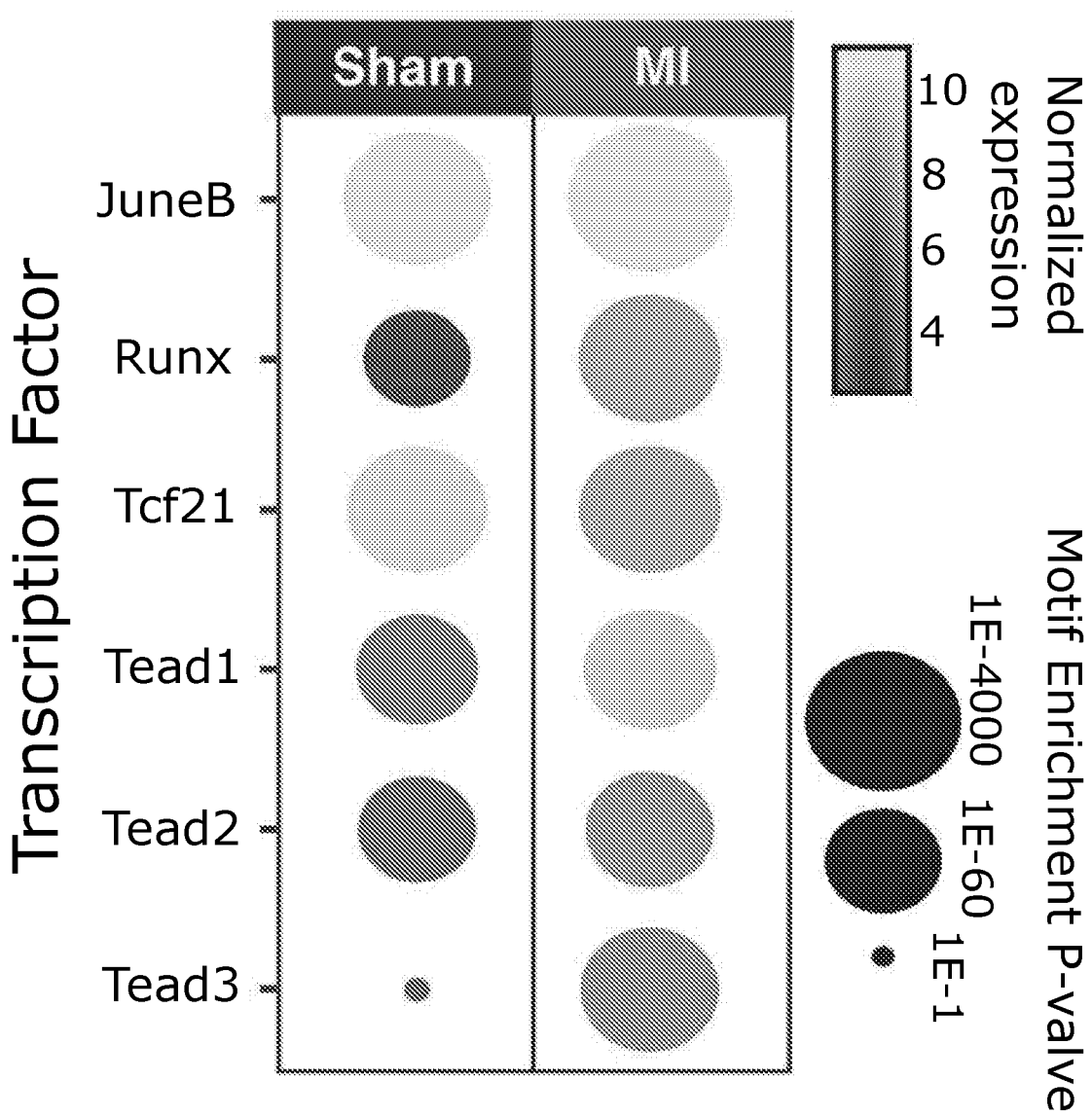

To identify the key transcriptional regulators involved in injury-induced CF differentiation, motif enrichment analysis was performed on the Fast-ATAC data (FIG. 15B). The Tcf21 motif was enriched and highly expressed in CFs from both sham and MI, indicating the successful sorting of Tcf21 lineage CFs. Post-MI there was strong enrichment of TEAD transcription factor motifs. TEAD transcription factors are DNA binding partners of the Yap transcriptional coactivator (Zhao et al., 2008; Moya and Halder, 2019). In addition to TEAD, motifs for the injury-associated transcription factors Runx and JunB were also enriched after MI. Correspondingly, the expression levels of these transcription factors were increased after MI (FIG. 15B). Indeed, AP1 complex components, such as JunB, have been shown to interact with TEAD and its transcriptional co-activator Yap at cis regulatory elements (Liu et al., 2016; Zanconato et al., 2015). Next, motif co-occurrence analysis was performed by looking at all TEAD motif containing ATAC peaks found in CFs after MI, and then investigating the density of AP1 and JunB motifs across these peaks (FIG. 22A). AP1 and JunB motifs were enriched at sites flanking TEAD motifs. The abundance of highly accessible TEAD and AP1-associated motifs, as well as their rapid increase at the transcriptional level 3 dPMI suggests a role for Yap and Hippo signaling in CFs during resting cardiac fibroblast differentiation.

Figure 15C:
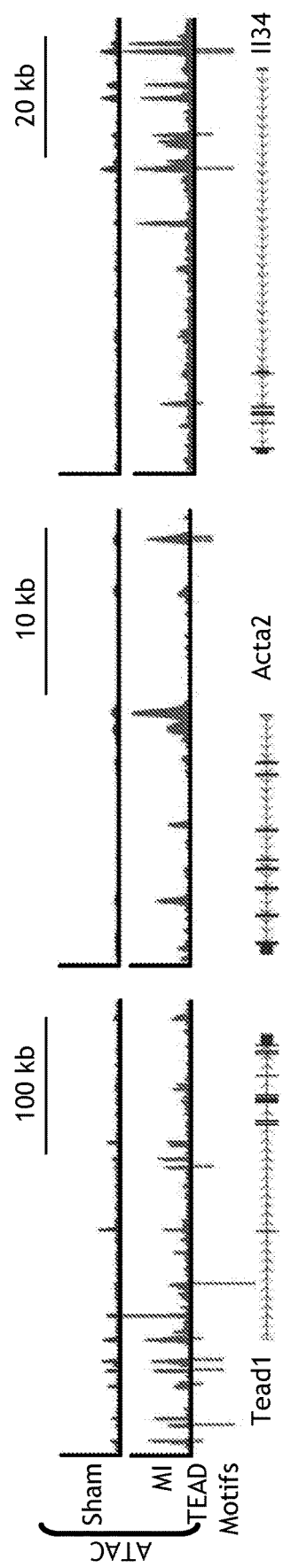
Figure 22B:
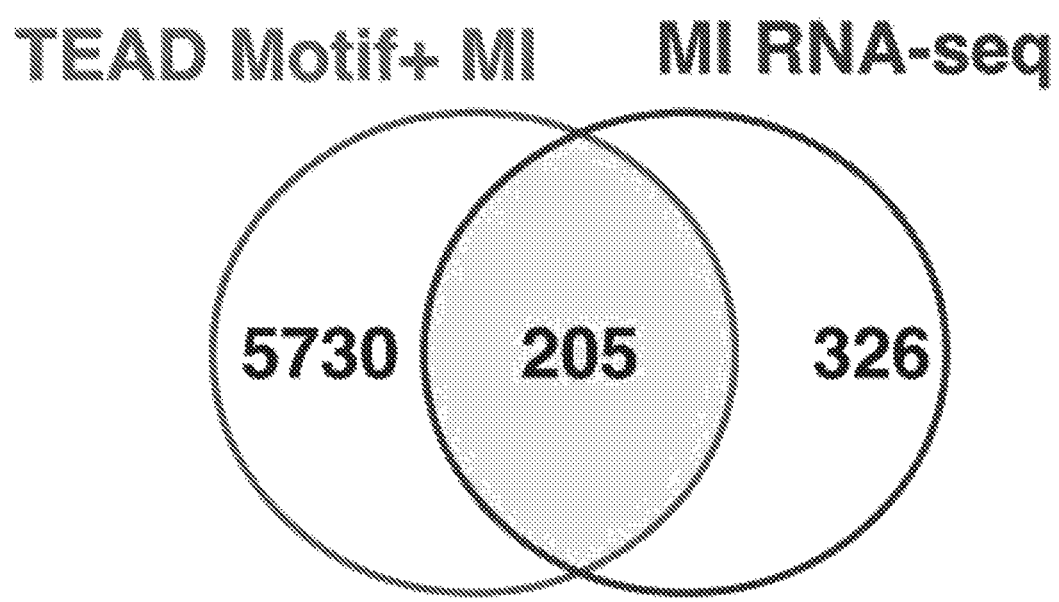
Figure 22C:
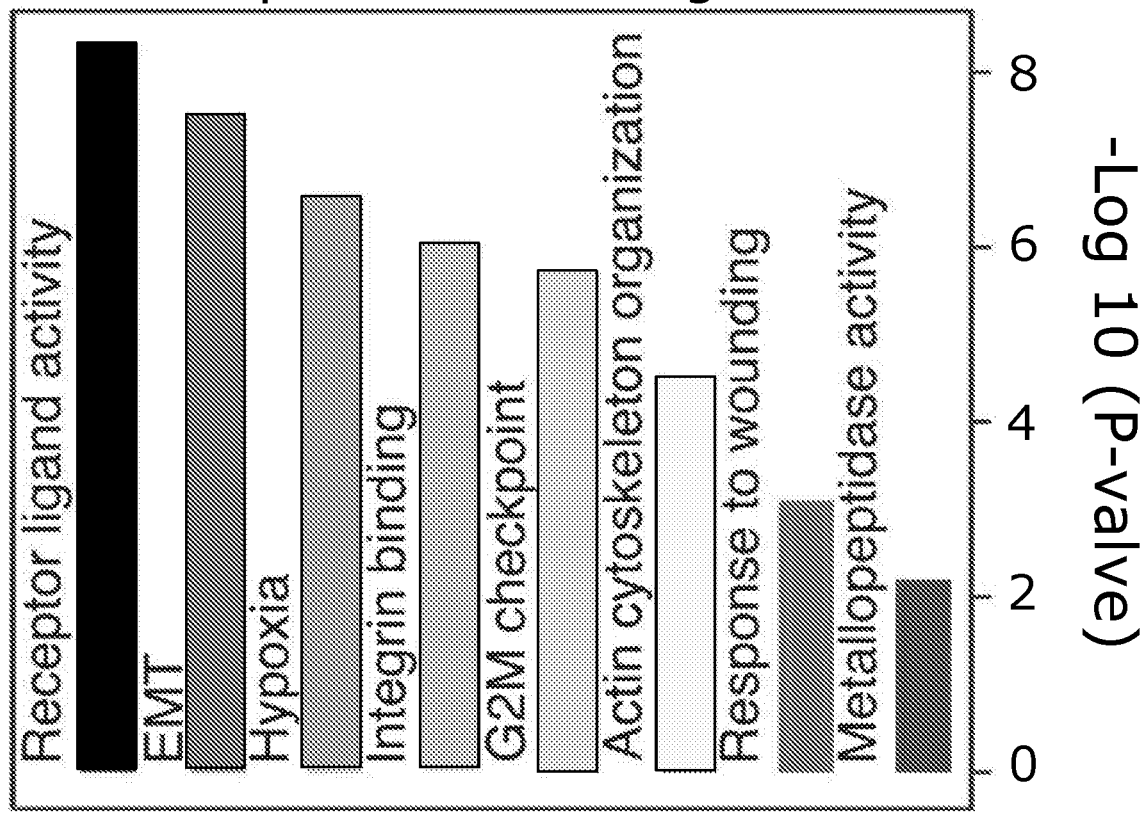

To characterize the Yap/Tead target genes and their respective molecular pathways and biological processes in CFs after MI, all TEAD motif containing Fast-ATAC peaks in CFs from 3d PMI hearts were annotated. These genes were overlaid with the up-regulated genes after MI and found that about one third of all up-regulated genes (205 genes out of 531 genes) contained ATAC peaks with a TEAD consensus motif (FIG. 22B). Gene ontology (GO) analysis revealed that upregulated genes with a TEAD motif are associated with injury response pathways such as epithelial-to-mesenchymal transition (EMT) and hypoxia. There were enriched terms like G2M checkpoint, which is consistent with recent work detailing the proliferation dynamics of cardiac fibroblasts after injury (Fu et al., 2018a; Kanisicak et al., 2016; Moore-Morris et al., 2018). Notably, the two most enriched gene categories were receptor ligand activity and chemotaxis (FIG. 22C), with enriched genes such as Anxa1, Edn1, Ccl7, Nov, and Il34, which are known mediators of inflammation and potential inducers of monocyte recruitment to the infarct site. Several known Yap/TEAD target genes were more accessible after MI, including Tead1 (FIG. 15C). Importantly, the myofibroblast identity gene Acta2 was also significantly upregulated after MI and contained an ATAC peak containing a TEAD motif (FIG. 15C).

Figure 15D:
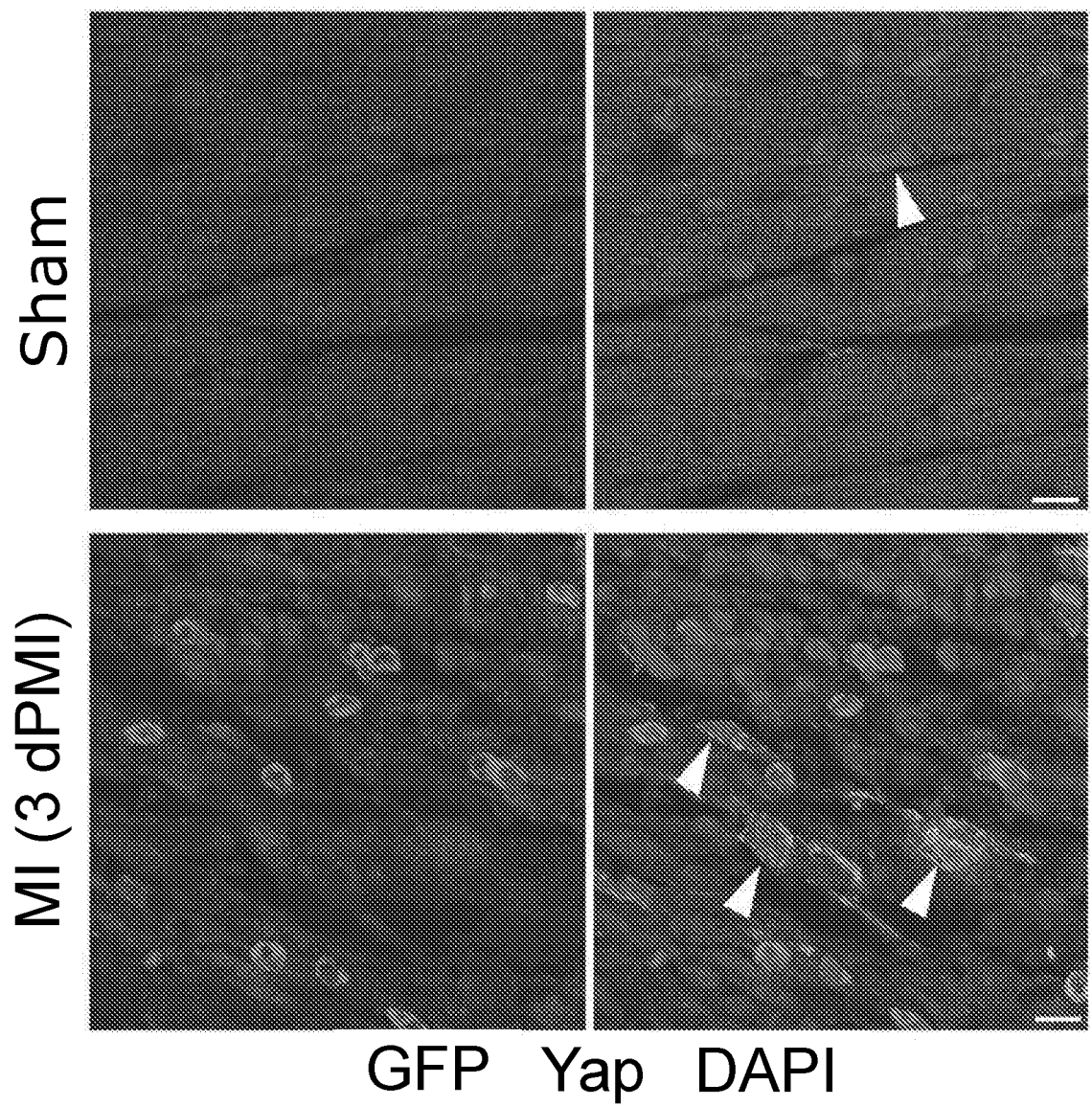
Figure 22D:
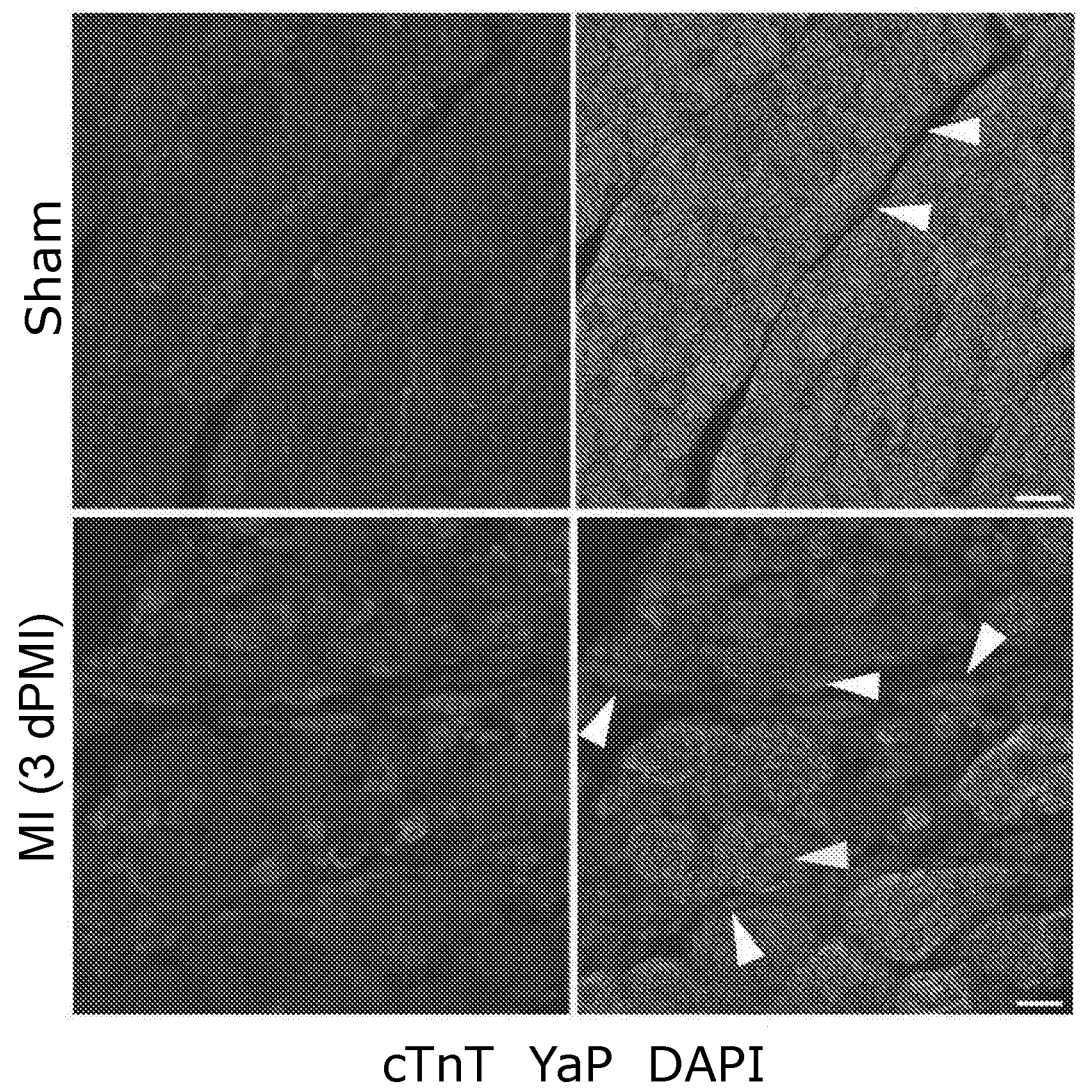

Since the global profiling suggested a role for Hippo-Yap signaling following MI in CFs, Yap subcellular localization was determined in CFs using confocal microscopy on immunofluorescent (IF) stained tissue sections. CFs were delineated as GFP positive cells derived from the Tcf21 lineage while cardiomyocytes were identified via their expression of cardiac troponin T (cTnT). CFs showed increased nuclear Yap at 3 dPMI (FIG. 15D). Consistent with previous findings (Del Re et al., 2013) there was enhanced nuclear Yap in a small number of cardiomyocytes 3 dPMI (FIG. 22D). This suggests that the Yap/TEAD gene regulatory network (GRN) in CFs is important for myofibroblast differentiation following MI.

Genome-Wide Myofibroblast Yap Chromatin Occupancy Mapping Via CUT&RUN

Figure 15E:
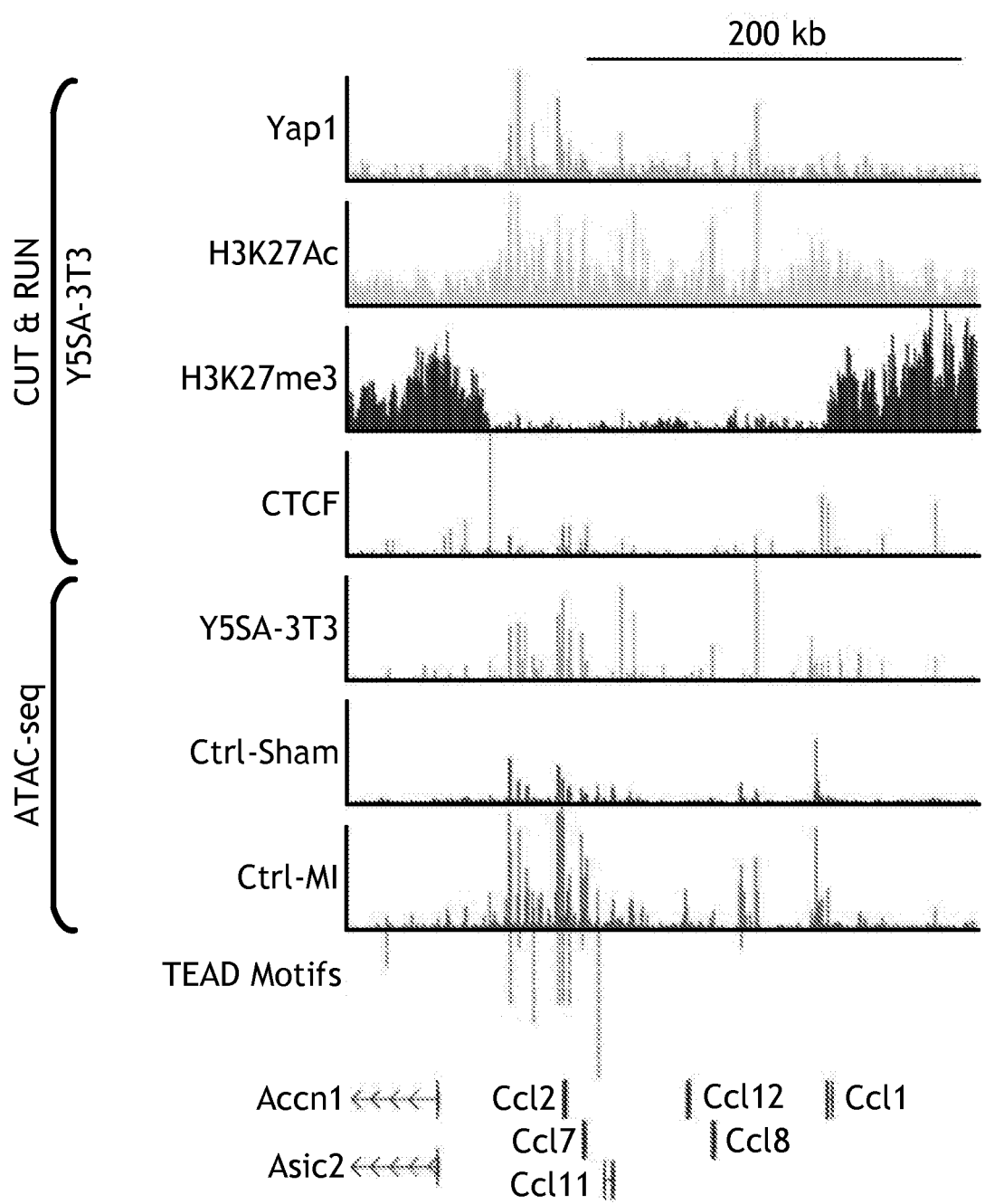

To gain insight into the direct transcriptional targets of Yap in fibroblasts CUT&RUN (Cleavage Under Targets and Release Using Nuclease) was performed, a protein-DNA interaction mapping methodology that relies on the antibody-based recruitment of micrococcal nuclease (Skene and Henikoff, 2017). This experiment was performed in NIH3T3 fibroblasts, which possess high Yap activity (Ota and Sasaki, 2008; Zhao et al., 2007), and express many myofibroblast markers. Also profiled were NIH3T3 fibroblasts stably expressing a YAP protein in which the serine residues phosphorylated by Lats1/2 have been mutated to alanine, referred to as YAP5SA. To comprehensively profile the epigenetic landscapes of the NIH3T3 fibroblasts, Fast-ATAC was performed to investigate chromatin accessibility in addition to H3K27ac, H3K4me3, and CTCF CUT&RUN profiling (FIG. 15E).

Figure 15F:
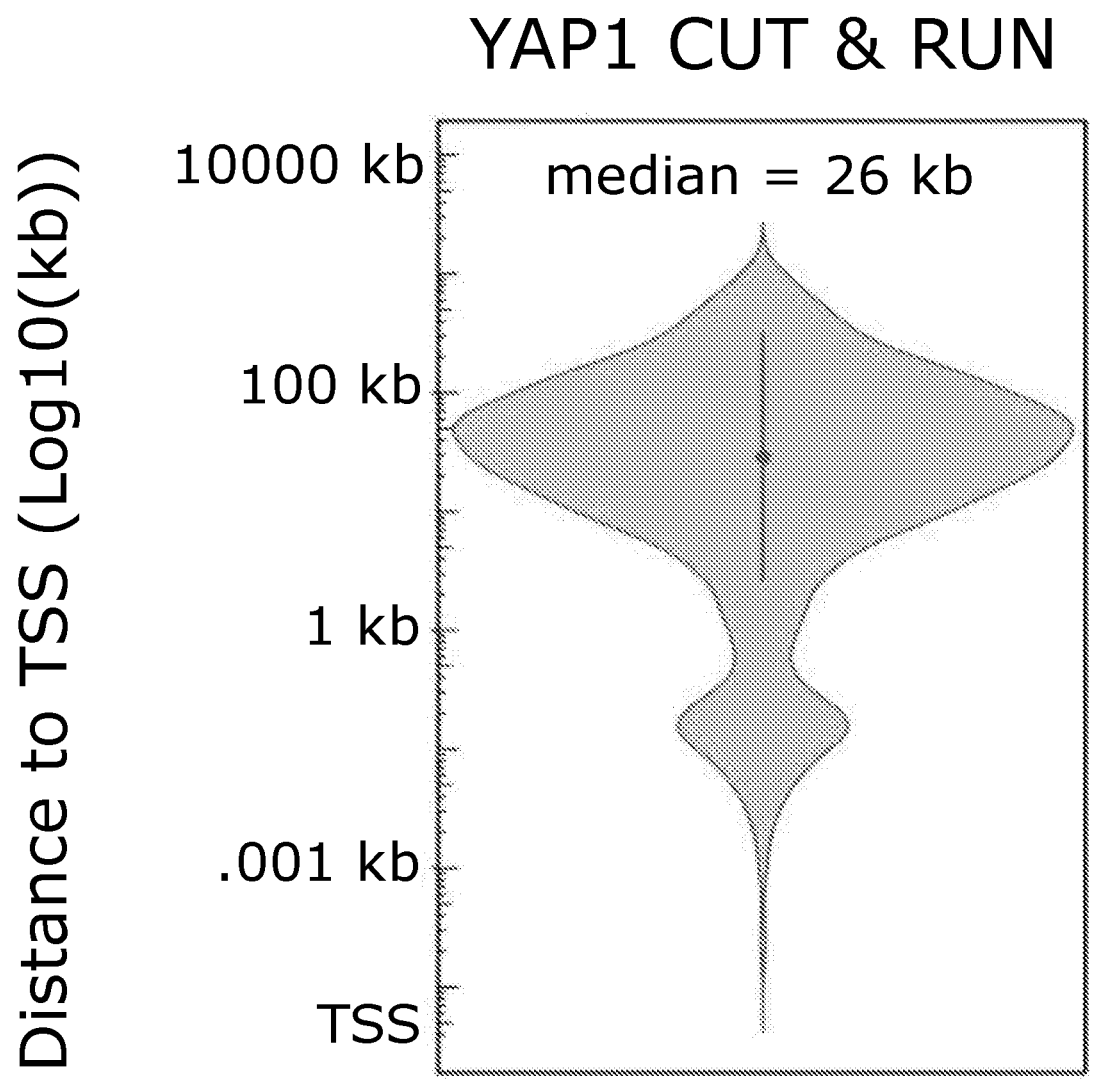
Figure 15G:
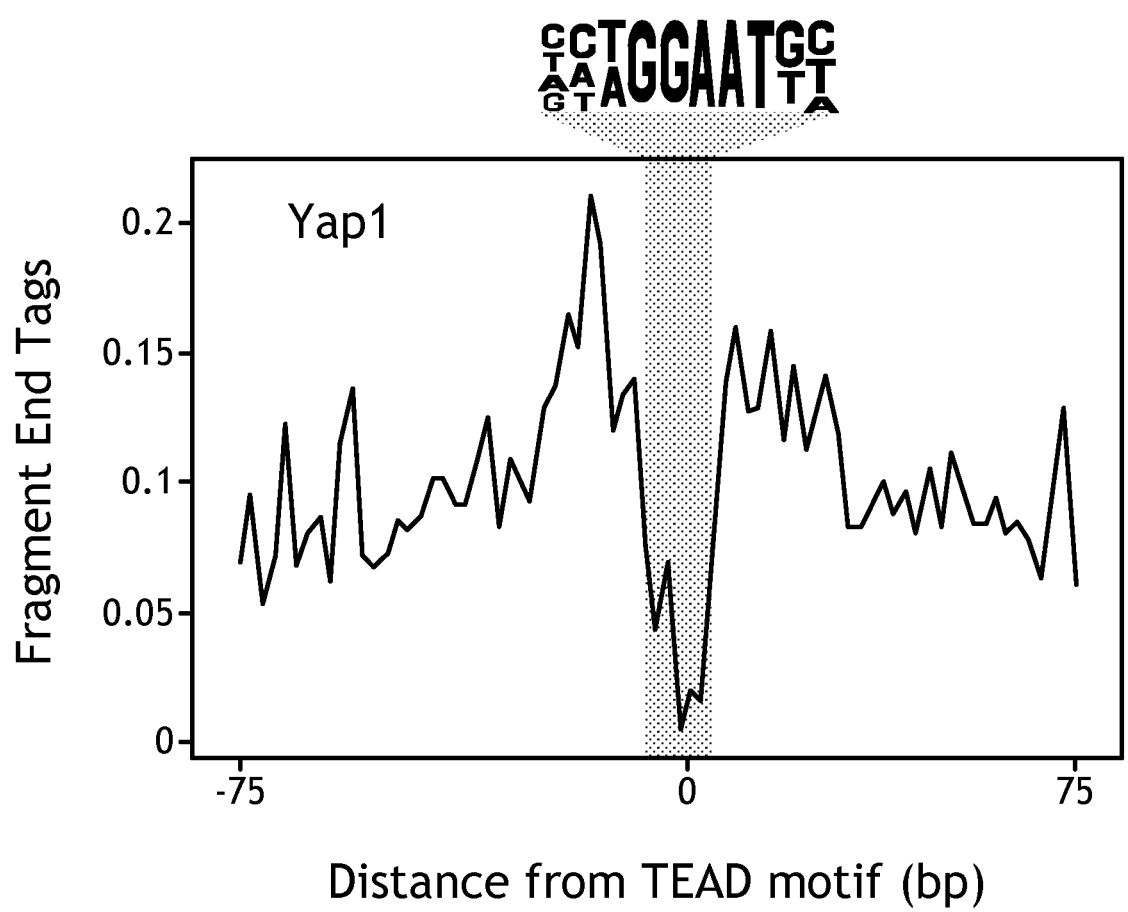
Figure 22E:
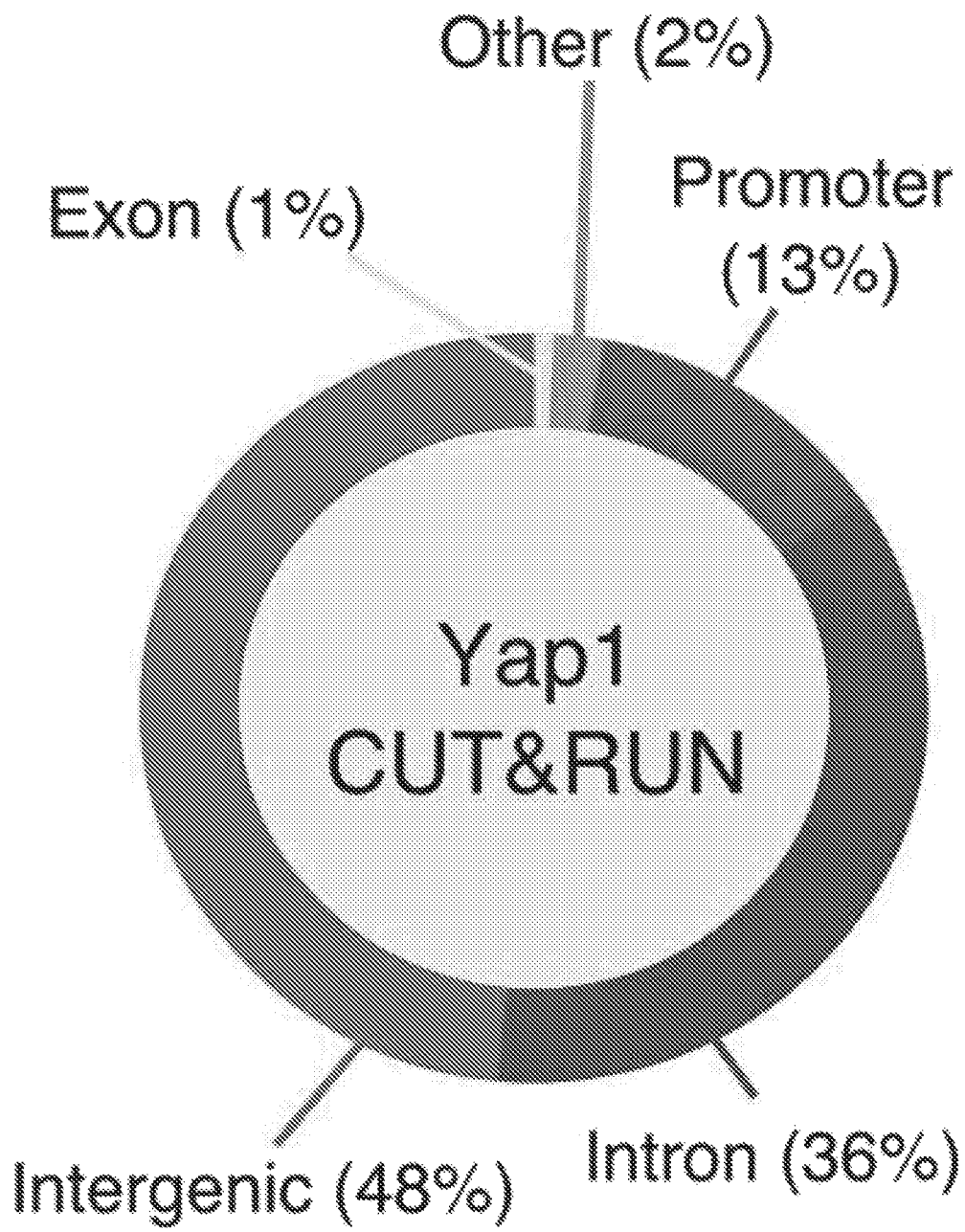
Figure 22F:
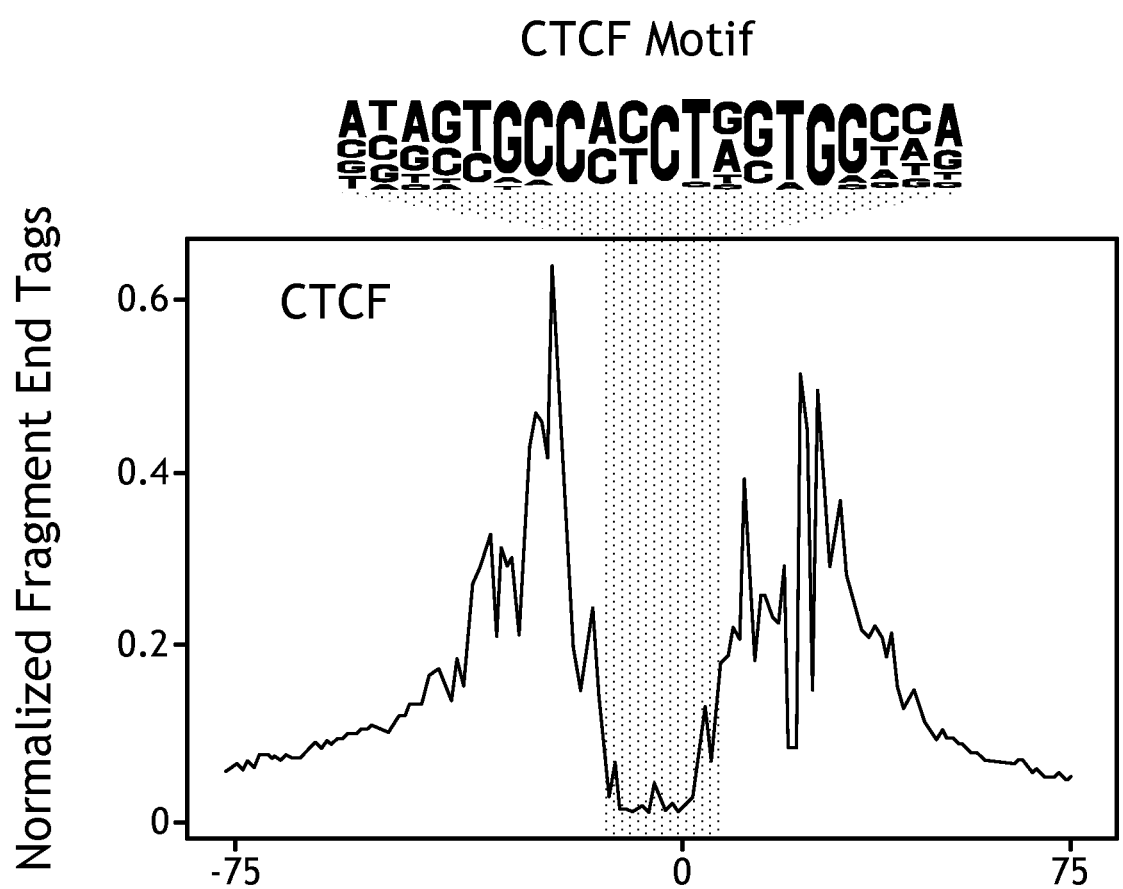

Yap binding was predominantly localized to intergenic and intronic regions (84% combined), and only 13% of peaks were found in promoters (FIG. 22E). The median distance of Yap to the transcriptional start site (TSS) was 29 kb (FIG. 15F), consistent with previous YAP epigenome occupancy profiling (Galli, et al. 2015). To estimate the resolution of CUT&RUN in fibroblasts, there was plotted the sequenced fragment ends centered around CTCF motifs and TEAD motifs. For CTCF, there was a large, approximately 20 bp footprint, characteristic of CTCF occupancy (FIG. 22F). The TEAD footprint at Yap-bound sites was half the size of the CTCF footprint, commensurate with the length of the Tead DNA binding motif, indicating that CUT&RUN maps Yap occupancy at TEAD motif containing regulatory elements with high precision.

Figure 15H:
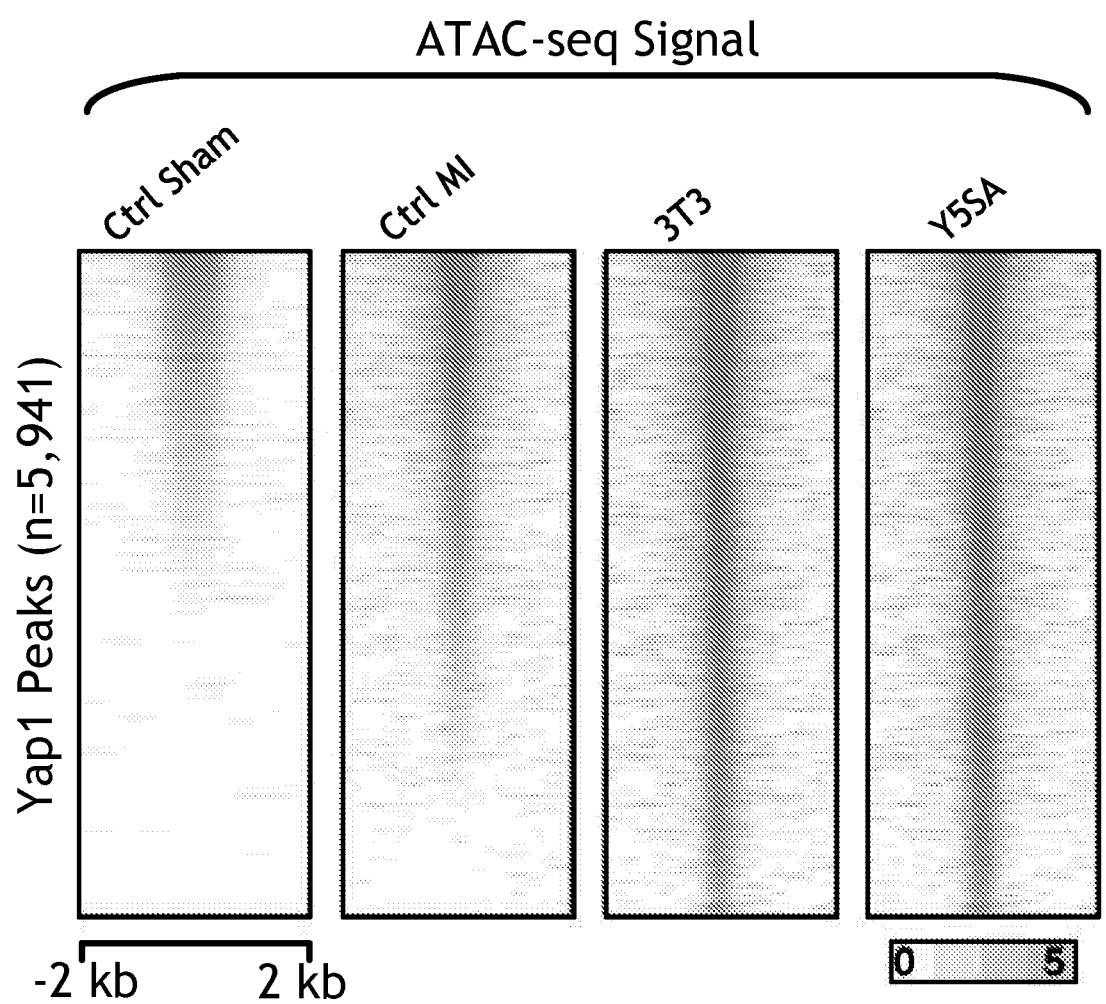
Figure 15I:
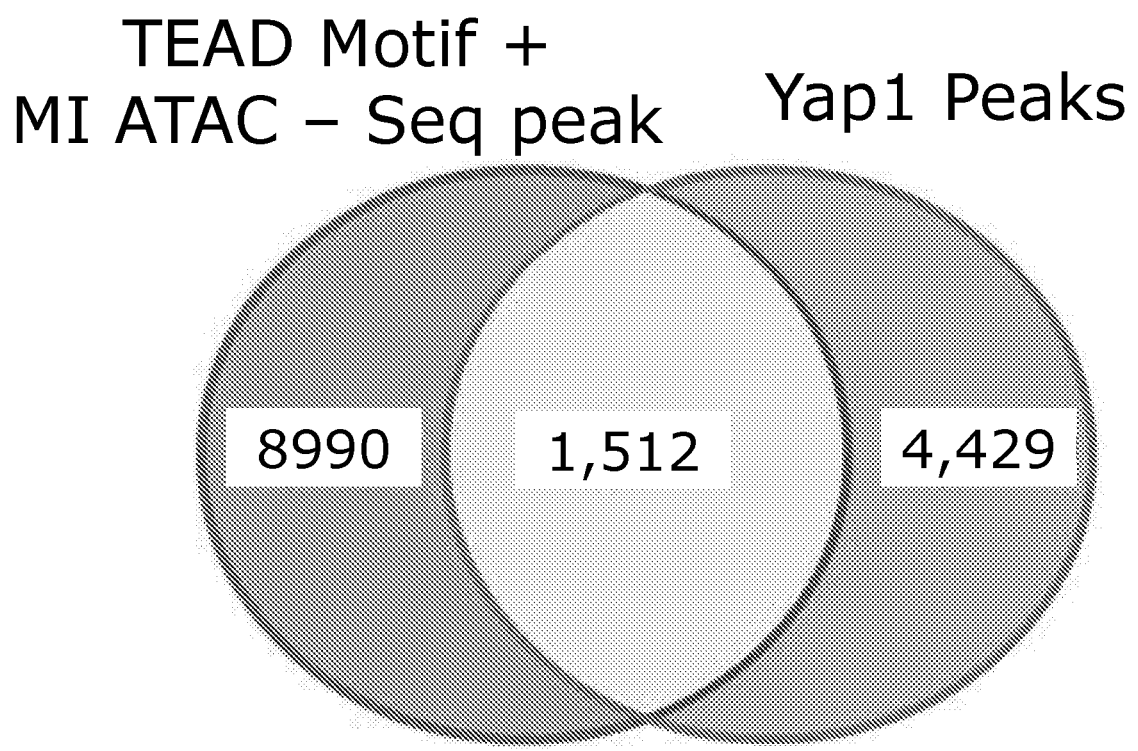
Figure 15J:
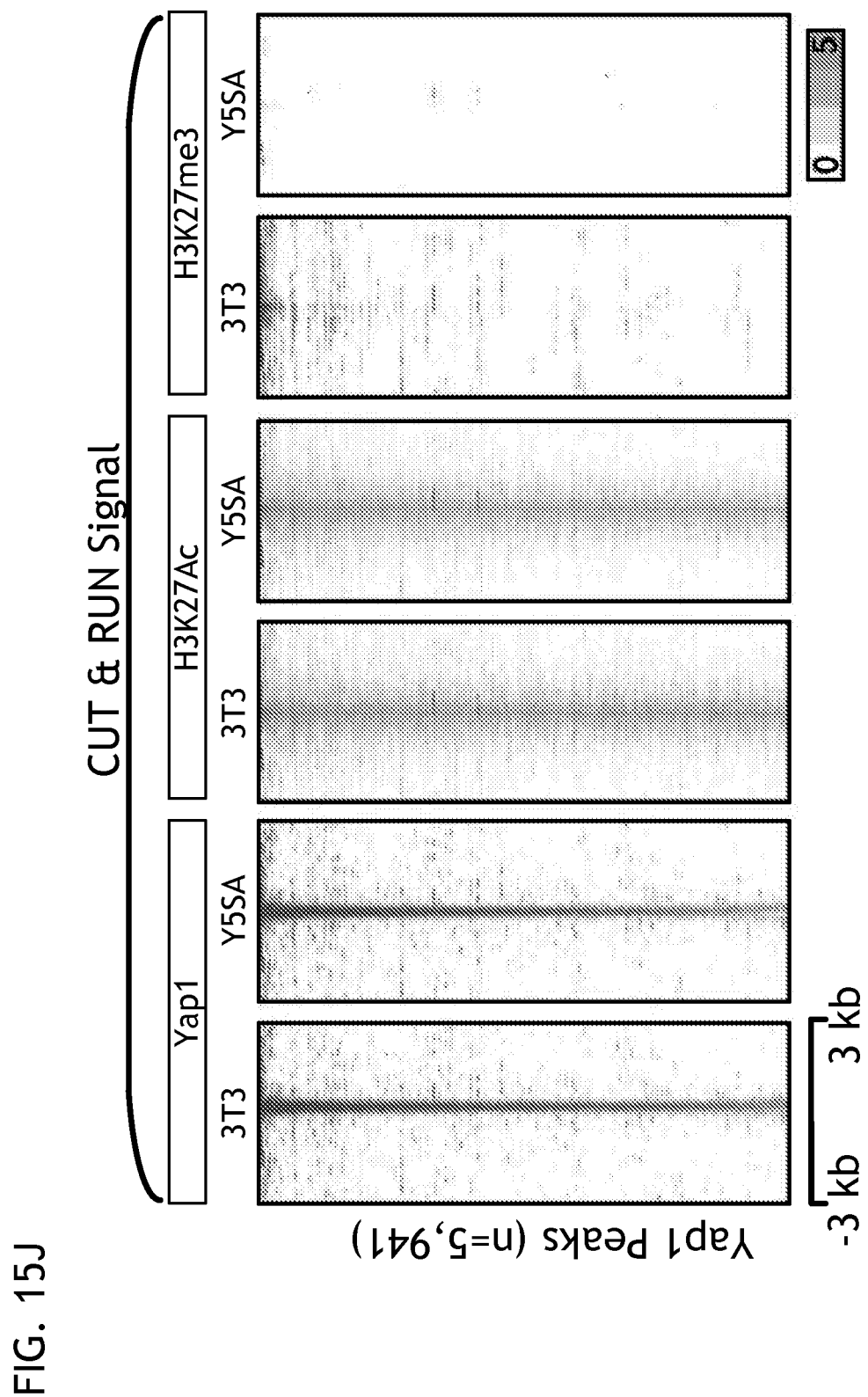

After peak calling and filtering (p-value<1e-5, see STAR methods), 5,941 Yap binding sites were identified in NIH3T3 fibroblasts. To interrogate the accessibility of these high confidence Yap sites in vivo, the ATAC-seq signal were looked at over these peaks in Sham CFs, MI CFs, NIH3T3 fibroblasts, and YAP5SA expressing NIH3T3 fibroblasts. While the highest chromatin accessibility of Yap sites was found in control NIH3T3 and YAP5SA NIH3T3 cells, the accessibility of Yap sites in CFs also increased after MI (FIG. 15H). Overall, 1,512 of the significant TEAD motif-containing ATAC peaks identified in vivo after MI in CFs (motif enrichment score>9.0) were also high confidence Yap binding sites (FIG. 15I). Moreover, Yap peaks possessed an active regulatory element status with high H3K27Ac enrichment and low H3K27me3 signal (FIG. 15J). Taken together, these data support the embodiment that Yap activity is increased in CFs after MI.

Yap Occupies Topologically Engaged Enhancers

Figure 16A:
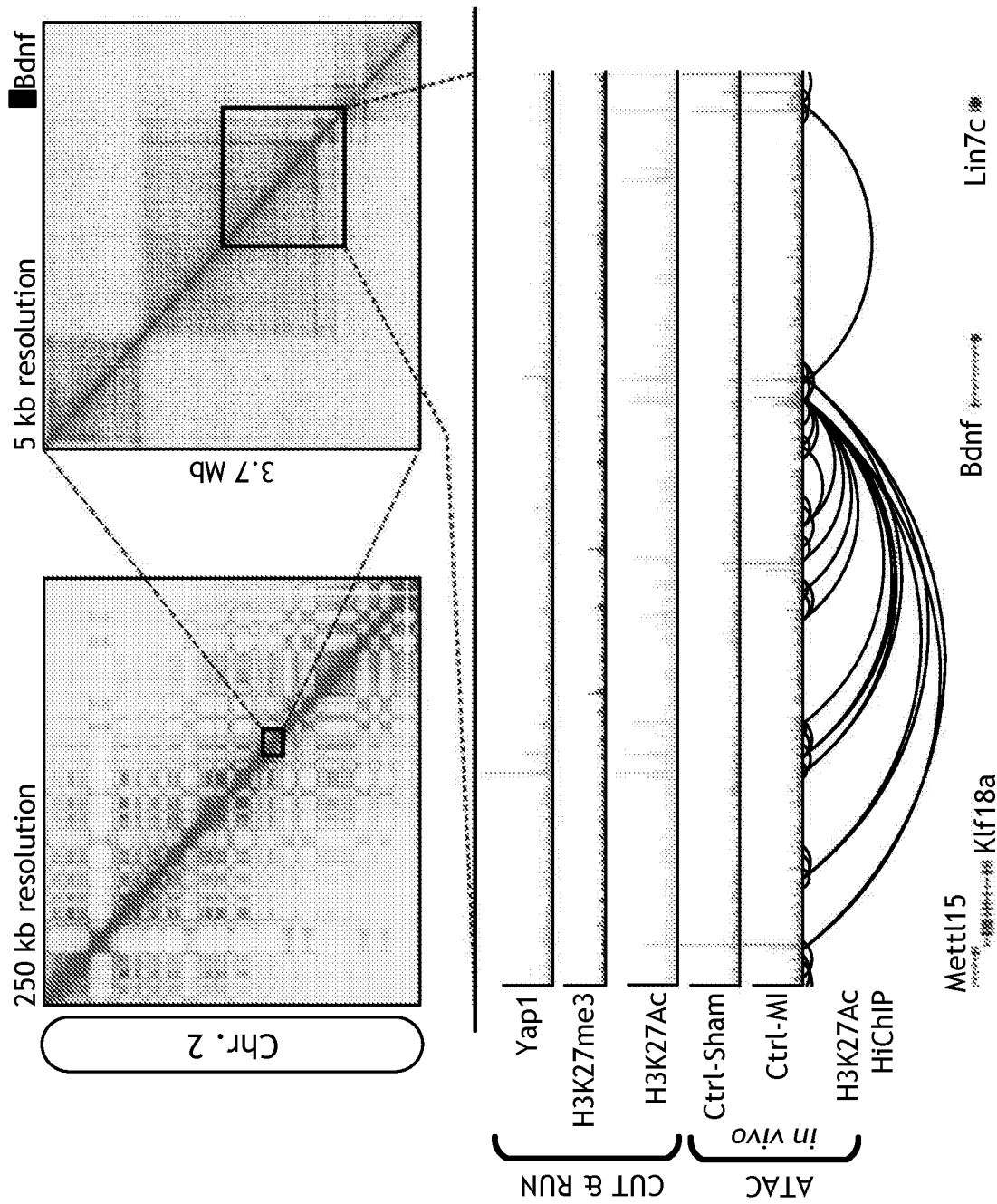
Figure 16B:
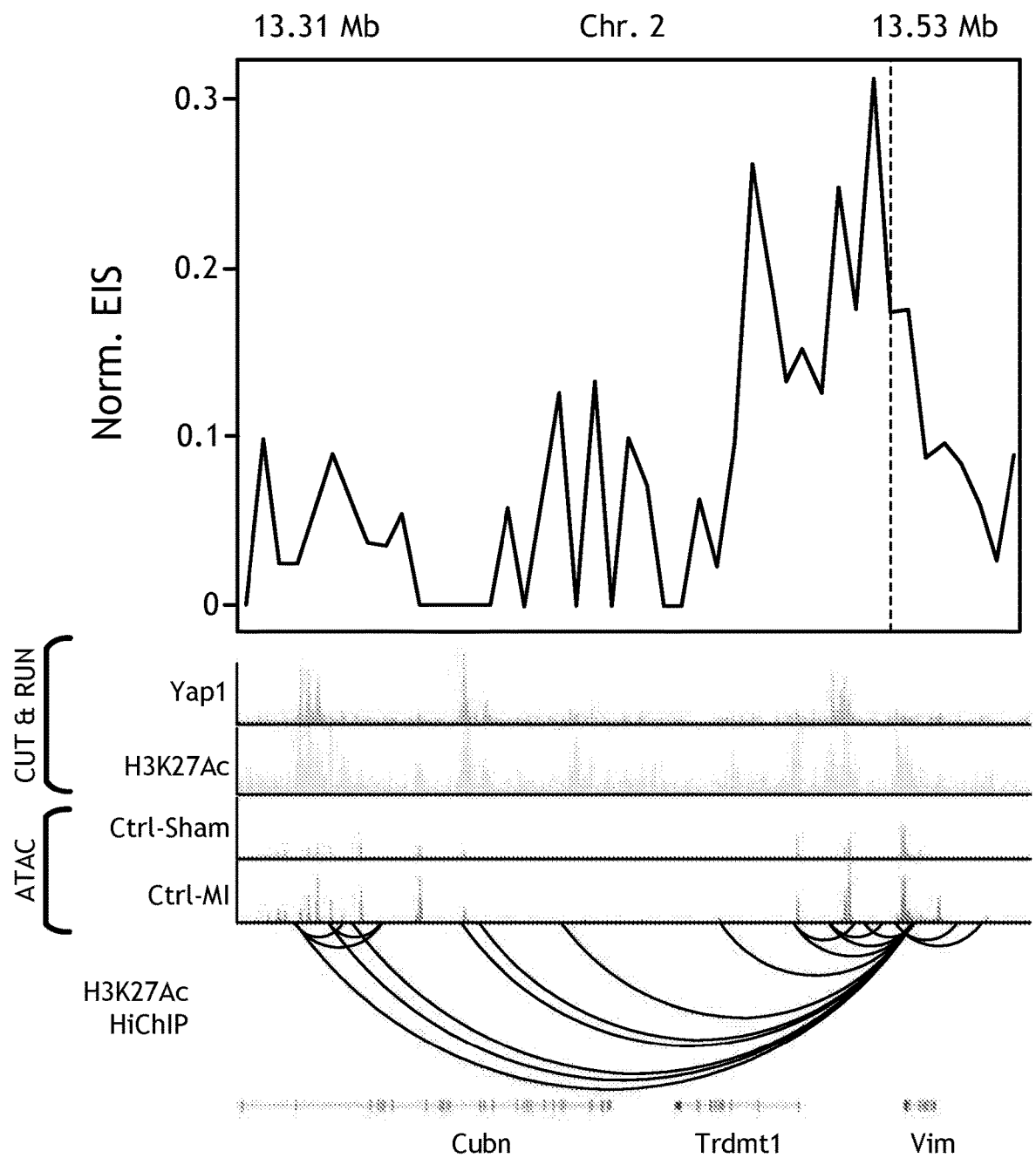
Figure 16C:
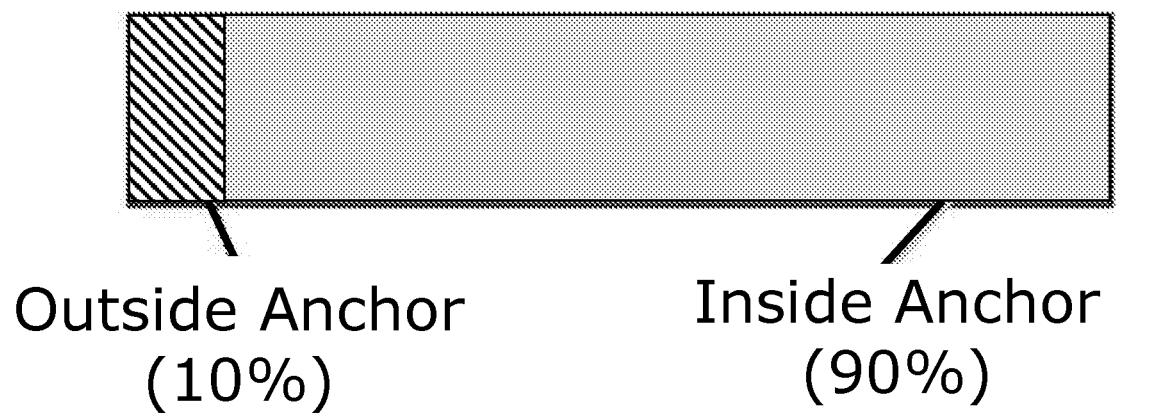
Figure 16D:
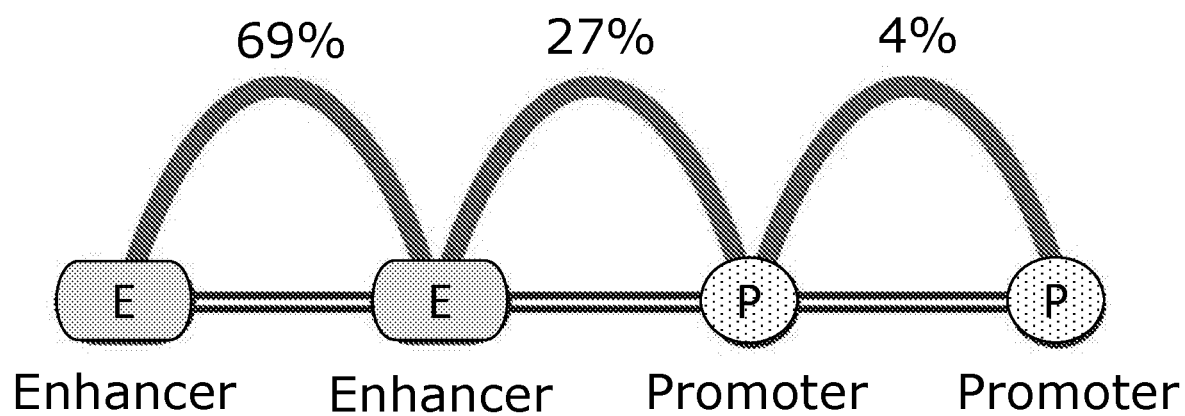
Figure 16E:
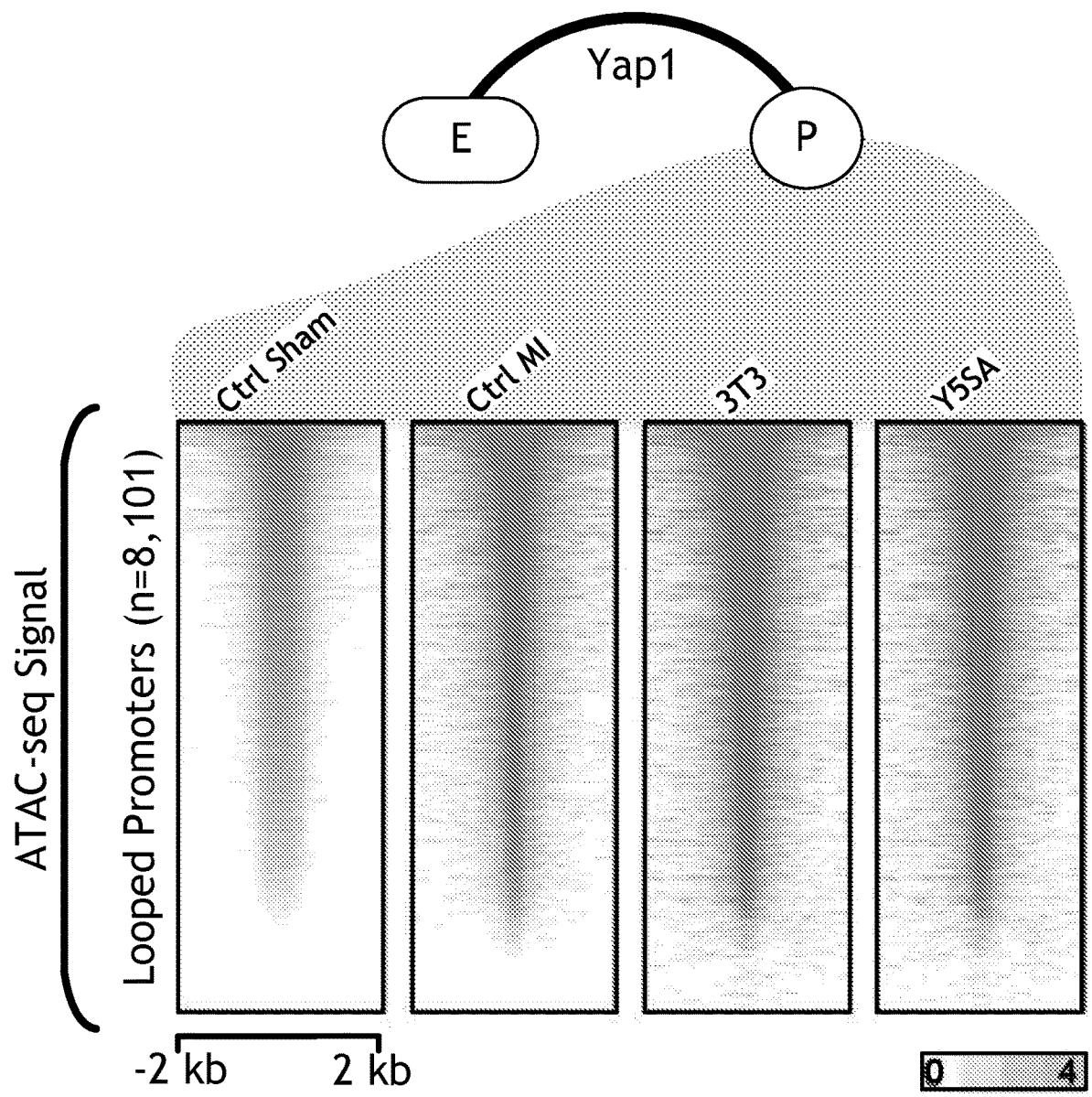

Yap binding sites contained high levels of H3K27Ac, consistent with their status as active regulatory elements as previously described in cancer cell lines (Galli et al., 2015; Zanconato et al., 2015). It is known that active distal enhancers form topological loops with promoters. The Yap-associated enhancer connectome was characterized in myofibroblasts using H3K27Ac HiChIP (Mumbach et al., 2017) (FIG. 16A). The HiChIP interaction matrix showed clear signs of chromatin compartments, topologically associated domains, and enhancer loops. The inventor identified the interaction of Yap occupied distal enhancers with the promoters of key myofibroblast genes and ligands, Bdnf and Vim (FIGS. 16A and 16B) that occurred through chromatin looping. Importantly, 90% of Yap peaks were positioned on H3K27Ac loop anchors (FIG. 16C). This experiment also revealed that Yap predominantly occupies enhancer-enhancer loops (69%), and enhancer-promoter loops (27%) (FIG. 16D). To investigate the activity of the identified Yap-occupied enhancer-promoter loops in vivo the accessibility was interrogated of the topologically linked promoters in CFs with and without injury. Promoters isolated from Yap occupied loops increased in chromatin accessibility after MI (FIG. 16E). Taken together, the results suggest that Yap occupies active enhancers in CFs and directly regulates the transcription of genes involved in the cardiac injury response.

Figure 17A:
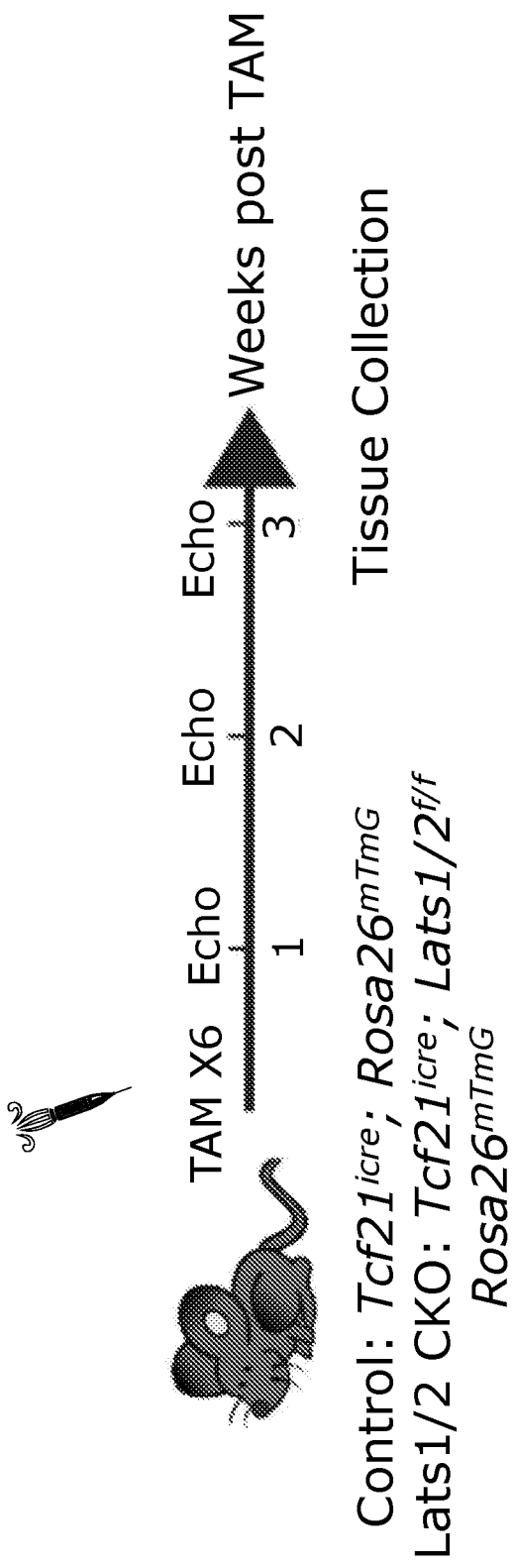
Figure 17B:
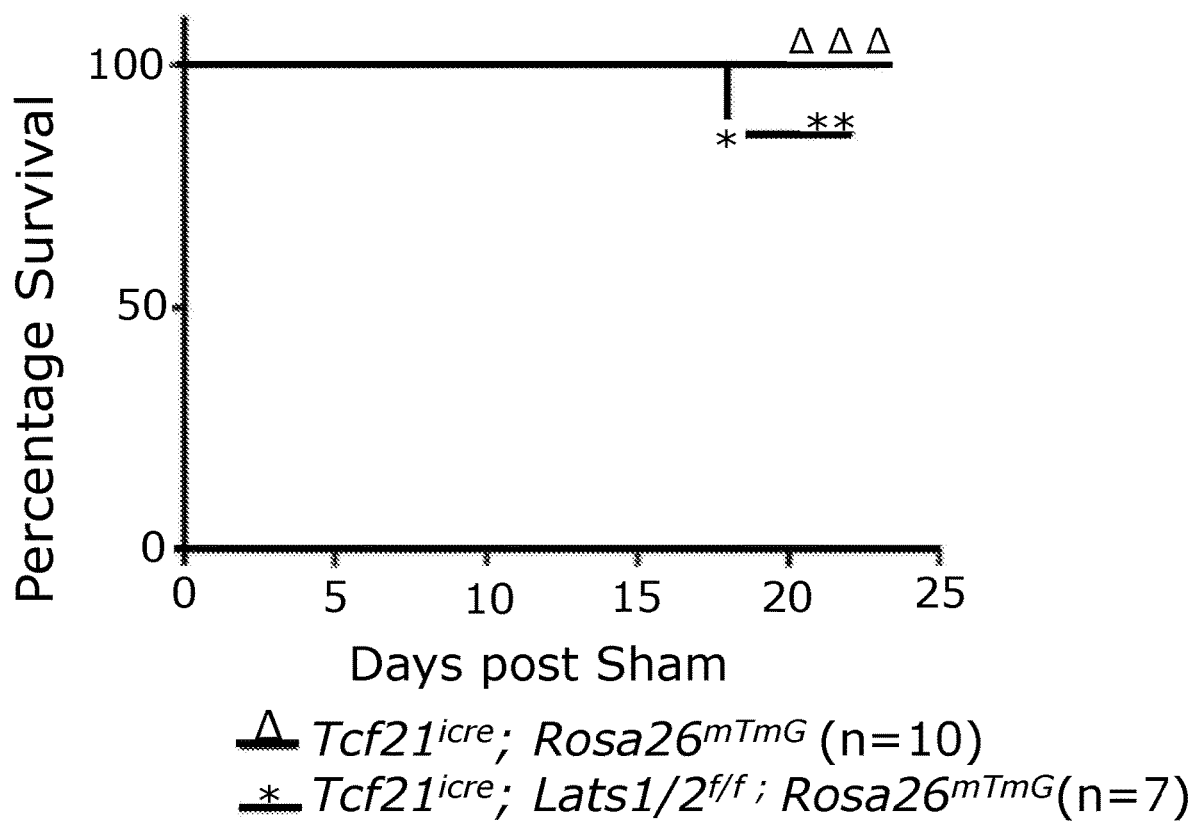
Figure 17C:
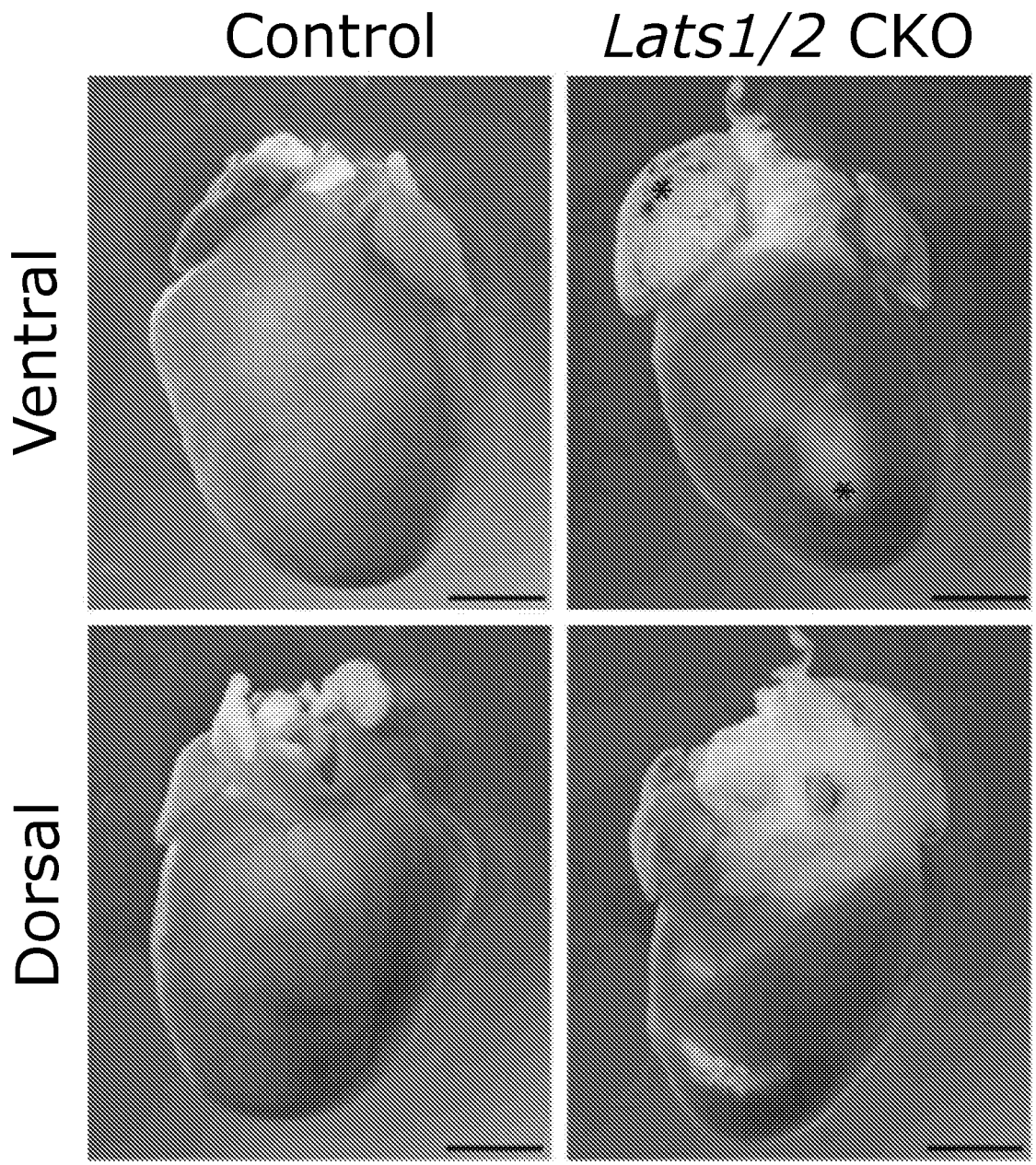
Figure 17D:
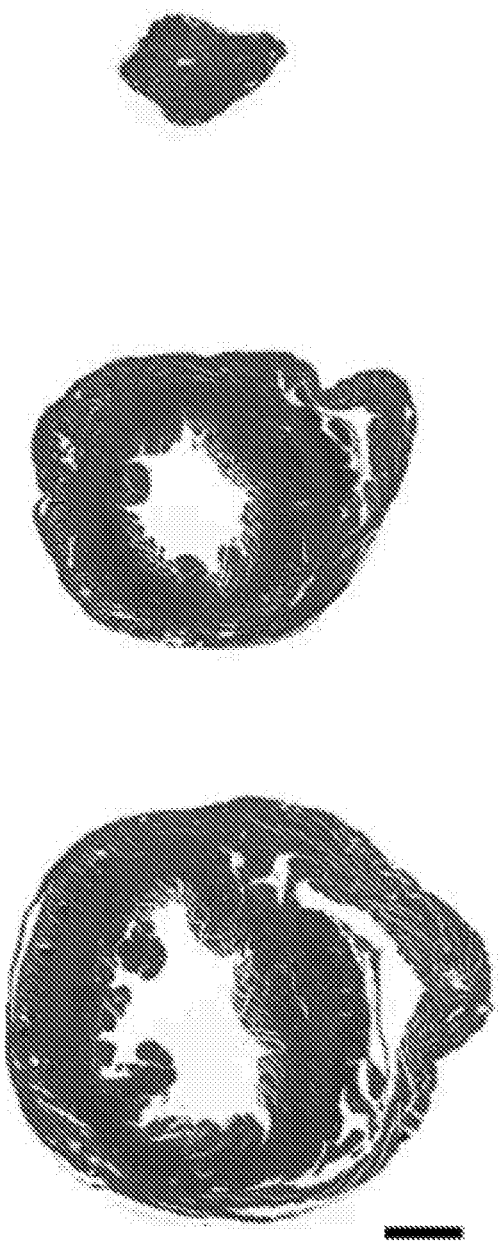
Figure 17D:
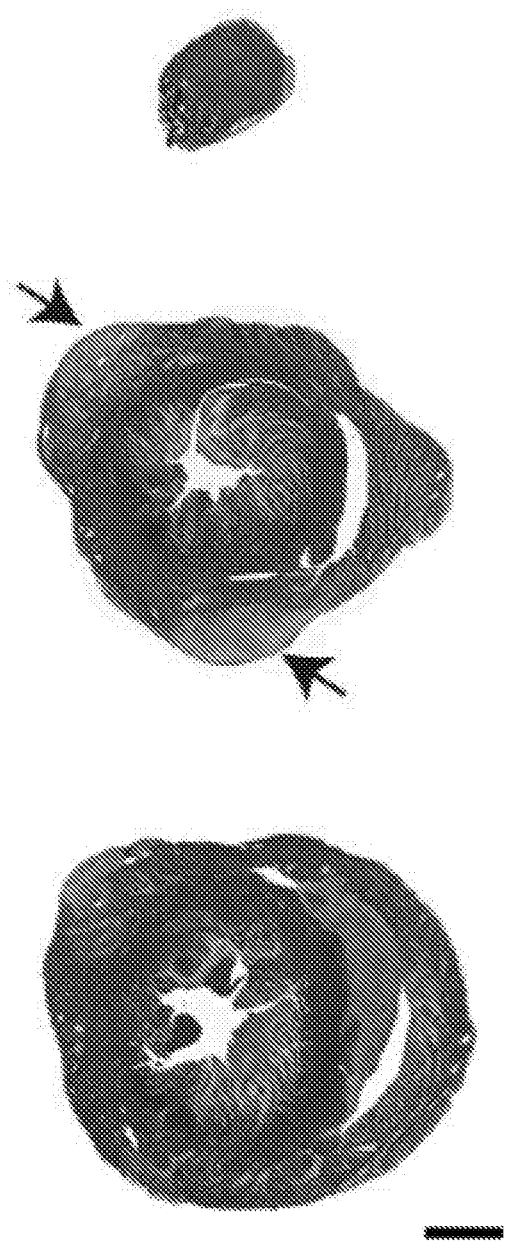
Figure 17E:
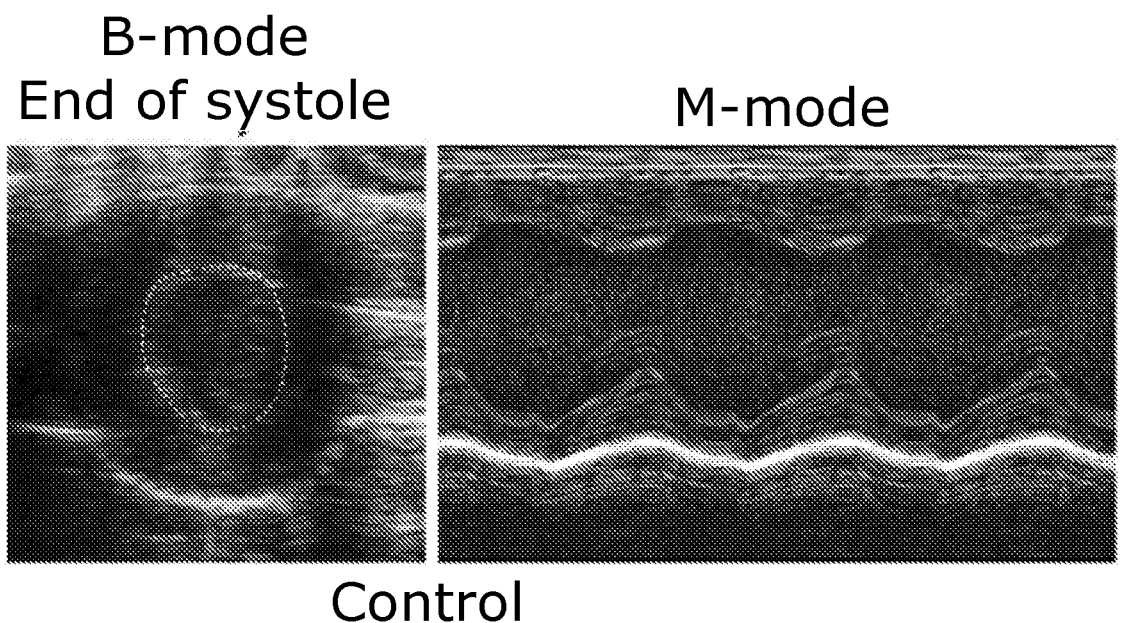
Figure 17E:
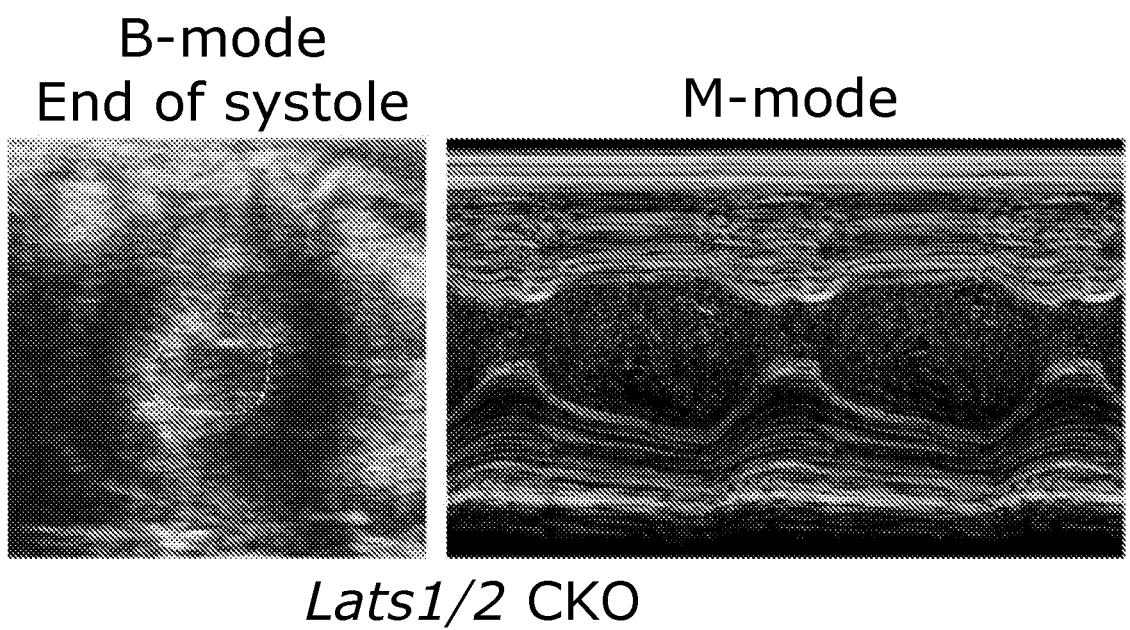
Figure 17F:
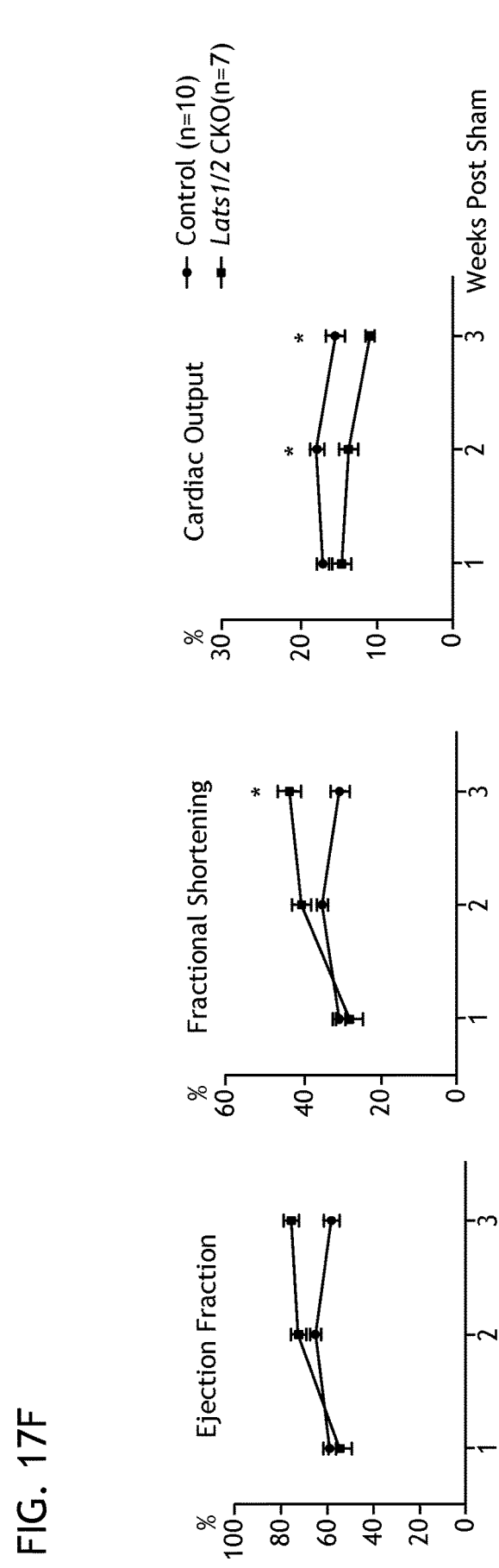

Inactivation of Lats1 and Lats2 in Resting Cardiac Fibroblasts Results in Fibrosis The nuclear activity of Yap is centrally repressed by the upstream Hippo pathway kinases Lats1 and Lats2 (Zhao et al., 2007). To directly investigate Lats1/2 function in resting CFs, Lats1 and Lats2 were disrupted in resting CFs using Tcf21iCre; Lats1$^{fl/fl}$; Lats2$^{fl/fl}$; mTmG mice, which henceforth is referred to as Lats1/2 CKO mice (FIG. 17A). The majority of Lats1/2 CKO animals survived until 3 weeks after inducing Cre activity (FIG. 17B). Strikingly, the gross heart morphology exhibited fibrosis in ventricles and atria and at the histologic level by Masson's Trichrome staining (FIGS. 17C and 17D). The aberrant fibrotic tissue observed in Lats1/2 CKO hearts was primarily localized to the outer and inner surfaces of the ventricular wall (FIG. 17D). Cardiac function was measured by echocardiography in control and Lats1/2 CKO hearts (FIGS. 17E and 17F). Three weeks after inactivating Lats1/2 in CFs, there was enhanced ejection fraction and fractional shortening with a reduction in cardiac output consistent with increased fibrosis in Lats1/2 CKO hearts. These data indicate that Lats1/2 expression in adult resting CFs prevents activation of the cardiac fibrotic response.

Lats1/2 Deletion in Cardiac Fibroblasts Disrupts Cardiac Tissue Composition

Cardiac tissue composition and transcriptional states were assessed to investigate in more depth if Lats1/2 repress the cardiac injury response, CF differentiation, and/or immuno-stimulation. To comprehensively capture the cellular heterogeneity, cell states, and cell state transitions in Lats1/2 CKO hearts, Drop-seq (Macosko et al., 2015) was performed 3-weeks following Tcf21-1Cre induction. After computational processing, batch correction, and unsupervised cell clustering (STAR Methods), the Tcf21-derived lineages were focused on, including epicardial cells and fibroblasts, as well as inflammatory cells.

Figure 18A:
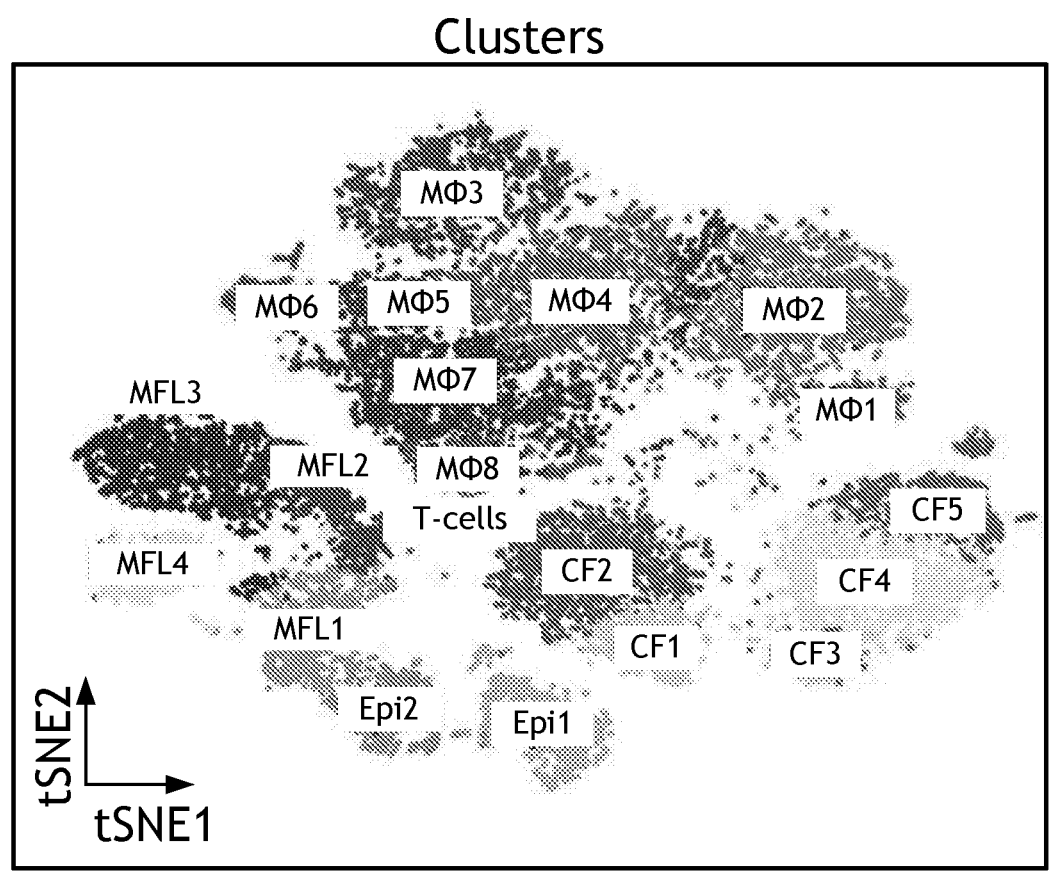
Figure 18B:
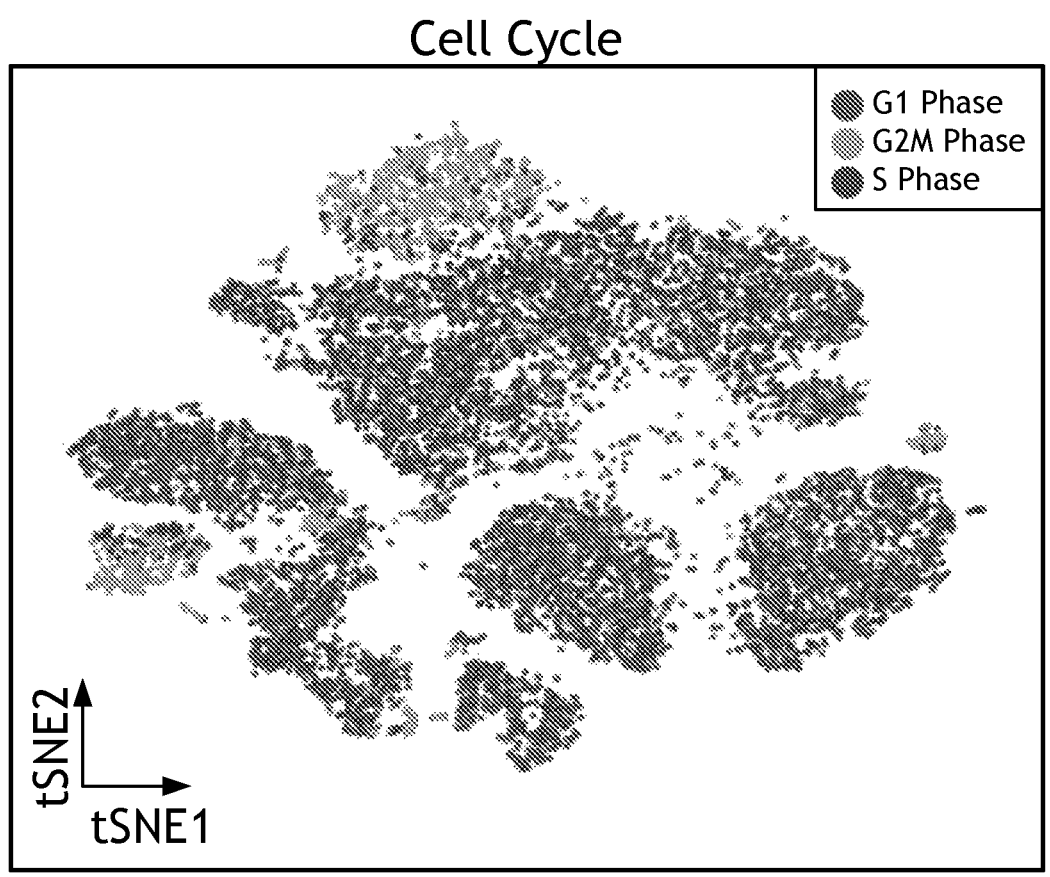
Figure 18C:
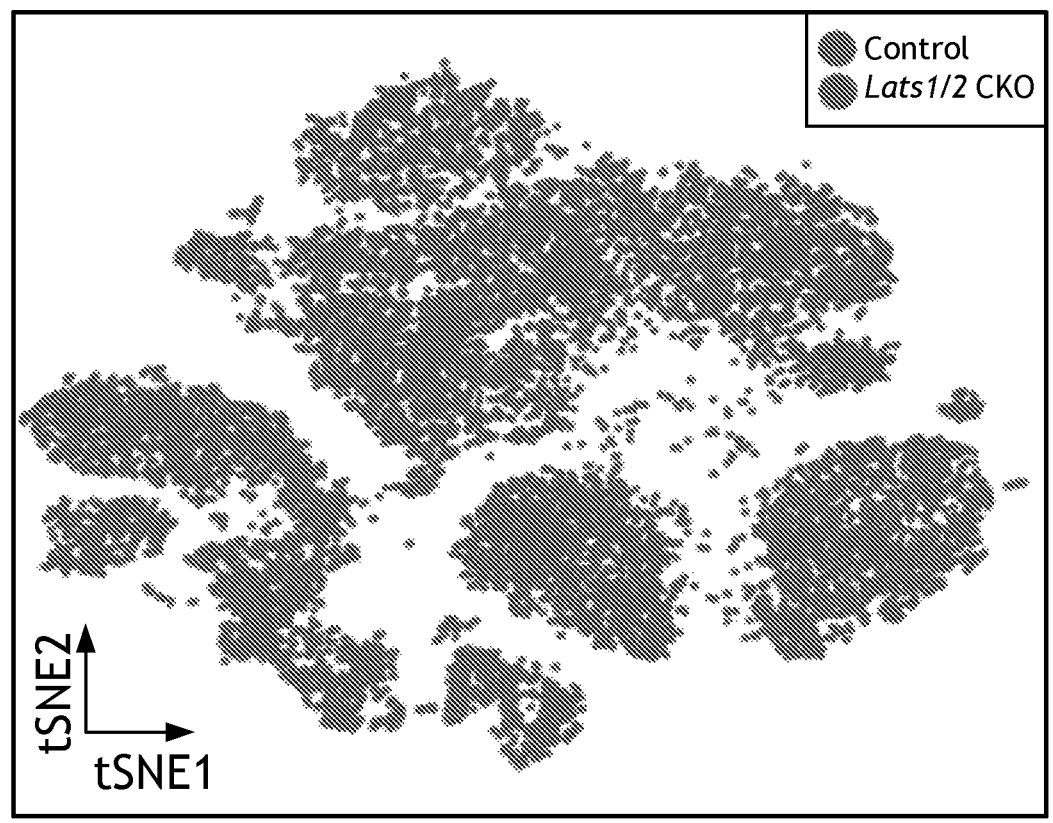
Figure 23A:
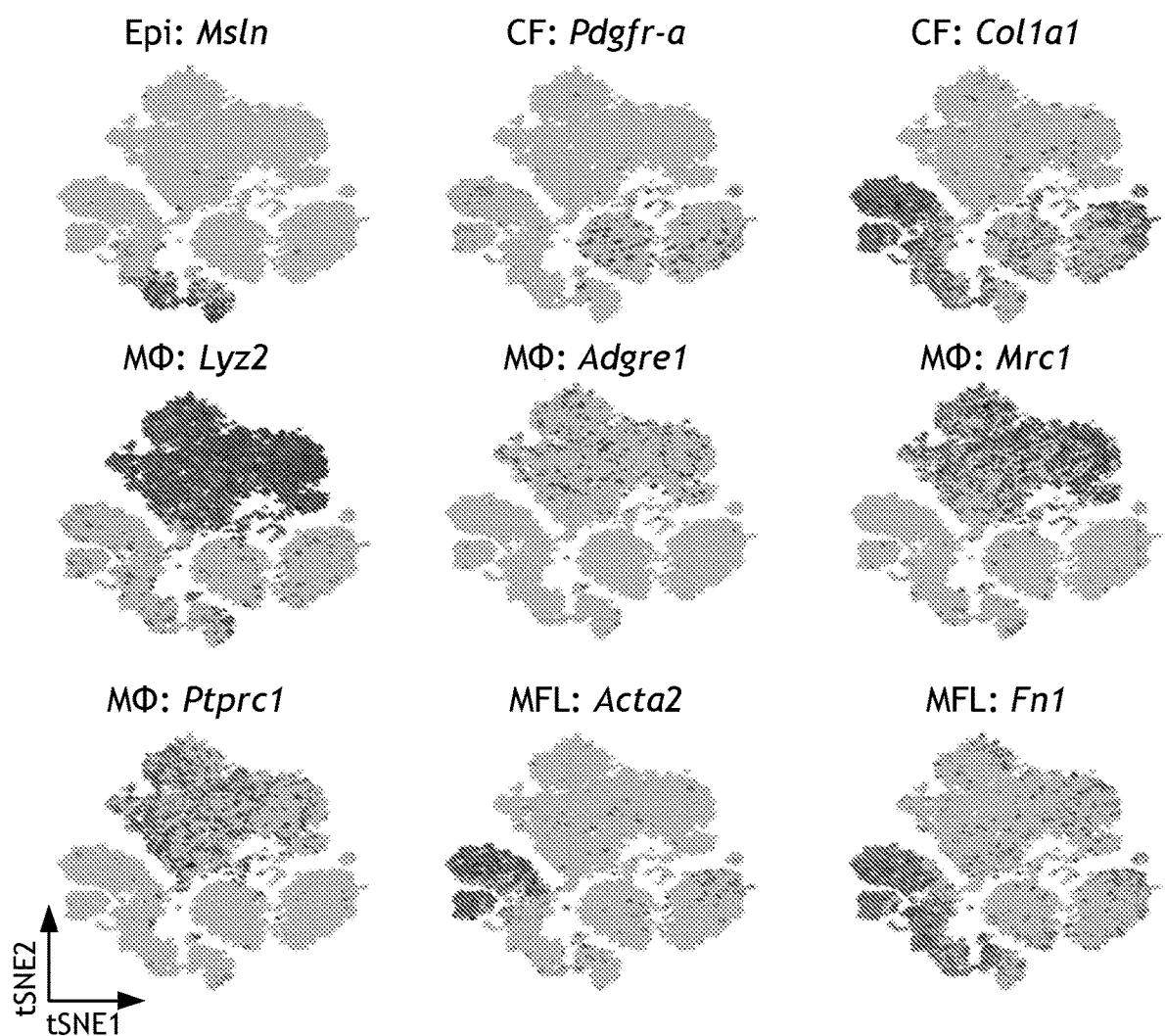
Figure 23B:
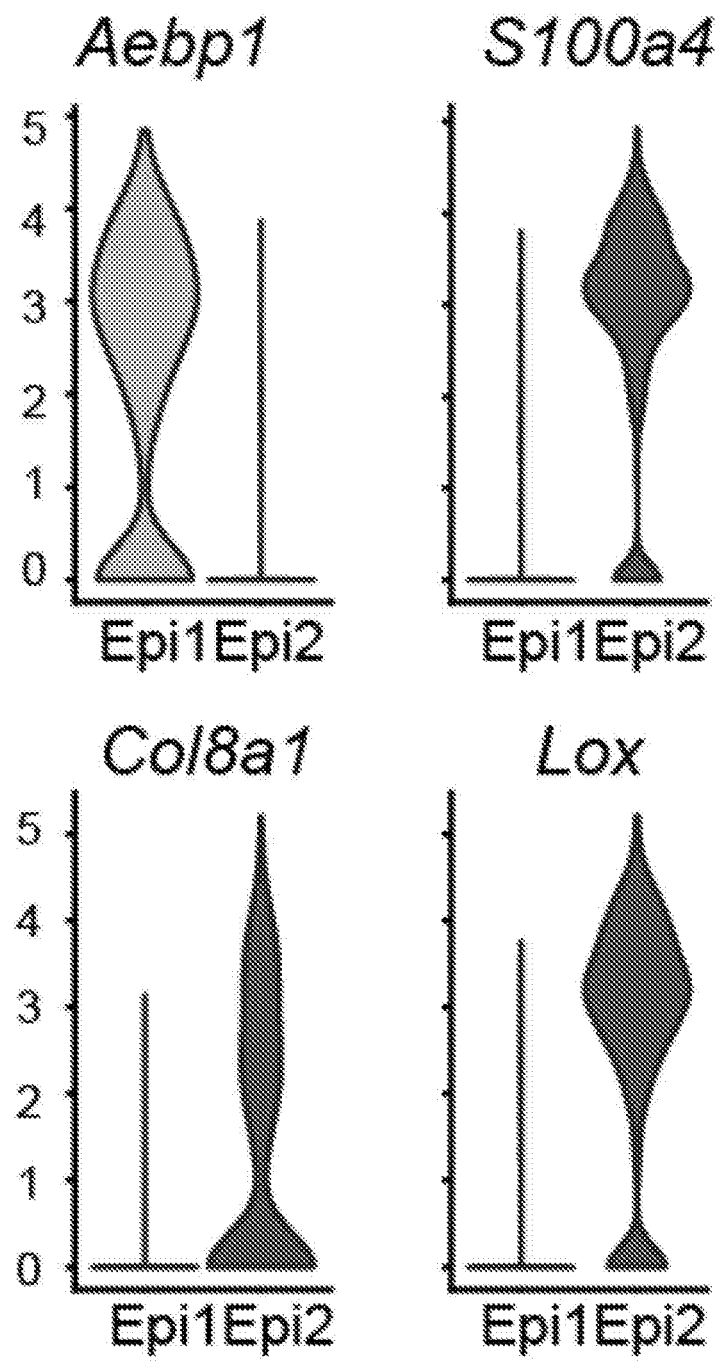

A total of 17,501 cells were captured that separated into 20 distinct clusters (FIG. 18A). There were two clusters of epicardial cells (Epi1-2) (Upk3b+ and Msln+), five clusters of cardiac fibroblasts (CF1-5) (Pdgfr-α+, Col1a1+), eight clusters of monocytes/macrophages (Mφ1-8) (Lyz2+, Adgre1+, Mrc1+, and Ptprc+), one cluster of T lymphocytes (T-cells)(Trbc2+ and Trac+) and four clusters of myofibroblast like cells (MFL1-4) (Acta2+ and Fn1+) (FIGS. 18A and 23A). MFLs, CF5, and Mφ3 were the most proliferative cell clusters based on transcriptional cell cycle phase determination analysis (see STAR Methods) (FIG. 18B). Strikingly, the differences in genotypic composition to each cluster were stark (FIG. 18C). Except T-cells and the Mφ8 cluster, all other clusters showed significantly different genotypic contributions as determined by chi-square statistical analysis (FIG. 18D).

The heterogeneity identified by Drop-seq was characterized. First, the two epicardial clusters Epi1 and Epi2 mainly comprised of cells from control and mutant hearts, respectively were evaluated (FIG. 18D). Compared to control-cell-dominant Epi1, the mutant-cell-dominant Epi2 cluster exhibited down-regulation of genes such as Aebp1 and the up-regulation of markers like S100a4, Col8a1, Lox (FIG. 23B), which have been shown to modulate fibrosis enhancing signals such as Tgf-β, Igf and Bmp signaling (Skrbic et al., 2015) suggesting that Lats1/2 CKO epicardial cells promote ECM collagen deposition in the Lats1/2 CKO heart.

Figure 18D:
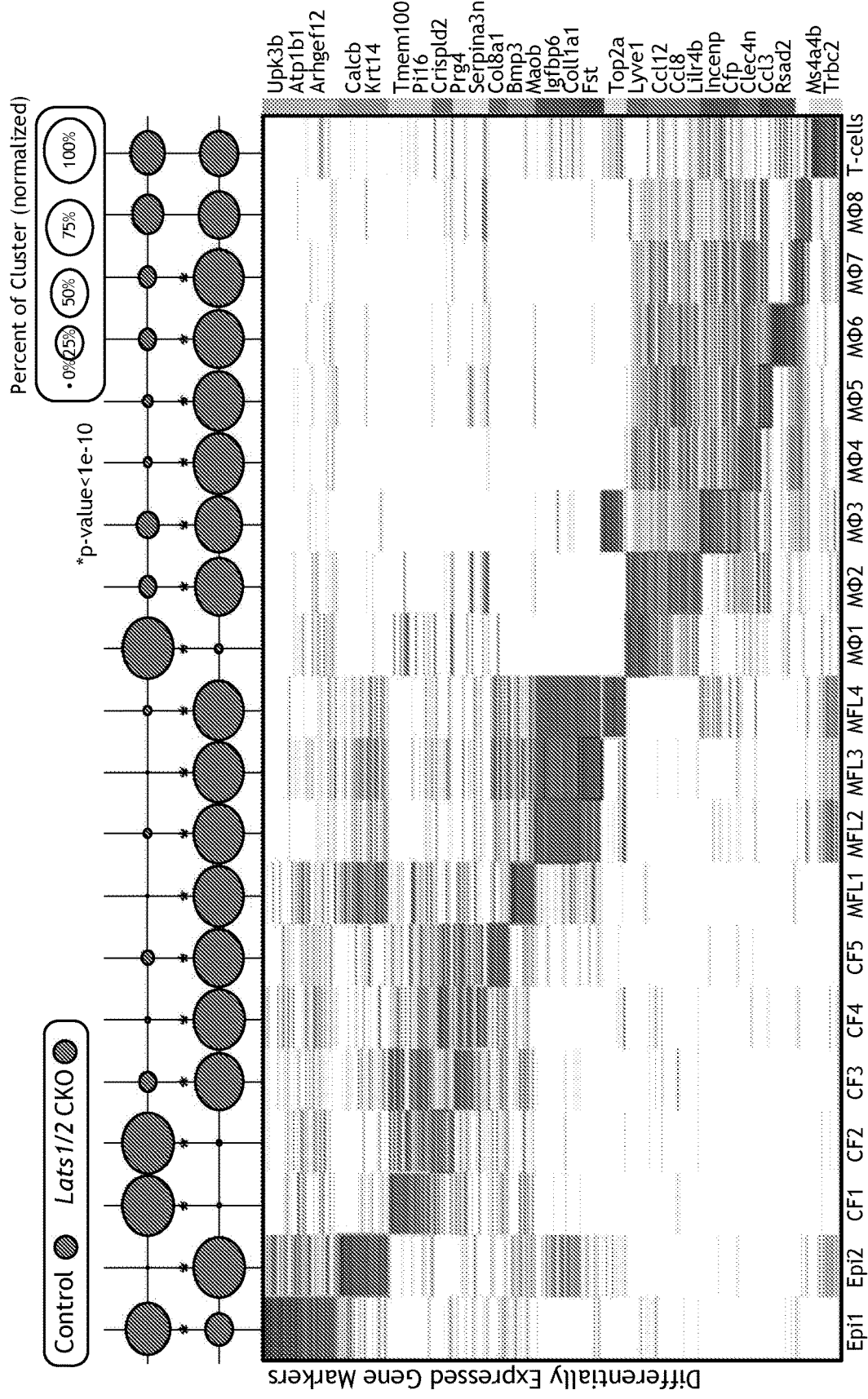

Among the five cardiac fibroblast clusters, there were two control heart-enriched subpopulations of fibroblasts, CF1 and CF2 revealing heterogeneity within resting control CFs (FIG. 18D). Interestingly, in addition to ECM associated genes such as Mgp, and Fbln5 (FIG. 23C) (Murshed et al., 2004; Zheng et al., 2007), several additional genes were enriched in CF2, such as Gpm6b, with known roles in cellular trafficking, and Apoe that is implicated in atherosclerosis and Alzheimer's disease (Fjorback et al., 2009; Mahley and Rall, 2000). However, the roles of Gpm6b and Apoe in CF homeostasis have yet to be uncovered. The other fibroblast cluster, CF1, exhibited high gene expression of Tmem100, Sema3c and Cd248 (FIGS. 18D and 23C) suggesting that these CFs may cross-talk with the cardiac vasculature (Khan et al., 2017; Somekawa et al., 2012; Yang et al., 2015).

Figure 23C:
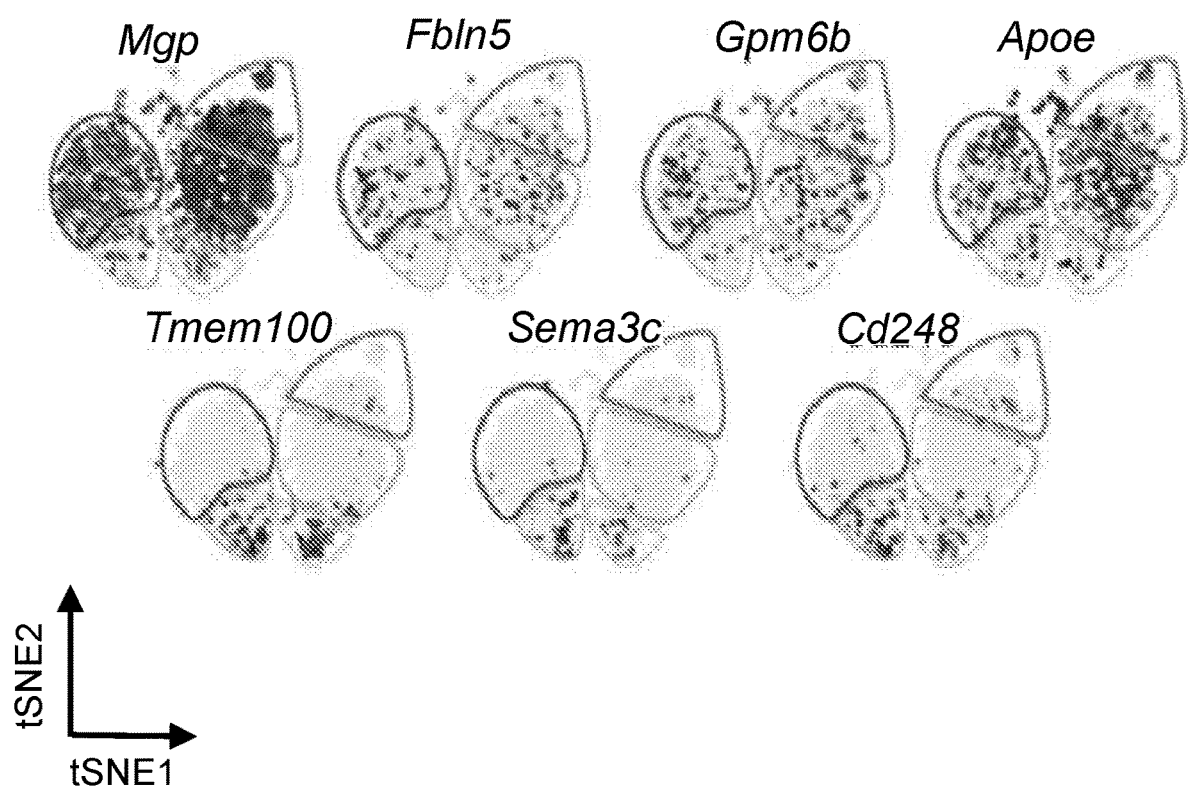
Figure 23D:
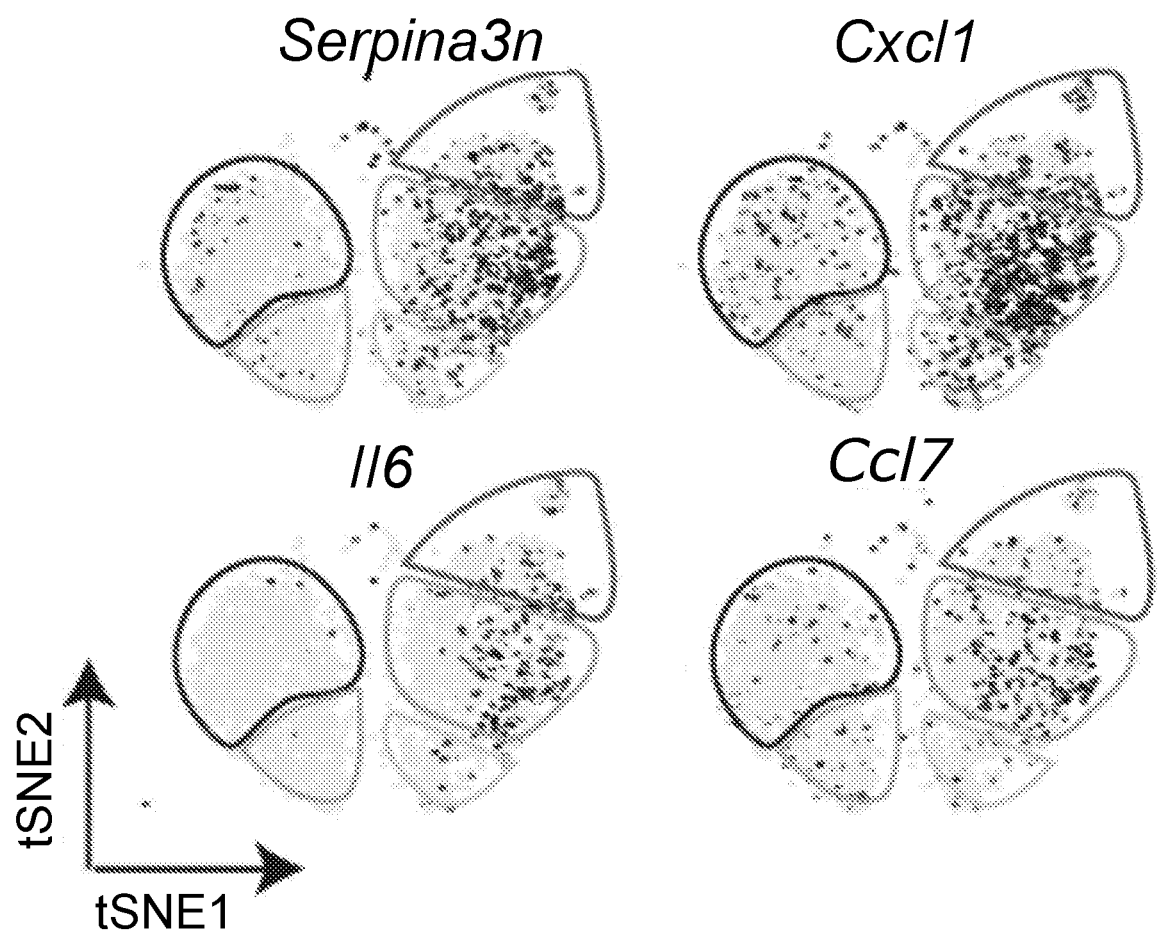

The gene features separating these two control fibroblast populations also distinguished mutant fibroblast clusters CF3 and CF4 (FIG. 23C). Additionally, the CF3 and CF4 fibroblast clusters, enriched in Lats1/2 CKO hearts, also possessed their own unique gene expression patterns consistent with an elevated inflammatory status, highlighted by the expression of Serpina3n, Cxcl1, Ccl7, and Il6 (FIG. 23D) (Shaftel et al., 2007; Tanaka et al., 2014; Vicuña et al., 2015). Notably, there was a third mutant CF subset, cluster CF5, that expressed elevated levels of Postn and Cilp that are both correlated with Tgf-β-induced signaling activation and the differentiation of fibroblasts to an active, fibrotic state (FIG. 23E) (Arpino et al., 2015; Khalil et al., 2017; Liu et al., 2013; van Nieuwenhoven et al., 2017). Collectively, these findings suggest that in the absence of injury, or any other stimulus, the deletion of Lats1/2 in resting CFs activated the cardiac injury response.

Figure 23E:
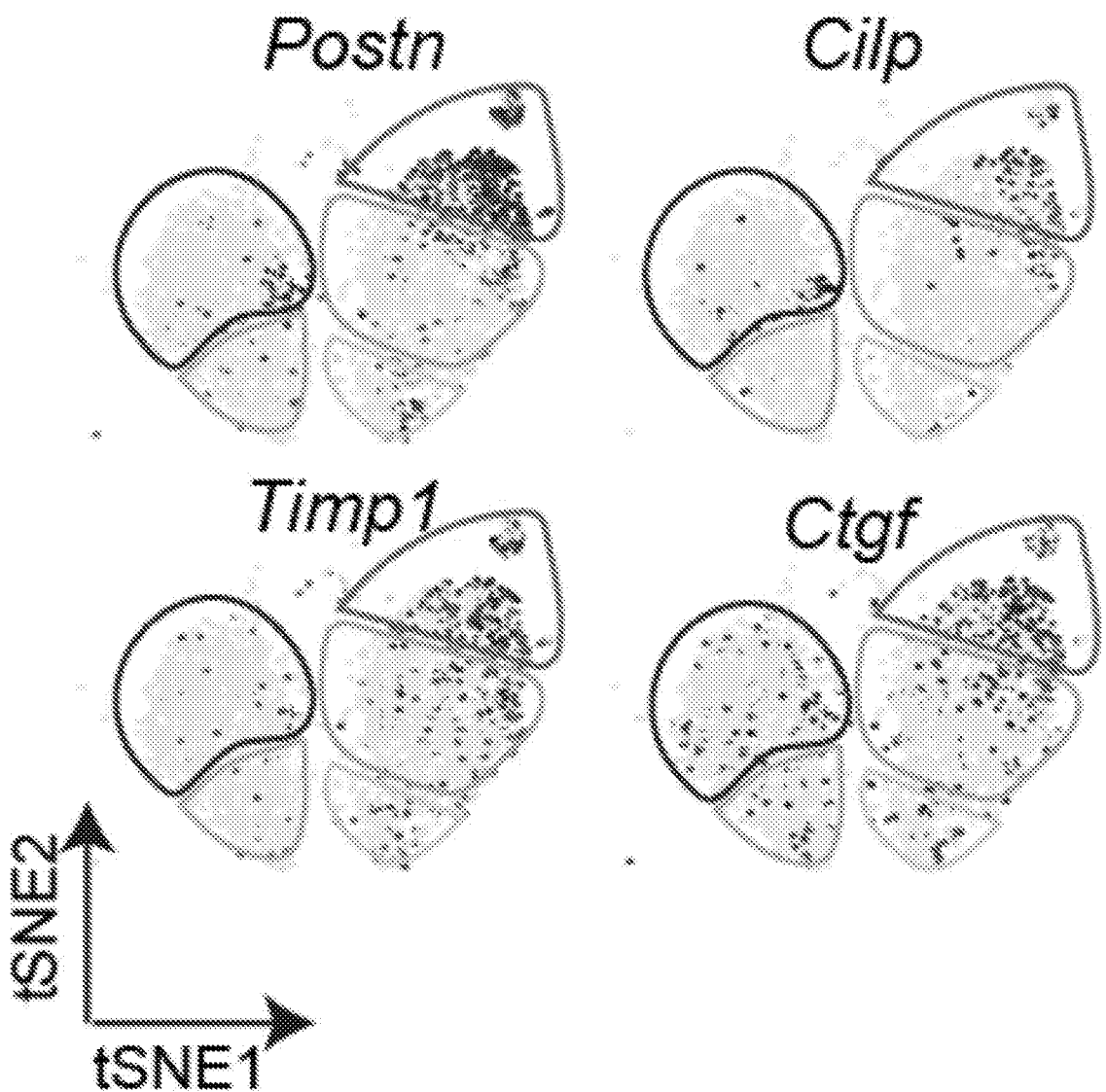
Figure 23F:
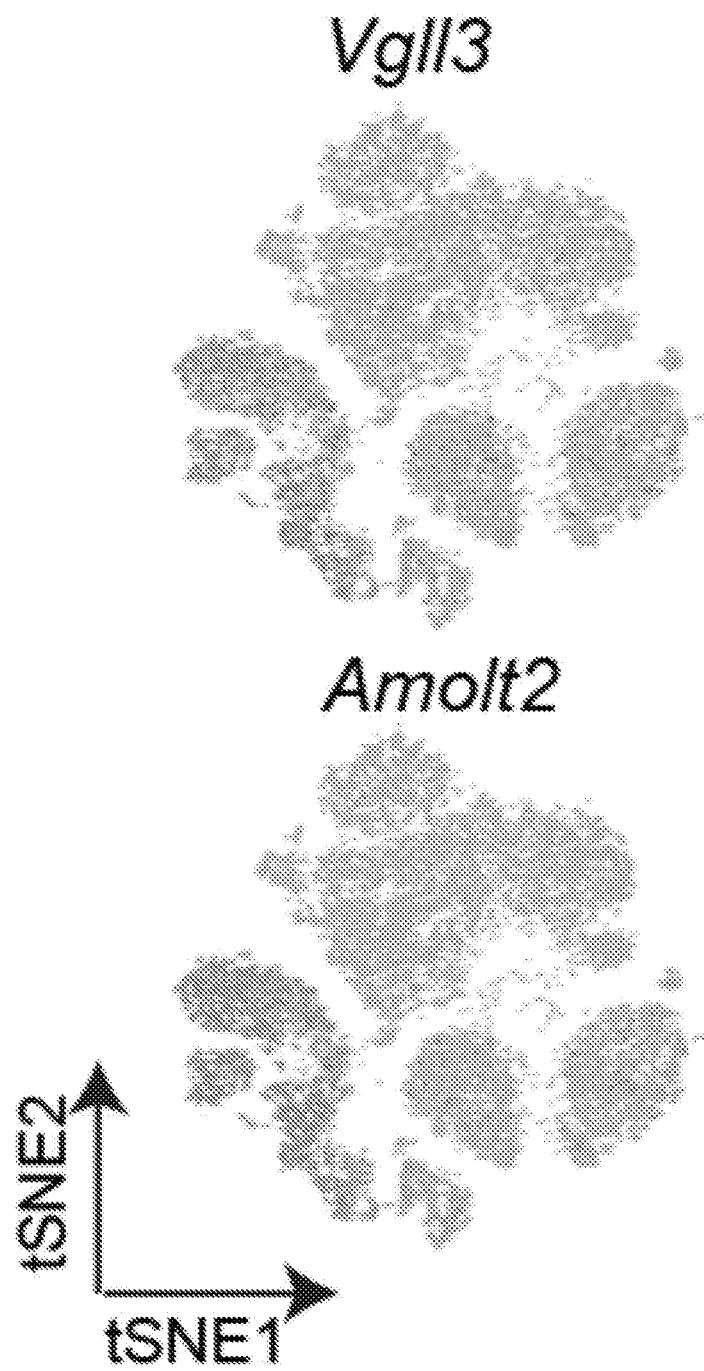
Figure 23G:
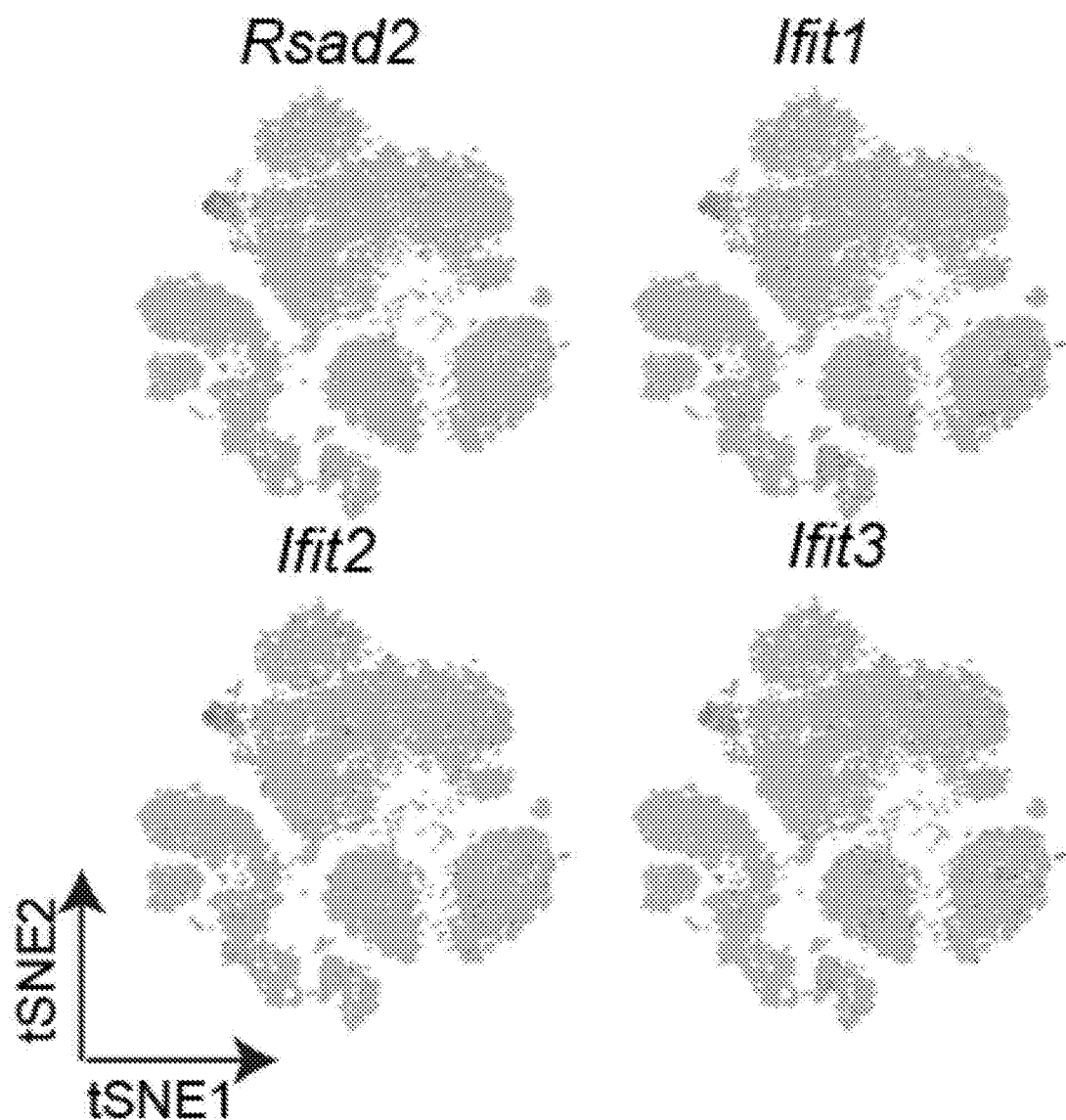
Figure 27A:
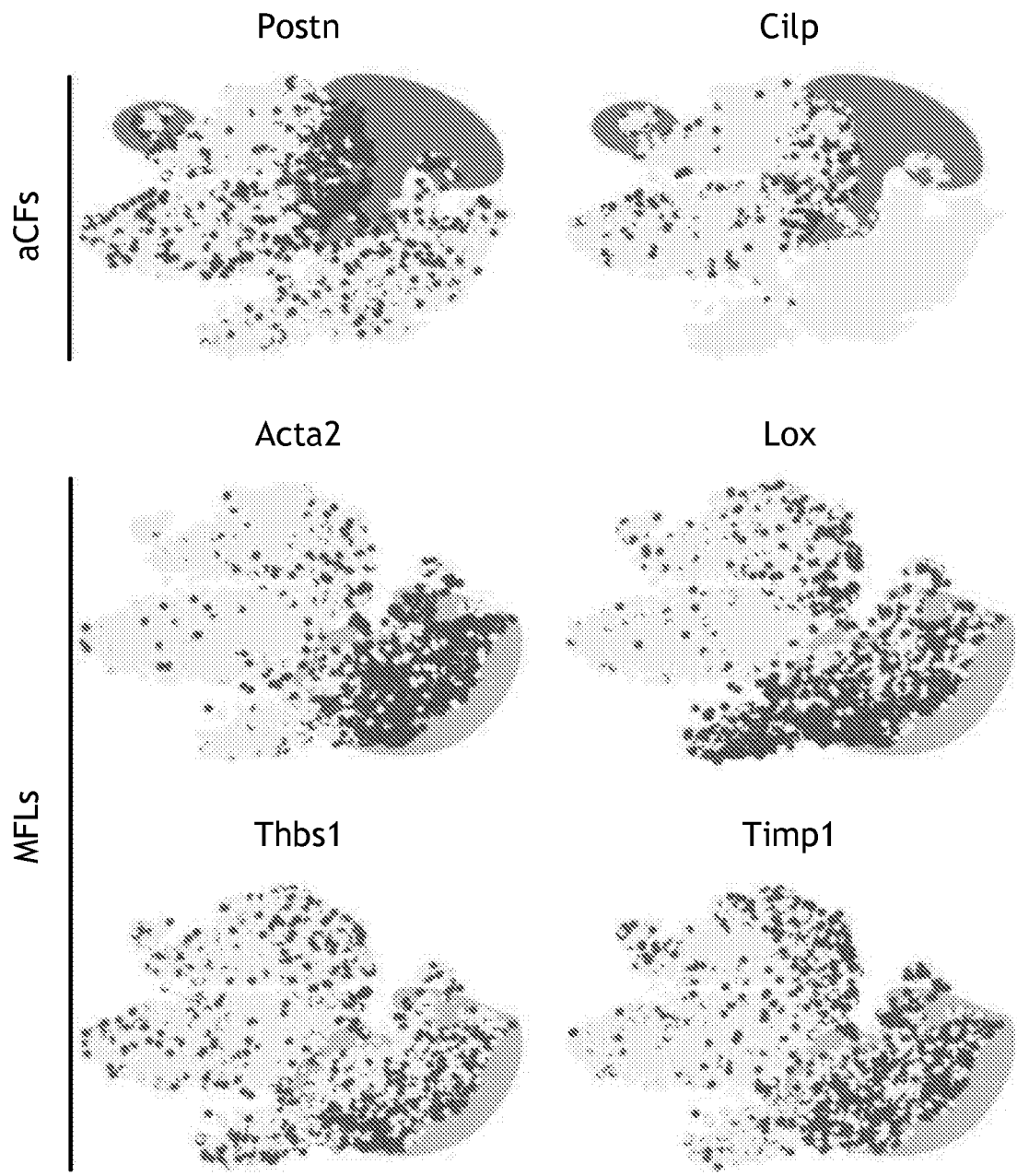
Figure 27B:
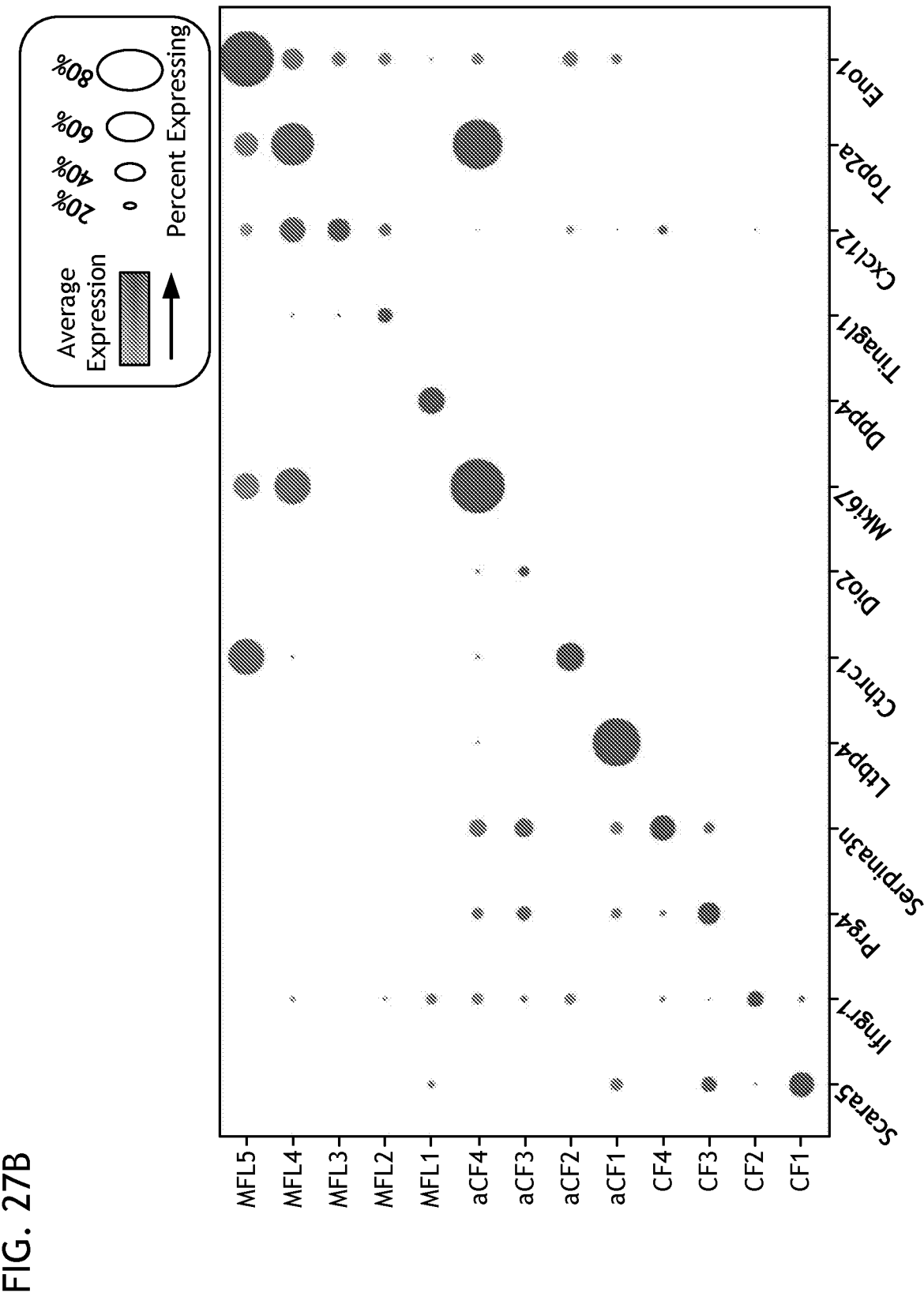
Figure 27C:
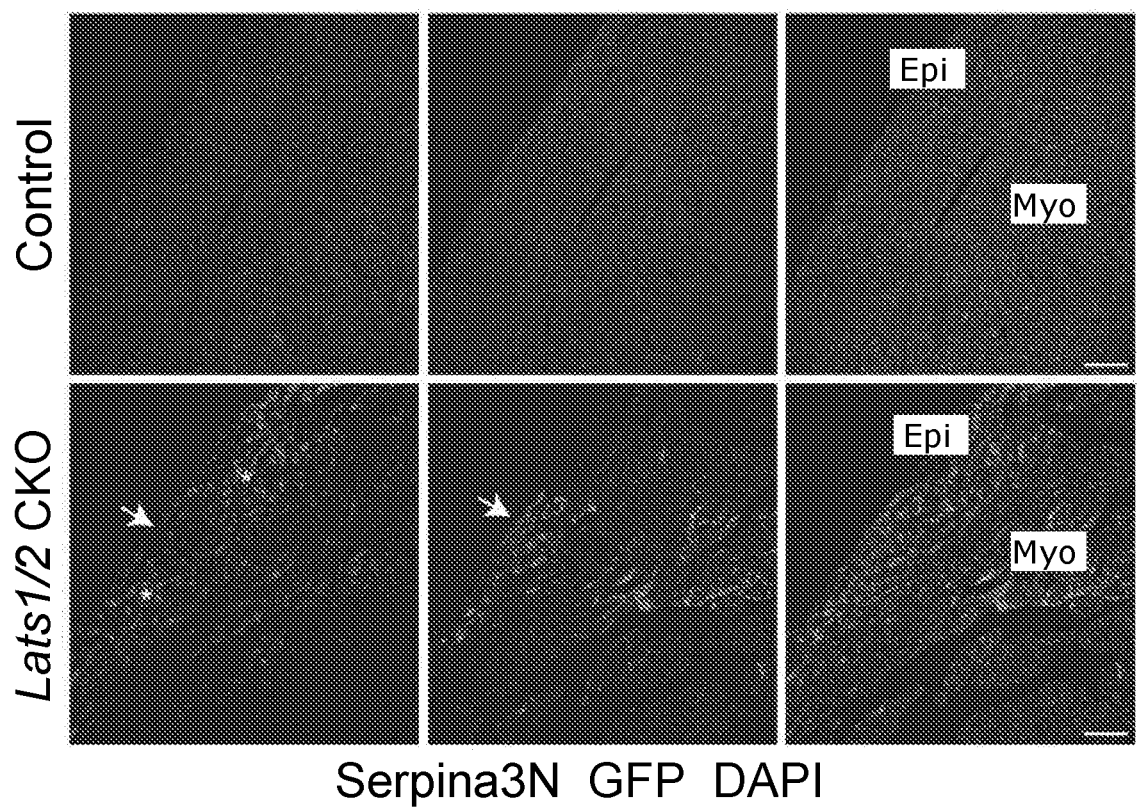

Lats1/2 Regulate Cardiac Fibroblast Cell States Both Autonomously and Non-Autonomously Lats1/2 CKO hearts contained two major mesenchymal populations. One population, including clusters CF3-5, more closely resembled resting cardiac fibroblasts (CF1-2) of control hearts, whereas the other mesenchymal population, including clusters MFL1-4, displayed strong expression of myofibroblast markers and Yap/TEAD targets (FIGS. 18D, 23A, and 23F). Thus, it was considered that clusters CF3-5 were composed of non-mutant CFs that escaped Cre-induced Lats1/2 deletion but were still responding to the fibrotic Lats1/2 CKO cardiac environment. The cardiac single-cell data revealed that Serpina3N, a gene encoding a granzyme B (GzmB) inhibitor expressed during the wound response (Hsu et al., 2014), marked clusters CF3-5 as compared to all other cardiac clusters, including MFLs (FIGS. 18D, and 23E). In situ hybridization with a Serpina3N probe revealed that Lats1/2 CKO hearts contained elevated numbers of Serpina3N positive cells compared to controls (FIG. 27C). Importantly, the majority of Serpina3N positive CFs were located adjacent to Tcf21-fibroblast lineage (GFP+) cells but were themselves Tcf21-fibroblast lineage negative (GFP−) (FIG. 27C). Thus, CF3-CF5 clusters are derived from resting CFs that escaped Lats1/2 deletion in the Lats1/2 CKO hearts.

Figure 18E:
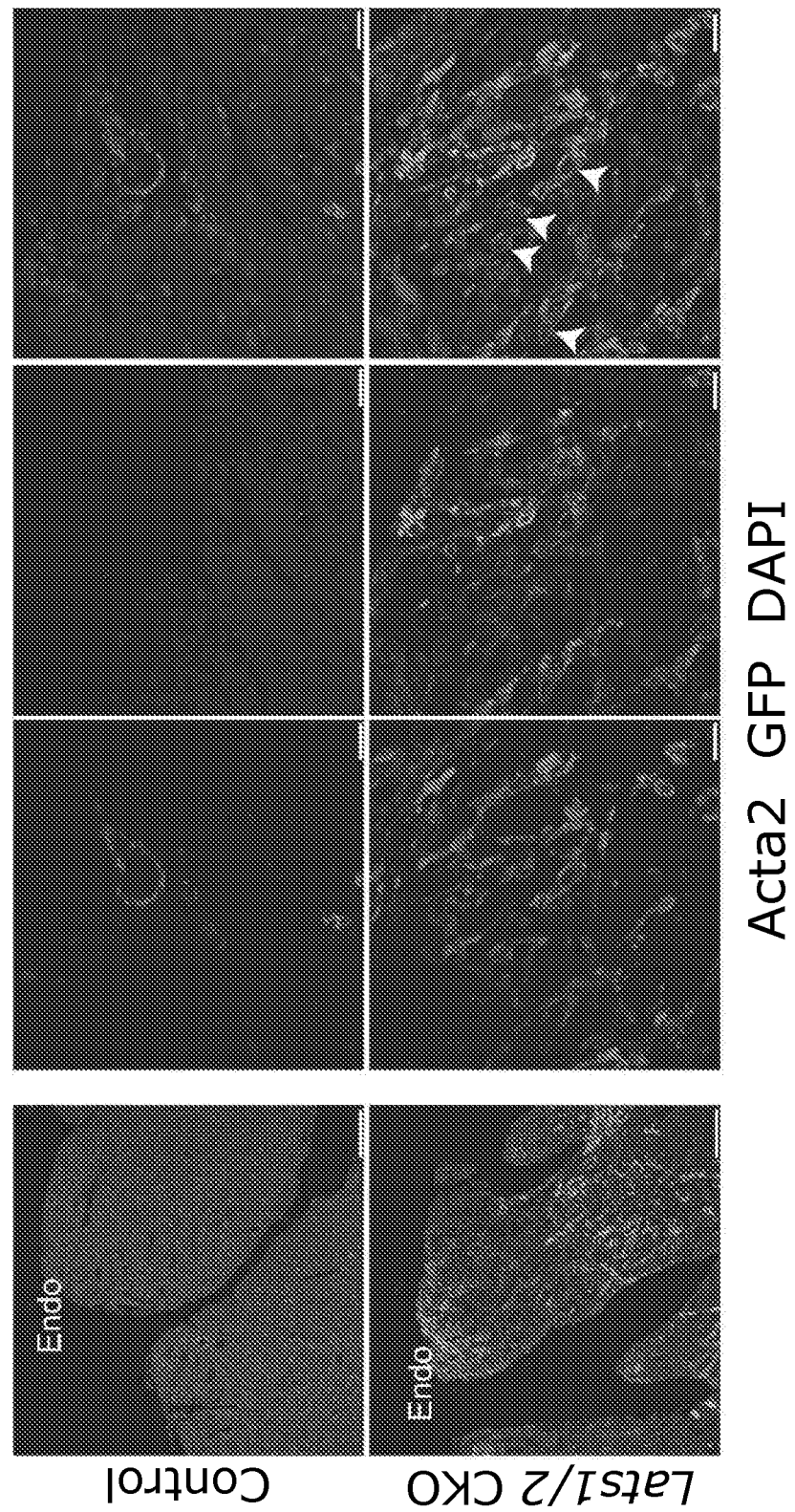

To characterize MFLs in Lats1/2 CKO hearts in greater depth, immunofluorescence (IF) experiments were used and high expression was observed of the myofibroblast marker Acta2 (αSMA) in Lats1/2 CKO tissue (FIG. 18E). Acta2 positive cells were highly aggregated in Lats1/2 CKO hearts, in contrast to controls in which only vascular smooth muscle cells expressed Acta2 (FIG. 18E). The majority of lineage-traced GFP positive cells exhibited Acta2 staining, further indicating that Lats1/2 deletion autonomously induces the myofibroblast cell fate (FIG. 18E).

Figure 24A:
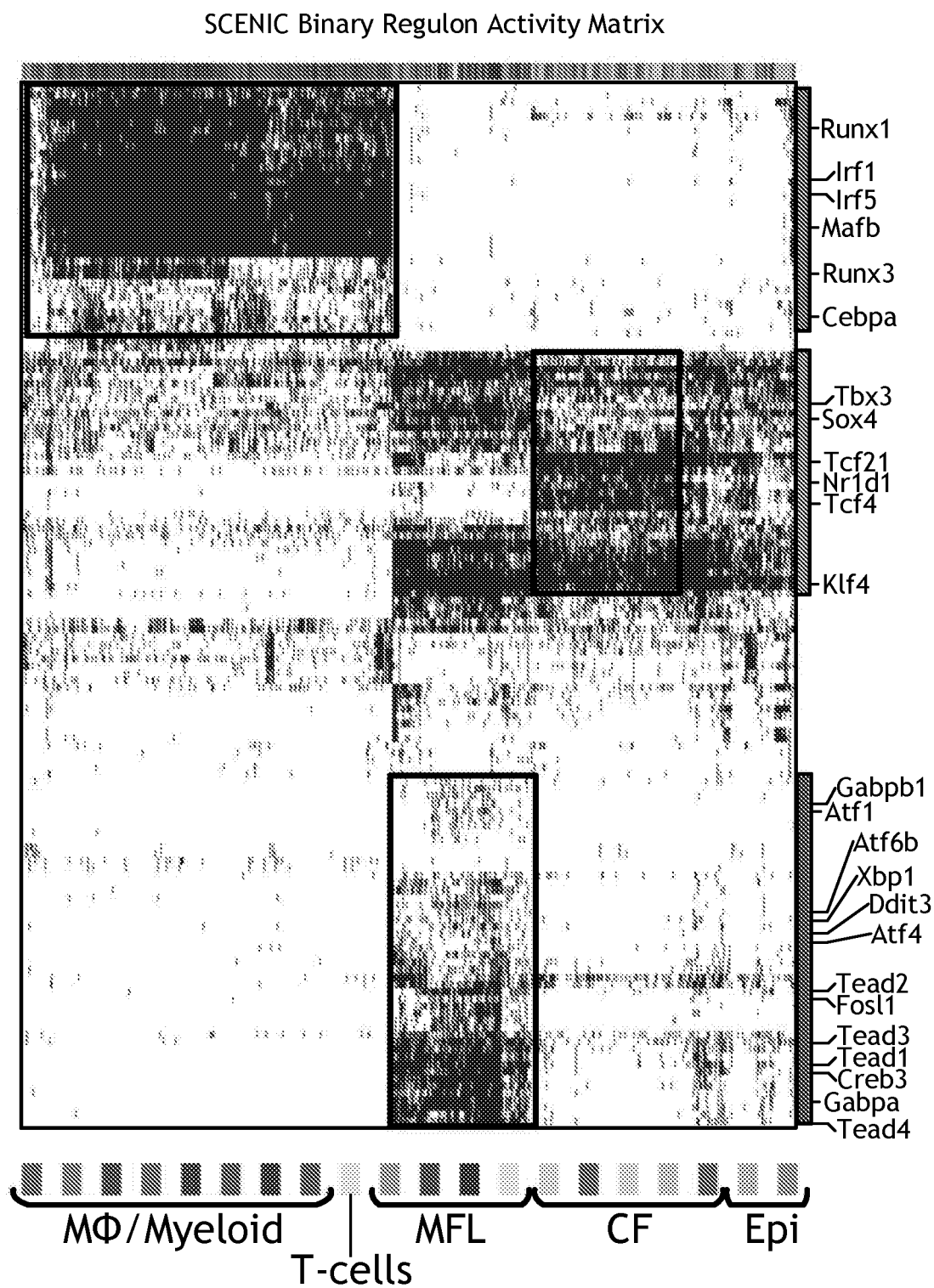
Figure 24B:
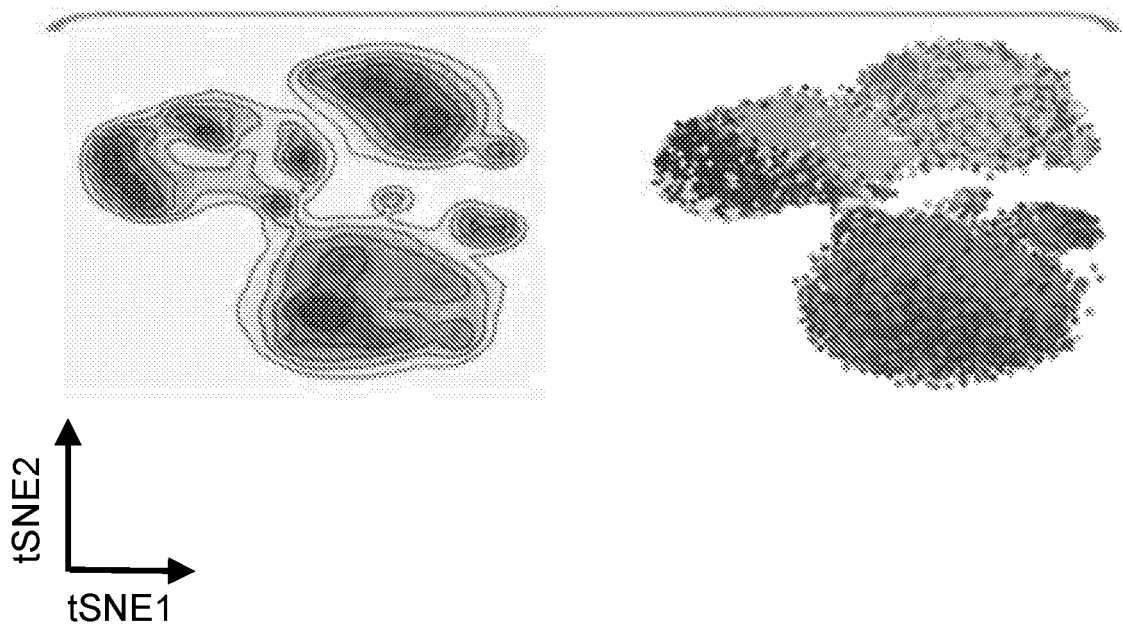
Figure 24C:
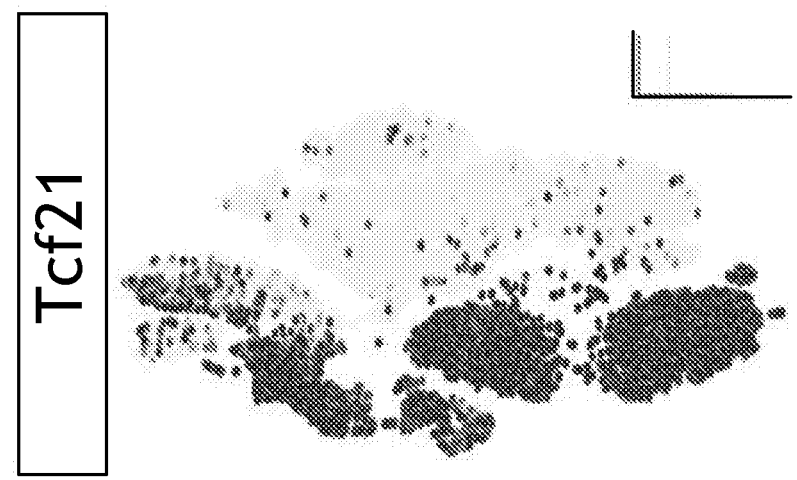
Figure 24C:
Figure 24C:

To further investigate the autonomous and non-autonomous effects of Lats1/2 deletion in CFs the single-cell regulatory network inference and clustering (SCENIC) computational pipeline was employed to map GRNs and the activity of transcription factors in the Drop-seq data set (Aibar et al., 2017) (see STAR METHODS). There were 541 active regulons out of the initial 1001 present in the transcription factor co-expression matrix. To compare the results of SCENIC with previous clustering analysis (FIG. 18A), tSNE was performed on the binary regulon matrix output from the SCENIC pipeline (FIG. 24A). The resulting tSNE revealed a distribution of cardiac cells that closely matched the expression-based tSNE (FIG. 24B). Indeed, cells of the myeloid lineage possessed Mafb, Runx3, Cebpa, and Cebpb regulons, while the cardiac fibroblasts showed Tcf21, Sox4, and Klf4 activity (FIG. 24A). Importantly, Tead1, Tead2, Tead3, and Tead4 regulons were active in MFLs (FIG. 24A), which is consistent the autonomous effects of Lats1/2 knockout in MFL cells. Surprisingly, other regulons present in MFLs were mainly those associated with the unfolded protein response (UPR), and the endoplasmic reticulum (ER) stress, including Xbp1, Atf1, Atf4, Atf6b, Ddit3, and Creb3. As predicted, the Tcf21 regulon was highly enriched across all fibroblast clusters and the epicardial and sub-epicardial cell types as well, while Atf4 and Tead1 were more specific to the mutant MFL sub-clusters (FIG. 24C).

Figure 24D:
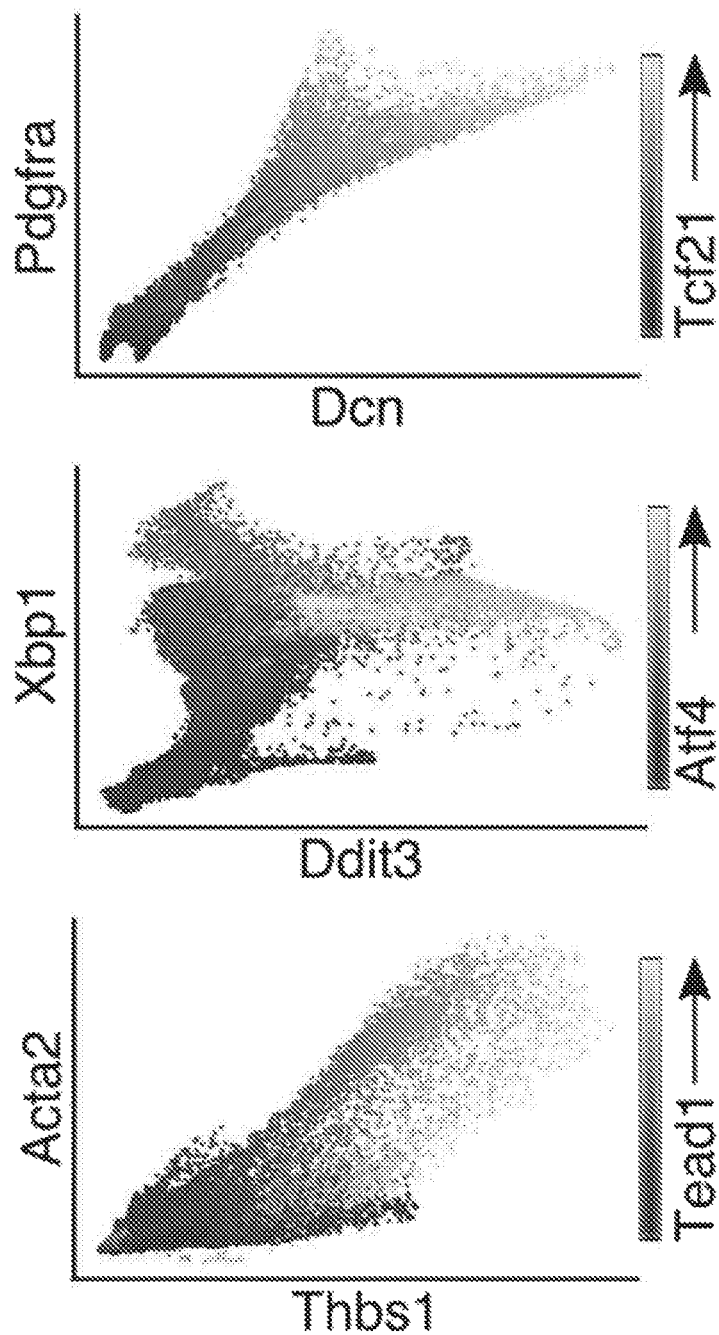
Figure 24E:
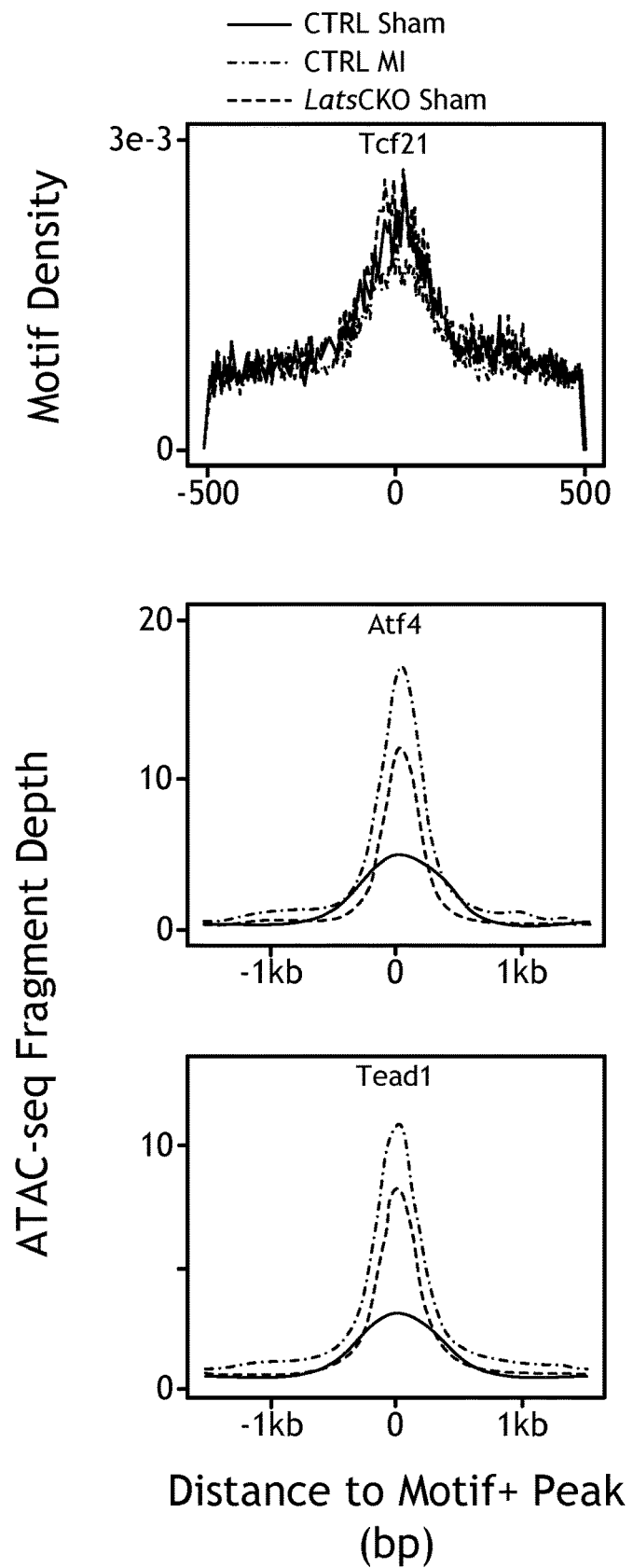

To further assess transcription factor activity from the Drop-seq data there was applied the Markov affinity based graph imputation of cells (MAGIC) algorithm (van Dijk et al., 2018) which is well suited for interrogating gene-gene relationships (FIG. 24D). Indeed, cells with high transcription factor expression displayed high target gene expression, indicating that regulon activity identified via SCENIC is robust for Tcf21, Atf4, and Tead1 regulons. Moreover, ATAC-seq data was analyzed to inspect regulon activity in cardiac fibroblasts. Globally Tcf21 motifs were enriched across all conditions: control sham, control MI, and Lats1/2 CKO sham (FIG. 24E, top). Atf4 and Tead1 motif positive peaks nearby genes identified in the SCENIC regulons were examined, and there was counted ATAC-seq fragments across these putative transcription factor binding sites. Both Atf4 and Tead1 sites were enriched in controls after MI, and in Lats1/2 CKO sham, but not in CFs from control sham. Taken together, these data demonstrated that in uninjured Lats1/2 CKO hearts MFLs and activated CFs were detected that are distinct from control resting fibroblasts.

Figure 18F:
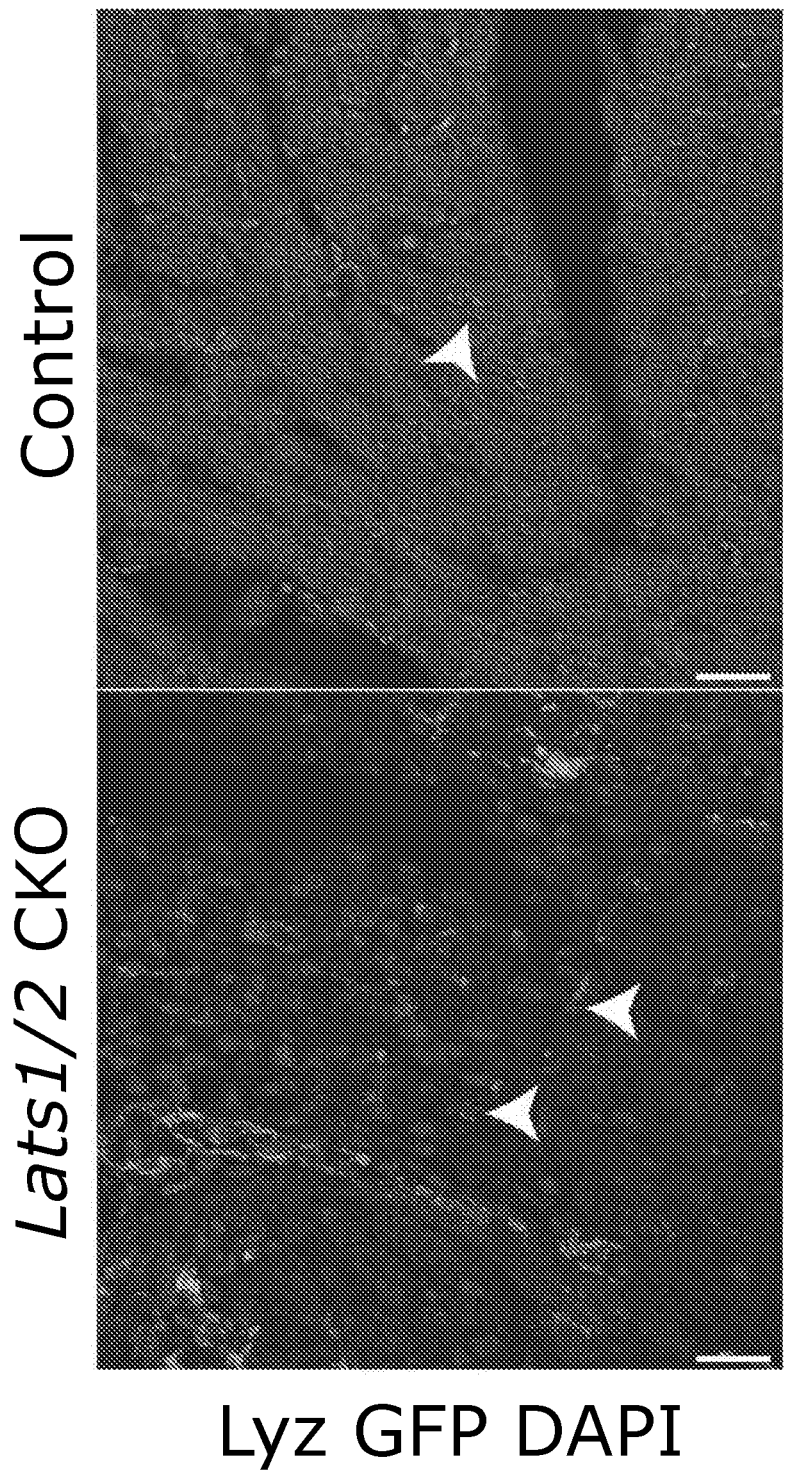

Lats1/2 Restrict Pro-Inflammatory Signaling Between Cardiac Fibroblasts and Myeloid Cells A prominent feature of the Lats1/2 CKO molecular phenotype was the large influx of immune cells from the myeloid lineage in the absence of injury (FIGS. 18C and 18D). Immunostaining with the macrophage marker Lyz, revealed increased numbers of macrophages within Lats1/2 CKO hearts (FIG. 18F). Indeed, the dramatic shift in cellular composition with an increased inflammatory component resembled an injured heart. The phenotypic expansion of myeloid cells in Lats1/2 CKO cardiac tissue is consistent with recent work where researchers performed scRNA-seq on purified leukocytes after MI and identified 8 clusters of myeloid cells, including a unique cluster of interferon-inducible cells (IFNICs) (King et al., 2017). Importantly, it was found that the cluster originally identified as Mφ6 were Rsad2+, Ifit1+, Ifit2+, and Ifit3+(FIG. 18D and FIG. 23F) and thus resembled ischemic injury induced IFNICs. These data suggest that Lats1/2 prevent the induction of a CF-derived pro-inflammatory cascade responsible for myeloid cell influx, activation, and phenotypic expansion.

Convergence of ER stress and unfolded protein response (UPR) pathways with the Tead GRN is consistent with a highly secretory cell state in Lats1/2 CKO CFs, as secretory cells, for example pancreatic β-cells, are known to carry a considerable synthetic burden (Eizirik and Cnop, 2010; Lipson et al., 2006; Qiu et al., 2010). Many Yap target genes induced in MFLs were secreted molecules. To investigate the crosstalk between MFLs and immune cells in Lats1/2 CKO hearts in more depth, intercellular communication network analysis was performed on groupings of cardiac cell clusters (FIG. 19A) based on the mouse orthologs of the FANTOM5 human ligand-receptor connectome (FIG. 19B) (Ramilowski et al., 2015) (see below). Strikingly, the mutant MFLs showed a larger number of significant ligand-receptor pairs (4.96-fold increase) compared to control CFs.

Figure 19A:
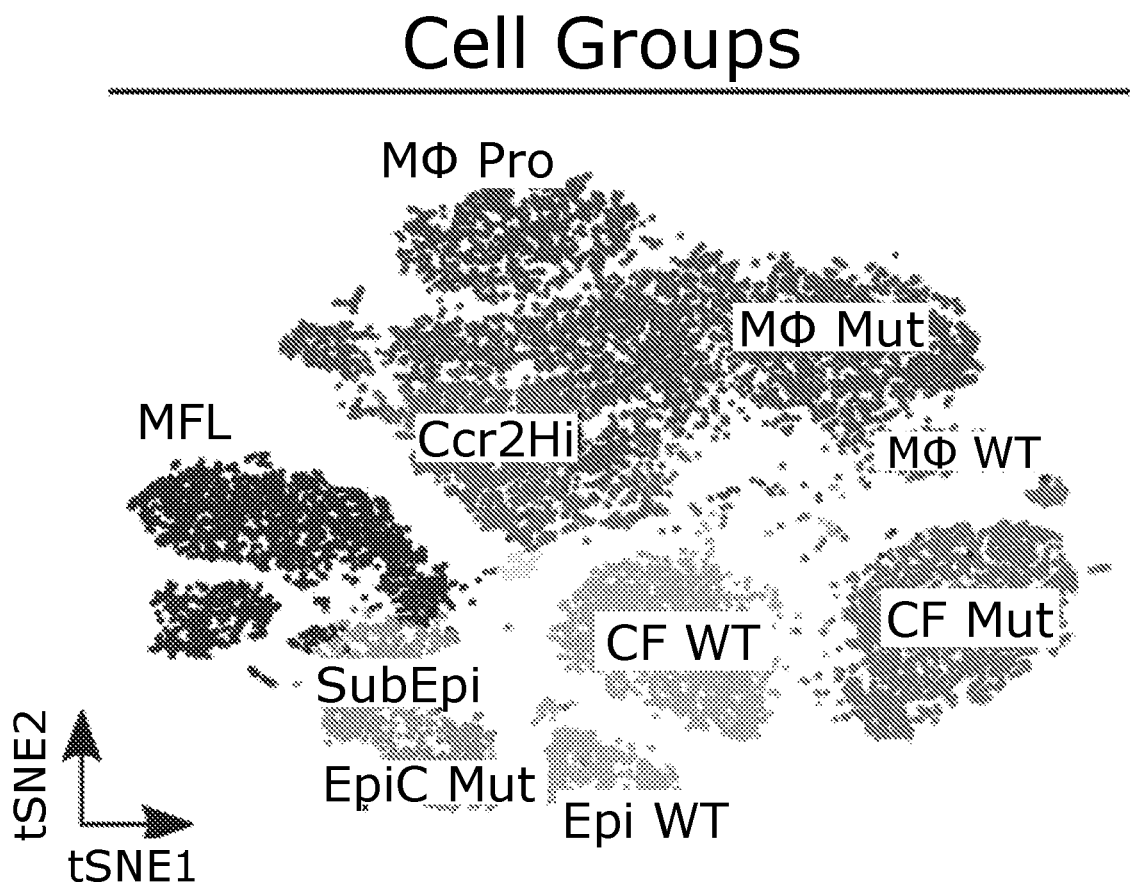
Figure 19B:
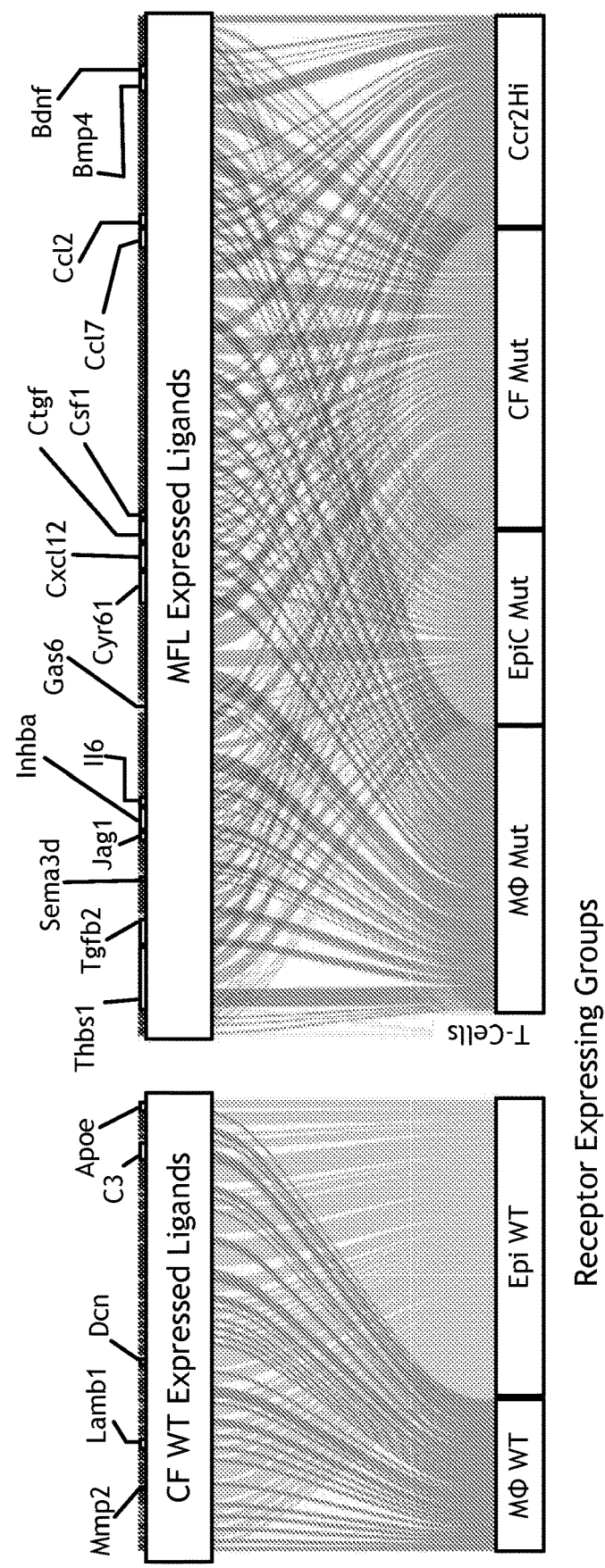
Figure 19C:
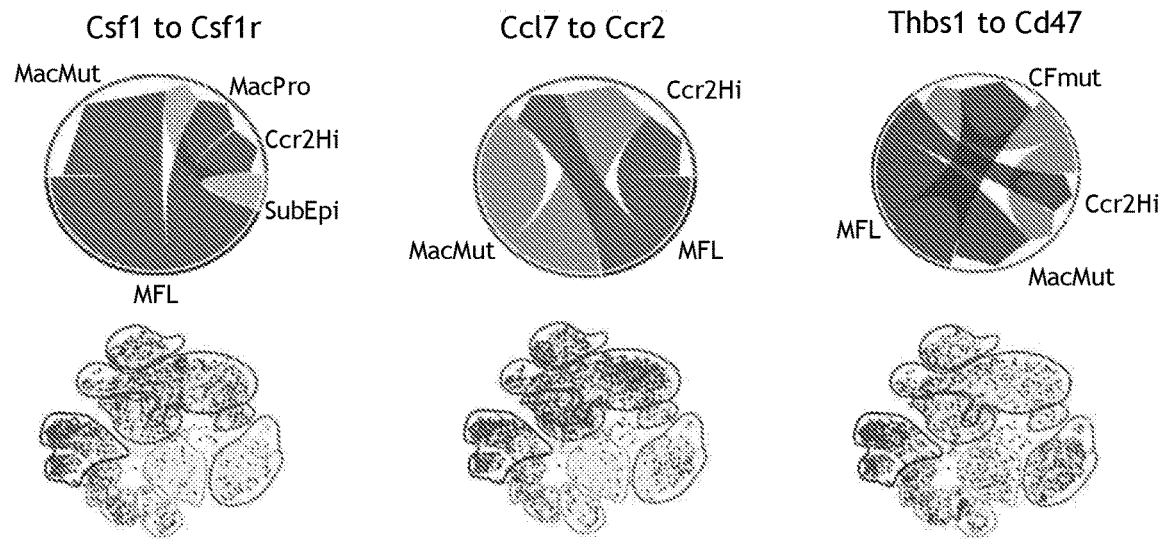
Figure 19C:
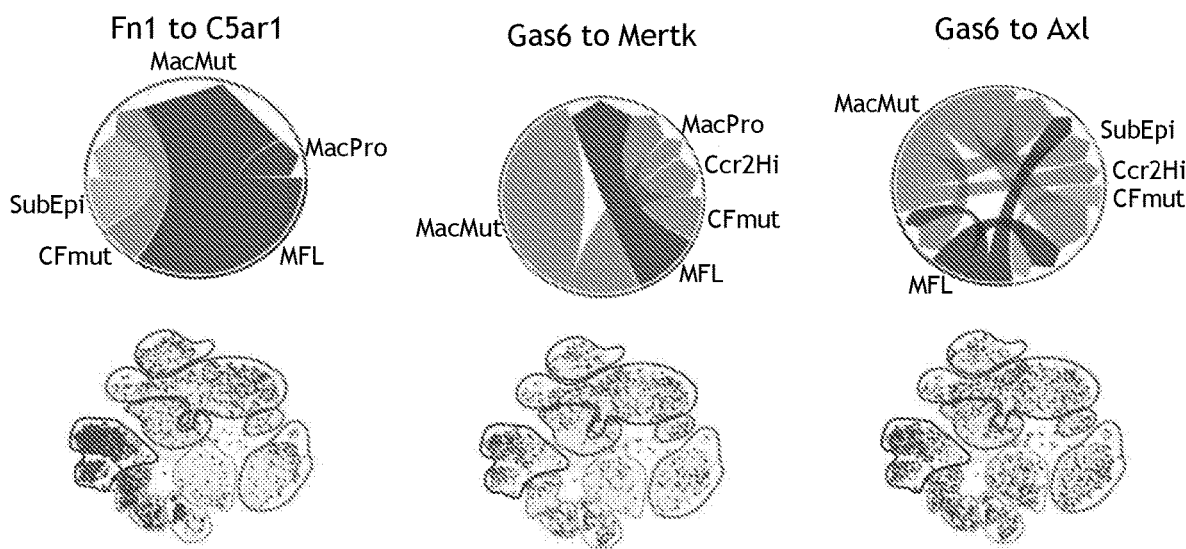

Many of the MFL expressed ligands were found to be hallmarks of the wound response (GO:0009611, p-value<$1.4 \times 10^{-15}$) such as Thbs1 (DiPietro et al., 1996), Serpine1 (Providence et al., 2002), Hbegf (Marikovsky et al., 1993) Ereg (Draper et al., 2003) and Timp1 (Vaalamo et al., 1996). Moreover, several MFL expressed ligands are Tgf-β family members or Tgf-β interactors, including Tgfb2, Inhba, Fst, and Thbs1 (FIG. 19B). Most notably, many of the top ligand-receptor pairs connect MFLs to myeloid cells (FIGS. 5B-5C). Prominent among the MFL-Mφ axis is the Csf1-Csf1r pair, which is partly responsible for linking fibroblasts and Mφs in a stable cell circuit in vitro (Zhou et al., 2018). Csf1 is also important for Mφ differentiation, chemotaxis, proliferation, function and survival (Hume and MacDonald, 2012). Moreover, the presence of the Ccl7-Ccr2 pair suggests that MFLs actively recruit monocytes into the myocardium (Jia et al., 2008). Furthermore, there was detected the mitogen Gas6 connected to its cognate TAM family receptor tyrosine kinases Mertk and Axl (Loges et al., 2010). Interestingly, both the MFLs and the mutant Mφ populations express high levels of the ligand and receptors suggesting the presence of both paracrine and autocrine pro-proliferative loops. Overall, these results suggest that Lats1/2 in CFs prevents the expression of a cadre of secreted proteins that function in wound repair, ECM organization, and immune cell recruitment.

Figure 19D:
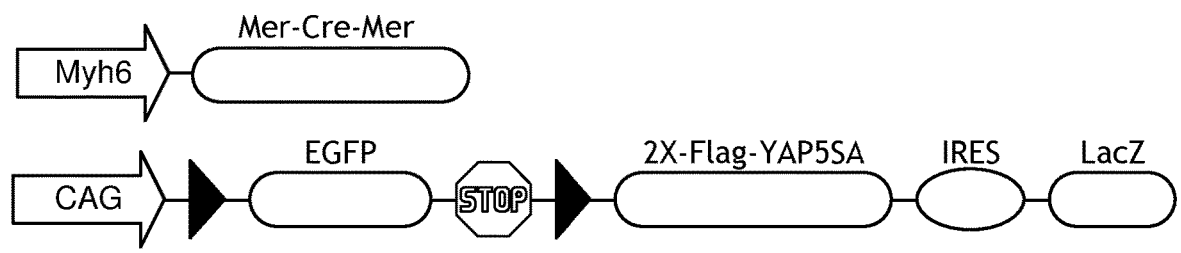

Uncoupling of the Hippo Pathway to Yap in Cardiomyocytes Promotes Myocardial Myeloid Cell Influx After MI, Yap is translocated to the nucleus of CFs, as well as a limited number of cardiomyocytes during the cardiac injury response (FIG. 22D). This led to investigation whether the injury-induced Yap gene program in CMs also orchestrates a non-autonomous effect on cardiac tissue composition. Thus, a Yap isoform was conditionally expressed that is incapable of being phosphorylated by Lats1/2, YAP5SA, in CMs using a mouse model that was described previously (Monroe et al., 2019). Drop-seq was performed on the hearts of Myh6-MerCreMer/+; YAP5SA-tg/+(hereafter referred to as YAP5SA-CM) mice, in addition to control animals (Myh6-MerCreMer/+) (FIG. 19D).

Figure 19E:
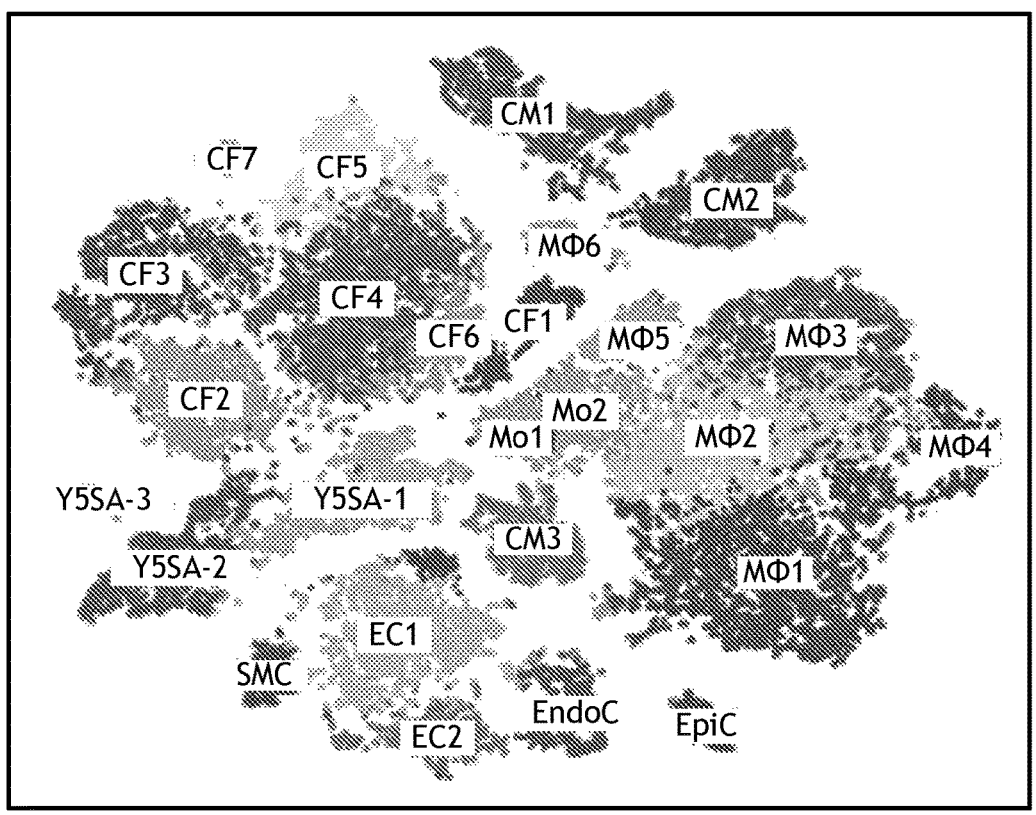
Figure 19F:
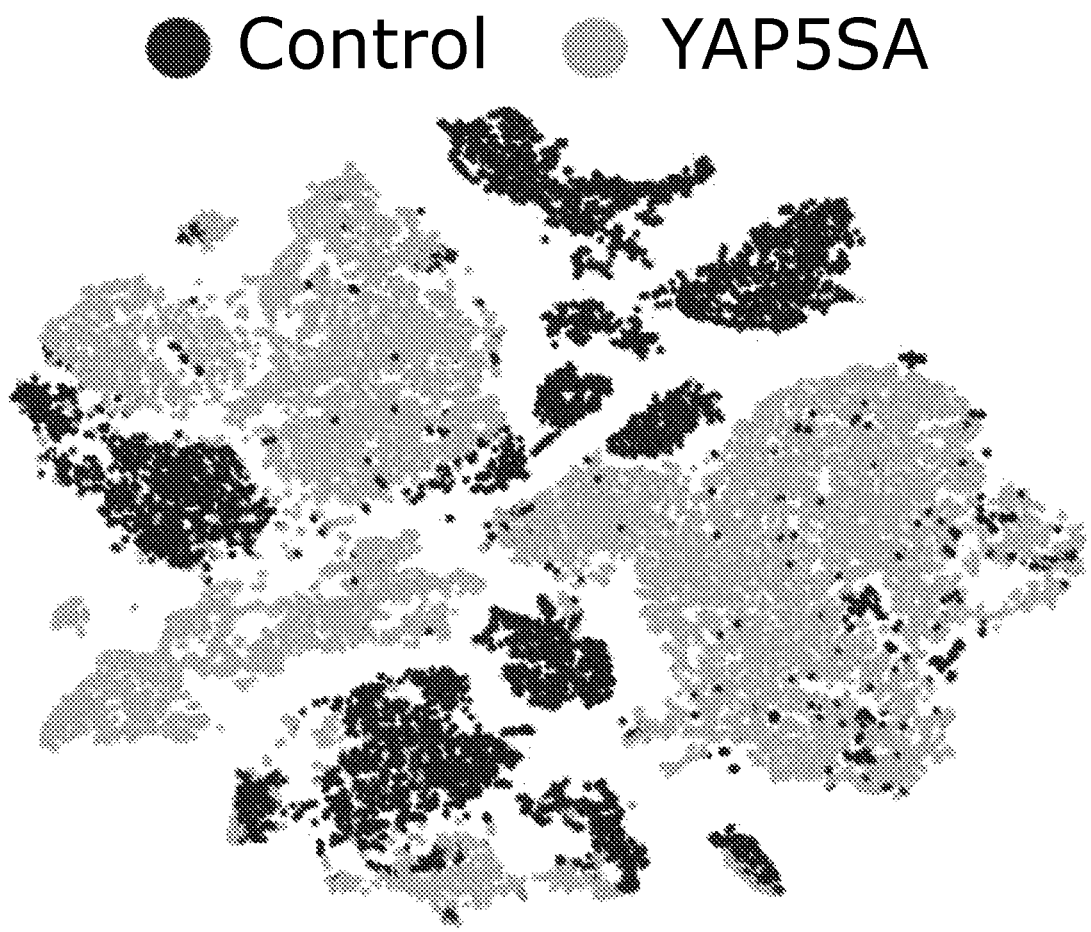
Figure 19G:
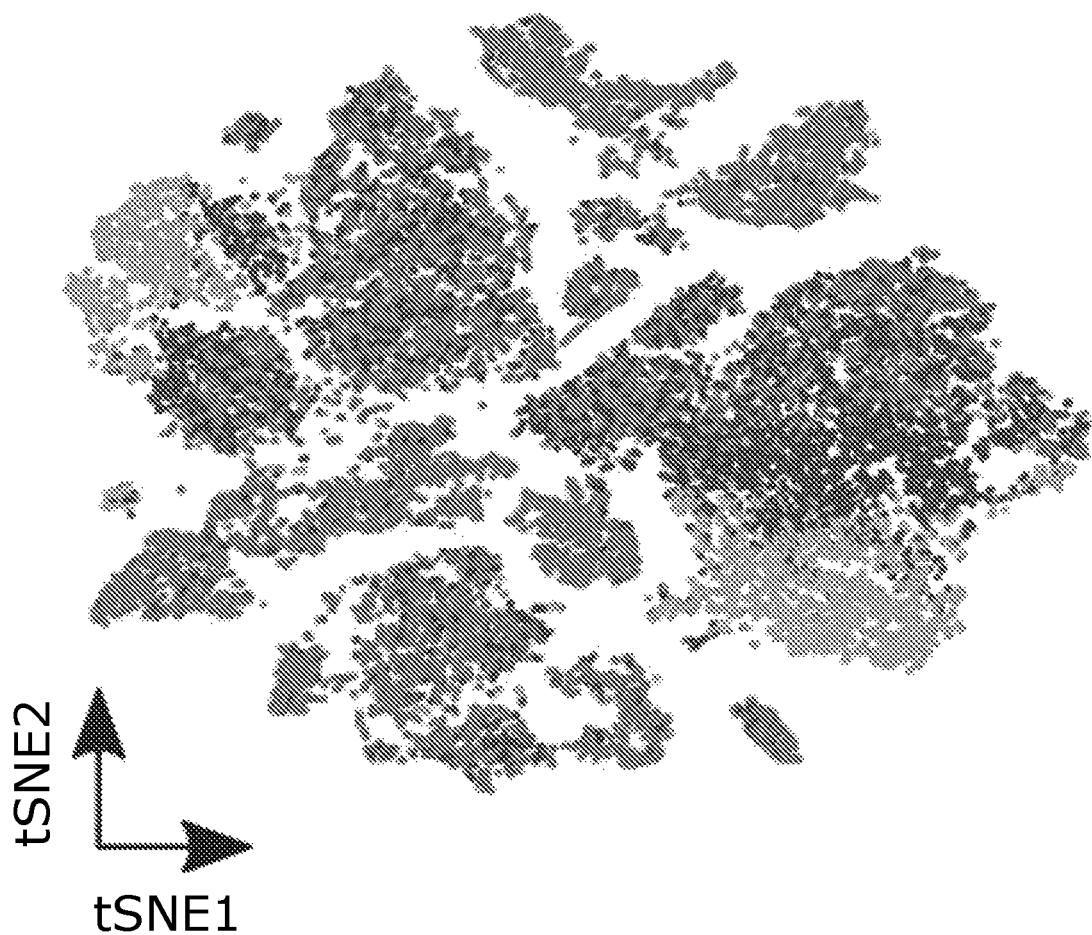
Figure 19H:
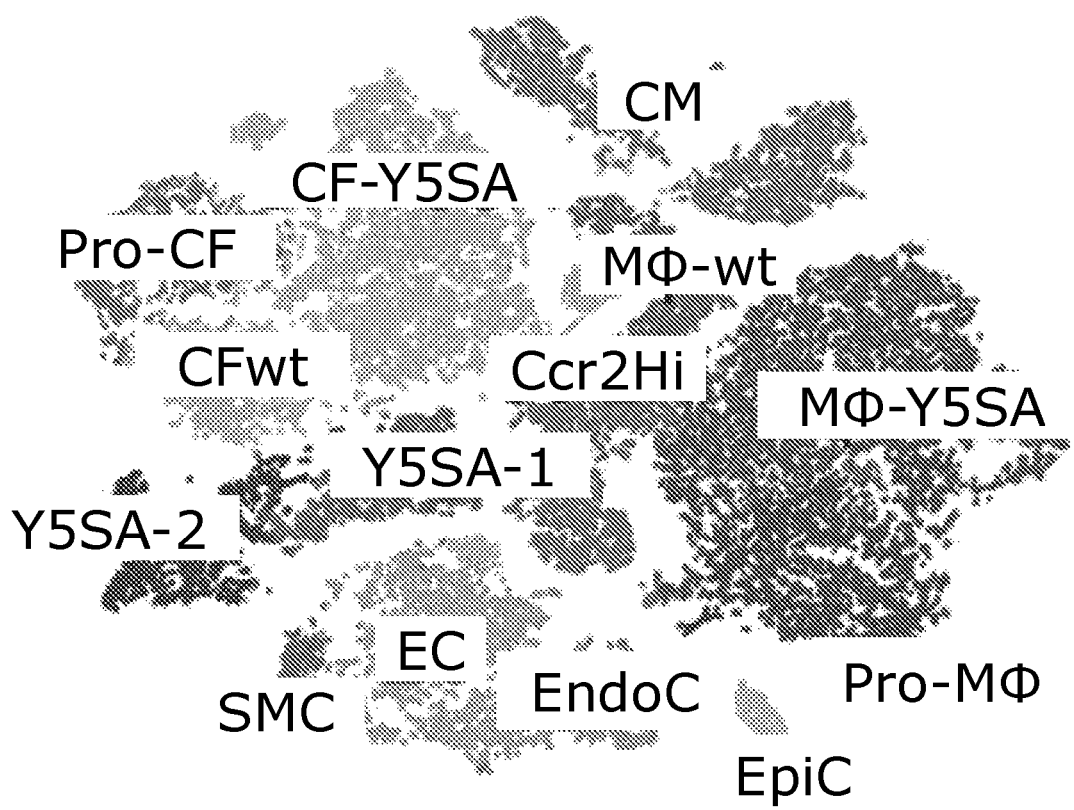
Figure 25A:
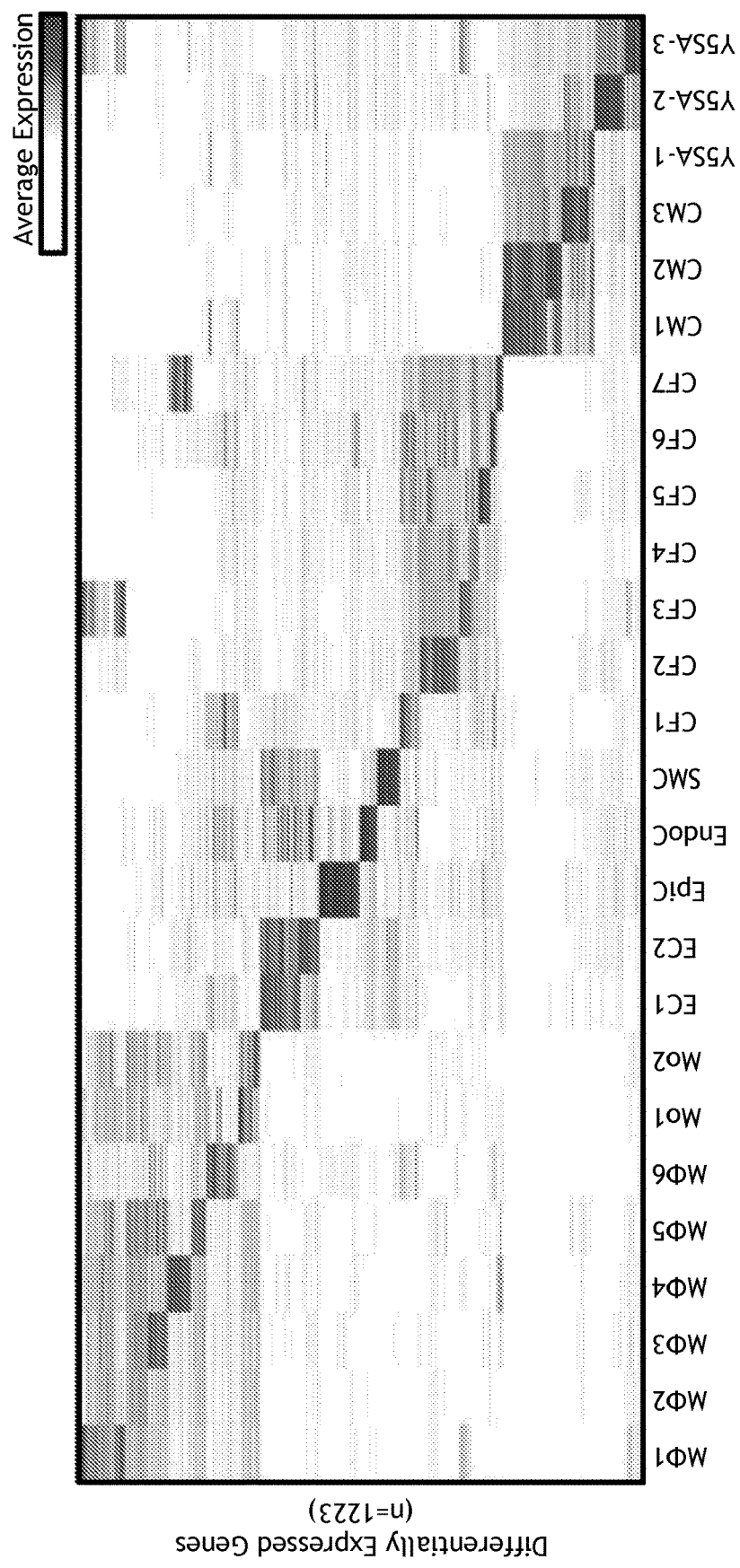
Figure 25C:
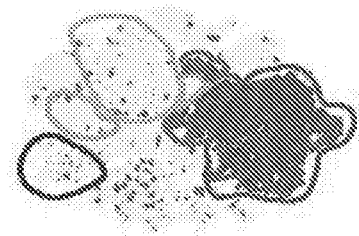
Figure 25C:
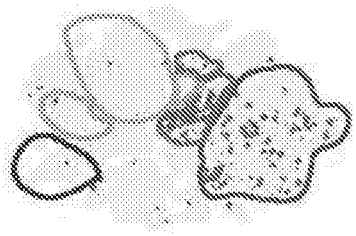
Figure 25C:
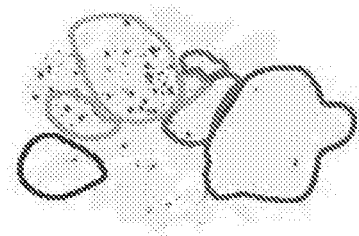
Figure 25C:
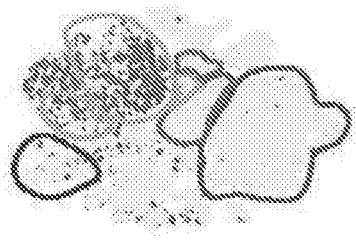
Figure 25C:
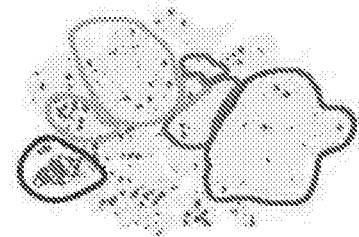
Figure 25C:
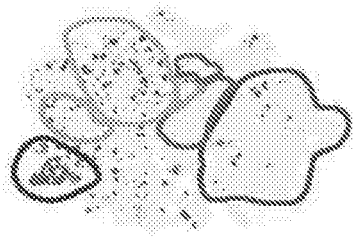
Figure 25C:
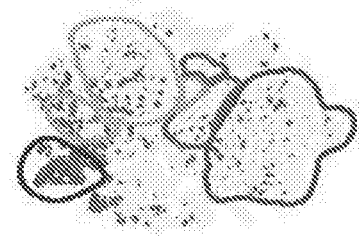
Figure 25C:
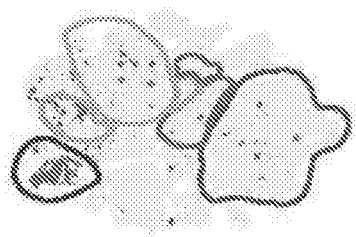

Over 24,000 single cell transcriptomes were profiled, and then the same computational analysis as described above was performed. After graph-based clustering and filtering there was identified 26 distinct cell clusters (FIGS. 19E, and 25A). Among these clusters, the YAP5SA CMs with the highest Yap activity as judged by Yap target gene expression, such as Amotl2, were identified as cluster Y5SA-2 (FIG. 25B). Similar to Lats1/2 CKO hearts, there was increased myeloid cell invasion, as well as a distinct transcriptional shift in the CFs residing in YAP5SA-CM hearts compared to controls (FIGS. 19F, 25B, and 25C). Moreover, YAP5SA-CMs (Y5SA-2) expressed some of the same genes identified in MFLs, including Acta2 and Col12a1 (FIG. 25C). There were proliferative adult cardiomyocytes (Y5SA-3), proliferative CFs, and proliferative myeloid cells (FIG. 19G).

Figure 19I:
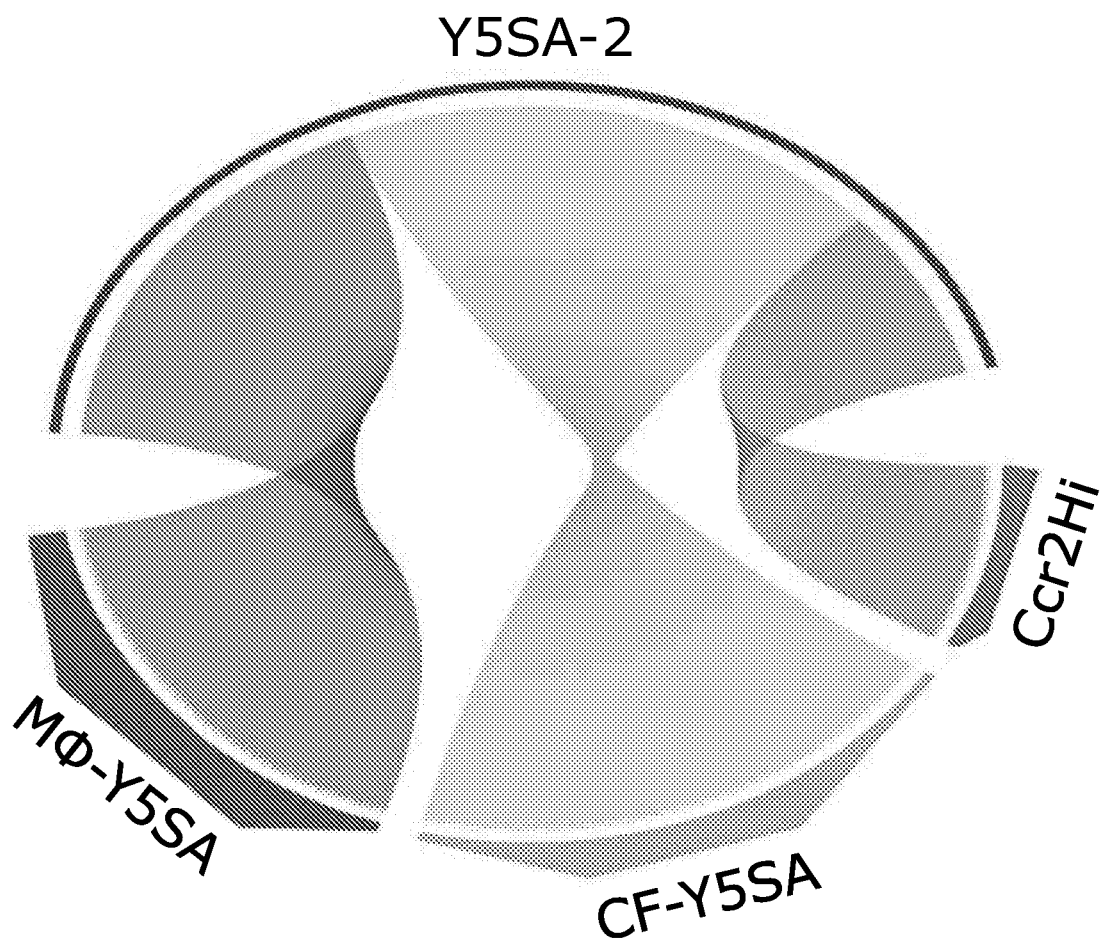
Figure 19J:
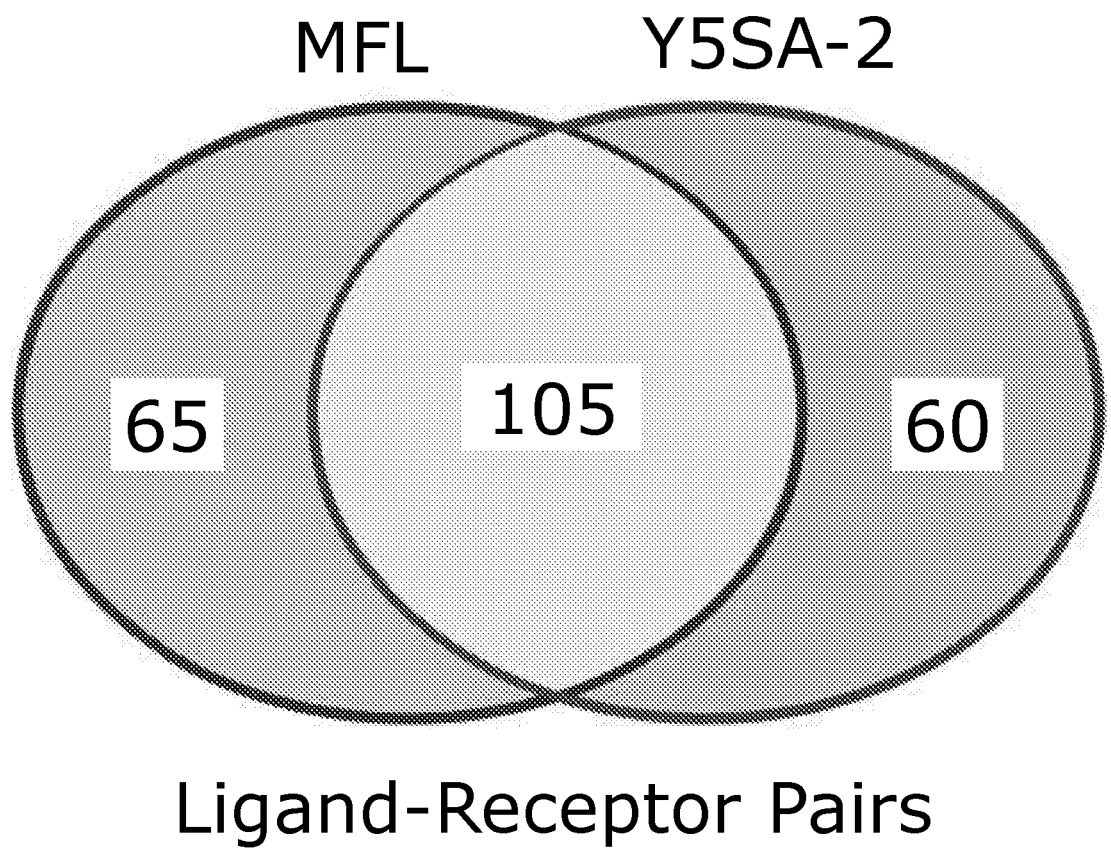
Figure 25D:
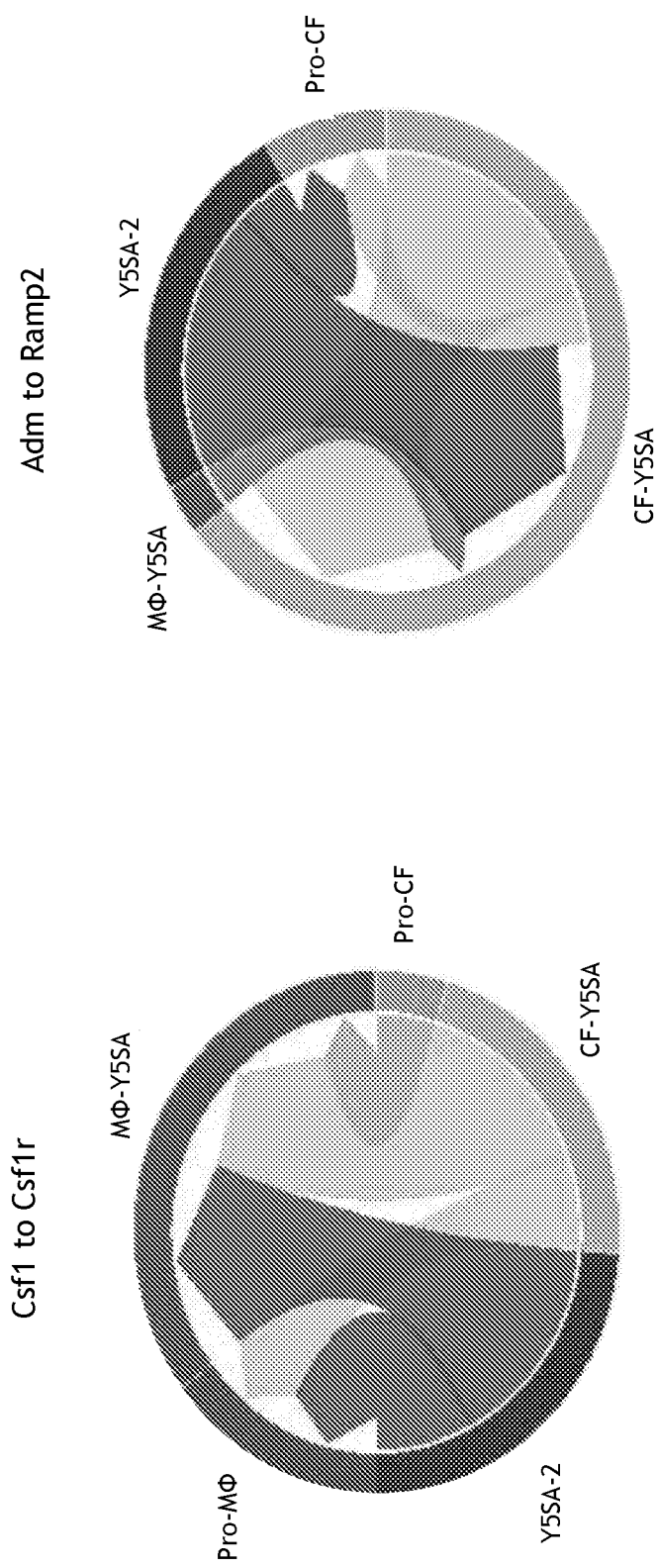
Figure 25E:
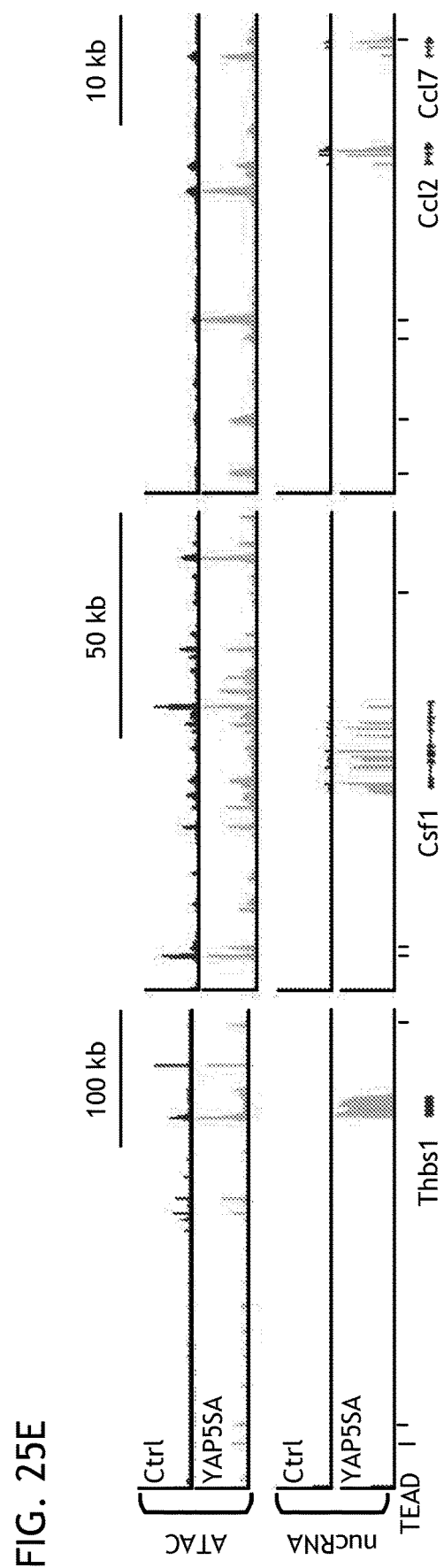

Next, clusters from YAP5SA-CM hearts were grouped together (FIG. 19H), and then there was performed ligand-receptor interaction network analysis with a focus on cardiac fibroblasts (CF-Y5SA), macrophages (Mϕ-Y5SA), and monocytes (Ccr2Hi) (FIG. 19I). Out of the total 165 ligand-receptor pairs directed from Y5SA-2, 105 (~64%) were shared with MFLs (FIGS. 19J and 25D). Moreover, CM-specific ATAC-seq and nuclear RNA-seq data were interrogated from control (Myh6-MCM only, tamoxifen treated) and YAP5SA hearts and it was found that many genes also exhibited epigenetic chromatin accessibility shifts at peaks containing conserved TEAD motifs, including Thbs1, Csf1, Ccl2, and Ccl7 (FIG. 24E).

Figure 19K:
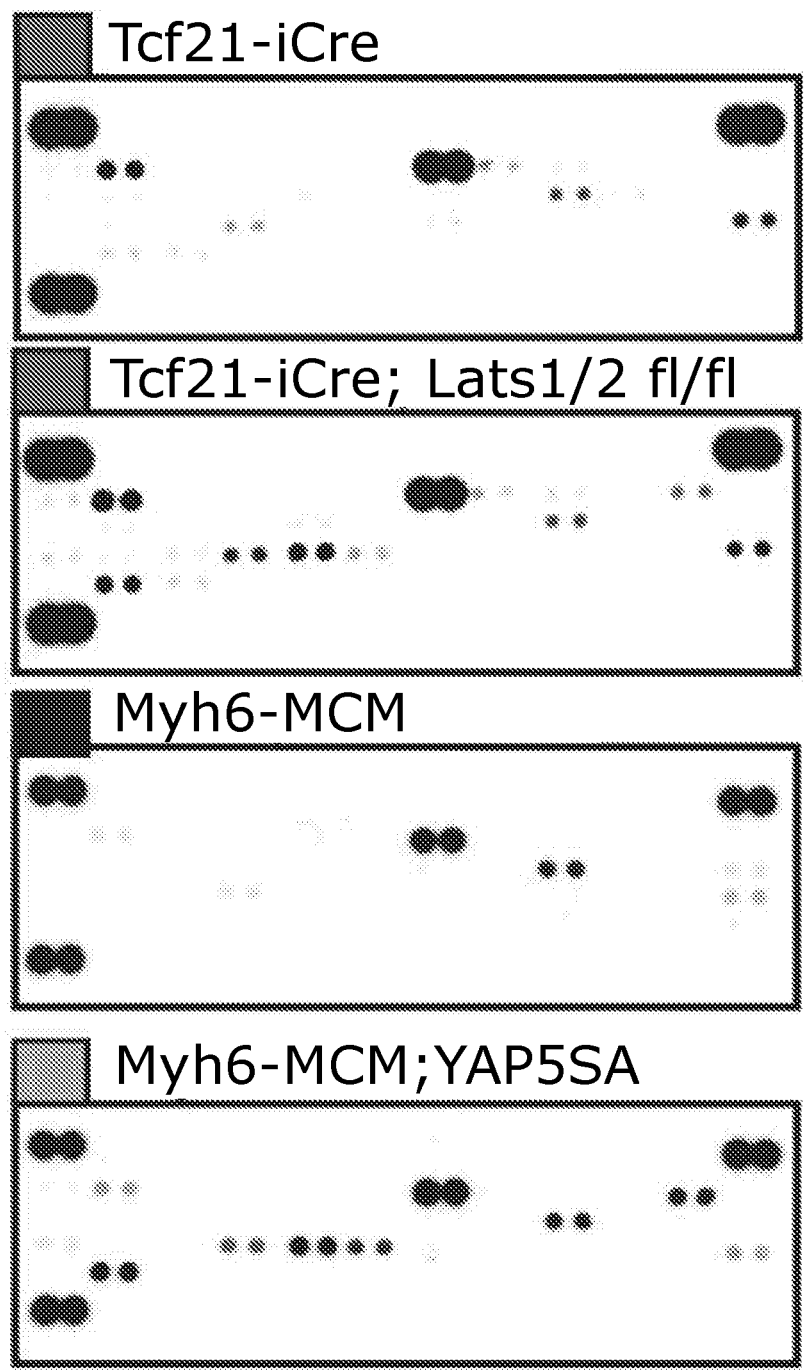
Figure 19L:
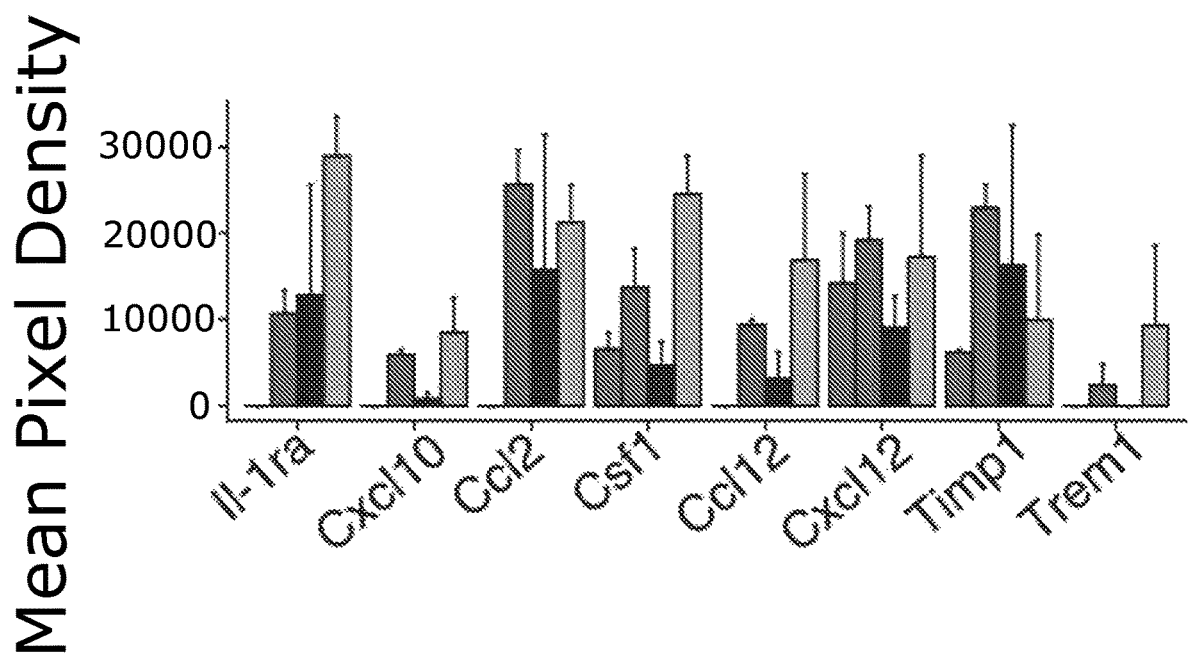

To validate the expression of key signaling molecules, the chemokine/cytokine production was measured of Lats1/2 CKO and YAP5SA-CM hearts, along with their respective controls. Protein lysates derived from the ventricles were harvested for cytokine array analysis (FIG. 19K). Among the 40 chemokines/cytokines analyzed, IL-1F3, Timp1, Cxcl1, Cxcl10, Cxcl12, Csf1, Ccl2 and Ccl12 were up-regulated in Lats1/2 CKO hearts. Furthermore, protein expression of Il-1ra, Cxcl10, Ccl2, Csf1, Ccl12, Cxcl12, and Trem1 were also upregulated in YAP5SA hearts (FIG. 19L). Thus, Lats1/2 inhibit a Yap-induced CM injury response and limit immune-cell infiltration into the heart.

Figure 20A:
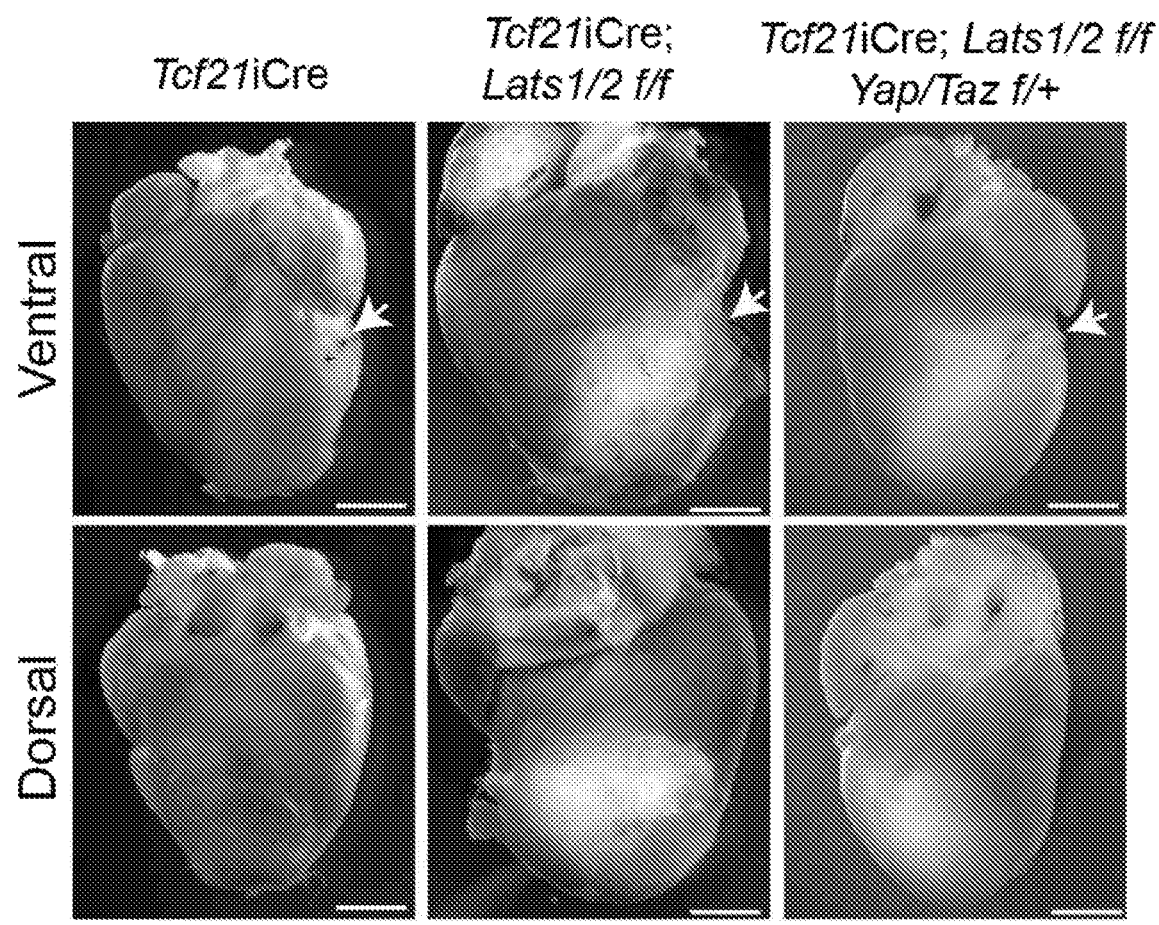
Figure 20B:
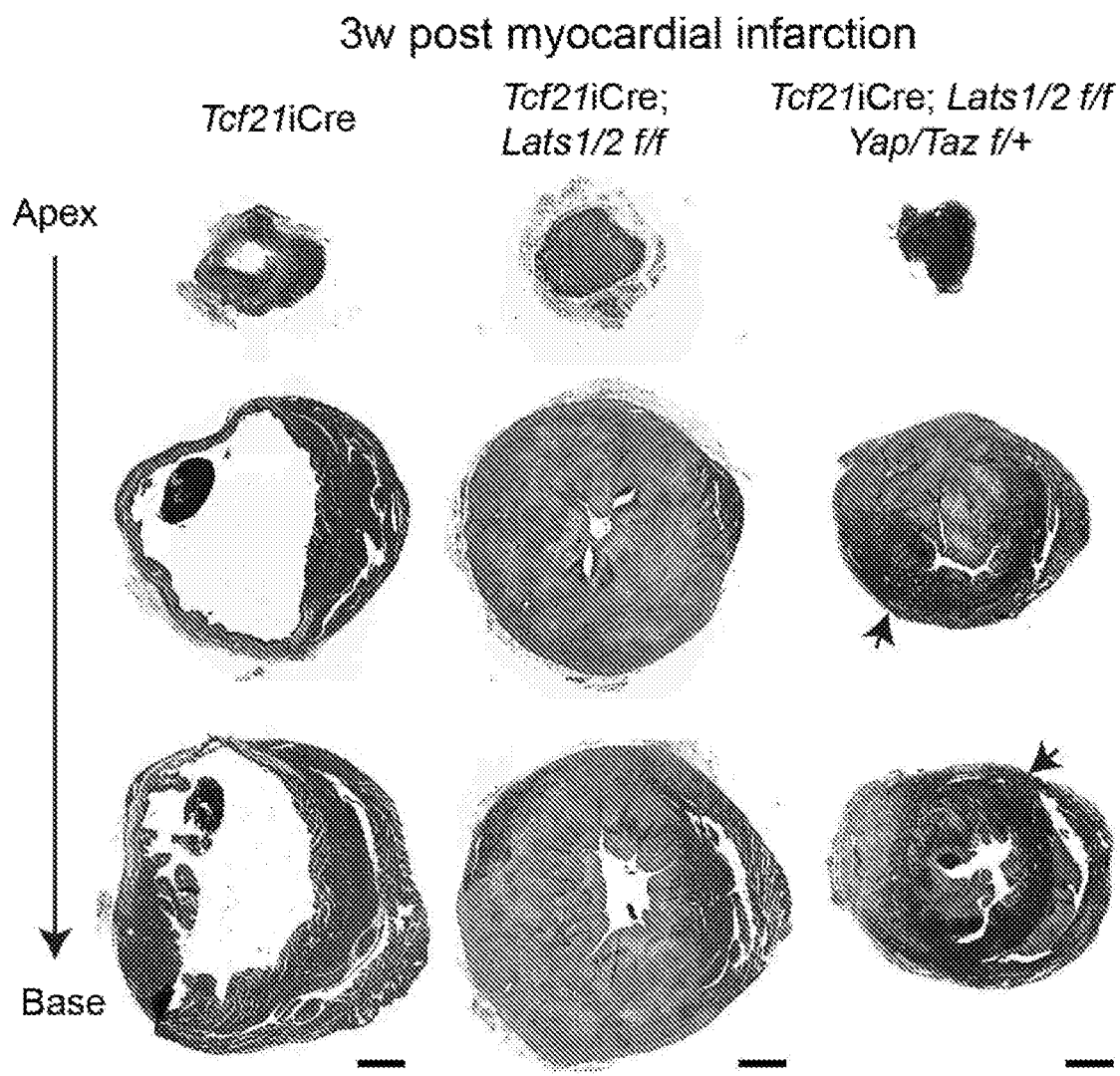
Figure 26A:
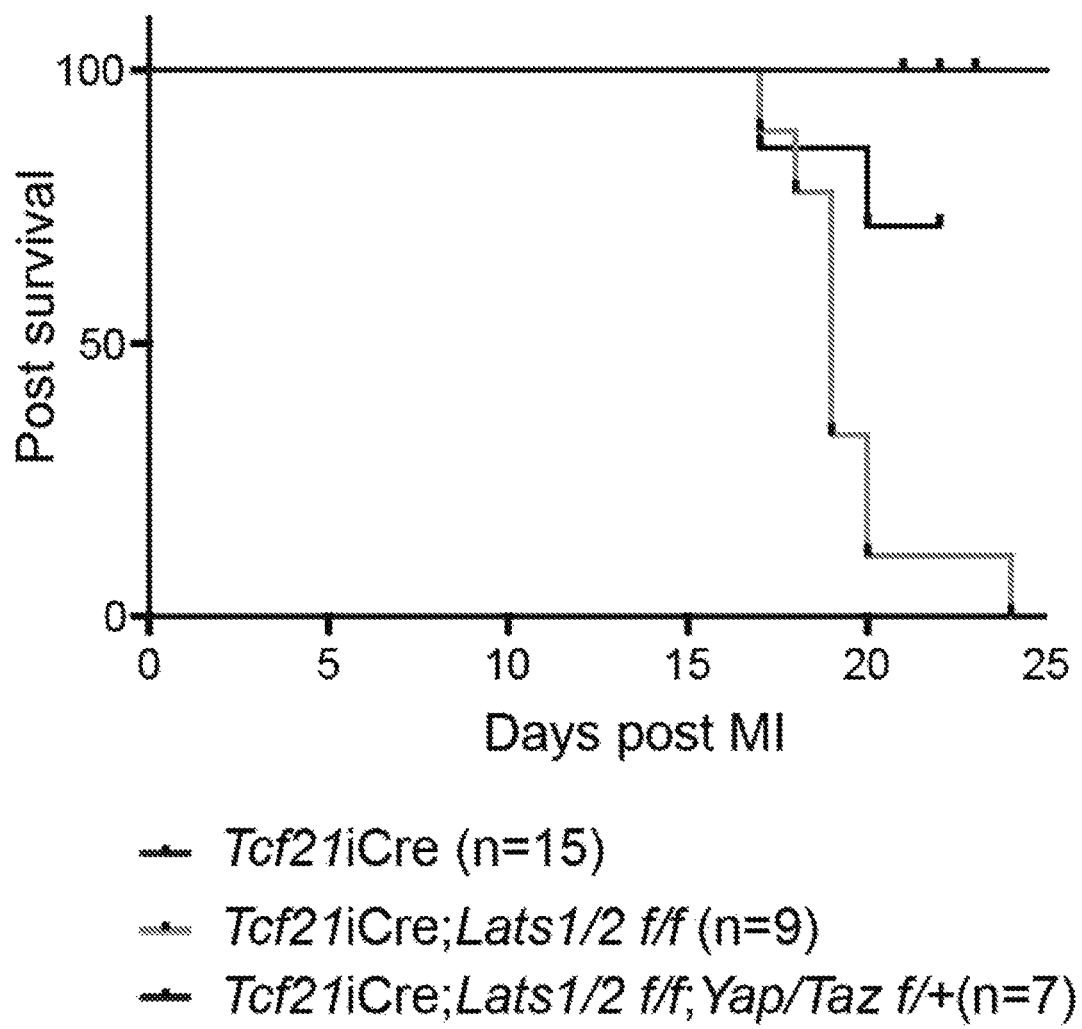

Lats1/2 Expression in Cardiac Fibroblasts is Required for Cardiac Scar Maturation Following Myocardial Infarction The cardiac myofibroblast cell state induced by MI is transitory, and differentiating cells typically lose Acta2 expression by 10 days after MI (Fu et al 2018 JCI). The data indicated that Lats1/2 deletion in resting CFs leads to Yap activation which promotes the resting CF to myofibroblast cell fate transition in the absence of MI. To study the injury-induced differentiation potential of Lats1/2 mutant CFs, MI was performed on Lats1/2 CKO hearts. Interestingly, all mutant mice died by 3 weeks after myocardial infarction (FIG. 26A), indicating that Lats1/2 are required for survival after MI. In Lats1/2 CKO hearts after MI, there was extensive fibrosis below the suture where artery occlusion was performed (FIG. 20A). Masson's trichrome staining and histological analysis in the Lats1/2 CKO post-MI hearts revealed profound expansion of fibrosis throughout the heart. Instead of forming a compact scar after MI, as in control hearts (FIG. 20B), the ischemic area and cardiac lumen of Lats1/2 CKO hearts after MI were almost completely replaced by fibrotic tissue (FIG. 20B). Yap and Taz were genetically reduced by generating Tcf21iCre; Lats1/2 f/f, Yap/Taz f/+ mice and the fibrosis phenotype was partially suppressed with improved survival post MI (FIG. 20B, FIG. 26A). This indicates that the fibrotic Lats1/2 CKO phenotype after MI is Yap and Taz-dependent.

Figure 26B:
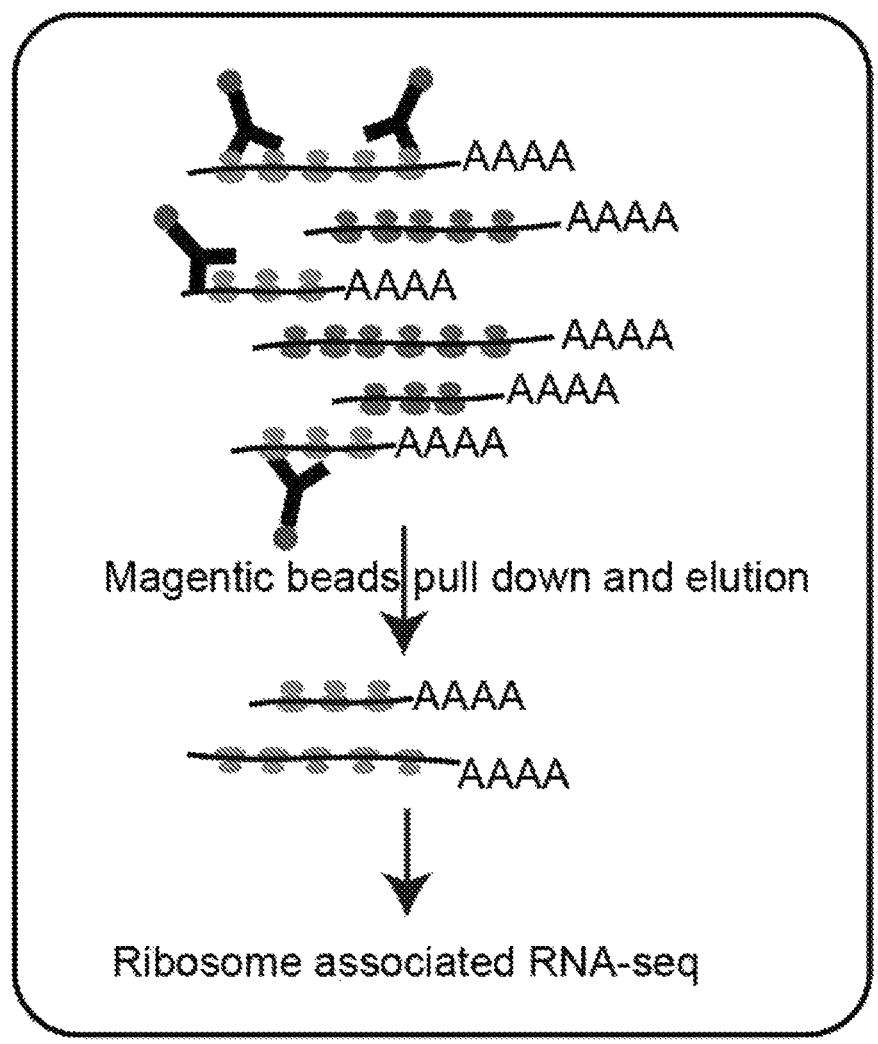
Figure 26C:
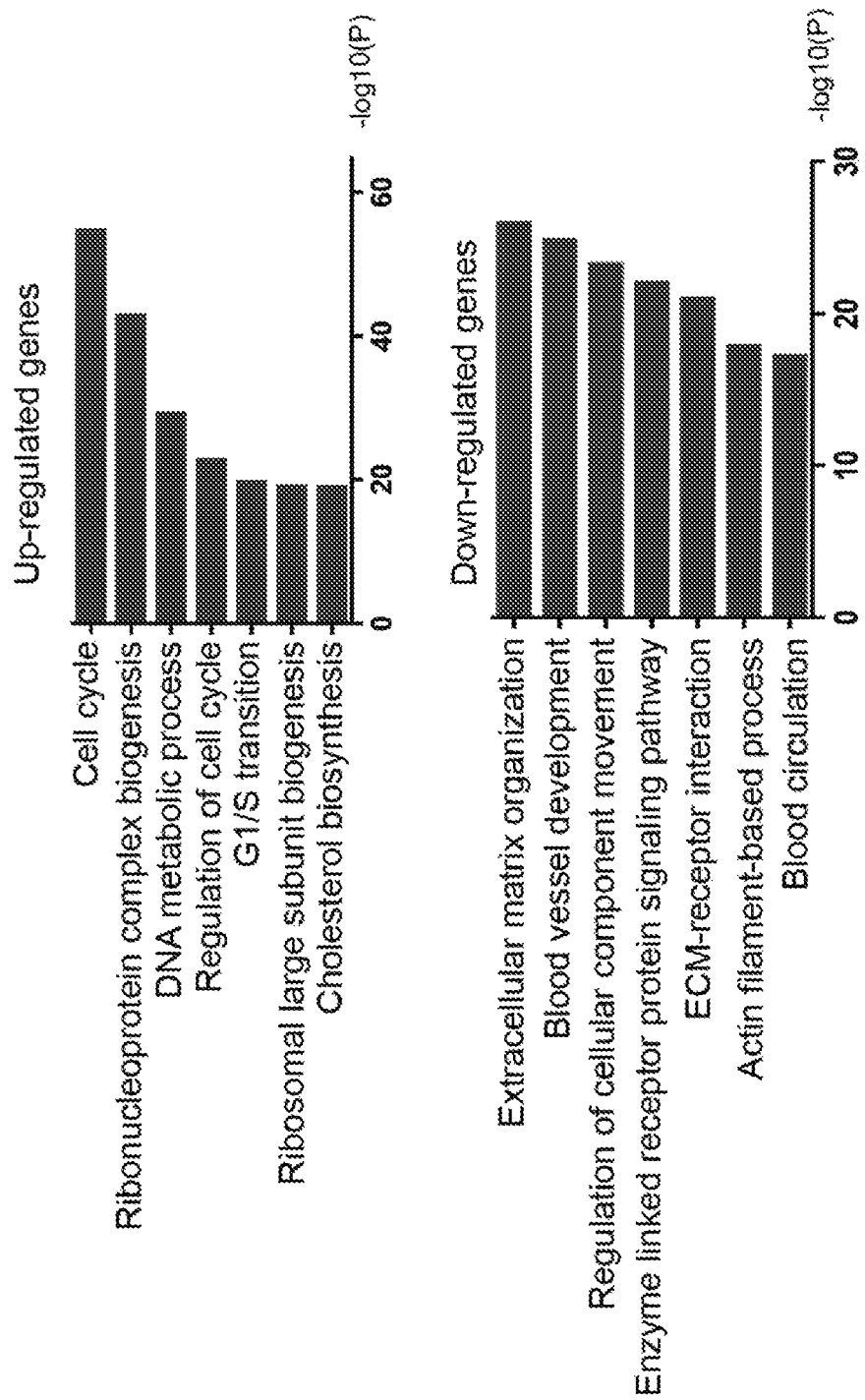

Translating Ribosome Affinity Purification followed by RNA-seq (TRAP-seq) was performed to interrogate genes actively being translated in CFs (Sanz et al., 2009). At 1 week post-MI, translating-ribosome-associated RNA was purified from control and Lats1/2 CKO hearts for RNA-seq (FIG. 26B). Gene Ontology (GO) analysis of differentially expressed genes showed genes associated with cell cycle, DNA metabolic processes, and ribosomal biogenesis were significantly up-regulated in Lats1/2 CKO hearts after MI, which is consistent with the known role of Lats1/2 in inhibiting proliferation (FIG. 26C).

Figure 20C:
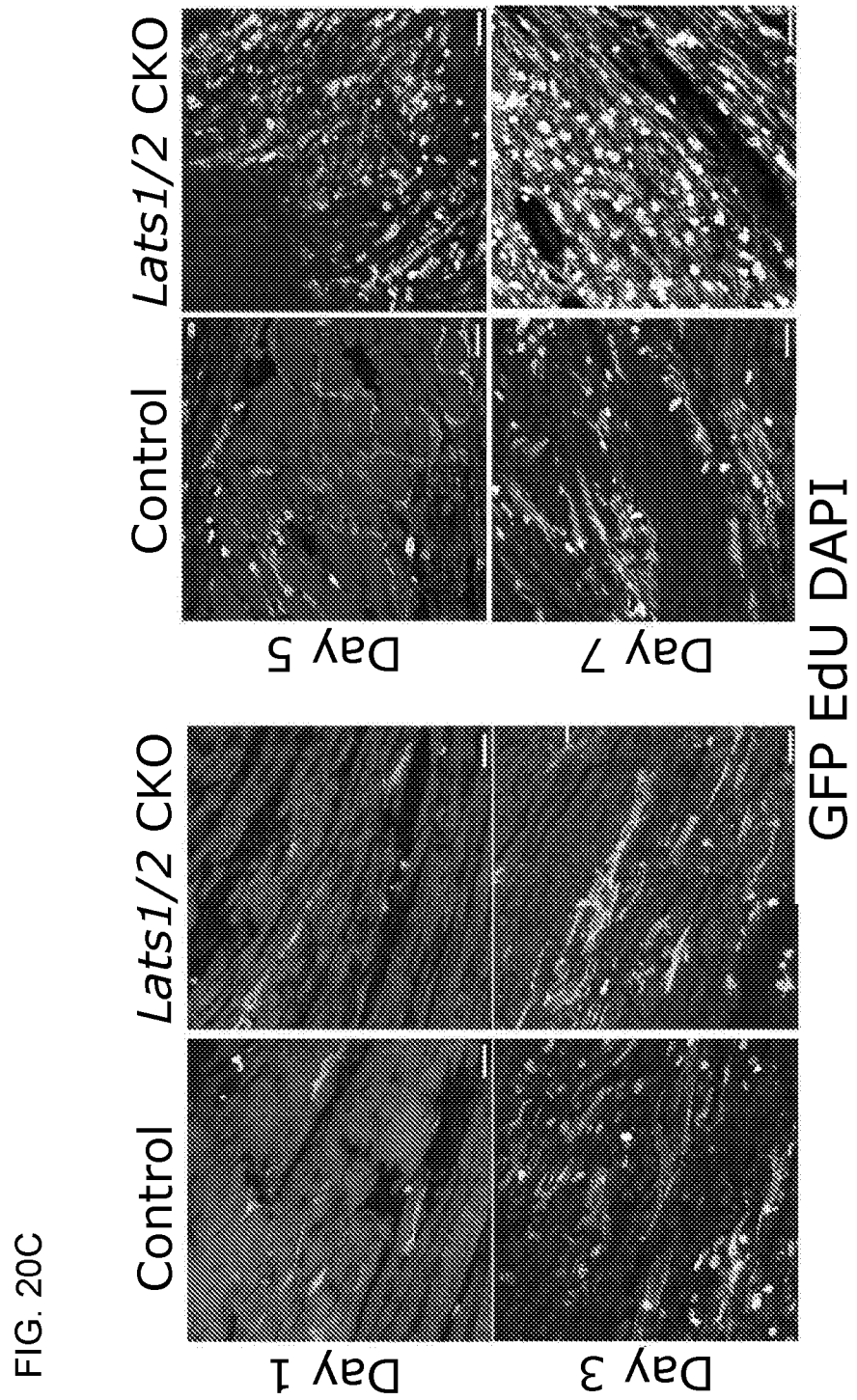
Figure 26D:
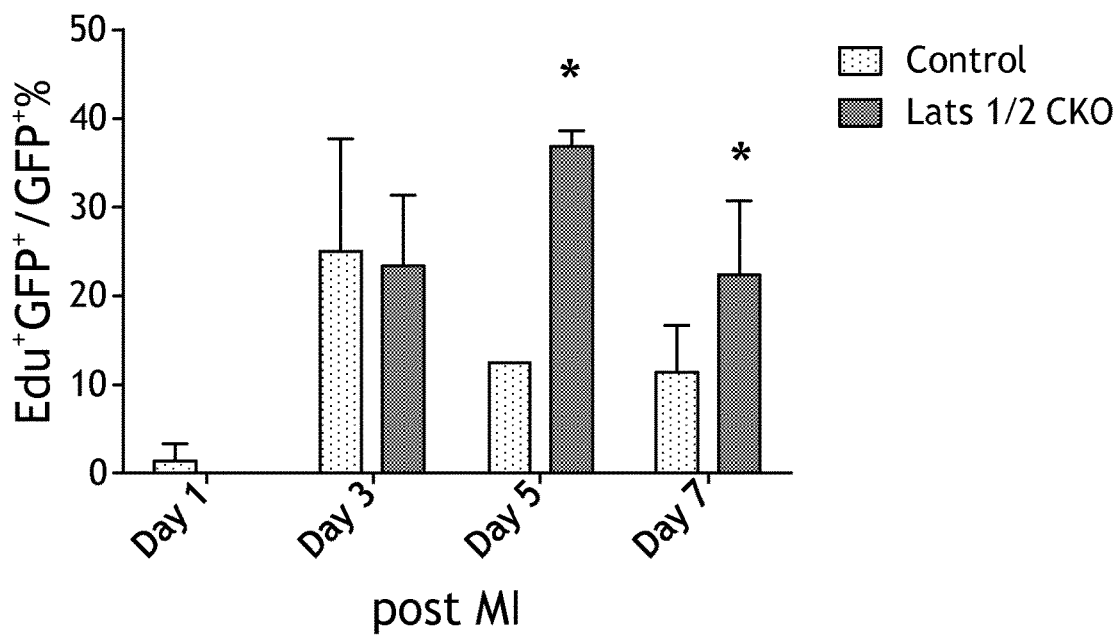
Figure 26E:
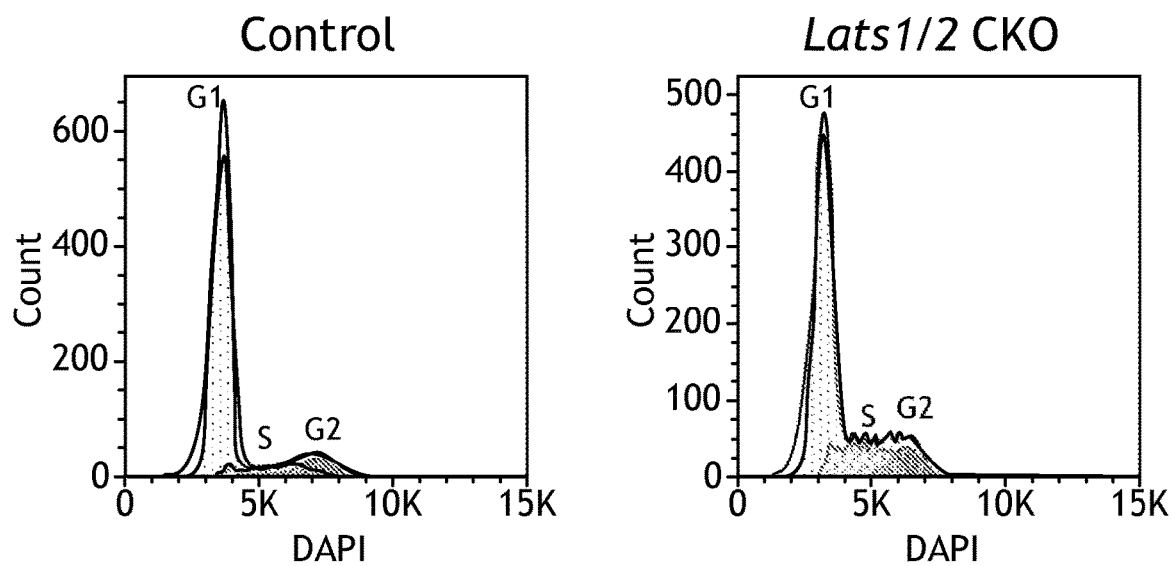
Figure 26F:
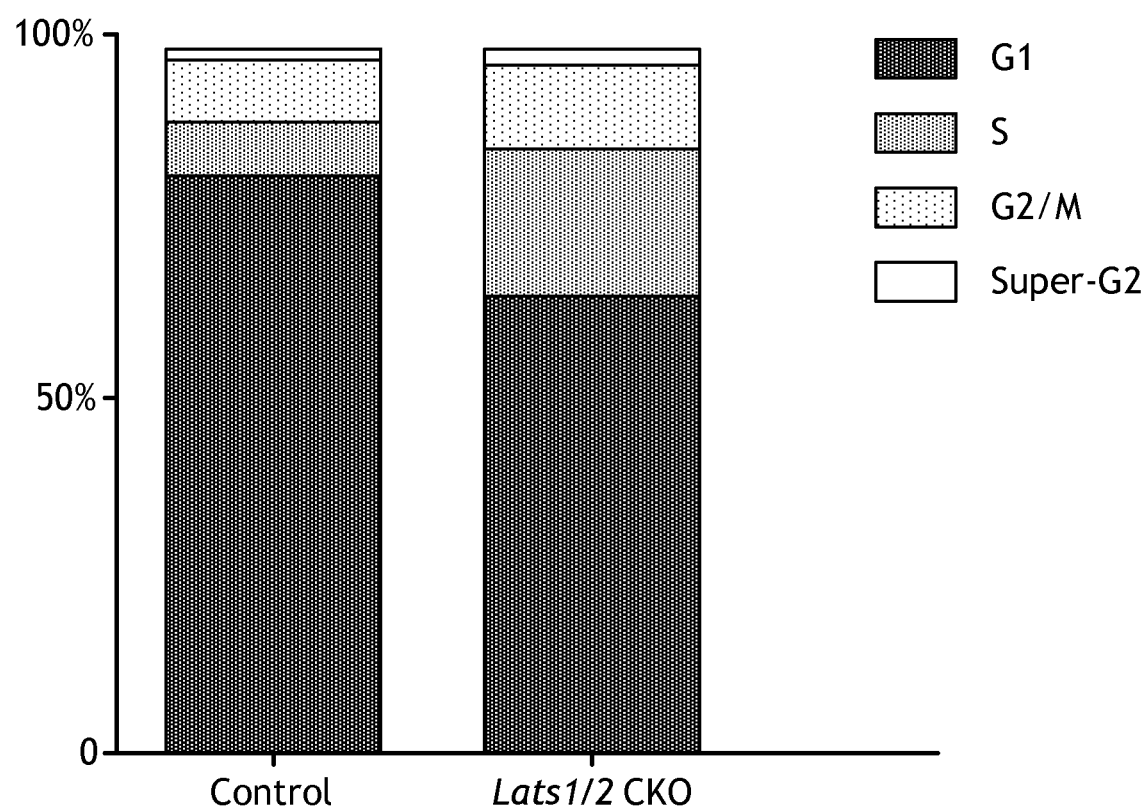

To examine the time-course of fibroblast expansion after MI, lineage tracing was performed in combination with EdU pulse incorporation at different timepoints during the resting CF to myofibroblast transition (FIG. 20C). EdU-labelling demonstrated a striking difference between control and Lats1/2 CKO hearts after MI. Further, Lats1/2 CKO hearts at 1-week post MI were comprised of GFP+ cells, which occupied the infarcted tissue regions (FIG. 20C). This indicates that the fibrotic tissue detected by Masson Trichrome staining mainly comes Tcf21-lineage derived Lats1/2 CKO CFs. In control CFs, there was a moderate increase of EdU incorporation that peaked at three days post MI and gradually tapered off by five days post MI. Lats1/2 CKO CFs had an increased EdU incorporation rate at both three days and five post MI, however, the number of Lats1/2 CKO EdU+ cells plateaued after five days post MI (FIGS. 20C and 26D). Injury induced CF cell cycle dynamics were further investigated by FACS analysis at 7 days post MI. Consistently, mutant MFLs showed a significant increase in the proportion of cells in S phase and a reduction of cells in G1 phase in contrast to control CFs (FIGS. 26E, 26F, and 26G). The proportion of cells in super G2 phase, a readout of polyploidy and genome instability, between control and mutant CFs is comparable. Collectively, the increased proliferation in Lats1/2 CKO CFs indicates an essential, inhibitory role for Lats1/2 in myofibroblast expansion after MI.

Figure 20D:
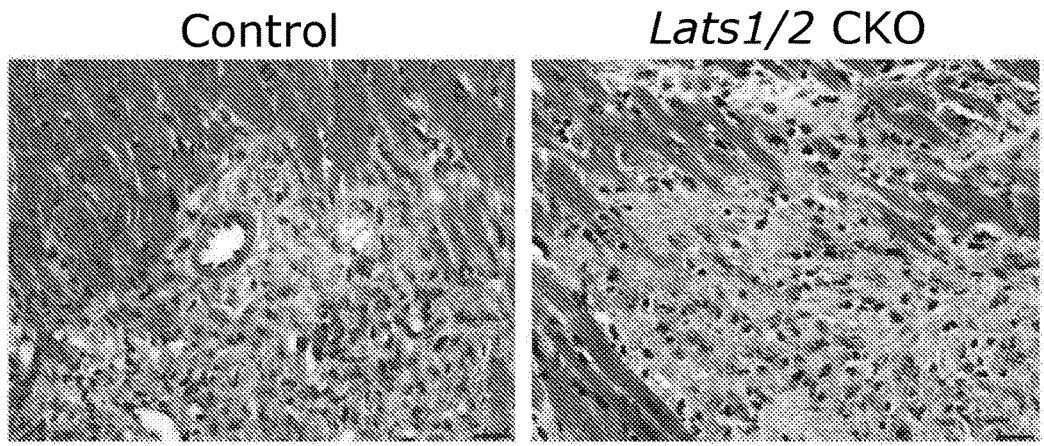

Cardiac scar maturation is associated with the deposition of a dense collagenous scar (Fu et al, 2018 JCI). The TRAP-seq data indicated that Lats1/2 CKO CFs after MI had reduced ECM gene translation. The genes associated with collagen synthesis assembly and modification, such as Col1a1, Col1a2, Col3a1, Bmp1, Plod1 and P3h2, were decreased in Lats1/2 CKO hearts after MI. Masson's Trichrome staining further corroborated that Lats1/2 CKO hearts three weeks post MI showed a reduction of total collagen content and lacked a compact scar after MI as compared to control after MI (FIGS. 20B and 20D). While Lats1/2 CKO hearts following MI did not possess compact or mature scars, scar tissue aggregated together (FIG. 20B). Moreover, this was also true for uninjured Lats1/2 CKO animals, where ectopic fibrotic tissue also was found to aggregate (FIG. 16D).

Figure 20E:
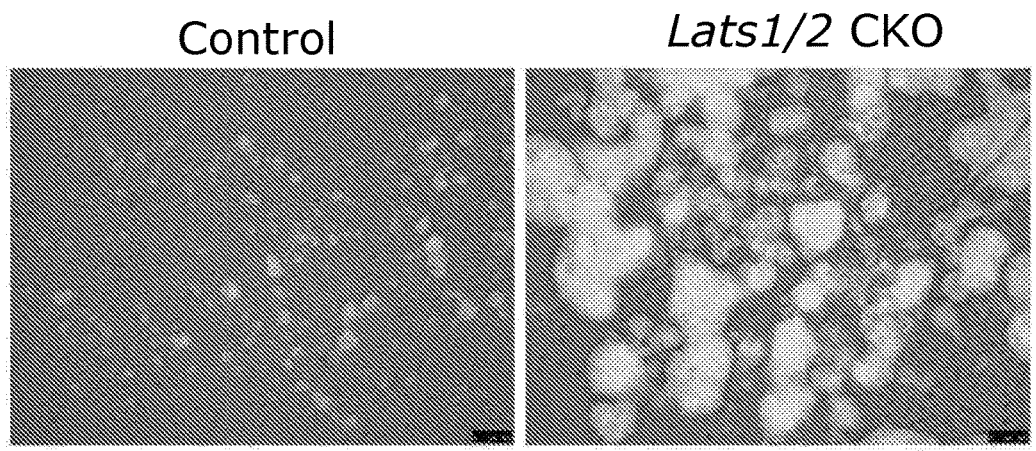

To further investigate the adhesive properties of Lats1/2 CKO CFs, FACS sorted GFP+ cells from hearts 3 weeks post-MI were plated them on low-attachment culture dishes for 24 hours (FIG. 20E). Lats1/2 CKO aggregates were much larger than controls, suggesting that Lats1/2 CKO CFs strongly interacted with one another in vitro as well as in vivo. These results suggest that Acta2 expressing myofibroblasts may functionally interact with each other after MI to form a supportive cellular network to prevent ventricular rupture. Overall, Lats1/2 are required in CFs for promoting proper myocardial scar deposition and maturation following ischemic injury.

Figure 21B:
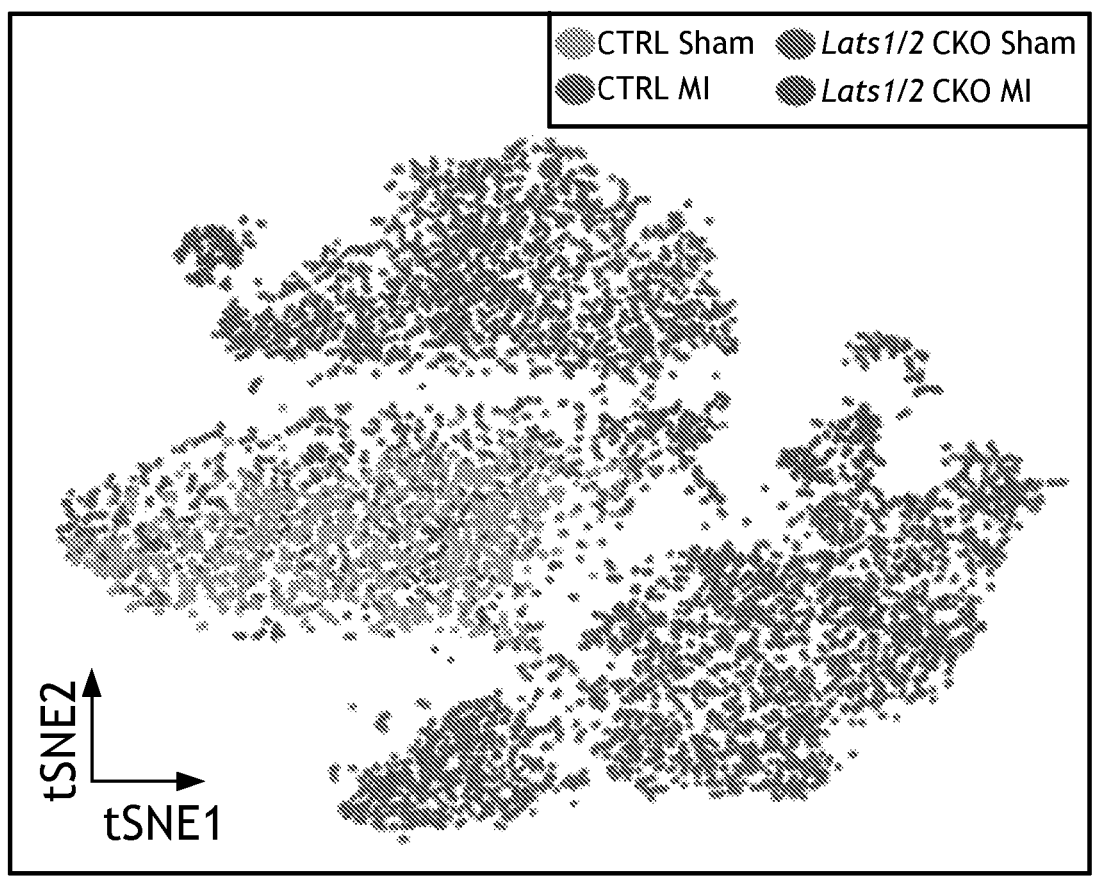
Figure 21C:
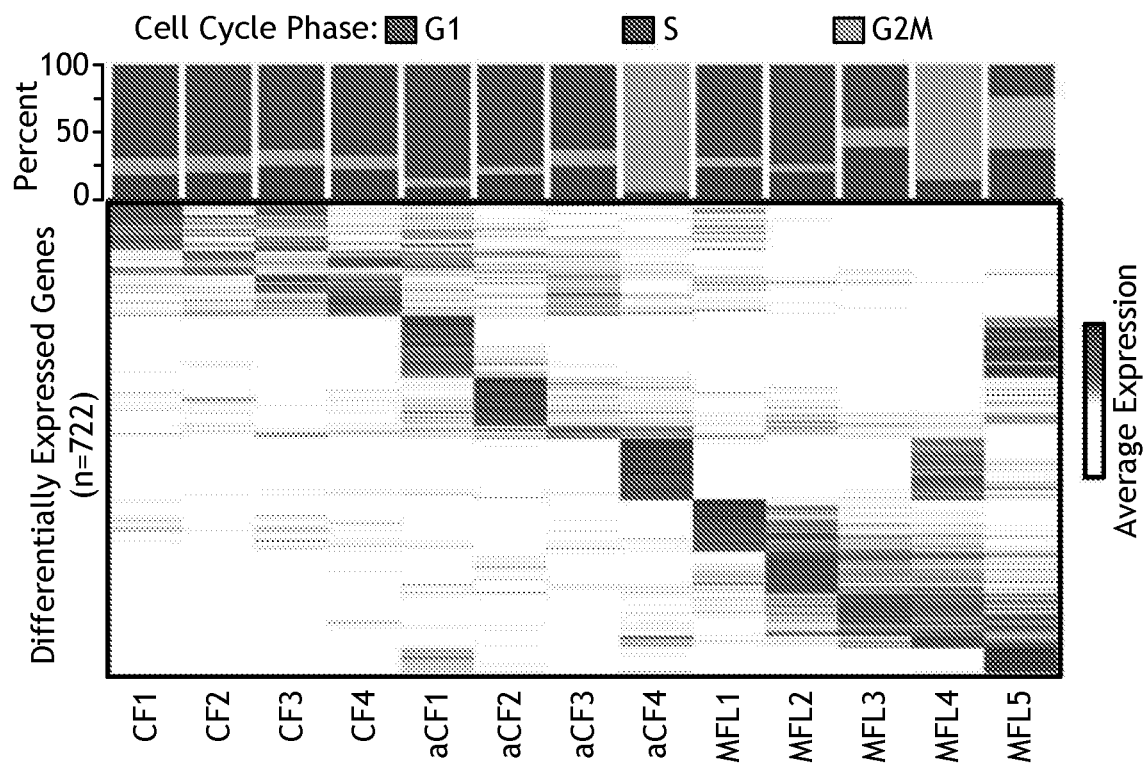

Cardiac Fibroblast and Myofibroblast Cell State Transitions After Myocardial Infarction The data suggested that Lats1/2 CKO CFs lack the ability to exit the myofibroblast cell state and cannot further differentiate into matrifibrocytes to deposit a mature scar. To better understand cardiac fibroblast cell states transitions following MI, Drop-seq was performed on Control and Lats1/2 CKO hearts 1 week after MI. There was filtered out all single-cell transcriptomes that were not fibroblasts after the digital gene expression matrices was merged with the sham scRNA-seq data, resulting in a comprehensive cardiac fibroblast data set consisting of 9,200 total cells (FIGS. 21A and 21B). From this, there was identified a total of thirteen transcriptionally distinct clusters of fibroblasts, including four resting cardiac fibroblast clusters (CF1-4), four activated fibroblast clusters (aCF1-4) expressing the highest levels of Postn and Cilp, and five MFL clusters (MFL1-5) expressing Acta2, Lox, Thbs1, and Timp1 (FIG. 27A). Differential expression analysis between each cluster (see STAR methods) identified 722 differentially expressed gene markers (FIGS. 21C and 27B). After computational determination of the cell cycle phase of each individual transcriptome (Kowalczyk et al., 2015), it was determined clusters aCF3 and MFL4-5 were the most proliferative cells (FIG. 21C). Thus, resting fibroblast proliferation is lowest compared to both activated CFs and myofibroblasts.

Figure 21D:
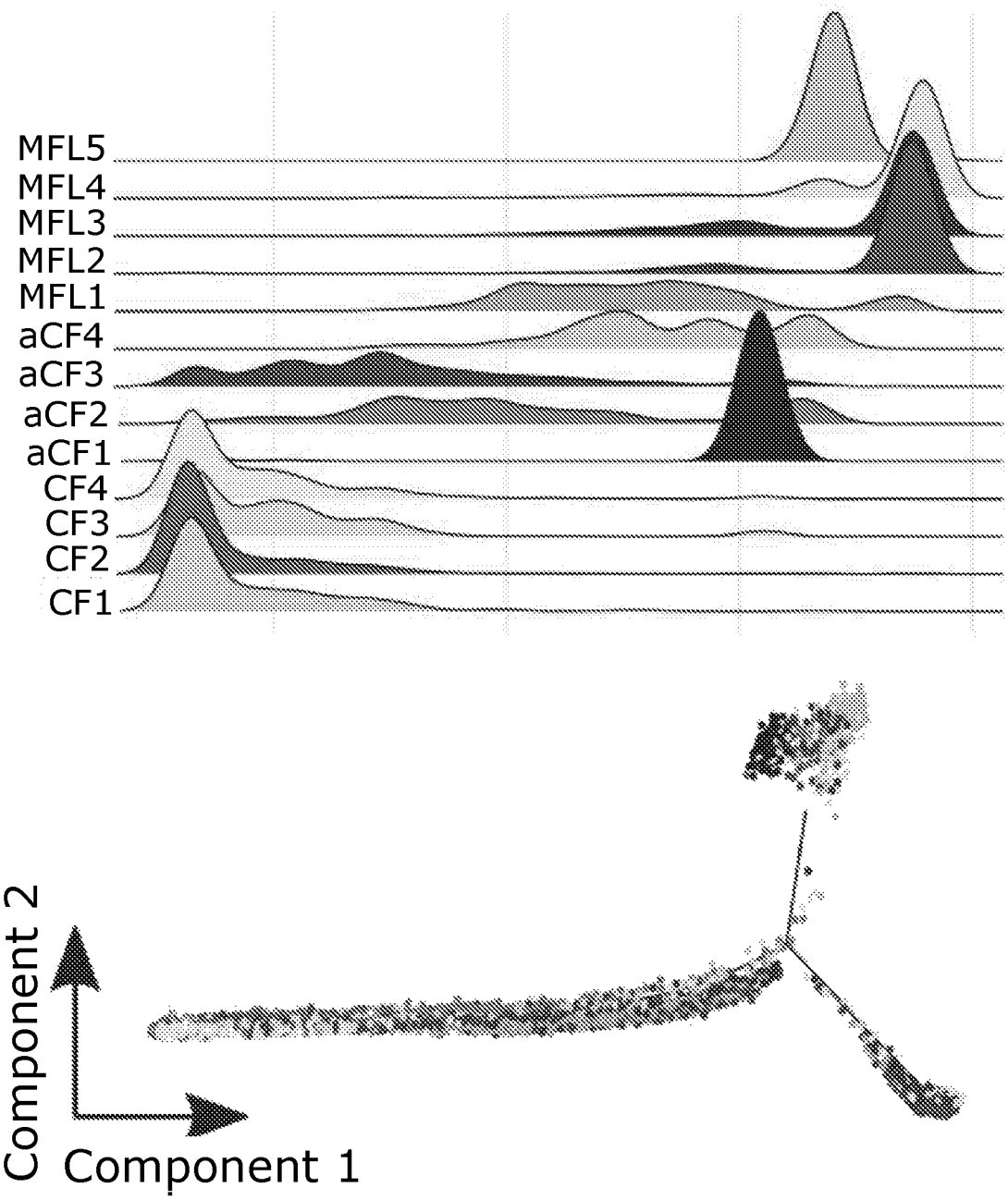
Figure 21E:
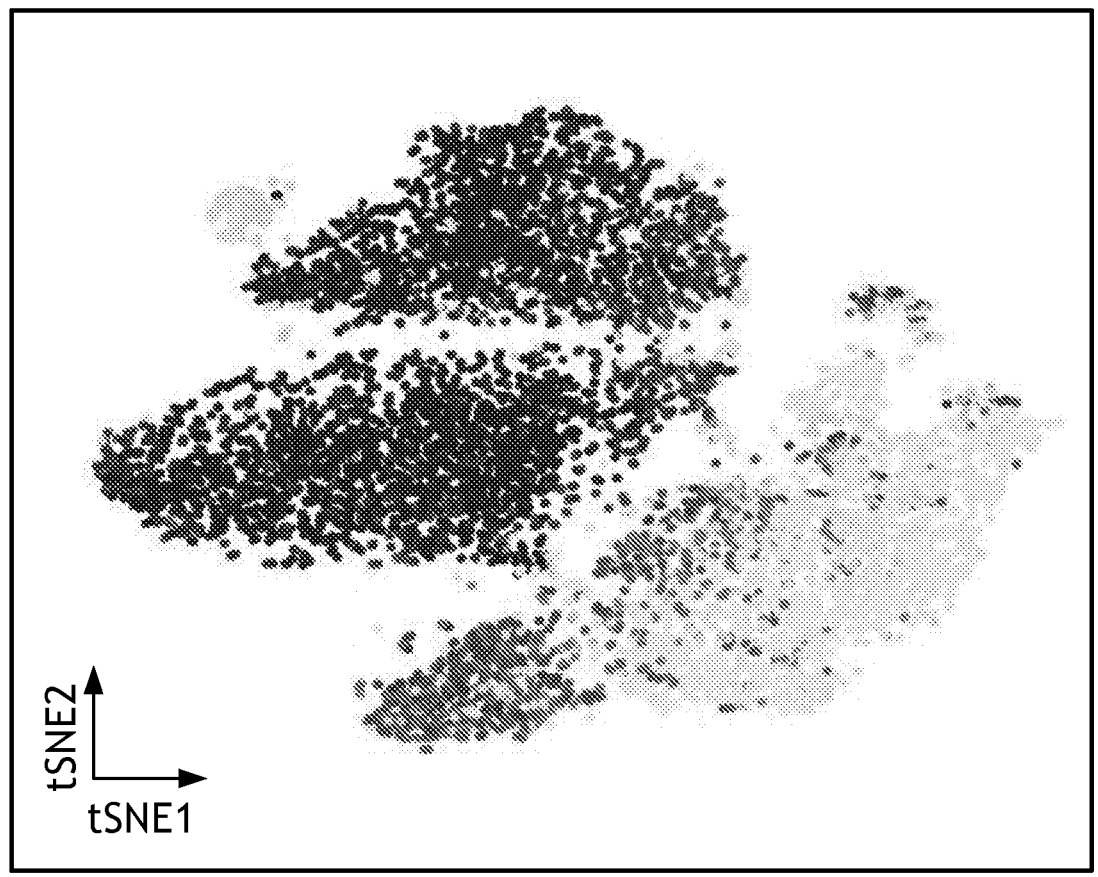
Figure 21E:
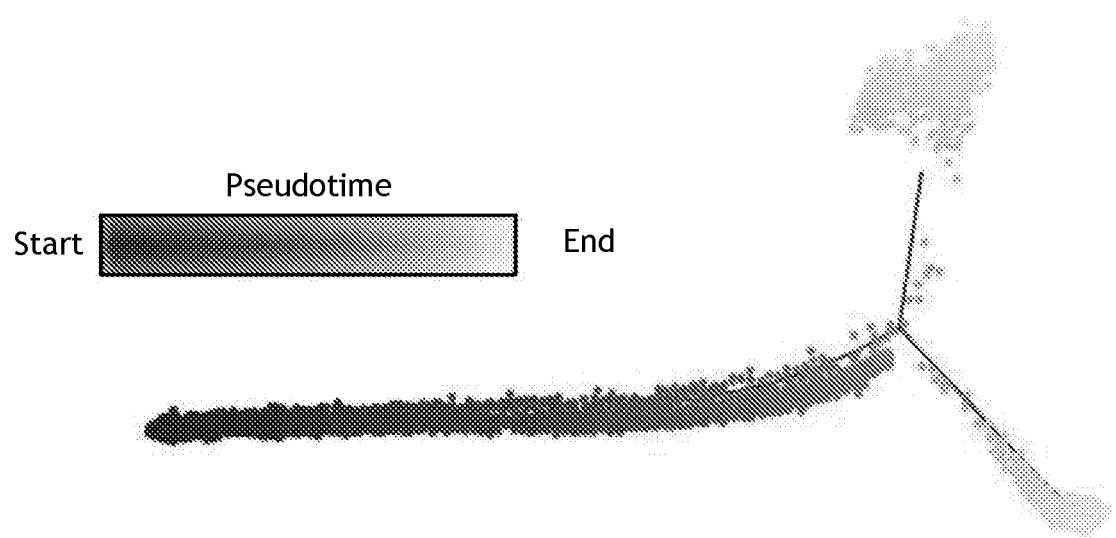
Figure 21F:
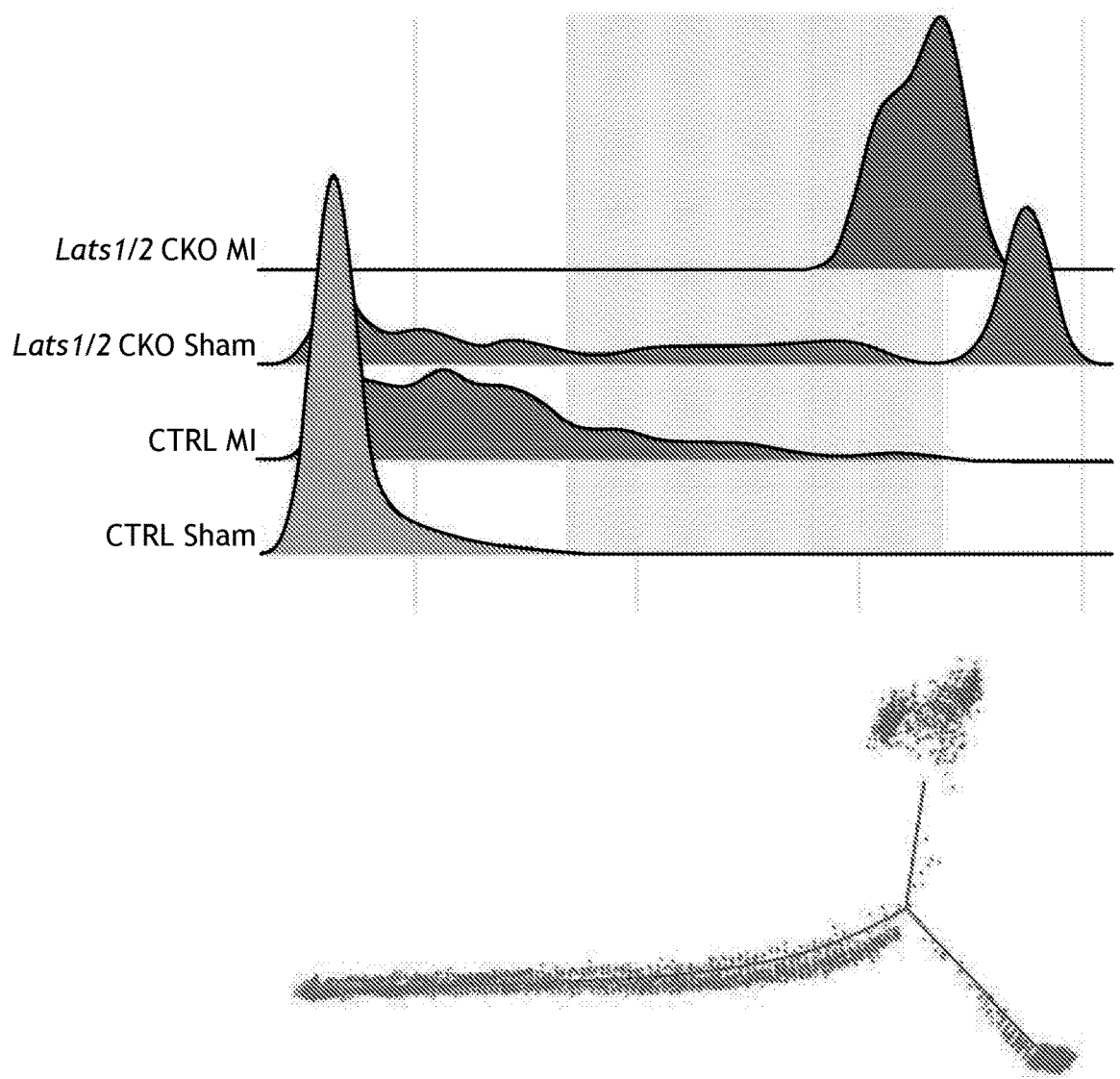

To investigate the dynamics of cardiac fibroblast cell fate transition states, the Monocle2 algorithm was employed to order cells along an unsupervised and unbiased differentiation axis (Li et al., 2017; Qiu et al., 2017). The cardiac fibroblasts ordered along a trajectory where resting CFs were localized at one extreme, active fibroblasts localized to an intermediate location, and finally MFLs occupied the other most distal portion of the minimum spanning tree (MST) (FIG. 21D). After projecting pseudotemporal positional values for individual cells across the tSNE from (FIG. 21A), the Monocle2 values were also very consistent with the graph-based clustering results (FIG. 21E). Next, the dynamics were compared of each transcriptome derived from the four experimental conditions across the differentiation trajectory. For this, the density was determined of all cells from each experiment across the MST (FIG. 21F). Consistent with the other data indicating that Lats1/2 repress a cardiac injury response, this analysis demonstrated that cardiac fibroblasts derived from Lats1/2 CKO sham animals more closely resembled CFs captured from control post-MI hearts as compared to normal uninjured CFs.

Figure 21G:
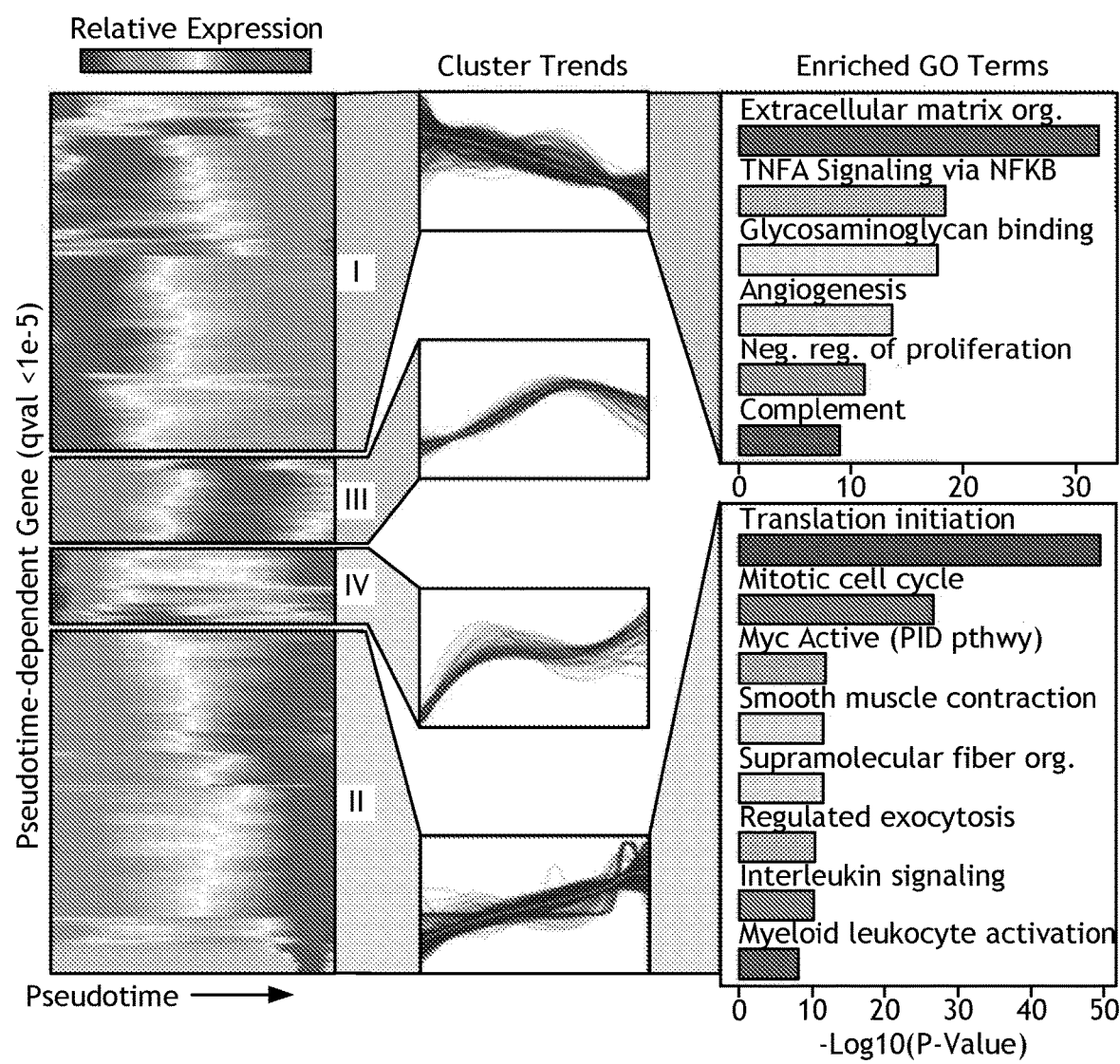
Figure 27D:
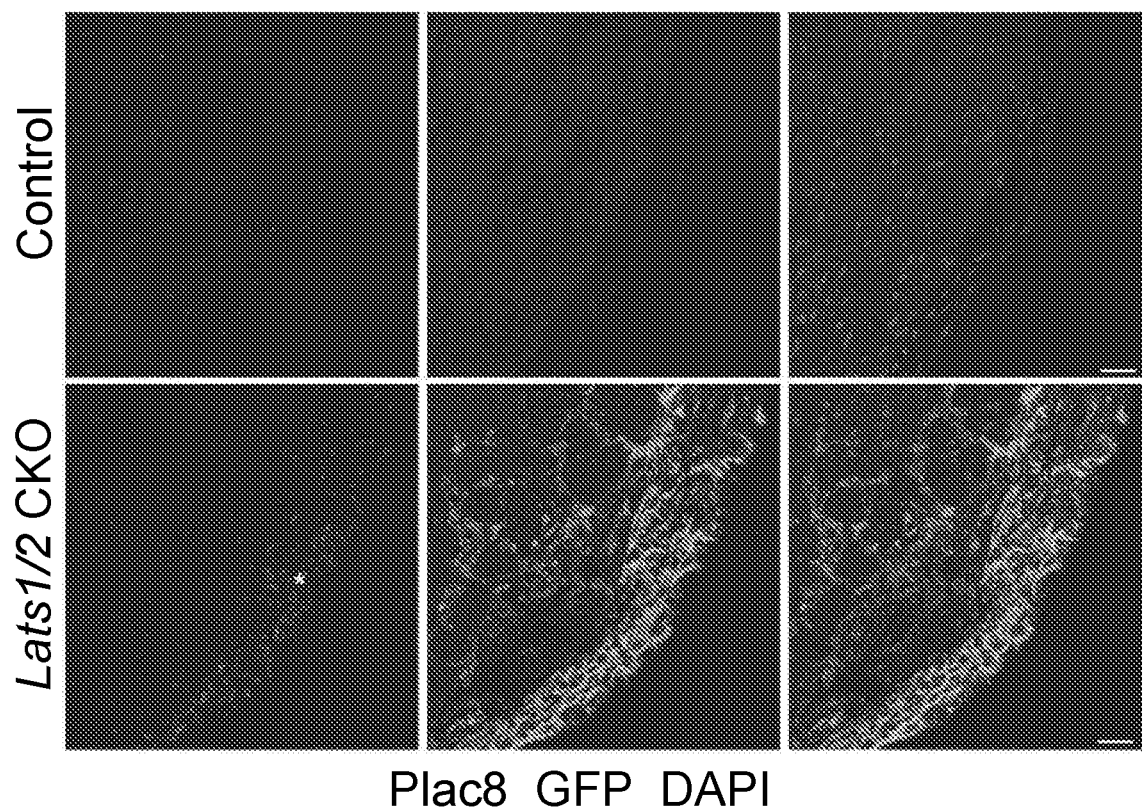

To detail the temporal transcriptional shifts occurring during injury induced cardiac fibroblast differentiation, the gene expression dynamics were determined that change as a function of progress (qvalue<1e-5) through the cardiac fibroblast differentiation axis (FIG. 21G). Hierarchical clustering was performed (nclust=4), to catalog genes by their overall dynamic trends (FIG. 21G). To validate these findings, IF and RNAscope in situ hybridization were performed. From cluster II, the cluster of genes increasing in expression with pseudotime progression that are primarily derived from Lats1/2 CKO cells, Plac8 was a suitable marker. In situ hybridization with a Plac8 probe in control and Lats1/2 CKO hearts revealed that Lats1/2 CKO GFP positive CFs expressed Plac8, while control CFs did not (FIG. 27D). GO analysis revealed that as CFs differentiate they shift their extracellular matrix expression patterns, decrease the expression of genes associated with pro-angiogenic signaling pathways, and inhibit the expression of many negative regulators of cell proliferation (FIG. 21G). Furthermore, CFs progressing to myofibroblasts increased the expression of several gene GO categories, including translation initiation, mitosis, exocytosis, interleukin signaling, and myeloid cell activation (FIG. 21G).

Figure 21H:
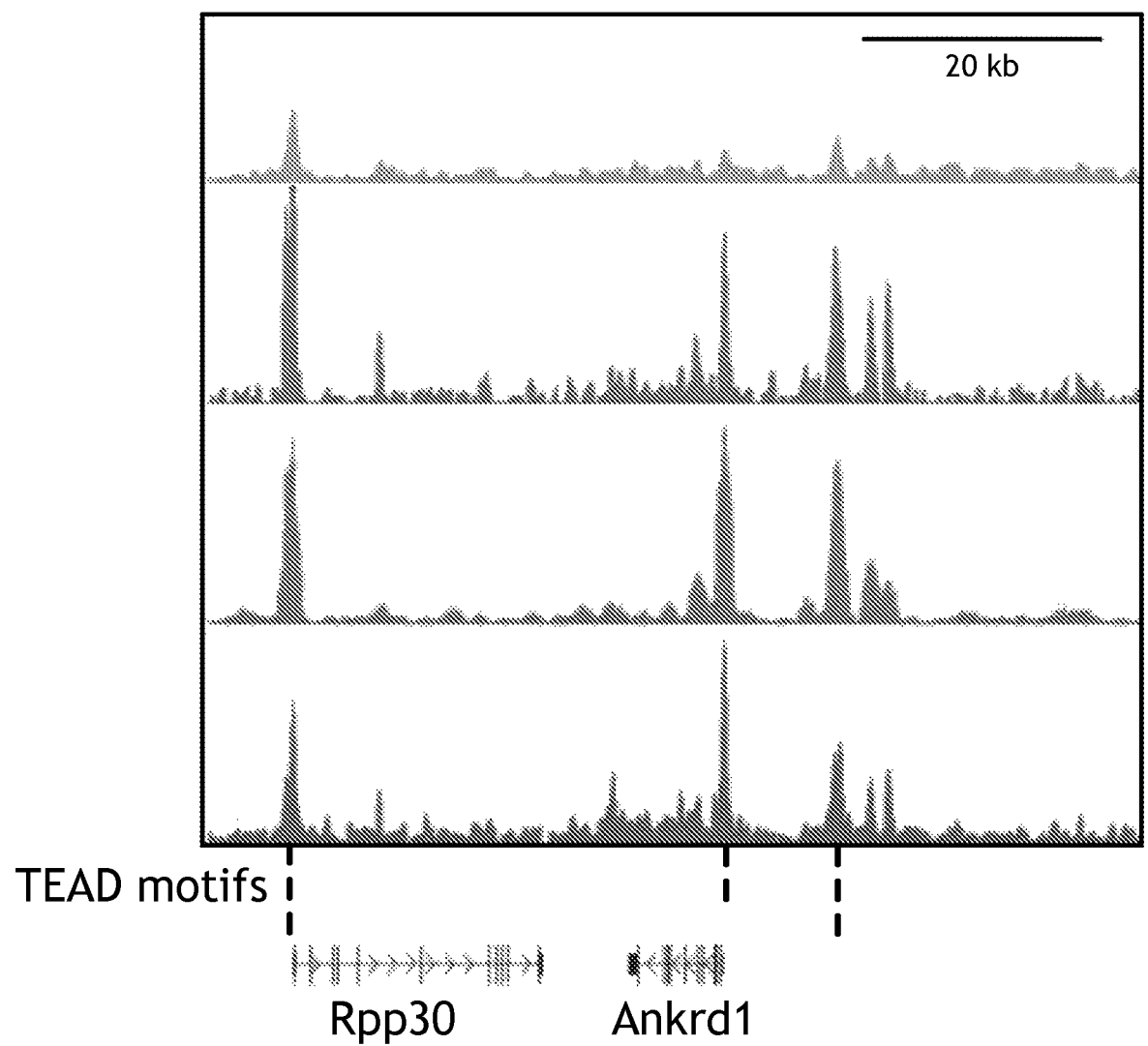
Figure 21I:
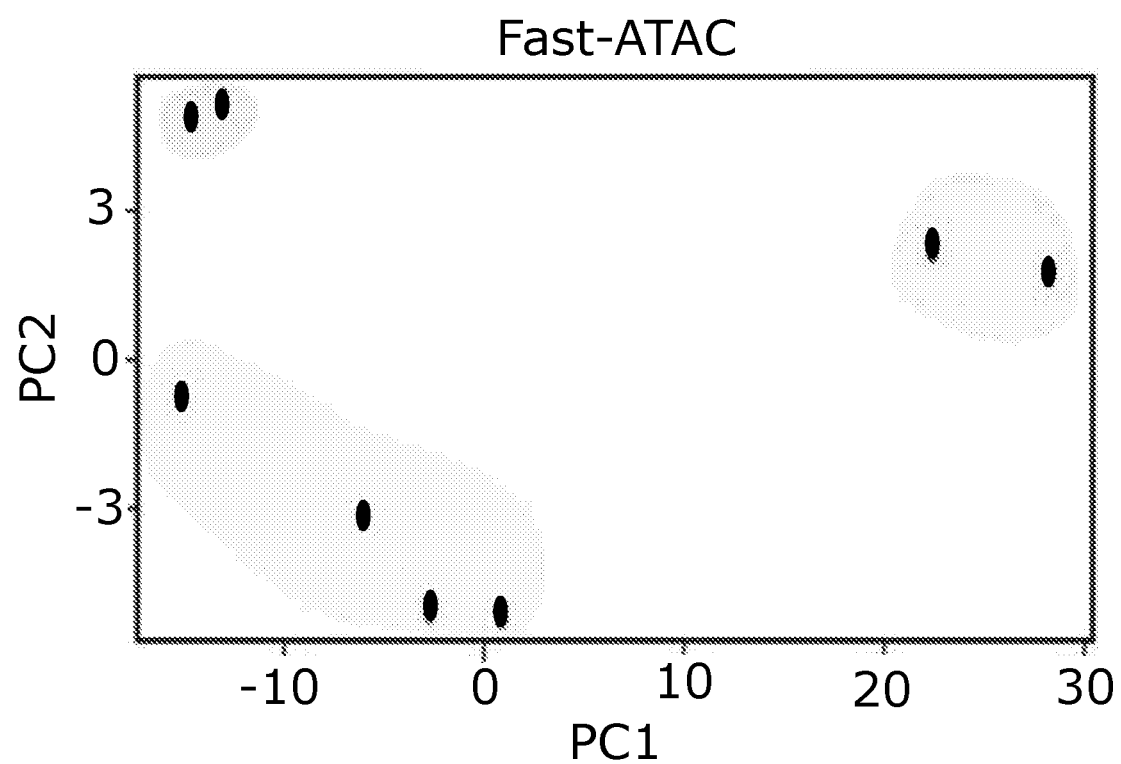
Figure 21J:
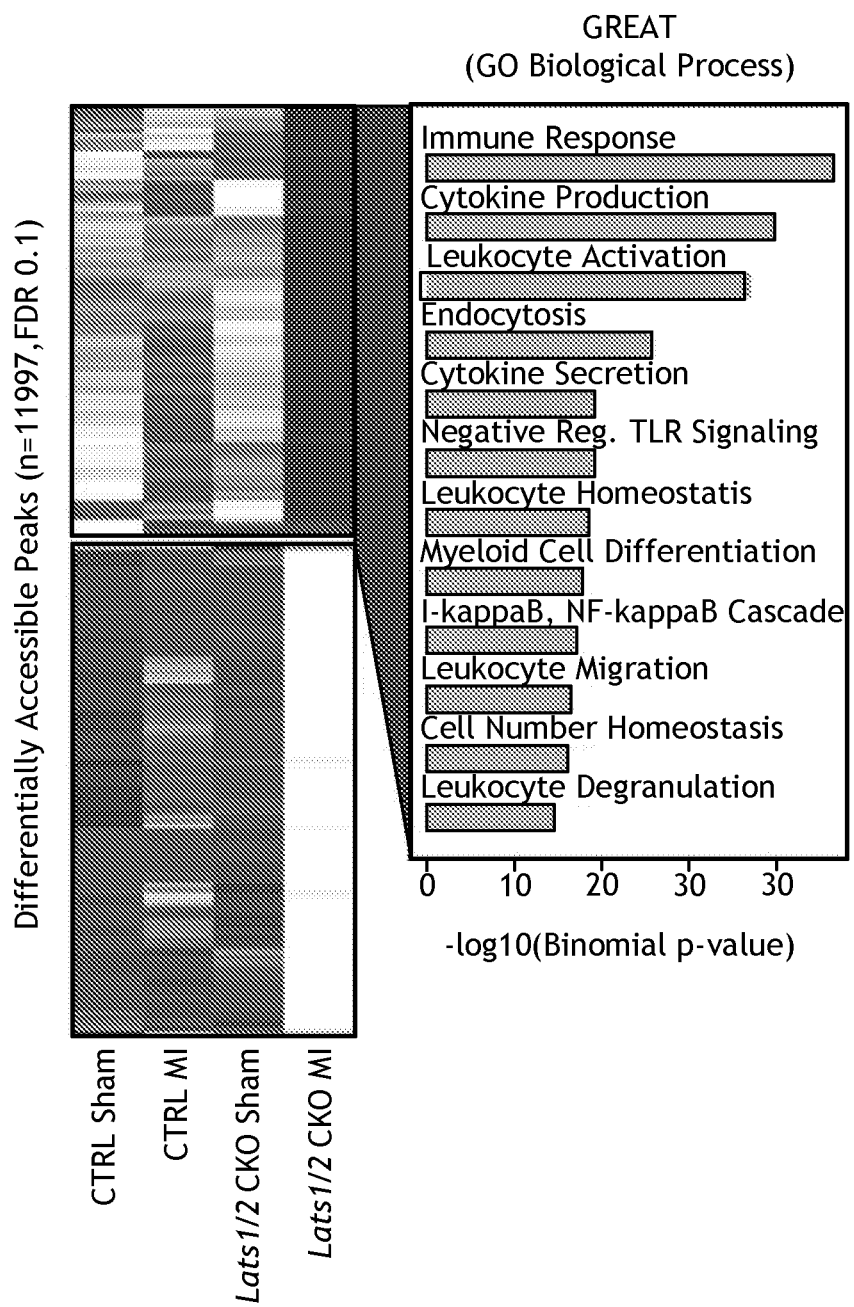

The gene expression findings were validated at the epigenetic level. Fast-ATAC was performed on sorted GFP positive Lats1/2 CKO CFs after MI, and then compared accessibility across all conditions. Importantly, Tead motifs proximal to Yap target genes, like Ankrd1, were highly accessible in Lats1/2 CKO MI samples (FIG. 21H). Comparative PCA carried out on the accessibility patterns across all ATAC peaks revealed distinct global chromatin signatures for control sham and Lats1/2 CKO MI, however, control MI and Lats1/2 CKO sham samples clustered together (FIG. 21I). To determine the accessible regions most enriched in post-MI Lats1/2 CKO fibroblasts, which confer their unique characteristics, and compare these global accessibility patterns and transcriptional dynamics identified via Monocle2, differential accessibility analysis was performed, and there were 11,997 (FDR set at 0.1) peaks differentially accessible between Lats1/2 CKO MI and the other conditions (FIG. 21J). The Genomic Regions Enrichment of Annotations Tool (GREAT) was implemented on the highest accessible cluster of peaks in post-MI Lats1/2 CKO cardiac fibroblasts, and found several statistically enriched GO terms, including cytokine production/secretion, and myeloid cell differentiation which were consistent with the Drop-seq analysis (FIG. 21J).

Figure 21K:
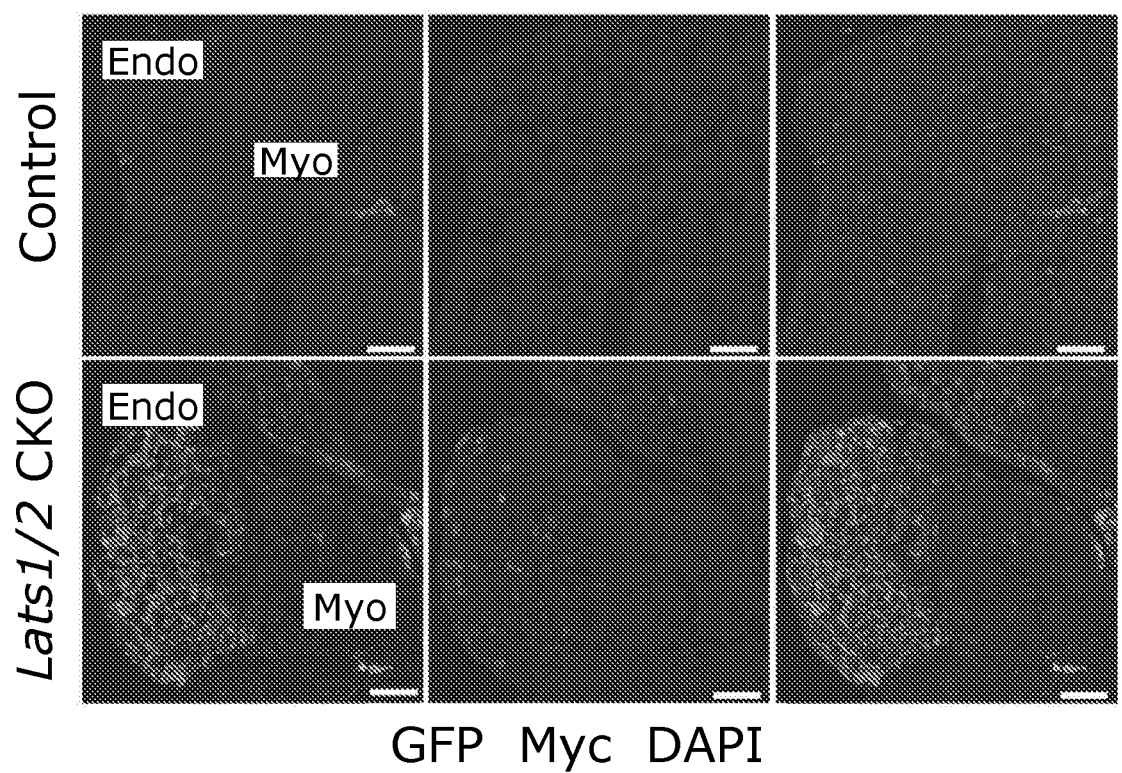
Figure 21L:
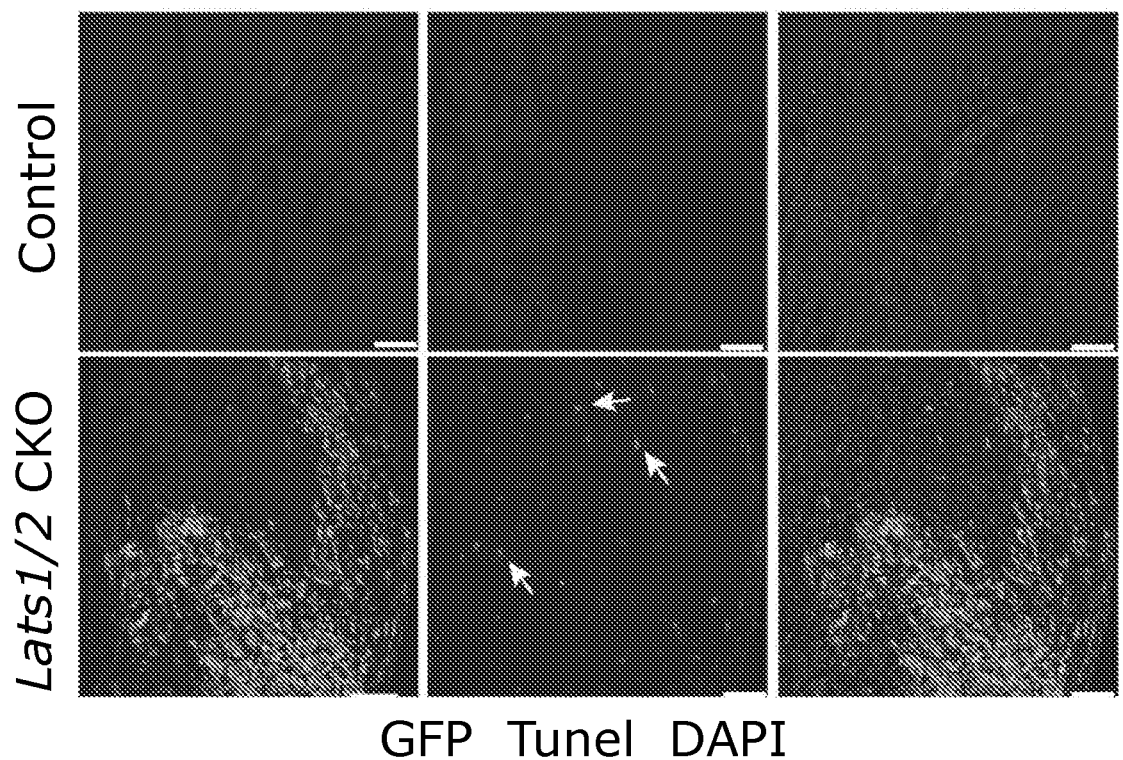
Figure 27E:
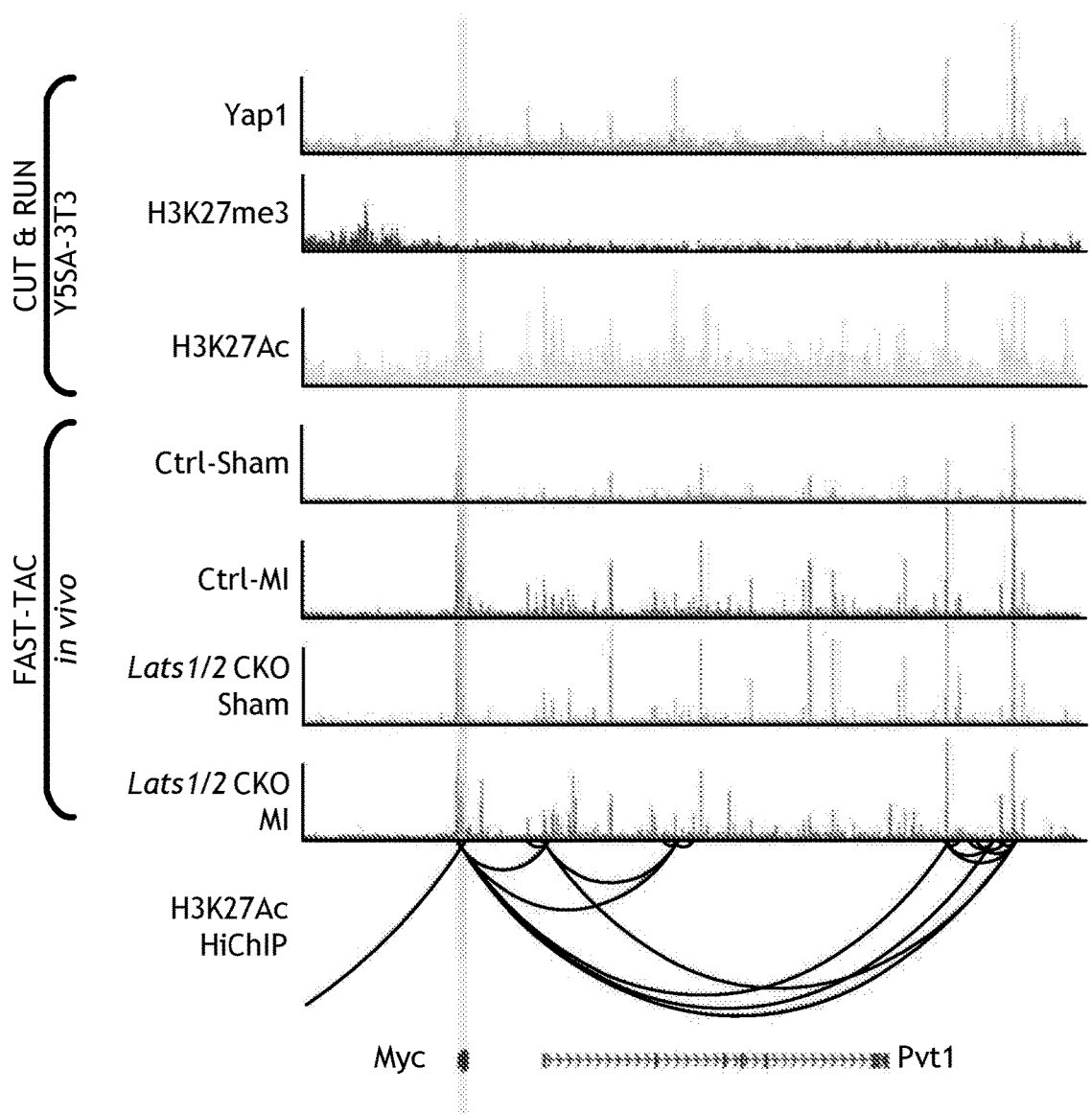
Figure 27F:
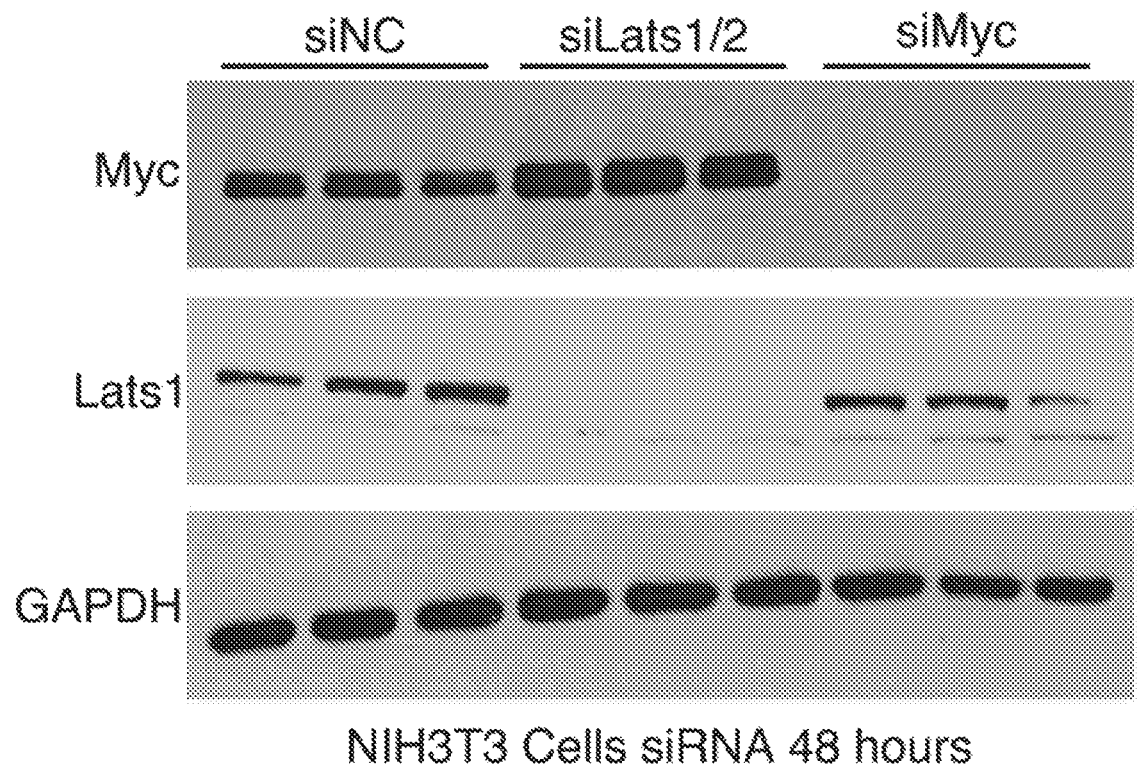
Figure 27G:
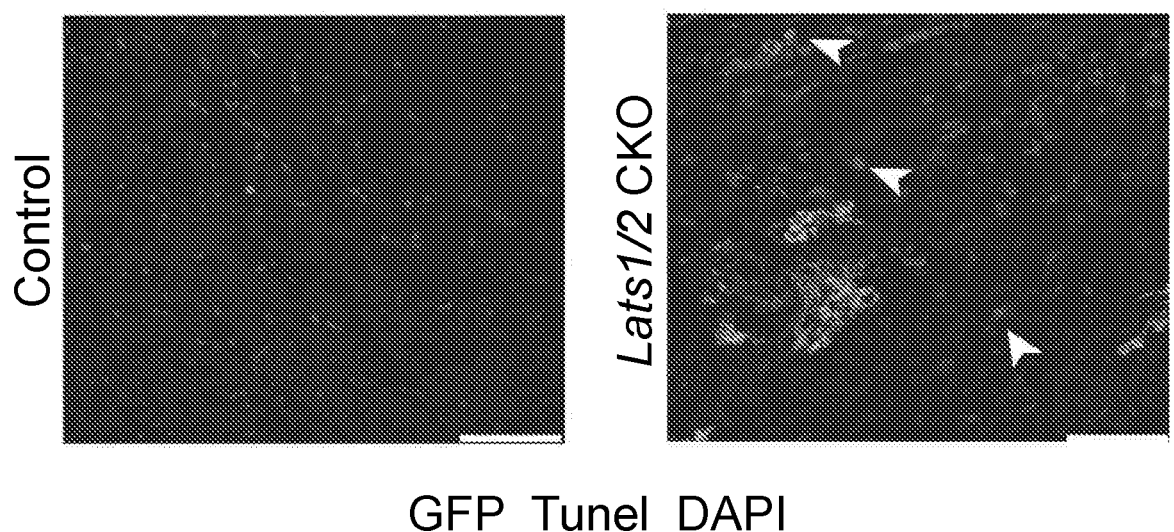

Myc activity was identified as a hallmark of injury induced CF differentiation (FIG. 21G) and, consistent with this, ribosomal biogenesis genes, which are regulated by Myc, were highly translated in mutant CFs (FIG. 26C). Further, in NIH3T3 fibroblasts and in CFs Myc was a direct Yap target, with a complex 3D enhancer 'clique' (FIG. 27E), as determined by H3K27Ac HiChIP and Yap CUT&RUN. Moreover, this enhancer was highly accessible after MI, and in Lats1/2 CKO mice (FIG. 27E). Consistent with the above findings, knockdown of Lats1/2 with siRNAs increased Myc protein levels in NIH3T3 fibroblasts (FIG. 27F). These results were further validated in vivo using IF experiments and it was determined that Lats1/2 CKO CFs possessed high levels of nuclear Myc expression (FIG. 21K). Interestingly, there was found epigenetic evidence for the activation of genes implicated in cell number homeostasis in myofibroblasts (FIG. 21J). Myc-induced cell competition has been shown to modify tissue composition via the induction of apoptosis of nearby cells with low expression of Myc during development (de la Cova et al., 2004). Hence, apoptosis was scored by TUNEL in Lats1/2 CKO hearts and there was increased apoptotic cells that were located peripheral to GFP+ cells consistent with the notion that high levels of Myc contributed to the dramatic expansion of Lats1/2 CKO CFs (FIGS. 21L and 27G). These results indicate that Lats1/2 inhibit Myc expression to limit CF expansion and maintain a physiologic cardiac tissue cellular composition.

Significance of Certain Embodiments

A motivation for characterizing CF cell fate transitions was to gain insight into multiple aspects of their biology that could yield clinically relevant treatment options for heart failure and heart disease that are also extendable to all forms of maladaptive fibrosis. It is demonstrated that following MI Yap is translocated to the nucleus of CFs where it deploys its' GRN and promotes the acquisition of the myofibroblast cell-state. Consistent with a model where Lats1 and Lats2 function as a cardiac injury sensor, the removal of these Hippo kinase components in uninjured CFs dramatically altered cardiac tissue composition and caused severe fibrosis. Moreover, after MI was applied to Lats1/2 CKO hearts proper cardiac scar formation and maturation did not occur. Drop-seq and computational analysis of non-injury-induced cardiac fibrosis identified mutant CFs as stimulators of myeloid cell influx. The recruited myeloid cells found in uninjured mutant hearts displayed a heterogeneous phenotypic expansion analogous to the ischemic myocardium. Overall, this work suggests that Hippo signaling in CFs is required to prevent precocious myofibroblast fate acquisition, as well as to promote the exit of this pro-inflammatory cell state as the scar matures.

Hippo Signaling Autonomously Inhibits Fibroblast Proliferation and the Myofibroblast Cell State Transition Hippo deficient (Lats1/2 CKO) CFs differentiated into MFLs without injury revealing an essential role for Lats1/2 in preventing the activation of the cardiac wound response. Previously, Drop-seq was applied to characterize the role of epicardial Hippo signaling during cardiac development, and found that the Hippo pathway functions to promote proper epicardial-to-CF differentiation (Xiao et al., 2018). Thus, Hippo signaling plays essential roles in the achievement of the resting CF cell identity during embryonic development and subsequently regulates essential CF fate transitions during postnatal homeostasis and injury response.

Lats1/2 Promote Resolution of the Cardiac Wound Response after Myocardial Infarction The data indicate that Hippo signaling in CFs prevents precocious myofibroblast fate acquisition and promotes exit of this pro-inflammatory cell state to the matrifibrocyte state. Cardiac myofibroblasts are highly proliferative and resistant to apoptosis, however, the cardiac myofibroblast cell state is transitory and lost by 10 days post-infarct (Fu et al., 2018). Consistent with the proliferative potential of myofibroblasts, removal of Lats1/2 in CFs resulted in increased cell proliferation. Notably, Lats1/2 CKO animals displayed an immense non-compacted scar in the after MI that was more severe than uninjured Lats1/2 CKO hearts. This observation suggests that there are other mechanisms, in addition to the Hippo kinases, that restrict Yap activity in CFs after MI. Mechanical cues are regulators of Yap activity (Aragona et al., 2013; Elosegui-Artola et al., 2017; Meng et al., 2018). Cardiac tissue matrix stiffness progressively increases following MI (Fomovsky and Holmes, 2010). Indeed, mechanotransduction induced by a stiff ECM has also been implicated in driving the myofibroblast phenotypic transition in pancreatic stellate cells (Lachowski et al., 2017). Moreover, the data support the finding that YAP and TAZ possess fibrogenic properties in pathologically stiff human lung tissue (Liu et al., 2015). Further experiments are required to determine the physiologic inputs that enhance Yap activity after MI.

Hippo Signaling Inhibits Myeloid Cell Recruitment During Cardiac Homeostasis

The role of Hippo-Yap in inducing the immune response is still poorly understood. While some have found evidence for Yap driven recruitment of M2 macrophages in the context of cancer (Guo et al., 2017), other labs found that overexpression of YAP5SA in the liver failed to induce myeloid invasion (Hagenbeek et al., 2018). Moreover, emerging data in a cancer model suggest that LATS1/2-null cells release vesicles packed with nucleic acids that engage circulating immune cells via type I Interferons and Toll-like receptors (Moroishi et al., 2016). Incidentally, IFNICs, or Interferon inducible cells, are considered post-phagocytic cardiac Mφs with high levels of self-DNA activated interferon regulatory factor 3 (Irf3) transcriptional activity were originally identified as being specific to the ischemic myocardium (King et al., 2017). In a specific embodiment, the increased cell death induced by Lats1/2 CKO cells and/or the release of pro-inflammatory vesicles may partly explain the injury-like myeloid cell phenotypic expansion and the appearance of IFNICs (Mφ6) during homeostasis. In some cases, CF-mediated cell competition is required for ventricular integrity after cardiac injury or is a maladaptive feature of their biology, where as in other cases it is not required.

Cell Competition May Contribute to Maintenance of Cardiac Cellular Composition

Cell competition is an evolutionarily conserved mechanism to maintain tissue homeostasis whereby "fit" cells ('winners') with higher anabolic capacity eliminate "unfit" cells ('losers') with lower anabolic capacity. In Lats1/2 deficient fibroblasts, there was pronounced Myc up-regulation, while non-mutant cells adjacent to these CFs in non-injured Lats1/2 CKO hearts displayed elevated levels of apoptosis, which agrees with the standard cell competition phenotype. This suggests a role for Hippo induced cell competition in CFs during homeostasis which is extendable to the post-infarct tissue environment. An intriguing possibility is that myofibroblast-mediated cell competition, a mechanism typically associated with the preservation of tissue fitness, promotes not only the removal of damaged cells post-MI, but also helps to generate a homogenous and expandable scar devoid of cardiac myocytes. Consistent with the non-autonomous activity of myofibroblasts, cell competition in *Drosophila* has been found to take place via Toll related receptors (TRRs) that are activated by cytokines to promote apoptosis in an NFKβ-dependent manner (Meyer et al., 2014). High-throughput CRISPR-Cas9 screens aimed at detailing the precise Yap and/or Myc target genes responsible for promoting CF-mediated cell competition are thus merited. Apoptosis initiated by competitive myofibroblasts ('winners') within and nearby the infarct is likely to promote local inflammation via the release of DAMPs, that in turn may elevate the local levels of interferons in the myocardium. Emerging data in a cancer model suggest that LATS1/2-null cells release vesicles packed with nucleic acids that engage circulating immune cells via type I Interferons and Toll-like receptors (Moroishi et al., 2016).

The Hippo Pathway as a Therapeutic Target for Cardiovascular Disease

Targeting the Hippo signaling pathway in CMs is a viable treatment option for promoting cardiac regeneration (Leach et al., 2017). In this study, however, it was found that inactivation of the Hippo pathway in CFs promotes cardiac fibrosis and adversely effects cardiac functional output. Conversely, a reduction in Yap activity suppressed the fibrotic phenotype observed in post-MI Lats1/2 CKO animals. Thus, in specific embodiments Yap and Hippo activity in CFs represent a therapeutic target for treating fibrosis and heart failure. Importantly, these results emphasize that highly cell type-specific therapeutic targeting of Hippo pathway components and Yap is useful for the treatment of heart failure. Further, there was uncovered many Yap target genes and other possible cellular targets that in specific embodiments allow for immune therapies geared toward promoting pro-inflammatory cell egress from the myocardium to restore homeostasis and curtail pathogenic CF activity after injury. Indeed, the modulation of myeloid cell numbers and phenotype to treat heart failure have been previously suggested (Nahrendorf, 2018) and recent work has found that stimulation of the cardiac lymphatic system may represent a potent therapeutically viable outlet for myeloid cells back into the circulation (Vieira et al., 2018). Surprisingly, mutant MFLs contained ER stress and UPR response signatures, which is consistent with their secretive nature. Interestingly, ER stress has been successfully targeted for the treatment of both arthritis and cancer (Li et al., 2017b; Qiu et al., 2017), and represents a promising targetable biological feature of myofibroblasts. However, cells with ER stress response induced Xbp1 activity have also been observed secreting vesicles with beneficial non-autonomous functions in C. elegans (Taylor and Dillin, 2013), and thus a cardio-protective role for the CF ER stress response exists as a legitimate possibility as well.

STAR Methods

Mice

Tcf21$^{iCre}$, Lats1/2$^{flox/flox}$, Yap/Taz$^{flox/flox}$, Rosa26$^{mTmG}$, Myh6-MCM, and YAP5SA-tg alleles have been described previously. Mice were on a mixed genetic background of C57BL/6 and 129SV. For Lats1/2 CKO and Tcf21iCre controls tamoxifen was dissolved in peanut oil with 5% ethanol at 10 mg/ml. 3 mg tamoxifen was administered to 6-8 week old mice by intraperitoneal injection for 6 days. For YAP5SA-CMs (Myh6-MCM/+; YAP5SA/+), daily tamoxifen intraperitoneal injections (40 µg/g) were administered for four consecutive days.

Echocardiography

Cardiac function was analyzed by echocardiography every week post-surgery. Imaging were performed on VisualSonics Vevo 2100 system with 550-s probe. B-mode images and M-mode images were captured on short-axis projection. Ejection fraction, fraction shortening, and cardiac output were calculated using cardiac measurement package installed in Vevo2100 system.

Histology and Immunofluorescence

Fibroblast-specific-Lats1/2 mutant mice (Lats1/2 CKO) were generated by crossing Tcf21$^{iCre}$ with Lats1/2$^{flox/flox}$; Rosa26$^{mTmG}$. Control were generated by crossing Tcf21$^{iCre}$ with Rosa26$^{mTmG}$. For histology and immunofluorescence staining, hearts were fixed in 4% PFA overnight at 4° C. and dehydrated in a serial ethanol, xylene and embedded in paraffin. Sections of 7 µm thick sections were prepared for staining. Masson's Trichrome staining was performed according to manufacturer's instruction (Sigma, HT15). Antibodies used for immunofluorescence staining were as follows: GFP (1:200, Abcam ab290, ab6673), c-Myc [Y69] (Abcam, ab32072), Yap (1:100, Novus, NB 110-58358), pYap (1:100, Cell signaling technologies 4911), α-smooth muscle actin (1:200, Sigma, C6198), Lyz (1:200, Abcam, ab108508). To visualize some antigens, Alexa-647 was employed. When applications required green and red co-staining, sections were pre-treated with 0.3% $H_2O_2$ in PBS for 20 min at room temperature to quench the endogenous GFP and Tomato signals, which come from the Rosa26$^{mTmG}$ reporter line. In some cases, Tyramide Signal Amplification Systems (1:100, Perkin Elmer) were used to amplify signal. TUNEL assay was performed according to manufacturer's instruction (Progema, G3250). Immunofluorescence images were captured on a Leica TCS SP5 confocal microscope.

EdU Incorporation Assay

Mice after MI were injected with EdU (0.5 mg) 24 hr before collecting heart tissue. Hearts were processed as described above. EdU incorporation was assayed by Click-it EdU imaging kit (Life Technologies C10340).

Western Blotting

Protein level was detected by Western Blotting. Mouse fibroblast cells line NIH3T3 was used for western blotting (ATCC®CRL-1658). siRNA used were as follows: Non-targeting siRNA (siNC) (Dharmacon, D-001810-02-05), Mouse Lats1 (siLats1) (Dharmacon, L-063467-00), mouse Lats2 (siLats2)(Dharmacon, L-044602-00) and mouse Myc (Dharmacon, M-040813-02-0005). RNAiMAX (Thermo Fisher Scientific) was used for transfection. Cells were treated with siRNA for 48 hours and harvest for protein detection. Antibody used for Western Blotting were as follows: anti-Myc (Abcam ab32072), anti-Lats1 (Cell Signaling Technology, 3477), Gapdh (Abcam ab9485).

Cytokine Arrays

Tissue lysate was prepared according to the manufacturer's instruction. Tcf21 iCre and Tcf21 iCre; Lats1/2 fl/fl hearts were collected at 10 days post tamoxifen injection. Myh6-MCM and Myh6-MCM; Yap5SA were collected 2 days post tamoxifen injection. Atria were removed and tissue were excised into small pieces. Tissue were further homogenized with dounce homogenizer in PBS supplemented with protease inhibitors. 10% Trion X-100 was added to make final concentration of 1%. Samples were frozen at −80 degree Celsius for 2 hours, thawed, and centrifuged at 10,000 g for 5 minutes. Supernatants were collected for protein array. Protein loading was normalized by GAPDH. Around 1000-2000 µg total protein was used for each sample.

FACS Analysis for Cell Cycle Scoring

According to DNA content, cells were assigned with 2N and 4N into G1 and G2/M phase respectively, cells with DAPI intensity in between 2N and 4N to S phase, and cell with DNA content more than 4N to super G2 phase.

Cardiac fibroblasts were isolated from hearts at 1 week post MI by langendorff perfusion. GFP positive cells were gated for analysis and DAPI were used for analyzing DNA content. FACS were performed on BD Biosciences SORP Aria I and BD Biosciences LSRII and cell cycle modelling were processed with FlowJo software.

Sphere-Forming Assay

GFP+ cells were FACS-sorted respectively from Tcf21 iCre; R26mTmG and Tcf21 iCre; Lats1/2 fl/fl; R26mTmG at 7 days post MI. 10,000-100,000 were seeded in one well/6 well ultra-low attachment plate (corning). Cell aggregation was observed 24 hours after seeding.

RNA Sequencing

For TRAP/Ribosome-associated RNA-seq, RNA pull-down from 1 week post MI hearts were performed according to McKnight Lab protocol (described on the McKnight laboratory website, University of Washington). Anti-HA antibody (Cell signaling technologies) were used for pull-down. Ribosome-associated mRNA was extracted using RNeasy Plus Micro Kit (Qiagen). mRNA was further purified by Dynabeads mRNA DIRECT Micro Kit (Life Technologies) and then converted to barcoded cDNA libraries for RNA sequencing on the Ion Proton System using Ion Total RNA-Seq Kit v2.0 (Life Technologies) and RNA-Seq Barcode 01-16 Kit (Life Technologies). RNA-seq was performed on Ion Proton. Around 12 million reads were generated for transcripts quantification in each sample. Paired-end RNA Seq reads were aligned to mm9 (*Mus musculus* assembly July 2007). Raw read counts were normalized and analyzed for differential gene expression by DESeq2. Metascape (available on the Metascape website) was used for Gene Ontology (GO) analysis to extract the information on gene set and gene network.

For FACS-sorted RNA-seq, GFP positive cells were isolated using Langendorff perfusion of heart 3 days after 6-dose tamoxifen injection. Because of limited GFP cells, sorted cells were directly collected in RLT lysis buffer from RNeasy Plus Micro Kit (Qiagen) and SMART-Seq Ultra Low Input RNA Kit to prepare RNA-seq library (Clonetech Laboratories). Sequencing and analysis procedures were same as above for TRAP RNA-seq.

RNAscope In Situ Hybridization

Formaldehyde-fixed paraffin-embedded heart sections were processed for RNA in situ detection using the RNAscope2.5 Assay (Advanced Cell Diagnostics, Inc.) according to the manufacturer's instructions. RNAscope probes used in this study: Serpina3n (430191), and Plac8 (532701).

Fast-ATAC

Approximately 10,000 FACS-sorted GFP+ cells were used as input for Fast-ATAC. Fast-ATAC was performed according to (Corces et al., 2016). Briefly, sorted cells were spun down, FACS buffer was removed, the pellet was then re-suspended in a transposase-containing reaction mixture complete with 0.05% digitonin prior to tagmentation at 37° C. with 1000 rpm agitation for 30 minutes. Next, transposed DNA was purified with a Qiagen PCR MinElute kit (Qiagen 28004). Fast-ATAC libraries were purified with a 1.8×SPR purification using AMPure XP beads following PCR amplification. Paired-end (75×75 bp) sequencing was performed on an Illumina Nextseq500 instrument.

ATAC-seq Analysis

Reads were mapped to the mouse genome (mm9) using Bowtie2 with default paired-end settings. Next, all non-nuclear and unmapped paired reads were discarded. Duplicated reads were removed with the picard MarkDuplicates function, default settings. Peak calling for differential accessibility analysis was carried out with Macs2 on the merged BAM file, Macs2 callpeak-nomodel –broad. Blacklisted regions, identified by ENCODE, from mm9 were removed from the comprehensive peak file using the bedtools subtract module. Reads were counted for each condition from the comprehensive peak file using the bedtools multicov module. PCA and differential accessibility analysis were performed with the DESeq2 R package using the multicov file as input. Motif enrichment analysis and individual condition peak calling (findPeaks—style factor) was conducted with Homer (findMotifsGenome.pl). Visualization of Fast-ATAC signals was done with Homer, and all reads were normalized by read count, where scores represent read count per bp per $1\times10^7$ reads.

Drop-Seq

Adult hearts from indicated genotypes were dissected, cannulated, and then dissociated into a single-cell suspension via collagenase digestion (Collagenase A, Roche) on a custom built Langendorff apparatus as described previously (Monroe et al., 2019) with minor modifications. In short, cardiomyocyte enrichment was performed whereby cardiomyocytes were allowed to settle by gravity for 5 minutes at room temperature after washes and the supernatant, containing non-CMs was put into new tube and spun down at 500×g and the pellet containing CMs was washed and spun down at 300×g. Finally, cells were combined in the final step and counted prior to dilution and input into Drop-seq rig. For YAP5SA-CM experiments, the inventor also performed CM-enrichment batches whereby only the CM enriched fractions were used for Drop-seq. Dissociated cells were diluted to a concentration of 200 cells per µL in PBS with 0.01% BSA. Drop-seq was then performed according to (Macosko et al., 2015). Here cells were co-encapsulated into nano-liter sized droplets containing barcoded microparticles (ChemGenes, catalog number Macosko 201110) and lysis buffer using a custom microfluidics device (FlowJEM, Toronto, Canada). After droplet breakage, reverse transcription (Thermo), and exonuclease treatment (NEB) all cDNA was PCR amplified (KAPA), pooled, purified with Ampure XP beads (Beckman Coulter), and ran on a Fragment analyzer (Advanced Analytical Technologies, Inc.) for quality control, quantification, and size determination. Library preparation was performed with the Illumina Nextera XT kit, and libraries were triple purified with Ampure XP beads (Beckman Coulter). All libraries were sequenced on an Illumina NextSeq500 instrument.

Single Cell RNA-Seq Data Analysis

The raw FastQ files were converted to BAMs with Picard tools (MergeSamFiles) and then used is input for STAR alignment, cell barcode correction, and digital gene expression (DGE) matrix generation via the Droplet-based RNA-seq tools software package (available at the Drop-seq website maintained by the McCarroll Lab). The minimum gene per cell threshold was set to 500 for inclusion into the final digital expression matrix. Subsequently, DGEs from each experiment were merged and then the comprehensive DGE was imported into Seurat (version 2.3.4) where normalization was performed according to package default settings. Batch effects were corrected for by regressing out the number of molecules per cell, the batch (i.e. orig. ident) and the percentage of mapped mitochondrial reads with the ScaleData function (Seurat package). Next, principle components analysis (PCA) was performed and significant PCs were used as input for graph-based clustering. Then 2-dimensional visualization of the multi-dimensional data set was done with tSNE. Differential expression of the individual clusters was performed using the likelihood-ratio test for single cell gene expression. To account for over-clustering, clusters that were not transcriptionally distinct were merged. Clusters that represented cell doublets were removed from the final data set. The approximate cell cycle phase of each cell was calculated using Seurat by scoring individual cells on their expression for S-phase, G1, and G2M genes (Kowalczyk et al., 2015). For pseudotemporal analysis, the normalized data from selected clusters were then passed directly into Monocle2 where density peak clustering and downstream analysis was performed. Chi-square statistical analysis between clusters was performed and visualized as described previously (Li et al., 2018). Gene interaction analysis requiring MAGIC analysis was carried out using the Rmagic package (version 1.0.0).

Within the SCENIC computational pipeline, there was identified all genes co-expressed with transcription factors using the GRNboost2 fast GRN inferencing algorithm (Friedman, 2002). Next, cis-regulatory motif enrichment analysis was performed on all co-expressed genes. This analysis cataloged putative transcription factor binding sites within the list of co-expressed genes, thereby allowing us to identify potential direct gene targets. Additionally, this enabled us to eliminate false positives and indirect transcriptional targets from the co-expression matrix. All combinations of transcription factors and direct gene targets with significant motif enrichment are referred to as regulons. Finally, the SCENIC AUCell algorithm was applied to calculate the activity of each regulon in every single-cell transcriptome (Aibar et al., 2017). Individual cells expressing many genes within a given regulon display the highest area under the curve (AUC) score, while those cells expressing few to none receive a low AUC score. The ranked distribution of AUCell scores across all of the cells for a given regulon is used to determine a threshold for active and inactive regulons, thus making the final output binary (active or inactive).

For ligand receptor connectome analysis, the scRNA-seq expression matrix was used to quantify the connections between cells that express ligand genes and cells that express receptor genes by counting the number of these ligand-receptor pairs for each cell to cell permutation. Similar to the analysis reported in (Camp et al 2017, Nature Multilineage communication regulate human liver bud development from pluripotency). Next, a cell to cell interaction matrix is generated from the sums of these counts. Finally, a matrix of ligand-receptor pair connection counts was created for each permutation of all cell groups and filtered those ligand-receptor pairs that had at least 100 cell-cell connections. The inventor further filtered this ligand receptor connectome to focus on the strongest interactions (greater than log(10)) differentially expressed between indicated cell types.

CUT&RUN

CUT&RUN experiments were carried out as described (Skene et al., 2018). Briefly, 200,000 NIH3T3 cells were washed in wash buffer (20 mM HEPES, pH7.5, 150 mM NaCl, 0.5 mM Spermidine and complete protease inhibitor (EDTA-free, Roche), captured with Concanavalin A beads (Polysciences, Warrington, Pa.) and incubated with primary antibodies overnight at 4° C. After washing with Dig-wash buffer (20 mM HEPES, pH7.5, 150 mM NaCl, 0.5 mM Spermidine, 0.08% Digitonin and protease inhibitors), cells were resuspended in 50 µL Digwash buffer and 2.5 µL of protein A-MNase (1:10 diluted, batch 6 from Steve Henikoff) and incubated at room temperature for 10 minutes. Cell pellets were washed again and placed in a 0° C. metal block, and 2 mM of CaCl2 was added and incubated for 45 minutes. MNase reaction was terminated by the addition of 2×STOP buffer and incubated at 37° C. 10 minutes. Samples were then digested by proteinase K at 70° C. for 10 minutes and DNA was extracted by ethanol precipitation. Library were prepared using KAPA Hyper Prep Kit (KAPA) and custom Y-shaped TruSeq adapters according to the manufacturer's instructions. All libraries were sequenced on a NextSeq 500 platform. Protein A-MNase (batch 6) and Yeast spike-in DNA were kindly provided by Dr. Steve Henikoff. The antibodies used were anti-Yap (Novus, NB110-58358), anti-H3K27ac (Abcam, ab4729), and H3K27me3 (Cell Signaling, 9733S).

CUT&RUN Data Analysis

Raw paired-end reads were aligned to the mm9 genome according to (Skene et al., 2018). Briefly, fastq files were mapped using Bowtie2 (version v2.2.5) with the following options: —local—very-sensitive-local—no-unal—no-mixed—no-discordant—phred33—I 10—X 700. For mapping Yeast spike-in fragments, the following options were used in addition to those stated directly above: —no-overlap—no-dovetail. Peak calling was performed as described in (Liu et al., 2018). In short, peaks were called from aligned BAM files using MACS2 callpeaks with the narrowPeak option and a P-value cutoff of 1e-5. Footprint detection was carried out by aligning all mapped read ends around motif containing peak centers. Peaks were centered around motifs using HOMER. Fragment ends were piled up using scripts previously published and available at: the GitHub website. For the final Yap CUT&RUN peak calling, mm9 aligned BAM files derived from both YAP5SA-NIH3T3 cells and control NIH3T3 cells were combined.

H3K27ac HiChIP

H3K27ac HiChIP was performed according to (Mumbach et al., 2017) with only minor modifications. Approximately 15 million NIH3T3 cells were used as input, and MboI digestion was carried out for 2 hours. Cells were sonicated for 10 cycles (30 seconds on, and 30 seconds off) using a Bioruptor Pico instrument (Diagenode). For biotin pull down 150 ng of chromatin was used as input, and tagmentation was performed using 4 uL of Tn5 transposase. For post-PCR size selection there was performed a double-sided size selection with Ampure XP beads (Beckmann-Coulter). All libraries were sequenced on a NextSeq 500 platform.

H3K27Ac HiChIP Analysis

H3K27ac HiChIP paired-end reads were aligned to the mm9 genome using HiC-Pro (Servant et al., 2015). Aligned reads were passed to the hichipper computational analysis pipeline (Lareau and Aryee, 2018), and loop calling was carried out with default parameters. For peak calling, "COMBINED, ALL" was used, and the MboI restriction fragment bed file for the mm9 genome was generated with the HiC-Pro digest_genome.py utility (digest_genome.py —r mboi). DNA loops that passed hichipper quality control were filtered to intrachromosomal loops with a minimum length of 5 Kbp and a maximum length of 2 Mbp. Tracks containing H3K27ac loop interactions calculated using the hichipper (—make-ucsc flag) were visualized using the WashU Epigenome browser and filtered according to interaction score. Virtual 4C (v4C) profiles were generated by visualizing dumped hic file outputs from Juicer (Durand et al., 2016a, 2016b) with a custom R script according to (Mumbach et al., 2017).

REFERENCES

Acharya, A., Baek, S. T., Huang, G., Eskiocak, B., Goetsch, S., Sung, C. Y., Banfi, S., Sauer, M. F., Olsen, G. S., Duffield, J. S., et al. (2012). The bHLH transcription factor Tcf21 is required for lineage-specific EMT of cardiac fibroblast progenitors. Development 139, 2139-2149.

Armulik, A., Genove, G., and Betsholtz, C. (2011). Pericytes: developmental, physiological, and pathological perspectives, problems, and promises. Dev Cell 21, 193-215.

Billings, S. E., Pierzchalski, K., Butler Tjaden, N. E., Pang, X. Y., Trainor, P. A., Kane, M. A., and Moise, A. R. (2013). The retinaldehyde reductase DHRS3 is essential for preventing the formation of excess retinoic acid during embryonic development. FASEB J 27, 4877-4889.

Bosada, F. M., Devasthali, V., Jones, K. A., and Stankunas, K. (2016). Wnt/beta-catenin signaling enables developmental transitions during valvulogenesis. Development 143, 1041-1054.

Braitsch, C. M., Combs, M. D., Quaggin, S. E., and Yutzey, K. E. (2012). Pod1/Tcf21 is regulated by retinoic acid signaling and inhibits differentiation of epicardium-derived cells into smooth muscle in the developing heart. Dev Biol 368, 345-357.

Cai, C. L., Martin, J. C., Sun, Y., Cui, L., Wang, L., Ouyang, K., Yang, L., Bu, L., Liang, X., Zhang, X., et al. (2008). A myocardial lineage derives from Tbx18 epicardial cells. Nature 454, 104-108.

Cambier, L., Plate, M., Sucov, H. M., and Pashmforoush, M. (2014). Nkx2-5 regulates cardiac growth through modulation of Wnt signaling by R-spondin3. Development 141, 2959-2971.

Campione, M., Ros, M. A., Icardo, J. M., Piedra, E., Christoffels, V. M., Schweickert, A., Blum, M., Franco, D., and Moorman, A. F. (2001). Pitx2 expression defines a left cardiac lineage of cells: evidence for atrial and ventricular molecular isomerism in the iv/iv mice. Dev Biol 231, 252-264.

Cavallero, S., Shen, H., Yi, C., Lien, C. L., Kumar, S. R., and Sucov, H. M. (2015). CXCL12 Signaling Is Essential for Maturation of the Ventricular Coronary Endothelial Plexus and Establishment of Functional Coronary Circulation. Dev Cell 33, 469-477.

Choy, M., and Lam, S. (2007). Sitagliptin: a novel drug for the treatment of type 2 diabetes. Cardiol Rev 15, 264-271.

Christopherson, K. W., 2nd, Hangoc, G., and Broxmeyer, H. E. (2002). Cell surface peptidase CD26/dipeptidylpeptidase IV regulates CXCL12/stromal cell-derived factor-1 alpha-mediated chemotaxis of human cord blood CD34+ progenitor cells. Journal of immunology (Baltimore, Md.: 1950) 169, 7000-7008.

Cruciat, C. M., and Niehrs, C. (2013). Secreted and transmembrane wnt inhibitors and activators. Cold Spring Harb Perspect Biol 5, a015081.

de la Cova C1, Abril M, Bellosta P, Gallant P, Johnston L A. (2004) Drosophila myc regulates organ size by inducing cell competition. Cell. April 2; 117(1):107-16.

DeLaughter, D. M., Bick, A. G., Wakimoto, H., McKean, D., Gorham, J. M., Kathiriya, I. S., Hinson, J. T., Homsy, J., Gray, J., Pu, W., et al. (2016). Single-Cell Resolution of Temporal Gene Expression during Heart Development. Dev Cell 39, 480-490.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

Dupont, S., Morsut, L., Aragona, M., Enzo, E., Giulitti, S., Cordenonsi, M., Zanconato, F., Le Digabel, J., Forcato, M., Bicciato, S., et al. (2011). Role of YAP/TAZ in mechanotransduction. Nature 474, 179-183.

Dyer, L. A., and Patterson, C. (2013). Isolation of embryonic ventricular endothelial cells. J Vis Exp.

Fang, W., Hartmann, N., Chow, D. T., Riegel, A. T., and Wellstein, A. (1992). Pleiotrophin stimulates fibroblasts and endothelial and epithelial cells and is expressed in human cancer. J Biol Chem 267, 25889-25897.

Galli GG1, Carrara M2, Yuan WC1, Valdes-Quezada C3, Gurung B4, Pepe-Mooney B5, Zhang T6, Geeven G3, Gray NS6, de Laat W3, Calogero RA2, Camargo FD7. (2015). YAP Drives Growth by Controlling Transcriptional Pause Release from Dynamic Enhancers. Mol Cell. October 15; 60(2):328-37.

Ghersi, G., Zhao, Q., Salamone, M., Yeh, Y., Zucker, S., and Chen, W. T. (2006). The protease complex consisting of dipeptidyl peptidase IV and seprase plays a role in the migration and invasion of human endothelial cells in collagenous matrices. Cancer Res 66, 4652-4661.

Gong, C., Qu, S., Lv, X. B., Liu, B., Tan, W., Nie, Y., Su, F., Liu, Q., Yao, H., and Song, E. (2014). BRMS1L suppresses breast cancer metastasis by inducing epigenetic silence of FZD10. Nature communications 5, 5406.

Guadix, J. A., Ruiz-Villalba, A., Lettice, L., Velecela, V., Munoz-Chapuli, R., Hastie, N. D., Perez-Pomares, J. M., and Martinez-Estrada, O. M. (2011). Wt1 controls retinoic acid signalling in embryonic epicardium through transcriptional activation of Raldh2. Development 138, 1093-1097.

Habets, P. E., Moorman, A. F., Clout, D. E., van Roon, M. A., Lingbeek, M., van Lohuizen, M., Campione, M., and Christoffels, V. M. (2002). Cooperative action of Tbx2 and Nkx2.5 inhibits ANF expression in the atrioventricular canal: implications for cardiac chamber formation. Genes Dev 16, 1234-1246.

Hagenbeek T J, Webster J D, Kljavin N M, Chang M T, Pham T, Lee H J, Klijn C, Cai A G, Totpal K, Ravishankar B, Yang N, Lee D H, Walsh K B, Hatzivassiliou G, de la Cruz C C, Gould S E, Wu X, Lee W P, Yang S, Zhang Z, Gu Q, Ji Q, Jackson E L, Lim D S, Dey A. (2018). The Hippo pathway effector TAZ induces TEAD-dependent liver inflammation and tumors. Sci Signal. September 11; 11(547).

Halder, G., and Johnson, R. L. (2011). Hippo signaling: growth control and beyond. Development 138, 9-22.

Hanna, M., Liu, H., Amir, J., Sun, Y., Morris, S. W., Siddiqui, M. A., Lau, L. F., and Chaqour, B. (2009). Mechanical regulation of the proangiogenic factor CCN1/CYR61 gene requires the combined activities of MRTF-A and CREB-binding protein histone acetyltransferase. J Biol Chem 284, 23125-23136.

Harrison, M. R., Bussmann, J., Huang, Y., Zhao, L., Osorio, A., Burns, C. G., Burns, C. E., Sucov, H. M., Siekmann, A. F., and Lien, C. L. (2015). Chemokine-guided angiogenesis directs coronary vasculature formation in zebrafish. Dev Cell 33, 442-454.

Hathaway, C. K., Grant, R., Hagaman, J. R., Hiller, S., Li, F., Xu, L., Chang, A. S., Madden, V. J., Bagnell, C. R., Rojas, M., et al. (2015). Endothelin-1 critically influences cardiac function via superoxide-MMP9 cascade. Proc Natl Acad Sci USA 112, 5141-5146.

He, L., Tian, X., Zhang, H., Wythe, J. D., and Zhou, B. (2014). Fabp4-CreER lineage tracing reveals two distinctive coronary vascular populations. J Cell Mol Med 18, 2152-2156.

Heallen, T., Morikawa, Y., Leach, J., Tao, G., Willerson, J. T., Johnson, R. L., and Martin, J. F. (2013). Hippo signaling impedes adult heart regeneration. Development 140, 4683-4690.

Heallen, T., Zhang, M., Wang, J., Bonilla-Claudio, M., Klysik, E., Johnson, R. L., and Martin, J. F. (2011). Hippo pathway inhibits Wnt signaling to restrain cardiomyocyte proliferation and heart size. Science 332, 458-461.

Hindley, C. J., Condurat, A. L., Menon, V., Thomas, R., Azmitia, L. M., Davis, J. A., and Pruszak, J. (2016). The Hippo pathway member YAP enhances human neural crest cell fate and migration. Scientific reports 6, 23208.

Hinkel, R., Trenkwalder, T., Petersen, B., Husada, W., Gesenhues, F., Lee, S., Hannappel, E., Bock-Marquette, I., Theisen, D., Leitner, L., et al. (2014). MRTF-A controls vessel growth and maturation by increasing the expression of CCN1 and CCN2. Nature communications 5, 3970.

Huang, G. N., Thatcher, J. E., McAnally, J., Kong, Y., Qi, X., Tan, W., DiMaio, J. M., Amatruda, J. F., Gerard, R. D., Hill, J. A., et al. (2012). C/EBP transcription factors mediate epicardial activation during heart development and injury. Science 338, 1599-1603.

Ito, S., and Nagata, K. (2017). Biology of Hsp47 (Serpin H1), a collagen-specific molecular chaperone. Seminars in cell & developmental biology 62, 142-151.

Janky, R., Verfaillie, A., Imrichova, H., Van de Sande, B., Standaert, L., Christiaens, V., Hulselmans, G., Herten, K., Naval Sanchez, M., Potier, D., et al. (2014). iRegulon: from a gene list to a gene regulatory network using large motif and track collections. PLoS Comput Biol 10, e1003731.

Jensen, B., Boukens, B. J., Postma, A. V., Gunst, Q. D., van den Hoff, M. J., Moorman, A. F., Wang, T., and Christoffels, V. M. (2012). Identifying the evolutionary building blocks of the cardiac conduction system. PLoS One 7, e44231.

Jiang, R., Lan, Y., Norton, C. R., Sundberg, J. P., and Gridley, T. (1998). The Slug gene is not essential for mesoderm or neural crest development in mice. Dev Biol 198, 277-285.

Jiang, X., Rowitch, D. H., Soriano, P., McMahon, A. P., and Sucov, H. M. (2000). Fate of the mammalian cardiac neural crest. Development 127, 1607-1616.

Katz, T. C., Singh, M. K., Degenhardt, K., Rivera-Feliciano, J., Johnson, R. L., Epstein, J. A., and Tabin, C. J. (2012). Distinct compartments of the proepicardial organ give rise to coronary vascular endothelial cells. Dev Cell 22, 639-650.

Khurana, S., Margamuljana, L., Joseph, C., Schouteden, S., Buckley, S. M., and Verfaillie, C. M. (2013). Glypican-3-mediated inhibition of CD26 by TFPI: a novel mechanism in hematopoietic stem cell homing and maintenance. Blood 121, 2587-2595.

Leek, J. T., Johnson, W. E., Parker, H. S., Jaffe, A. E., and Storey, J. D. (2012). The sva package for removing batch effects and other unwanted variation in high-throughput experiments. Bioinformatics 28, 882-883.

Lepilina, A., Coon, A. N., Kikuchi, K., Holdway, J. E., Roberts, R. W., Burns, C. G., and Poss, K. D. (2006). A dynamic epicardial injury response supports progenitor cell activity during zebrafish heart regeneration. Cell 127, 607-619.

Li, G., Xu, A., Sim, S., Priest, J. R., Tian, X., Khan, T., Quertermous, T., Zhou, B., Tsao, P. S., Quake, S. R., et al. (2016). Transcriptomic Profiling Maps Anatomically Patterned Subpopulations among Single Embryonic Cardiac Cells. Dev Cell 39, 491-507.

Li, P., Cavallero, S., Gu, Y., Chen, T. H., Hughes, J., Hassan, A. B., Bruning, J. C., Pashmforoush, M., and Sucov, H. M. (2011). IGF signaling directs ventricular cardiomyocyte proliferation during embryonic heart development. Development 138, 1795-1805.

Liebner, S., Cattelino, A., Gallini, R., Rudini, N., Iurlaro, M., Piccolo, S., and Dejana, E. (2004). Beta-catenin is required for endothelial-mesenchymal transformation during heart cushion development in the mouse. The Journal of cell biology 166, 359-367.

Liu, Q., Hu, T., He, L., Huang, X., Tian, X., Zhang, H., He, L., Pu, W., Zhang, L., Sun, H., et al. (2015). Genetic targeting of sprouting angiogenesis using Apln-CreER. Nature communications 6, 6020.

Lu, M. H., Huang, C. C., Pan, M. R., Chen, H. H., and Hung, W. C. (2012). Prospero homeobox 1 promotes epithelial-mesenchymal transition in colon cancer cells by inhibiting E-cadherin via miR-9. Clinical cancer research: an official journal of the American Association for Cancer Research 18, 6416-6425.

Ma, L., Lu, M. F., Schwartz, R. J., and Martin, J. F. (2005). Bmp2 is essential for cardiac cushion epithelial-mesenchymal transition and myocardial patterning. Development 132, 5601-5611.

Maaten, L., and Hinton, G. (2008). Visualizing data using t-SNE. J Mach Learn Res 9.

Macosko, E. Z., Basu, A., Satija, R., Nemesh, J., Shekhar, K., Goldman, M., Tirosh, I., Bialas, A. R., Kamitaki, N., Martersteck, E. M., et al. (2015). Highly Parallel Genome-wide Expression Profiling of Individual Cells Using Nanoliter Droplets. Cell 161, 1202-1214.

Majkut, S., Idema, T., Swift, J., Krieger, C., Liu, A., and Discher, D. E. (2013). Heart-specific stiffening in early embryos parallels matrix and myosin expression to optimize beating. Curr Biol 23, 2434-2439.

McDavid, A., Finak, G., Chattopadyay, P. K., Dominguez, M., Lamoreaux, L., Ma, S. S., Roederer, M., and Gottardo, R. (2013). Data exploration, quality control and testing in single-cell qPCR-based gene expression experiments. Bioinformatics 29, 461-467.

McKean, D. M., Homsy, J., Wakimoto, H., Patel, N., Gorham, J., DePalma, S. R., Ware, J. S., Zaidi, S., Ma, W., Patel, N., et al. (2016). Loss of RNA expression and allele-specific expression associated with congenital heart disease. Nature communications 7, 12824.

Monroe T O, Hill M C, Morikawa Y, Leach J P, Heallen T, Cao S, Krijger PHL, de Laat W, Wehrens XHT, Rodney G G, Martin J F (2019). YAP Partially Reprograms Chromatin Accessibility to Directly Induce Adult Cardiogenesis In Vivo. Dev Cell. March 25; 48(6):765-779.

Morikawa, Y., Zhang, M., Heallen, T., Leach, J., Tao, G., Xiao, Y., Bai, Y., Li, W., Willerson, J. T., and Martin, J. F. (2015). Actin cytoskeletal remodeling with protrusion formation is essential for heart regeneration in Hippo-deficient mice. Sci Signal 8, ra41.

Moya I M and Halder G. (2019) Hippo-YAP/TAZ signalling in organ regeneration and regenerative medicine. Nat Rev Mol Cell Biol. April; 20(4):211-226.

Mukouyama, Y. S., James, J., Nam, J., and Uchida, Y. (2012). Whole-mount confocal microscopy for vascular branching morphogenesis. Methods in molecular biology 843, 69-78.

Muzumdar, M. D., Tasic, B., Miyamichi, K., Li, L., and Luo, L. (2007). A global double-fluorescent Cre reporter mouse. Genesis 45, 593-605.

Nusse, R., and Clevers, H. (2017). Wnt/beta-Catenin Signaling, Disease, and Emerging Therapeutic Modalities. Cell 169, 985-999.

Ou, X., O'Leary, H. A., and Broxmeyer, H. E. (2013). Implications of DPP4 modification of proteins that regulate stem/progenitor and more mature cell types. Blood 122, 161-169.

Pinto, A. R., Ilinykh, A., Ivey, M. J., Kuwabara, J. T., D'Antoni, M. L., Debuque, R., Chandran, A., Wang, L., Arora, K., Rosenthal, N. A., et al. (2016). Revisiting Cardiac Cellular Composition. Circ Res 118, 400-409.

Puig-Hervas, M. T., Temtamy, S., Aglan, M., Valencia, M., Martinez-Glez, V., Ballesta-Martinez, M. J., Lopez-Gonzalez, V., Ashour, A. M., Amr, K., Pulido, V., et al. (2012). Mutations in PLOD2 cause autosomal-recessive connective tissue disorders within the Bruck syndrome—osteogenesis imperfecta phenotypic spectrum. Human mutation 33, 1444-1449.

Qiu, X., Hill, A., Packer, J., Lin, D., Ma, Y. A., and Trapnell, C. (2017). Single-cell mRNA quantification and differential analysis with Census. Nat Methods 14, 309-315.

Ramjee, V., Li, D., Manderfield, L. J., Liu, F., Engleka, K. A., Aghajanian, H., Rodell, C. B., Lu, W., Ho, V., Wang, T., et al. (2017). Epicardial YAP/TAZ orchestrate an immunosuppressive response following myocardial infarction. J Clin Invest 127, 899-911.

Red-Horse, K., Ueno, H., Weissman, I. L., and Krasnow, M. A. (2010). Coronary arteries form by developmental reprogramming of venous cells. Nature 464, 549-553.

Rudat, C., Grieskamp, T., Rohr, C., Airik, R., Wrede, C., Hegermann, J., Herrmann, B. G., Schuster-Gossler, K., and Kispert, A. (2014). Upk3b is dispensable for development and integrity of urothelium and mesothelium. PLoS One 9, e112112.

Rudat, C., and Kispert, A. (2012). Wt1 and epicardial fate mapping. Circ Res 111, 165-169.

Rutkovskiy, A., Valen, G., and Vaage, J. (2013). Cardiac aquaporins. Basic Res Cardiol 108, 393.

Salazar, V. S., Gamer, L. W., and Rosen, V. (2016). BMP signalling in skeletal development, disease and repair. Nature reviews Endocrinology 12, 203-221.

Satija, R., Farrell, J. A., Gennert, D., Schier, A. F., and Regev, A. (2015). Spatial reconstruction of single-cell gene expression data. Nat Biotechnol 33, 495-502.

Shamloo, A., Mohammadaliha, N., Heilshorn, S. C., and Bauer, A. L. (2016). A comparative study of collagen matrix density effect on dndothelial sprout formation using experimental and computational approaches. Ann Biomed Eng 44, 929-941.

Shaul, Y. D., Freinkman, E., Comb, W. C., Cantor, J. R., Tam, W. L., Thiru, P., Kim, D., Kanarek, N., Pacold, M. E., Chen, W. W., et al. (2014). Dihydropyrimidine accumulation is required for the epithelial-mesenchymal transition. Cell 158, 1094-1109.

Shekhar, K., Lapan, S. W., Whitney, I. E., Tran, N. M., Macosko, E. Z., Kowalczyk, M., Adiconis, X., Levin, J. Z., Nemesh, J., Goldman, M., et al. (2016). Comprehensive classification of retinal bipolar neurons by single-cell transcriptomics. Cell 166, 1308-1323 e1330.

Singh, A., Ramesh, S., Cibi, D. M., Yun, L. S., Li, J., Li, L., Manderfield, L. J., Olson, E. N., Epstein, J. A., and Singh, M. K. (2016). Hippo Signaling Mediators Yap and Taz Are Required in the Epicardium for Coronary Vasculature Development. Cell Rep 15, 1384-1393.

Singhal, N., and Martin, P. T. (2015). A role for Galgt1 in skeletal muscle regeneration. Skeletal muscle 5, 3.

Skelly, D. A., Squiers, G. T., McLellan, M. A., Bolisetty, M. T., Robson, P., Rosenthal, N. A., and Pinto, A. R. (2018). Single-Cell Transcriptional Profiling Reveals Cellular Diversity and Intercommunication in the Mouse Heart. Cell Rep 22, 600-610.

Smart, N., Bollini, S., Dube, K. N., Vieira, J. M., Zhou, B., Davidson, S., Yellon, D., Riegler, J., Price, A. N., Lythgoe, M. F., et al. (2011). De novo cardiomyocytes from within the activated adult heart after injury. Nature 474, 640-644.

Sridurongrit, S., Larsson, J., Schwartz, R., Ruiz-Lozano, P., and Kaartinen, V. (2008). Signaling via the Tgf-beta type I receptor Alk5 in heart development. Dev Biol 322, 208-218.

Trapnell, C., Cacchiarelli, D., Grimsby, J., Pokharel, P., Li, S., Morse, M., Lennon, N.J., Livak, K. J., Mikkelsen, T. S., and Rinn, J. L. (2014). The dynamics and regulators of cell fate decisions are revealed by pseudotemporal ordering of single cells. Nat Biotechnol 32, 381-386.

Tripathi, S., Pohl, M. O., Zhou, Y., Rodriguez-Frandsen, A., Wang, G., Stein, D. A., Moulton, H. M., DeJesus, P., Che, J., Mulder, L. C., et al. (2015). Meta- and Orthogonal Integration of Influenza "OMICs" Data Defines a Role for UBR4 in Virus Budding. Cell Host Microbe 18, 723-735.

Tse, J. R., and Engler, A. J. (2010). Preparation of hydrogel substrates with tunable mechanical properties. Current protocols in cell biology/editorial board, Juan S Bonifacino [et al] Chapter 10, Unit 10 16.

Ulmer, B., Hagenlocher, C., Schmalholz, S., Kurz, S., Schweickert, A., Kohl, A., Roth, L., Sela-Donenfeld, D., and Blum, M. (2013). Calponin 2 acts as an effector of noncanonical Wnt-mediated cell polarization during neural crest cell migration. Cell Rep 3, 615-621.

Viragh, S., and Challice, C. E. (1981). The origin of the epicardium and the embryonic myocardial circulation in the mouse. Anat Rec 201, 157-168.

Volz, K. S., Jacobs, A. H., Chen, H. I., Poduri, A., McKay, A. S., Riordan, D. P., Kofler, N., Kitajewski, J., Weissman, I., and Red-Horse, K. (2015). Pericytes are progenitors for coronary artery smooth muscle. Elife 4.

Wang, S., Yu, J., Jones, J. W., Pierzchalski, K., Kane, M. A., Trainor, P. A., Xavier-Nieto, J., and Moise, A. R.

(2018). Retinoic Acid Signaling Promotes the Cytoskeleton Rearrangement of Embryonic Epicardial Cells Faseb J In Press.

Wessels, A., and Perez-Pomares, J. M. (2004). The epicardium and epicardially derived cells (EPDCs) as cardiac stem cells. Anat Rec A Discov Mol Cell Evol Biol 276, 43-57.

Xin, M., Kim, Y., Sutherland, L. B., Qi, X., McAnally, J., Schwartz, R. J., Richardson, J. A., Bassel-Duby, R., and Olson, E. N. (2011). Regulation of insulin-like growth factor signaling by Yap governs cardiomyocyte proliferation and embryonic heart size. Sci Signal 4, ra70.

Zhang, H., Pu, W., Li, G., Huang, X., He, L., Tian, X., Liu, Q., Zhang, L., Wu, S. M., Sucov, H. M., et al. (2016). Endocardium Minimally Contributes to Coronary Endothelium in the Embryonic Ventricular Free Walls. Circ Res 118, 1880-1893.

Zhou, B., Honor, L. B., He, H., Ma, Q., Oh, J. H., Butterfield, C., Lin, R. Z., Melero-Martin, J. M., Dolmatova, E., Duffy, H. S., et al. (2011). Adult mouse epicardium modulates myocardial injury by secreting paracrine factors. J Clin Invest 121, 1894-1904.

Zhou, B., Ma, Q., Rajagopal, S., Wu, S. M., Domian, I., Rivera-Feliciano, J., Jiang, D., von Gise, A., Ikeda, S., Chien, K. R., et al. (2008). Epicardial progenitors contribute to the cardiomyocyte lineage in the developing heart. Nature 454, 109-113.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of inhibiting fibrosis and/or inflammation in cardiac tissue, the method comprising the step of contacting cardiac fibroblasts in the cardiac tissue with an agent that increases the level of at least one of Large tumor suppressor kinase 1 (LATS1) or Large tumor suppressor kinase 2 (LATS2) in the cardiac tissue;
wherein the agent that increases the level of LATS1 is a LATS1 polypeptide comprising an amino acid sequence at least 95% identical to SEQ ID NO: 2 or a nucleic acid encoding the LATSI polypeptide; and
wherein the agent that increases the level of LATS2 is a LATS2 polypeptide comprising an amino acid sequence at least 95% identical to SEQ ID NO: 4 or a nucleic acid encoding the LATS2 polypeptide.

2. The method of claim 1, wherein the fibrosis is from a myocardial infarction.

3. The method of claim 1, wherein the agent is a nucleic acid encoding the LATS1 polypeptide or the LATS2 polypeptide.

4. The method of claim 3, wherein the nucleic acid is a vector comprising an expression construct that encodes LATS1, an expression construct that encodes LATS2, or an expression construct the encodes LATS1 and LATS2 separated by a 2A or IRES element.

5. The method of claim 1, wherein the nucleic acid encoding the LATS1 polypeptide comprises SEQ ID NO: 1.

6. The method of claim 1, wherein the nucleic acid encoding the LATS2 polypeptide comprises SEQ ID NO:3.

7. The method of claim 4, wherein the vector is a viral vector.

8. The method of claim 7, wherein the viral vector is an adenoviral vector, an adeno-associated viral vector, a lentiviral vector, or a retroviral vector.

9. The method of claim 4, wherein the vector is a plasmid, retrotransposon, nanoparticle, liposome, or combination thereof.

10. The method of claim 1, wherein the agent is at least one of a LATS1 polypeptide comprising SEQ ID NO: 2 or a LATS2 polypeptide comprising SEQ ID NO: 4.

11. The method of claim 1, which is an in vitro method.

* * * * *

UNITED STATES PATENT AND TRADEMARK OFFICE
CERTIFICATE OF CORRECTION

| | | |
|---|---|---|
| PATENT NO. | : 12,268,704 B2 | Page 1 of 1 |
| APPLICATION NO. | : 17/049891 | |
| DATED | : April 8, 2025 | |
| INVENTOR(S) | : James F. Martin | |

It is certified that error appears in the above-identified patent and that said Letters Patent is hereby corrected as shown below:

In the Claims

Column 87 Claim 1, Line 57, delete "LATSI" and replace with LATS1.

Signed and Sealed this
Twentieth Day of May, 2025

Coke Morgan Stewart
*Acting Director of the United States Patent and Trademark Office*

SEQUENCE LISTING

<160> NUMBER OF SEQ ID NOS: 10

<210> SEQ ID NO 1
<211> LENGTH: 7362
<212> TYPE: DNA
<213> ORGANISM: Homo sapiens

<400> SEQUENCE: 1

```
agcggagtgc ggcggcggcg acactgagtg gaaggcaaaa tggcggcggc ggcggcggtg      60
gcctggtgtt aaggggagag ccaggtcctc acgacccctg ggacgggccg cgctggcccg     120
cggcagcccc cccgttcgtc tccccgctct gccccaccag ggatacttgg ggttgctggg     180
acggactctg gccgcctcag cgtccgccct caggcccgtg gccgctgtcc aggagctctg     240
ctctcccctc cagagttaat tatttatatt gtaaagaatt ttaacagtcc tggggacttc     300
cttgaaggat cattttcact tttgctcaga agaaagctct ggatctatca aataaagaag     360
tccttcgtgt gggctacata tatagatgtt ttcatgaaga ggagtgaaaa gccagaagga     420
tatagacaaa tgaggcctaa gacctttcct gccagtaact atactgtcag tagccggcaa     480
atgttacaag aaattcggga atcccttagg aatttatcta aaccatctga tgctgctaag     540
gctgagcata acatgagtaa aatgtcaacc gaagatcctc gacaagtcag aaatccaccc     600
aaatttggga cgcatcataa agccttgcag gaaattcgaa actctctgct tccatttgca     660
aatgaaacaa attcttctcg gagtacttca gaagttaatc cacaaatgct tcaagacttg     720
caagctgctg gatttgatga ggatatggtt atacaagctc ttcagaaaac taacaacaga     780
agtatagaag cagcaattga attcattagt aaaatgagtt accaagatcc tcgacgagag     840
cagatggctg cagcagctgc cagacctatt aatgccagca tgaaaccagg gaatgtgcag     900
caatcagtta accgcaaaca gagctggaaa ggttctaaag aatccttagt tcctcagagg     960
catggcccgc cactaggaga aagtgtggcc tatcattctg agagtcccaa ctcacagaca    1020
gatgtaggaa gacctttgtc tggatctggt atatcagcat ttgttcaagc tcaccctagc    1080
aacggacaga gagtgaaccc cccaccacca cctcaagtaa ggagtgttac tcctccacca    1140
cctccaagag gccagactcc ccctccaaga ggtacaactc cacctccccc ttcatgggaa    1200
```

```
ccaaactctc aaacaaagcg ctattctgga aacatggaat acgtaatctc ccgaatctct    1260
cctgtcccac ctggggcatg gcaagagggc tatcctccac cacctctcaa cacttccccc    1320
atgaatcctc ctaatcaagg acagagaggc attagttctg ttcctgttgg cagacaacca    1380
atcatcatgc agagttctag caaatttaac tttccatcag ggagacctgg aatgcagaat    1440
ggtactggac aaactgattt catgatacac caaaatgttg tccctgctgg cactgtgaat    1500
cggcagccac cacctccata tcctctgaca gcagctaatg acaaagccc ttctgcttta    1560 caaacagggg gatctgctgc tccttcgtca tatacaaatg gaagtattcc tcagtctatg    1620
atggtgccaa acagaaatag tcataacatg gaactatata acattagtgt acctggactg    1680
caaacaaatt ggcctcagtc atcttctgct ccagcccagt catccccgag cagtgggcat    1740
gaaatcccta catggcaacc taacatacca gtgaggtcaa attcttttaa taacccatta    1800
ggaaatagag caagtcactc tgctaattct cagccttctg ctacaacagt cactgcaatt    1860
acaccagctc ctattcaaca gcctgtgaaa agtatgcgtg tattaaaacc agagctacag    1920
actgctttag cacctacaca cccttcttgg ataccacagc caattcaaac tgttcaaccc    1980
agtccttttc ctgagggaac cgcttcaaat gtgactgtga tgccacctgt tgctgaagct    2040
ccaaactatc aaggaccacc accaccctac ccaaaacatc tgctgcacca aaacccatct    2100
gttcctccat acgagtcaat cagtaagcct agcaaagagg atcagccaag cttgcccaag    2160
gaagatgaga gtgaaaagag ttatgaaaat gttgatagtg gggataaaga aaagaaacag    2220
attacaactt cacctattac tgttaggaaa acaagaaag atgaagagcg aagggaatct    2280
cgtattcaaa gttattctcc tcaagcattt aaattcttta tggagcaaca tgtagaaaat    2340
gtactcaaat ctcatcagca gcgtctacat cgtaaaaaac aattagagaa tgaaatgatg    2400
cgggttggat tatctcaaga tgcccaggat caaatgagaa agatgctttg ccaaaaagaa    2460
tctaattaca tccgtcttaa aagggctaaa atggacaagt ctatgtttgt gaagataaag    2520
acactaggaa taggagcatt tggtgaagtc tgtctagcaa gaaaagtaga tactaaggct    2580
ttgtatgcaa caaaaactct tcgaaagaaa gatgttcttc ttcgaaatca agtcgctcat    2640
gttaaggctg agagagatat cctggctgaa gctgacaatg aatgggtagt tcgtctatat    2700
tattcattcc aagataagga caatttatac tttgtaatgg actacattcc tgggggtgat    2760
atgatgagcc tattaattag aatgggcatc tttccagaaa gtctggcacg attctacata    2820
gcagaactta cctgtgcagt tgaaagtgtt cataaaatgg gttttattca tagagatatt    2880
aaacctgata atatttttga ttgatcgtgat ggtcatatta aattgactga ctttggcctc    2940
tgcactggct tcagatggac acacgattct aagtactatc agagtggtga ccatccacgg    3000
caagatagca tggatttcag taatgaatgg ggggatccct caagctgtcg atgtggagac    3060
agactgaagc cattagagcg gagagctgca cgccagcacc agcgatgtct agcacattct    3120 ttggtttggga ctcccaatta tattgcacct gaagtgttgc tacgaacagg atacacacag    3180
ttgtgtgatt ggtggagtgt tggtgttatt cttttttgaaa tgttggtggg acaacctcct    3240
ttcttggcac aaaacaccat tagaaacacaa atgaaggtta tcaactggca aacatctctt    3300
cacattccac cacaagctaa actcagtcct gaagcttctg atcttattat taaactttgc    3360
cgaggacccg aagatcgctt aggcaagaat ggtgctgatg aaataaaagc tcatccattt    3420
tttaaaacaa ttgacttctc cagtgacctg agacagcagt ctgcttcata cattcctaaa    3480
atcacacacc caacagatac atcaaatttt gatcctgttg atcctgataa attatggagt    3540
```

```
gatgataacg aggaagaaaa tgtaaatgac actctcaatg gatggtataa aaatggaaag      3600
catcctgaac atgcattcta tgaatttacc ttccgaaggt tttttgatga caatggctac      3660
ccatataatt atccgaagcc tattgaatat gaatacatta attcacaagg ctcagagcag      3720
cagtcggatg aagatgatca aaacacaggc tcagagatta aaaatcgcga tctagtatat      3780
gtttaacaca ctagtaaata aatgtaatga ggatttgtaa aagggcctga aatgcgaggt      3840
gttttgaggt tctgagagta aaattatgca aatatgacag agctatatat gtgtgctctg      3900
tgtacaatat tttattttcc taaattatgg gaaatccttt taaaatgtta atttattcca      3960 gccgttttaaa tcagtattta gaaaaaaatt gttataagga aagtaaatta tgaactgaat     4020
attatagtca gttcttggta cttaaagtac ttaaaataag tagtgctttg tttaaaagga      4080
gaaacctggt atctatttgt atatatgcta ataattttta aaatacaaga gttttttgaaa     4140 tttttttgaa agacagtttt agtttatct tgctttaacc aaatatgaaa catacccct        4200 attttacaga gctctttttt cccctcataa ccttgttttt ggtagaaaat aagctagaga      4260
aattaagcca tcgtgttggt gagtgttcct aggctaatga taatctgtat aattcacatc     4320
ctgaaactaa ggaatacagg gttgaaaaaa tattaatatg tttgtcagaa ggaaaaataa      4380
tgcatttatc ttcccccca ccccccgccc catgaaatat ttaatctatt taatcttctt       4440
gcatttattt ctcaagaatt actggcttta aaagaagcca aagcactact agctttttt       4500 ccatattggt attttttgatg ctgcttccaa ttttaaaagg gaacaaagct gccataaatc     4560
gaaatgttca atactaaaag ctaaaatatt tctcaccatc ctaagcagat aattattta       4620 attttcatat acttttcctg tatagtaact attttgatta tatcatcaat gttacctgtt     4680
tcctctttca gaacagtgct gcatatacag attgttattg gcaaaggaaa atctggctat      4740
ctggcaatat tttacctaag cgcagattaa ttggtgaaaa aattaactct taagatggcc      4800
attaataatt aggaaagttt acagagtggt cttagtagaa aattcaagtc ctcctaattt     4860
atttaaggtt caataatgcg ttcaacatgc ctgttatgta taacgcttag gttctaagga     4920
agattaaggt ttcataccaa aatacatgta gcttatcttt taggaagggg aaaaaggctc      4980 catttttgacc atagtaaaat ttgtgttgtg tttatttcc tttcttaag ctccactgat       5040 aagggattgt ttttatcaaa agttactatt tgtagattgg aggcataatt ttagtgattt      5100
tcatactttt agctttcttc gcataaaagc taattgaaac cgtatatgta gtaaaattaa      5160
aggcagagct gttgcagttg aattggagag ttagggcaaa gaacacttat tagcccacac     5220
ttcccacctt tctacaggtg gtcctttcag agctcagcct gaaaacccac tactgtgtta     5280
tcgtgcgtct tttgggggtta gtggttcttt tgagaatctg aaggaagctg tggactcttc    5340
ctagaaaaaa aaaccacaca tacacataca atgttgcatg cagtttcaag ggattttgga     5400
catattgaaa cctatcacag gctgtaggtt atggacctct gtgccatgag aaaattgata     5460
cattaaacta agaactttgt ttttaactta ccaatcacta ctcagcacat cttatataag     5520
ctgataattt gtgatggaaa aggtctgtag catgtgtatat aaggtgacct tatgaatgcc    5580
tctcttgctg gtacattaag ttgtttaat atatcatttg gagggactg aaatgttagg       5640 ctcattacaa gctgataca gaaatatttc tgaaggatt ctaatcagaa ttgtaaaaca       5700
atgtgctatc atgaaatcgc agtcttcacc tcatggttca tggaacattt ggttagtccc     5760
ataaaatcct atgcaaaaca aagtagttca agaatttta ggtgggtagt cacatttata      5820
aggtattcct cttactcttt gggcttttc agtctgattt atttaaattt tcatttagtt      5880
gttttacttt tggactaagg tgcaatacag tagaagataa cttttgttaca tttatgttgt   5940
```

```
aggaaaacta aggtgctgtc cctcccct tcccttccca caaaatctgt attcccccta    6000
ttgctgaaat gtaacagaca ctacaaattt tgtattcttt ttttgttttt tgttttgaga    6060
cagggtctca ctctgtcacc caggctggag ggcagtggcg cttcacagct cactgcatcc    6120
tcaaccttgg gggctcacgc agtcctcccg cctcagcctc ccaagtagct gggcatgcgc    6180
caccaagccc agctaatttt tgtatcttta gtagagatgg ggtttcgcca tgttgcccag    6240
gttggtgtgg aattcctggg ctccagttat atgcccacct cagcctccca aagtgctggg    6300
attacagacg tgacccaccg cgcctggcgc aaatatgtat tcttttaaaa tttcctctga    6360
tactataagc ttttttgcatt tatctgaagc agtatacatg cctttggtat cagcaatttt    6420
aacagtttgg atatacttat cagctatctt attccaaaac tacatctact tcttccagta    6480
tagaatctgt tgcttcctga ccaaaaagat gagaaaaaca atgttaaaaa tatagatgct    6540
ttccattgaa atggagtgaa acattggtt ctatatgttt tcttttaaaa taattttctt    6600
attaaaaact tgctgtcttt attatactta cccttttat gcatatcaat agtatttata    6660
agatgtgttc tataattatg taattgtaga tactgttatg cattgtccag tgacatcata    6720
aggcaggccc tactgctgta tcttttctac cttcttattt gtaatagaaa ctatagaatg    6780
tatgactaaa aagtcacttt gagattgact ttttaaaaa gttattaccct tctgctgttg    6840 caaagtgcaa aactgtgagt ggaattgttt tattctgact taatgtgtta gaaattagag    6900
aatacagtgg gaggatttt agacattgct gctgctgtta cccaaggtat tttagataaa    6960 aaattttaa taaacatccc tttggtattt aaagtggaac atttagcctg ttcattttaa    7020
tctaaagcaa aaagtaattt gggtcaaaat attggtatat ttgtaaagcg ccttaatata    7080
tccctttgtg gaaggcacta cacagtttac ttttatattg tattgtgtat ataagtatt    7140 tgtattaaaa ttgaatcagt ggcaacatta aagtttttata aaatcatgct ttgttagaaa    7200
aagaattaca gctttgcaat ataactaatt gtttcgcata attctgaatg taatagatat    7260
gaataatcag cctgtgtttt taatgaactt atttgtattt tcccaatcat tttctctagt    7320
gtaatgtttg ctgggataat aaaaaaaatt caaatctttc aa    7362

<210> SEQ ID NO 2
<211> LENGTH: 1130
<212> TYPE: PRT
<213> ORGANISM: Homo sapiens

<400> SEQUENCE: 2

Met Lys Arg Ser Glu Lys Pro Glu Gly Tyr Arg Gln Met Arg Pro Lys
1               5                   10                  15

Thr Phe Pro Ala Ser Asn Tyr Thr Val Ser Ser Arg Gln Met Leu Gln
                20                  25                  30

Glu Ile Arg Glu Ser Leu Arg Asn Leu Ser Lys Pro Ser Asp Ala Ala
            35                  40                  45

Lys Ala Glu His Asn Met Ser Lys Met Ser Thr Glu Asp Pro Arg Gln
        50                  55                  60

Val Arg Asn Pro Pro Lys Phe Gly Thr His His Lys Ala Leu Gln Glu
65                  70                  75                  80

Ile Arg Asn Ser Leu Leu Pro Phe Ala Asn Glu Thr Asn Ser Ser Arg
                85                  90                  95

Ser Thr Ser Glu Val Asn Pro Gln Met Leu Gln Asp Leu Gln Ala Ala
                100                 105                 110
```

-continued

Gly Phe Asp Glu Asp Met Val Ile Gln Ala Leu Gln Lys Thr Asn Asn
            115                 120                 125

Arg Ser Ile Glu Ala Ala Ile Glu Phe Ile Ser Lys Met Ser Tyr Gln
        130                 135                 140

Asp Pro Arg Arg Glu Gln Met Ala Ala Ala Ala Arg Pro Ile Asn
145                 150                 155                 160

Ala Ser Met Lys Pro Gly Asn Val Gln Gln Ser Val Asn Arg Lys Gln
                165                 170                 175

Ser Trp Lys Gly Ser Lys Glu Ser Leu Val Pro Gln Arg His Gly Pro
            180                 185                 190

Pro Leu Gly Glu Ser Val Ala Tyr His Ser Glu Ser Pro Asn Ser Gln
        195                 200                 205

Thr Asp Val Gly Arg Pro Leu Ser Gly Ser Gly Ile Ser Ala Phe Val
210                 215                 220

Gln Ala His Pro Ser Asn Gly Gln Arg Val Asn Pro Pro Pro Pro Pro
225                 230                 235                 240

Gln Val Arg Ser Val Thr Pro Pro Pro Pro Arg Gly Gln Thr Pro
                245                 250                 255

Pro Pro Arg Gly Thr Thr Pro Pro Pro Ser Trp Glu Pro Asn Ser
            260                 265                 270

Gln Thr Lys Arg Tyr Ser Gly Asn Met Glu Tyr Val Ile Ser Arg Ile
            275                 280                 285

Ser Pro Val Pro Pro Gly Ala Trp Gln Glu Gly Tyr Pro Pro Pro Pro
        290                 295                 300

Leu Asn Thr Ser Pro Met Asn Pro Pro Asn Gln Gly Gln Arg Gly Ile
305                 310                 315                 320

Ser Ser Val Pro Val Gly Arg Gln Pro Ile Ile Met Gln Ser Ser Ser
                325                 330                 335

Lys Phe Asn Phe Pro Ser Gly Arg Pro Gly Met Gln Asn Gly Thr Gly
            340                 345                 350

Gln Thr Asp Phe Met Ile His Gln Asn Val Val Pro Ala Gly Thr Val
        355                 360                 365

Asn Arg Gln Pro Pro Pro Tyr Pro Leu Thr Ala Ala Asn Gly Gln
370                 375                 380

Ser Pro Ser Ala Leu Gln Thr Gly Gly Ser Ala Ala Pro Ser Ser Tyr
385                 390                 395                 400

Thr Asn Gly Ser Ile Pro Gln Ser Met Met Val Pro Asn Arg Asn Ser
                405                 410                 415

His Asn Met Glu Leu Tyr Asn Ile Ser Val Pro Gly Leu Gln Thr Asn
            420                 425                 430

Trp Pro Gln Ser Ser Ala Pro Ala Gln Ser Ser Pro Ser Ser Gly
        435                 440                 445

His Glu Ile Pro Thr Trp Gln Pro Asn Ile Pro Val Arg Ser Asn Ser
450                 455                 460

Phe Asn Asn Pro Leu Gly Asn Arg Ala Ser His Ser Ala Asn Ser Gln
465                 470                 475                 480

Pro Ser Ala Thr Thr Val Thr Ala Ile Thr Pro Ala Pro Ile Gln Gln
                485                 490                 495

Pro Val Lys Ser Met Arg Val Leu Lys Pro Glu Leu Gln Thr Ala Leu
            500                 505                 510

Ala Pro Thr His Pro Ser Trp Ile Pro Gln Pro Ile Gln Thr Val Gln
        515                 520                 525

```
Pro Ser Pro Phe Pro Glu Gly Thr Ala Ser Asn Val Thr Met Pro
    530                 535                 540

Pro Val Ala Glu Ala Pro Asn Tyr Gln Gly Pro Pro Pro Tyr Pro
545                 550                 555                 560

Lys His Leu Leu His Gln Asn Pro Ser Val Pro Pro Tyr Glu Ser Ile
                565                 570                 575

Ser Lys Pro Ser Lys Glu Asp Gln Pro Ser Leu Pro Lys Glu Asp Glu
            580                 585                 590

Ser Glu Lys Ser Tyr Glu Asn Val Asp Ser Gly Asp Lys Glu Lys Lys
        595                 600                 605

Gln Ile Thr Thr Ser Pro Ile Thr Val Arg Lys Asn Lys Lys Asp Glu
    610                 615                 620

Glu Arg Arg Glu Ser Arg Ile Gln Ser Tyr Ser Pro Gln Ala Phe Lys
625                 630                 635                 640

Phe Phe Met Glu Gln His Val Glu Asn Val Leu Lys Ser His Gln Gln
                645                 650                 655

Arg Leu His Arg Lys Lys Gln Leu Glu Asn Glu Met Met Arg Val Gly
                660                 665                 670

Leu Ser Gln Asp Ala Gln Asp Gln Met Arg Lys Met Leu Cys Gln Lys
        675                 680                 685

Glu Ser Asn Tyr Ile Arg Leu Lys Arg Ala Lys Met Asp Lys Ser Met
690                 695                 700

Phe Val Lys Ile Lys Thr Leu Gly Ile Gly Ala Phe Gly Glu Val Cys
705                 710                 715                 720

Leu Ala Arg Lys Val Asp Thr Lys Ala Leu Tyr Ala Thr Lys Thr Leu
                725                 730                 735

Arg Lys Lys Asp Val Leu Leu Arg Asn Gln Val Ala His Val Lys Ala
                740                 745                 750

Glu Arg Asp Ile Leu Ala Glu Ala Asp Asn Glu Trp Val Val Arg Leu
            755                 760                 765

Tyr Tyr Ser Phe Gln Asp Lys Asp Asn Leu Tyr Phe Val Met Asp Tyr
        770                 775                 780

Ile Pro Gly Gly Asp Met Met Ser Leu Leu Ile Arg Met Gly Ile Phe
785                 790                 795                 800

Pro Glu Ser Leu Ala Arg Phe Tyr Ile Ala Glu Leu Thr Cys Ala Val
                805                 810                 815

Glu Ser Val His Lys Met Gly Phe Ile His Arg Asp Ile Lys Pro Asp
            820                 825                 830

Asn Ile Leu Ile Asp Arg Asp Gly His Ile Lys Leu Thr Asp Phe Gly
        835                 840                 845

Leu Cys Thr Gly Phe Arg Trp Thr His Asp Ser Lys Tyr Tyr Gln Ser
    850                 855                 860

Gly Asp His Pro Arg Gln Asp Ser Met Asp Phe Ser Asn Glu Trp Gly
865                 870                 875                 880

Asp Pro Ser Ser Cys Arg Cys Gly Asp Arg Leu Lys Pro Leu Glu Arg
                885                 890                 895

Arg Ala Ala Arg Gln His Gln Arg Cys Leu Ala His Ser Leu Val Gly
            900                 905                 910

Thr Pro Asn Tyr Ile Ala Pro Glu Val Leu Leu Arg Thr Gly Tyr Thr
        915                 920                 925

Gln Leu Cys Asp Trp Trp Ser Val Gly Val Ile Leu Phe Glu Met Leu
    930                 935                 940
```

```
Val Gly Gln Pro Pro Phe Leu Ala Gln Thr Pro Leu Glu Thr Gln Met
945                 950                 955                 960

Lys Val Ile Asn Trp Gln Thr Ser Leu His Ile Pro Pro Gln Ala Lys
            965                 970                 975

Leu Ser Pro Glu Ala Ser Asp Leu Ile Ile Lys Leu Cys Arg Gly Pro
        980                 985                 990

Glu Asp Arg Leu Gly Lys Asn Gly Ala Asp Glu Ile Lys Ala His Pro
    995                 1000                1005

Phe Phe Lys Thr Ile Asp Phe Ser Ser Asp Leu Arg Gln Gln Ser
1010                1015                1020

Ala Ser Tyr Ile Pro Lys Ile Thr His Pro Thr Asp Thr Ser Asn
1025                1030                1035

Phe Asp Pro Val Asp Pro Lys Leu Trp Ser Asp Asp Asn Glu
1040                1045                1050

Glu Glu Asn Val Asn Asp Thr Leu Asn Gly Trp Tyr Lys Asn Gly
1055                1060                1065

Lys His Pro Glu His Ala Phe Tyr Glu Phe Thr Phe Arg Arg Phe
1070                1075                1080

Phe Asp Asp Asn Gly Tyr Pro Tyr Asn Tyr Pro Lys Pro Ile Glu
1085                1090                1095

Tyr Glu Tyr Ile Asn Ser Gln Gly Ser Glu Gln Gln Ser Asp Glu
1100                1105                1110

Asp Asp Gln Asn Thr Gly Ser Glu Ile Lys Asn Arg Asp Leu Val
1115                1120                1125

Tyr Val
1130

<210> SEQ ID NO 3
<211> LENGTH: 5546
<212> TYPE: DNA
<213> ORGANISM: Homo sapiens

<400> SEQUENCE: 3
gacgcccgtg gaatgccaac aatgtagcga atgtcccact tgggtctgcg ctttggaacc      60
gcggcgtgag cgccccggga agatggagca gtcgccgtcc acgccaccgc cgccgcccgg     120
ggctcccccg tccctgcggg gccagcagca gctccagcca ccagtgcccg gtctcccggc     180
gcgagaggcc cgggagccgc cggccaggac gcccccgagg gtgtagaccg cgcccctgga     240
gagagtgata atcttcaaaa tgaagacttt ggaaaatttt aggttctcta taggaactac     300
aaaaatggaa ggaaagaaca ttttcaaaag gaaattattt tgaaagtatg tttacaacaa     360
actgatacta ttgacagttt ttttttttaa ataataaaac actttaagaa gattgtattt     420
atggtaaaag gaaactggac taacaatgag gccaaagact tttcctgcca cgacttattc     480
tggaaatagc cggcagcgac tgcaagagat tcgtgagggg ttaaaacagc catccaagtc     540
ttcggttcag ggctacccg caggaccaaa cagtgacact tccctggatg ccaaagtcct     600
ggggagcaaa gatgccacca ggcagcagca gcagatgaga gccacccaa agttcggacc     660 ttatcagaaa gccttgaggg aaatcagata ttccttgttg ccttttgcta atgaatcggg     720
cacctctgca gctgcagaag tgaaccggca aatgctgcag gaactggtga acgcaggatg     780
cgaccaggag atggctggcc gagctctcaa gcagactggc agcaggagca tcgaggccgc     840
cctggagtac atcagcaaga tgggctacct ggacccgagg aatgagcaga ttgtgcgggt     900
cattaagcag acctccccag gaaagggggct catgccaacc ccagtgacgc ggaggcccag     960
```

```
cttcgaagga accggcgatt cgtttgcgtc ctaccaccag ctgagcggta ccccctacga    1020
gggcccaagc ttcggcgctg acggccccac ggcgctggag gagatgccgc ggccgtacgt    1080
ggactacctt ttccccggag tcggccccca cgggcccggc caccagcacc agcacccacc    1140
caagggctac ggtgccagcg tagaggcagc aggggcacac ttcccgctgc agggcgcgca    1200
ctacgggcgg ccgcacctgc tggtgcctgg ggaaccctg ggctacggag tgcagcgcag    1260
cccctccttc cagagcaaga cgccgccgga gaccggggt tacgccagcc tgcccacgaa    1320
gggccaggga ggaccgccag gcgccggcct cgctttccca ccccctgccg ccgggctcta    1380
cgtgccgcac ccacaccaca agcaggccgg tcccgcggcc caccagctgc atgtgctggg    1440
ctcccgcagc caggtgttcg ccagcgacag ccccccgcag agcctgctca ctccctcgcg    1500
gaacagcctc aacgtggacc tgtatgaatt gggcagcacc tccgtccagc agtgccggc    1560 tgccaccctg gcccgccggg actccctgca gaagccgggc ctggaggcgc cgccgcgcgc    1620
gcacgtggcc ttccggcctg actgcccagt gcccagcagg accaactcct tcaacagcca    1680
ccagccgcgg cccggtccgc ctggcaaggc cgagccctcc ctgcccgccc caacaccgt    1740 gacggctgtc acgccgcgc acatcttgca cccggtgaag agcgtgcgtg tgctgaggcc    1800
ggagccgcag acggctgtgg ggccctcgca ccccgcctgg gtgcccgcgc ctgccccggc    1860
ccccgccccc gccccgccc cggctgcgga gggcttggac gccaaggagg agcatgccct    1920
ggcgctgggc ggcgcaggcg ccttcccgct ggacgtggag tacgaggcc cagaccggag    1980 gtgcccgcct ccgccctacc cgaagcacct gctgctgcgc agcaagtcgg agcagtacga    2040
cctggacagc ctgtgcgcag gcatggagca gagcctccgt gcgggcccca acgagcccga    2100
gggcggcgac aagagccgca aaagcgccaa ggggacaaa gcggaaagg ataaaaagca    2160 gattcagacc tctcccgttc ccgtccgcaa aaacagcaga gacgaagaga agagagagtc    2220
acgcatcaag agctactcgc atacgcctt taagttcttc atggagcagc acgtggagaa    2280
tgtcatcaaa acctaccagc agaaggttaa ccggaggctg cagctggagc aagaaatggc    2340
caaagctgga ctctgtgaag ctgagcagga gcagatgcgg aagatcctct accagaaaga    2400
gtctaattac aacaggttaa agagggccaa gatggacaag tctatgtttg tcaagatcaa    2460
aaccctgggg atcggtgcct ttggagaagt gtgccttgct tgtaaggtgg acactcacgc    2520
cctgtacgcc atgaagaccc taaggaaaaa ggatgtcctg aaccggaatc aggtggccca    2580
cgtcaaggcc gagagggaca tcctggccga ggcagacaat gagtgggtgg tcaaactcta    2640
ctactccttc caagacaaag acagcctgta ctttgtgatg gactacatcc ctgggtgga    2700 catgatgagc ctgctgatcc ggatggaggt cttccctgag cacctggccc ggttctacat    2760
cgcagagctg actttggcca ttgagagtgt ccacaagatg ggcttcatcc accgagacat    2820
caagcctgat aacattttga tagatctgga tggtcacatt aaactcacag atttcggcct    2880
ctgcactggg ttcaggtgga ctcacaattc caaatattac cagaaaggga ccatgtcag    2940 acaggacagc atggagccca gcgacctctg ggatgatgtg tctaactgtc ggtgtgggga    3000
caggctgaag accctagagc agagggcgcg gaagcagcac cagaggtgcc tggcacattc    3060
actggtgggg actccaaact acatcgcacc cgaggtgctc tccgcaaag gtacactca    3120 actctgtgac tggtggagtg ttggagtgat tctcttcgag atgctggtgg ggcagccgcc    3180 cttttttggca cctactccca cagaaaccca gctgaaggtg atcaactggg agaacacgct    3240
ccacattcca gcccaggtga agctgagccc tgaggccagg gacctcatca ccaagctgtg    3300
```

```
ctgctccgca gaccaccgcc tggggcggaa tggggccgat gacctgaagg cccacccctt    3360
cttcagcgcc attgacttct ccagtgacat ccggaagcag ccagcccct acgttcccac     3420 catcagccac cccatggaca cctcgaattt cgaccccgta gatgaagaaa gcccttggaa    3480
cgatgccagc gaaggtagca ccaaggcctg ggacacactc acctcgccca ataacaagca    3540
tcctgagcac gcattttacg aattcacctt ccgaaggttc tttgatgaca atggctaccc    3600
ctttcgatgc ccaaagcctt caggagcaga agcttcacag gctgagagct cagatttaga    3660
aagctctgat ctggtggatc agactgaagg ctgccagcct gtgtacgtgt agatggggc     3720 caggcacccc caccactcgc tgcctcccag gtcagggtcc cggagccggt gccctcacag    3780
gccaataggg aagccgaggg ctgttttgtt ttaaattagt ccgtcgatta cttcacttga    3840
aattctgctc ttcaccaaga aacccaaac aggacacttt tgaaaacagg actcagcatc     3900
gctttcaata ggcttttcag gaccttcact gcattaaaac aatatttttg aaaatttagt    3960
acagtttaga aagagcactt attttgttta tatccatttt ttcttactaa attatagggga   4020 ttaactttga caaatcatgc tgctgttatt ttctacatttt gtattttatc catagcactt   4080
attcacattt aggaaaagac ataaaaactg aagaacattg atgagaaatc tctgtgcaat    4140
aatgtaaaaa aaaaaaaaga taacactctg ctcaatgtca cggagaccat tttatccaca    4200
caatggtttt tgtttttttat ttttttcccat gtttcaaat tgtgatataa tgatataatg   4260
ttaaaagctg cttttttttgg cttttgcat atctagtata ataggaagtg tgagcaaggt    4320
gatgatgtgg ctgtgatttc cgacgtctgg tgtgtggaga gtactgcatg agcagagttc    4380
ttctattata aaattaccat atcttgccat tcacagcagg tcctgtgaat acgttttac     4440 tgagtgtctt taaatgaggt gttctagaca gtgtgctgat aatgtattgt gcgggtgacc    4500
tcttcgctat gattgtatct cttactgttt tgttaaagaa atgcagatgt gtaactgaga    4560
agtgatttgt gtgtgtgtct tggttgtgat tggattcttt gggggggggg aactgaaaca    4620
tttgtcatat actgaactta tatacatcaa aagggattaa tacagcgatg ccaaaaagtt    4680
taatcacgga cacatgtccg tttctgtagt ccgtatgctc tttcattctt ggtagagctg    4740
gtatgtggaa tgccataacct ctgaccctac tacttacctt tttactgaca gactgcccac   4800
actgaaagct tcagtgaatg ttcttagtcc tgttttcttc tgttactgtc aggaaactga    4860
gtgatctaat ggttctctca ctttttttttt gttcttttag tgtactttga agtatcaaat    4920
cttaacttgg tttaaacaat acatattcct aacctttgta aaaaagcaaa gattcttcaa    4980
aatgacattg aaataaaaag taagcctac gtattttctt agaagtatag atgtatgtgc     5040
gtgtatacac acacacacac acacacagag ataaacacaa tattccttat ttcaaattag    5100
tatgattcct atttaaagtg atttatattt gagtaaaaag ttcaattctt ttttgctttt    5160
taaaaaatct gatgcttcat aattttcatt atattattcc acatatttt ccttgaagtt     5220 cttagcataa tgtatccatt acttagtata tatctaggca acaacactta gaagtttatc    5280 agtgttttaaa ctaaaaaaat aaagattcct gtgtactggt ttcatttgt gtgagtggca    5340 tactcaagtc tgctgtgcct gtcgtcgtga ctgtcagtat tctcgctatt ttatagtcgt    5400
gccatgttgt tactcacagc gctctgacat actttcatgt ggtaggttct ttctcaggaa    5460
ctcagtttaa ctattattta ttgatatatc attacctttg aaaagcttct actggcacaa    5520
tttattatta aaattttgaa tccaaa                                         5546

<210> SEQ ID NO 4
<211> LENGTH: 1088
```

```
<212> TYPE: PRT
<213> ORGANISM: Homo sapiens

<400> SEQUENCE: 4
```

| | | | | | | | | | | | | | | |
|---|---|---|---|---|---|---|---|---|---|---|---|---|---|---|

Met Arg Pro Lys Thr Phe Pro Ala Thr Thr Tyr Ser Gly Asn Ser Arg
1               5                   10                  15

Gln Arg Leu Gln Glu Ile Arg Glu Gly Leu Lys Gln Pro Ser Lys Ser
            20                  25                  30

Ser Val Gln Gly Leu Pro Ala Gly Pro Asn Ser Asp Thr Ser Leu Asp
        35                  40                  45

Ala Lys Val Leu Gly Ser Lys Asp Ala Thr Arg Gln Gln Gln Gln Met
50                  55                  60

Arg Ala Thr Pro Lys Phe Gly Pro Tyr Gln Lys Ala Leu Arg Glu Ile
65                  70                  75                  80

Arg Tyr Ser Leu Leu Pro Phe Ala Asn Glu Ser Gly Thr Ser Ala Ala
                85                  90                  95

Ala Glu Val Asn Arg Gln Met Leu Gln Glu Leu Val Asn Ala Gly Cys
            100                 105                 110

Asp Gln Glu Met Ala Gly Arg Ala Leu Lys Gln Thr Gly Ser Arg Ser
        115                 120                 125

Ile Glu Ala Ala Leu Glu Tyr Ile Ser Lys Met Gly Tyr Leu Asp Pro
130                 135                 140

Arg Asn Glu Gln Ile Val Arg Val Ile Lys Gln Thr Ser Pro Gly Lys
145                 150                 155                 160

Gly Leu Met Pro Thr Pro Val Thr Arg Arg Pro Ser Phe Glu Gly Thr
                165                 170                 175

Gly Asp Ser Phe Ala Ser Tyr His Gln Leu Ser Gly Thr Pro Tyr Glu
            180                 185                 190

Gly Pro Ser Phe Gly Ala Asp Gly Pro Thr Ala Leu Glu Glu Met Pro
        195                 200                 205

Arg Pro Tyr Val Asp Tyr Leu Phe Pro Gly Val Gly Pro His Gly Pro
210                 215                 220

Gly His Gln His Gln His Pro Pro Lys Gly Tyr Gly Ala Ser Val Glu
225                 230                 235                 240

Ala Ala Gly Ala His Phe Pro Leu Gln Gly Ala His Tyr Gly Arg Pro
                245                 250                 255

His Leu Leu Val Pro Gly Glu Pro Leu Gly Tyr Gly Val Gln Arg Ser
            260                 265                 270

Pro Ser Phe Gln Ser Lys Thr Pro Glu Thr Gly Gly Tyr Ala Ser
        275                 280                 285

Leu Pro Thr Lys Gly Gln Gly Gly Pro Gly Ala Gly Leu Ala Phe
290                 295                 300

Pro Pro Pro Ala Ala Gly Leu Tyr Val Pro His Pro His His Lys Gln
305                 310                 315                 320

Ala Gly Pro Ala Ala His Gln Leu His Val Leu Gly Ser Arg Ser Gln
                325                 330                 335

Val Phe Ala Ser Asp Ser Pro Pro Gln Ser Leu Leu Thr Pro Ser Arg
            340                 345                 350

Asn Ser Leu Asn Val Asp Leu Tyr Glu Leu Gly Ser Thr Ser Val Gln
        355                 360                 365

Gln Trp Pro Ala Ala Thr Leu Ala Arg Arg Asp Ser Leu Gln Lys Pro
370                 375                 380

Gly Leu Glu Ala Pro Pro Arg Ala His Val Ala Phe Pro Arg Asp Cys
385                 390                 395                 400

```
Pro Val Pro Ser Arg Thr Asn Ser Phe Asn Ser His Gln Pro Arg Pro
            405                 410                 415

Gly Pro Pro Gly Lys Ala Glu Pro Ser Leu Pro Ala Pro Asn Thr Val
            420                 425                 430

Thr Ala Val Thr Ala Ala His Ile Leu His Pro Val Lys Ser Val Arg
            435                 440                 445

Val Leu Arg Pro Glu Pro Gln Thr Ala Val Gly Pro Ser His Pro Ala
    450                 455                 460

Trp Val Pro Ala Pro Ala Pro Ala Pro Ala Pro Ala Pro Ala Pro Ala
465                 470                 475                 480

Ala Glu Gly Leu Asp Ala Lys Glu Glu His Ala Leu Ala Leu Gly Gly
                485                 490                 495

Ala Gly Ala Phe Pro Leu Asp Val Glu Tyr Gly Gly Pro Asp Arg Arg
                500                 505                 510

Cys Pro Pro Pro Tyr Pro Lys His Leu Leu Arg Ser Lys Ser
                515                 520                 525         Ser

Glu Gln Tyr Asp Leu Asp Ser Leu Cys Ala Gly Met Glu Gln Ser Leu
    530                 535                 540

Arg Ala Gly Pro Asn Glu Pro Glu Gly Gly Asp Lys Ser Arg Lys Ser
545                 550                 555                 560

Ala Lys Gly Asp Lys Gly Gly Lys Asp Lys Lys Gln Ile Gln Thr Ser
                565                 570                 575

Pro Val Pro Val Arg Lys Asn Ser Arg Asp Glu Glu Lys Arg Glu Ser
                580                 585                 590

Arg Ile Lys Ser Tyr Ser Pro Tyr Ala Phe Lys Phe Phe Met Glu Gln
                595                 600                 605

His Val Glu Asn Val Ile Lys Thr Tyr Gln Gln Lys Val Asn Arg Arg
    610                 615                 620

Leu Gln Leu Glu Gln Glu Met Ala Lys Ala Gly Leu Cys Glu Ala Glu
625                 630                 635                 640

Gln Glu Gln Met Arg Lys Ile Leu Tyr Gln Lys Glu Ser Asn Tyr Asn
                645                 650                 655

Arg Leu Lys Arg Ala Lys Met Asp Lys Ser Met Phe Val Lys Ile Lys
                660                 665                 670

Thr Leu Gly Ile Gly Ala Phe Gly Glu Val Cys Leu Ala Cys Lys Val
                675                 680                 685

Asp Thr His Ala Leu Tyr Ala Met Lys Thr Leu Arg Lys Lys Asp Val
    690                 695                 700

Leu Asn Arg Asn Gln Val Ala His Val Lys Ala Glu Arg Asp Ile Leu
705                 710                 715                 720

Ala Glu Ala Asp Asn Glu Trp Val Val Lys Leu Tyr Tyr Ser Phe Gln
                725                 730                 735

Asp Lys Asp Ser Leu Tyr Phe Val Met Asp Tyr Ile Pro Gly Gly Asp
                740                 745                 750

Met Met Ser Leu Leu Ile Arg Met Glu Val Phe Pro Glu His Leu Ala
                755                 760                 765

Arg Phe Tyr Ile Ala Glu Leu Thr Leu Ala Ile Glu Ser Val His Lys
    770                 775                 780

Met Gly Phe Ile His Arg Asp Ile Lys Pro Asp Asn Ile Leu Ile Asp
785                 790                 795                 800

Leu Asp Gly His Ile Lys Leu Thr Asp Phe Gly Leu Cys Thr Gly Phe
                805                 810                 815
```

```
Arg Trp Thr His Asn Ser Lys Tyr Tyr Gln Lys Gly Ser His Val Arg
            820                 825                 830

Gln Asp Ser Met Glu Pro Ser Asp Leu Trp Asp Val Ser Asn Cys
835                 840                 845

Arg Cys Gly Asp Arg Leu Lys Thr Leu Glu Gln Arg Ala Arg Lys Gln
850                 855                 860

His Gln Arg Cys Leu Ala His Ser Leu Val Gly Thr Pro Asn Tyr Ile
865                 870                 875                 880

Ala Pro Glu Val Leu Leu Arg Lys Gly Tyr Thr Gln Leu Cys Asp Trp
                885                 890                 895

Trp Ser Val Gly Val Ile Leu Phe Glu Met Leu Val Gly Gln Pro Pro
                900                 905                 910

Phe Leu Ala Pro Thr Pro Thr Glu Thr Gln Leu Lys Val Ile Asn Trp
                915                 920                 925

Glu Asn Thr Leu His Ile Pro Ala Gln Val Lys Leu Ser Pro Glu Ala
930                 935                 940

Arg Asp Leu Ile Thr Lys Leu Cys Cys Ser Ala Asp His Arg Leu Gly
945                 950                 955                 960

Arg Asn Gly Ala Asp Asp Leu Lys Ala His Pro Phe Phe Ser Ala Ile
                965                 970                 975

Asp Phe Ser Ser Asp Ile Arg Lys Gln Pro Ala Pro Tyr Val Pro Thr
                980                 985                 990

Ile Ser His Pro Met Asp Thr Ser Asn Phe Asp Pro Val Asp Glu Glu
                995                 1000                1005

Ser Pro Trp Asn Asp Ala Ser Glu Gly Ser Thr Lys Ala Trp Asp
    1010                1015                1020

Thr Leu Thr Ser Pro Asn Asn Lys His Pro Glu His Ala Phe Tyr
    1025                1030                1035

Glu Phe Thr Phe Arg Arg Phe Phe Asp Asp Asn Gly Tyr Pro Phe
    1040                1045                1050

Arg Cys Pro Lys Pro Ser Gly Ala Glu Ala Ser Gln Ala Glu Ser
    1055                1060                1065

Ser Asp Leu Glu Ser Ser Asp Leu Val Asp Gln Thr Glu Gly Cys
    1070                1075                1080

Gln Pro Val Tyr Val
    1085

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggaggaagat tatgcacaac aac                                          23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgtggagaca tgaaagacta agg                                          23
```

```
<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggagctcatg aatgcctgat t                                              21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctgcagaaga actgtgctct ta                                             22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cctacccaca caagacatca a                                              21

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctcaggagat gatccaacaa gaa                                            23
```